United States Patent [19]
Warren et al.

[11] Patent Number: 5,840,868
[45] Date of Patent: Nov. 24, 1998

[54] PESTICIDAL PROTEINS AND STRAINS

[75] Inventors: Gregory W. Warren; Michael G. Koziel, both of Cary; Martha A. Mullins, Raleigh; Brian Carr; Nalini M. Desai, both of Cary; Kristy Kostichka, Durham, all of N.C.

[73] Assignee: Novartis Finance Corporation, New York, N.Y.

[21] Appl. No.: 471,044

[22] Filed: Jun. 6, 1995

Related U.S. Application Data

[60] Division of Ser. No. 463,483, Jun. 5, 1995, which is a continuation-in-part of Ser. No. 314,594, Sep. 28, 1994, abandoned, which is a continuation-in-part of Ser. No. 218,018, Mar. 23, 1994, abandoned, which is a continuation-in-part of Ser. No. 37,057, Mar. 25, 1993, abandoned.

[51] Int. Cl.$^6$ .......................... C07H 21/02; C07H 21/04; C12Q 1/68; C07K 1/00
[52] U.S. Cl. ........................... 536/23.1; 536/24.1; 435/6; 435/320.1; 530/350
[58] Field of Search ................. 536/23.1, 24.1; 435/252.3, 320.1, 6; 530/350

[56] References Cited

U.S. PATENT DOCUMENTS

| | | | |
|---|---|---|---|
| 3,632,747 | 1/1972 | Satohiro et al. | 424/93 |
| 3,651,215 | 3/1972 | Satohiro et al. | 424/93 |
| 4,996,155 | 2/1991 | Sick et al. | 435/252.3 |
| 5,262,323 | 11/1993 | Baird et al. | 435/252.5 |

FOREIGN PATENT DOCUMENTS

| | | |
|---|---|---|
| 0498537A2 | 1/1992 | European Pat. Off. . |
| 0501650A2 | 2/1992 | European Pat. Off. . |
| WO88/08880 | 11/1988 | WIPO . |
| WO90/13651 | 11/1990 | WIPO . |
| WO91/16432 | 10/1991 | WIPO . |
| WO91/16434 | 10/1991 | WIPO . |
| WO 94/21795 | 9/1994 | WIPO . |

OTHER PUBLICATIONS

Arellano, A., et al., "Evidence of a New *Bacillus thuringiensis* Toxin Active Against the Australian Sheep Blowfly *Lucilla cuprina*", *Proceedings and Abstracts of the 5th International Colloquium on Invertebrate Pathology and Microbial Control, Adelaide, Austrailia*, 20–24 Aug., 1990, p. 291.

Beecher, Douglas J., et al., "A Novel Bicomponent Hemolysin from *Bacillus cereus*", *Inspection and Immunity*, 58(7):2220–2227 (1990).

Faust, R.M., "Bacterial Diseases", In: *Insect Diseases*, G. Cantwell, ed., Marcel Dekker, NY 1974, pp. 90–102.

Faust, R.M., et al., "Bacteria and Their Toxins as Insecticides", In: *Microbial and Viral Pesticides*, E. Kurstak, Ed., Marcel Dekker, NY, 1982, pp. 84–89, 108–120.

Gilmore, Michael S., et al., "A *Bacillus cereus* Cytolytic Determinant, Cereolysin AB, Which Comprises the Phospholipase C and Sphingomyelinase Genes: Nucleotide Sequence and Genetic Linkage", *Journal of Bacteriology*, 171(2):744–753 (1989).

Heimpel, A.M., "The pH in the Gut and Blood of the Larch Sawfly, *Pristiphora erichsonii* (HTG.), and Other Insects with Reference to the Pathogenicity of *Bacillus cereus* FR. and FR.", *Can. J. Zool.*, 33:99–106 (1955).

Heimpel, A.M., "Investigations of the Mode of Action of Strains of *Bacillus cereus* FR. and FR. Pathogenic for the Larch Sawfly, *Pristiphora erichsonii* (HTG.)", *Can. J. Zool.*, 33:311–326 (1995).

Hofte, H., et al., "Insecticidal Crystal Proteins of *Bacillus thuringiensis*", *Microbiological Reviews*, 53(2):242–255 (1989).

Koziel, M.G., et al., "Field Performance of Elite Tansgenic Maize Plants Expressing an Insecticidal Protein Derived from *Bacillus thuringiensis*", *Bio/Technology*, 11:194–200 (1993).

Krieg, A., "Thuricin, a Bacteriocin Produced by *Bacillus thuringiensis*", *J. Invert. Path.*, 15:291 (1970).

Krieg, A., "Concerning Alpha–exotoxin Produced by Vegetative Cells of *Bacillus thuringiensis* and *Bacillus cereus*", *J. Invert. Path.*, 17:134–135 (1971).

Kushner, D.J., et al., "Lecithinase Production by Strains of *Bacillus cereus* FR. and FR. Pathogenic for the Larch Sawfly, *Pristiphora erichsonii* (HTG.)", *Can. J. Microbiol.*, 3:547–551 (1957).

Luthy, P., et al., "*Bacillus thuringiensis* as a Bacterial Insecticide: Basic Consideration and Application", In: *Microbial and Viral Pesticides*, E. Kurstak, Ed., Marcel Dekker, NY 1982, pp. 37–39, 54–56.

Myers, P.S., et al., "Localization of a Mosquito–Larval Toxin of *Bacillus sphaericus* 1593", *Appl. Enviro. Microbiol.*, 39(1):1205–1211 (1980).

Porter, A.G., et al., "Mosquitocidal Toxins of Bacilli and Their Genetic Manipulation for Effective Biological Control of Mosquitoes", *Microbiological Reviews*, 57(4):838–861 (1993).

Sekar, V., "The Insecticidal Crystal Protein Gene is Expressed in Vegetative Cells of *Bacillus thuringiensis* var. temebropmos", *Current Microbiology*, 17:347–349.

Shivakumar, A.G., et al., Abstract,:Cloned Crystal Protein Genes Express Vegetatively in *Bacillus subtilis*, *Plasmid*, 16(3):230 (1986).

Thanabalu, T., et al., "Proteolytic Processing of the Mosquitocidal Toxin from *Bacillus sphaericus* SSII–1", *J. Bateriol.*, 174(15):5051–5056 (1992).

(List continued on next page.)

*Primary Examiner*—Nancy Degen
*Assistant Examiner*—Andrew Wang
*Attorney, Agent, or Firm*—Gary M. Pace

[57] ABSTRACT

The present invention is drawn to pesticidal strains and proteins. Bacillus strains which are capable of producing pesticidal proteins and auxiliary proteins during vegetative growth are provided. Also provided are the purified proteins, nucleotide sequences encoding the proteins and methods for using the strains, proteins and genes for controlling pests.

10 Claims, 1 Drawing Sheet

OTHER PUBLICATIONS

Yoshisue, H., et al., "Effects of *Bacillus thuringiensis* var. israelensis 20 kDa Protein on Production of the Bti 130–kDa Crystal Protein in *Escherichia coli*", *Bioscience, Biotechnology, and Biochemistry,* 56(9):1429–1433 (1992).

Bernier et al., "*Bacillus Thuringiensis* Strains A20 and A29 and Insecticidal Compounds Therefrom, and Compositions Containing These Compounds", Abstract No. 227249, *New Zealand Patent Office Journal,* 80(6):798, (1988).

Jellis et al., "*Bacillus Thuringiensis* δ–Endotoxin Variants and Insecticidal Compositions", Abstract No. 228108, *New Zealand Patent Office Journal,* 81(3):359, (1992).

Schurter et al., "Genetic Manifpulation of *B.thuringiensis* and *B.cereus* Vectors and Insecticidal Composition", Abstract No. 229191, *New Zealand Patent Office Journal,* 81(3):363, (1992).

Tayabali et al., "Semiautomated Quantification of Cytotoxic Damage Induced in Cultured Insect Cells Exposed to Commercial *Bacillus thuringiensis* Biopesticides", *Journal of Applied Toxicology,* 15(5):365–373 (1995).

Thanabalu et al., "Cytotoxicity and ADP–Ribosylating Activity of the Mosquitocidal Toxin from *Bacillus sphaericus* SSII–1: Possible Roles of the 27– and 70–Kilodalton Peptides", *Journal of Bacteriology,* 175(8):2314–2320 (1993).

Vaithlingam et al., "Anti–Coleopteran Toxin and Gene", Abstract No. 226442, *New Zealand Patent Office Journal,* 80(7):931, (1991).

Wahisaka et al., "Bacillus Thuringiensis Mutant and Bacterial Insecticide", Abstract No. 199725, *New Zealand Patent Office Journal,* (1982).

Walther et al., "Analysis of Mosquito Larvicidal Potential Exhibited by Vegetative Cells of *Bacillus thuringiensis* subsp. israelensis", *Applied and Environmental Microbiology,* 52(4): 650–653 (1986).

Ward et al., "*Bacillus thuringiensis* var. israelensis δ–Endotoxin Cloning and Expression of the Toxin in Sporogenic and Asporogenic Strains of *Bacillus subtilis*", *Journal of Molecular Biology,* 191(1):13–22 (1986).

Figure 1

Characterization of pCIB6022

| | Activity vs. WCRW |
|---|---|
| pCIB6022 | +++ |
| pCIB6203 | — |
| pCIB6023 | — |
| pCIB6206 | — |
| pCIB6024 | — |

Functional Complementation of VIP Clones

| | Activity vs. WCRW |
|---|---|
| pCIB6203 + pCIB6023 | +++ |
| pCIB6203 + pCIB6206 | +++ |
| pCIB6023 + pCIB6024 | +++ |

PESTICIDAL PROTEINS AND STRAINS

This is a divisional application of Ser. No. 08/463,483, filed Jun. 5, 1995 which is a continuation-in-part of Ser. No. 08/314,594 filed Sep. 28, 1994, now abandoned, which is a continuation-in-part of Ser. No. 08/218,018, filed Mar. 23, 1994, now abandoned, which is a continuation-in-part of Ser. No. 08/037,057, filed Mar. 25, 1993, now abandoned.

FIELD OF THE INVENTION

The present invention is drawn to methods and compositions for controlling plant and non-plant pests.

BACKGROUND OF THE INVENTION

Insect pests are a major factor in the loss of the world's commercially important agricultural crops. Broad spectrum chemical pesticides have been used extensively to control or eradicate pests of agricultural importance. There is, however, substantial interest in developing effective alternative pesticides.

Microbial pesticides have played an important role as alternatives to chemical pest control. The most extensively used microbial product is based on the bacterium *Bacillus thuringiensis* (Bt). Bt is a gram-positive spore forming Bacillus which produces an insecticidal crystal protein (ICP) during sporulation.

Numerous varieties of Bt are known that produce more than 25 different but related ICP's. The majority of ICP's made by Bt are toxic to larvae of certain insects in the orders Lepidoptera, Diptera and Coleoptera. In general, when an ICP is ingested by a susceptible insect the crystal is solubilized and transformed into a toxic moiety by the insect gut proteases. None of the ICP's active against coleopteran larvae such as Colorado potato beetle (*Leptinotarsa decemlineata*) or Yellow mealworm (*Tenebrio molitor*) have demonstrated significant effects on members of the genus Diabrotica particularly *Diabrotica virgifera virgifera*, the western corn rootworm (WCRW) or *Diabrotica longicornis barberi*, the northern corn rootworm.

*Bacillus cereus* (Bc) is closely related to Bt. A major distinguishing characteristic is the absence of a parasporal crystal in Bc. Bc is a widely distributed bacterium that is commonly found in soil and has been isolated from a variety of foods and drugs. The organism has been implicated in the spoilage of food.

Although Bt has been very useful in controlling insect pests, there is a need to expand the number of potential biological control agents.

BRIEF DESCRIPTION OF THE FIGURE

FIG. 1: Characterization of pCIB6022. Boxed regions represent the extent of VIP1A(a) and VIP2A(a). White box represents the portion of VIP1 encoding the 80 kDa peptide observed in Bacillus. Dark box represents the N-terminal 'propeptide' of VIP1A(a) predicted by DNA sequence analysis. Stippled box represents the VIP2A(a) coding region. Large 'X' represents the location of the frameshift mutation introduced into VIP1A(a). Arrows represent constructs transcribed by the beta-galactosidase promoter. Restriction Sites: C-Cla I; X-Xba I; S-Sca I; RI- Eco RI; B-Bgl II; RV-Eco RV.

SUMMARY OF THE INVENTION

The present invention is drawn to compositions and methods for controlling plant and non-plant pests. Particularly, new pesticidal proteins are disclosed which are isolatable from the vegetative growth stage of Bacillus. Bacillus strains, proteins, and genes encoding the proteins are provided.

The methods and compositions of the invention may be used in a variety of systems for controlling plant and non-plant pests.

DETAILED DESCRIPTION OF THE INVENTION

Compositions and methods for controlling plant pests are provided. In particular, novel pesticidal proteins are provided which are produced during vegetative growth of Bacillus strains. The proteins are useful as pesticidal agents.

The present invention recognizes that pesticidal proteins are produced during vegetative growth of Bacillus strains. To date, all of the identified pesticidal proteins of the invention are secreted from the cell. Prior to the present invention, there was no recognition in the art that a class or classes of pesticidal proteins are produced during vegetative growth of Bacillus. The only report was of a single mosquitocidal toxin from *Bacillus sphaericus* SSII-1 by Myers and Yousten in *Infect. Immun.*, 19:1047–1053 (1978). Having recognized that such a class exists, the present invention embraces all vegetative insecticidal proteins, hereinafter referred to as VIPs, except for the mosquitocidal toxin from *B. sphaericus*.

The present VIPs are not abundant after sporulation and are particularly expressed during log phase growth before stationary phase. For the purpose of the present invention vegetative growth is defined as that period of time before the onset of sporulation. Genes encoding such VIPs can be isolated, cloned and transformed into various delivery vehicles for use in pest management programs.

For purposes of the present invention, pests include but are not limited to insects, fungi, bacteria, nematodes, mites, ticks, protozoan pathogens, animal-parasitic liver flukes, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera and Lepidoptera.

Tables 1–10 gives a list of pests associated with major crop plants and pests of human and veterinary importance. Such pests are included within the scope of the present invention.

TABLE 1

| Lepidoptera (Butterflies and Moths) |
|---|
| Maize |
| *Ostrinia nubilalis*, European corn borer<br>*Agrotis ipsilon*, black cutworm<br>*Helicoverpa zea*, corn earworm<br>*Spodoptera frugiperda*, fall armyworm<br>*Diatraea grandiosella*, southwestern corn borer<br>*Elasmopalpus lignosellus*, lesser cornstalk borer<br>*Diatraea saccharalis*, sugarcane borer |
| Sorghum |
| *Chilo partellus*, sorghum borer<br>*Spodoptera frugiperda*, fall armyworm<br>*Helicoverpa zea*, corn earworm |

TABLE 1-continued

Lepidoptera (Butterflies and Moths)

*Elasmopalpus lignosellus*, lesser cornstalk borer
*Feltia subterranea*, granulate cutworm
Wheat

*Pseudaletia unipunctata*, army worm
*Spodoptera frugiperda*, fall armyworm
*Elasmopalpus lignosellus*, lesser cornstalk borer
*Agrotis orthogonia*, pale western cutworm
*Elasmopalpus lignosellus*, lesser cornstalk borer
Sunflower

*Suleima helianthana*, sunflower bud moth
*Homoeosoma electellum*, sunflower moth
Cotton

*Heliothis virescens*, cotton boll worm
*Helicoverpa zea*, cotton bollworm
*Spodoptera exigua*, beet armyworm
*Pectinophora gossypiella*, pink bollworm
Rice

*Diatraea saccharalis*, sugarcane borer
*Spodoptera frugiperda*, fall armyworm
*Helicoverpa zea*, corn earworm
Soybean

*Pseudoplusia includens*, soybean looper
*Anticarsia gemmatalis*, velvetbean caterpillar
*Plathypena scabra*, green cloverworm
*Ostrinia nubilalis*, European corn borer
*Agrotis ipsilon*, black cutworm
*Spodoptera exigua*, beet armyworm
*Heliothis virescens*, cotton boll worm
*Helicoverpa zea*, cotton bollworm
Barley

*Ostrinia nubilalis*, European corn borer
*Agrotis ipsilon*, black cutworm

TABLE 2

Coleoptera (Beetles)

Maize

*Diabrotica virgifera virgifera*, western corn rootworm
*Diabrotica longicornis barberi*, northern corn rootworm
*Diabrotica undecimpunctata howardi*, southern corn rootworm
*Melanotus* spp., wireworms
*Cyclocephala borealis*, northern masked chafer (white grub)
*Cyclocephala immaculata*, southern masked chafer (white grub)
*Popillia japonica*, Japanese beetle
*Chaetocnema pulicaria*, corn flea beetle
*Sphenophorus maidis*, maize billbug
Sorghum

*Phyllophaga crinita*, white grub
*Eleodes, Conoderus,* and *Aeolus* spp., wireworms
*Oulema melanopus*, cereal leaf beetle
*Chaetocnema pulicaria*, corn flea beetle
*Sphenophorus maidis*, maize billbug
Wheat

*Oulema melanopus*, cereal leaf beetle
*Hypera punctata*, clover leaf weevil
*Diabrotica undecimpunctata howardi*, southern corn rootworm
Sunflower

*Zygogramma exclamationis*, sunflower beetle
*Bothyrus gibbosus*, carrot beetle

TABLE 2-continued

Coleoptera (Beetles)

Cotton

*Anthonomus grandis*, boll weevil
Rice

*Colaspis brunnea*, grape colaspis
*Lissorhoptrus oryzophilus*, rice water weevil
*Sitophilus oryzae*, rice weevil
Soybean

*Epilachna varivestis*, Mexican bean beetle

TABLE 3

Homoptera (Whiteflies, Aphids etc.)

Maize

*Rhopalosiphum maidis*, corn leaf aphid
*Anuraphis maidiradicis*, corn root aphid
Sorghum

*Rhopalosiphum maidis*, corn leaf aphid
*Sipha flava*, yellow sugarcane aphid
Wheat Russian wheat aphid
*Schizaphis graminum*, greenbug
*Macrosiphum avenae*, English grain aphid
Cotton

*Aphis gossypii*, cotton aphid
*Pseudatomoscelis seriatus*, cotton fleahopper
*Trialeurodes abutilonea*, bandedwinged whitefly
Rice

*Nephotettix nigropictus*, rice leafhopper
Soybean

*Myzus persicae*, green peach aphid
*Empoasca fabae*, potato leafhopper
Barley

*Schizaphis graminum*, greenbug
Oil Seed Rape

*Brevicoryne brassicae*, cabbage aphid

TABLE 4

Hemiptera (Bugs)

Maize

*Blissus leucopterus leucopterus*, chinch bug
Sorghum

*Blissus leucopterus leucopterus*, chinch bug
Cotton

*Lygus lineolaris*, tarnished plant bug
Rice

*Blissus leucopterus leucopterus*, chinch bug
*Acrosternum hilare*, green stink bug
Soybean

*Acrosternum hilare*, green stink bug

TABLE 4-continued

Hemiptera (Bugs)

Barley

*Blissus leucopterus leucopterus*, chinch bug
*Acrosternum hilare*, green stink bug
*Euschistus servus*, brown stink bug

TABLE 5

Orthoptera (Grasshoppers, Crickets, and Cockroaches)

Maize

*Melanoplus femurrubrum*, redlegged grasshopper
*Melanoplus sanguinipes*, migratory grasshopper
Wheat

*Melanoplus femurrubrum*, redlegged grasshopper
*Melanoplus differentialis*, differential grasshopper
*Melanoplus sanguinipes*, migratory grasshopper
Cotton

*Melanoplus femurrubrum*, redlegged grasshopper
*Melanoplus differentialis*, differential grasshopper
Soybean

*Melanoplus femurrubrum*, redlegged grasshopper
*Melanoplus differentialis*, differential grasshopper
Structural/Household

*Periplaneta americana*, American cockroach
*Blattella germanica*, German cockroach
*Blatta orientalis*, oriental cockroach

TABLE 6

Diptera (Flies and Mosquitoes)

Maize

*Hylemya platura*, seedcorn maggot
*Agromyza parvicornis*, corn blotch leafminer
Sorghum

*Contarinia sorghicola*, sorghum midge
Wheat

*Mayetiola destructor*, Hessian fly
*Sitodiplosis mosellana*, wheat midge
*Meromyza americana*, wheat stem maggot
*Hylemya coarctata*, wheat bulb fly
Sunflower

*Neolasioptera murtfeldtiana*, sunflower seed midge
Soybean

*Hylemya platura*, seedcorn maggot
Barley

*Hylemya platura*, seedcorn maggot
*Mayetiola destructor*, Hessian fly
Insects attacking humans and animals and disease carriers

*Aedes aegypti*, yellowfever mosquito
*Aedes albopictus*, forest day mosquito
*Phlebotomus papatasii*, sand fly
*Musca domestica*, house fly
*Tabanus atratus*, black horse fly
*Cochliomyia hominivorax*, screwworm fly

TABLE 7

Thysanoptera (Thrips)

Maize

*Anaphothrips obscurus*, grass thrips
Wheat

*Frankliniella fusca*, tobacco thrips
Cotton

*Thrips tabaci*, onion thrips
*Frankliniella fusca*, tobacco thrips
Soybean

*Sericothrips variabilis*, soybean thrips
*Thrips tabaci*, onion thrips

TABLE 8

Hymenoptera (Sawflies, Ants, Wasps, etc.)

Maize

*Solenopsis milesta*, thief ant
Wheat

*Cephus cinctus*, wheat stem sawfly

TABLE 9

Other Orders and Representative Species

Dermaptera (Earwigs)

*Forficula auricularia*, European earwig
Isoptera (Termites)

*Reticulitermes flavipes*, eastern subterranean termite
Mallophaga (Chewing Lice)

*Cuclotogaster heterographa*, chicken head louse
*Bovicola bovis*, cattle biting louse
Anoplura (Sucking Lice)

*Pediculus humanus*, head and body louse
Siphonaptera (Fleas)

*Ctenocephalides felis*, cat flea

TABLE 10

Acari (Mites and Ticks)

Maize

*Tetranychus urticae*, twospotted spider mite
Sorghum

*Tetranychus cinnabarinus*, carmine spider mite
*Tetranychus urticae*, twospotted spider mite
Wheat

*Aceria tulipae*, wheat curl mite
Cotton

*Tetranychus cinnabarinus*, carmine spider mite
*Tetranychus urlicae*, twospotted spider mite
Soybean

*Tetranychus turkestani*, strawberry spider mite
*Tetranychus urticae*, twospotted spider mite

TABLE 10-continued

Acari (Mites and Ticks)

Barley

*Petrobia latens*, brown wheat mite
Important human and animal Acari

*Demacentor variabilis*, American dog tick
*Argas persicus*, fowl tick
*Dermatophagoides farinae*, American house dust mite
*Dermatophagoides pteronyssinus*, European house dust mite Now that it has been recognized that pesticidal proteins can be isolated from the vegetative growth phase of Bacillus, other strains can be isolated by standard techniques and tested for activity against particular plant and non-plant pests. Generally Bacillus strains can be isolated from any environmental sample, including soil, plant, insect, grain elevator dust, and other sample material, etc., by methods known in the art. See, for example, Travers et al. (1987) Appl. Environ. Microbiol. 53:1263–1266; Saleh et al. (1969) Can J. Microbiol. 15:1101–1104; DeLucca et al. (1981) Can. J. Microbiol. 27:865–870; and Norris, et al. (1981) "The genera Bacillus and Sporolactobacillus," In Starr et al; (eds.), The Prokaryotes: A Handbook on Habitats, Isolation, and Identification of Bacteria, Vol. II, Springer-Verlog Berlin Heidelberg. After isolation, strains can be tested for pesticidal activity during vegetative growth. In this manner, new pesticidal proteins and strains can be identified.

Such Bacillus microorganisms which find use in the invention include *Bacillus cereus* and *Bacillus thuringiensis*, as well as those Bacillus species listed in Table 11.

TABLE 11

List of Bacillus species

| Morphological Group 1 | Unassigned Strains |
|---|---|
| B. megaterium | Subgroup A |
| B. cereus* | B. apiarus* |
| B. cereus var. mycoides | B. filicolonicus |
| B. thuringiensis* | B. thiaminolyticus |
| B. licheniformis | B. alcalophilus |
| B. subtilis* | Subgroup B |
| B. pumilus | B. cirroflagellosus |
| B. firmus* | B. chitinosporus |
| B. coagulans | B. lentus |
| Morphological Group 2 | Subgroup C |
| B. polymyxa | B. badius |
| B. macerans | B. aneurinolyticus |
| B. circulans | B. macroides |
| B. stearothermophilus | B. freundenreichii |
| B. alvei* | Subgroup D |
| B. laterosporus* | B. pantothenticus |
| B. brevis | B. epiphytus |
| B. pulvifaciens | Subgroup E1 |
| B. popilliae* | B. aminovorans |
| B. lentimorbus* | B. globisporus |
| B. larvae* | B. insolitus |

TABLE 11-continued

List of Bacillus species

| Morphological Group 3 | B. psychrophilus |
|---|---|
| B. sphaericus* | Subgroup E2 |
| B. pasteurii | B. psychrosaccharolyticus |
| | B. macquariensis |

*= Those Bacillus strains that have been previously found associated with insects Grouping according to Parry, J. M. et al. (1983) Color Atlas of Bacillus species, Wolfe Medical Publications, London.

In accordance with the present invention, the pesticidal proteins produced during vegetative growth can be isolated from Bacillus. In one embodiment, insecticidal proteins produced during vegetative growth, can be isolated. Methods for protein isolation are known in the art. Generally, proteins can be purified by conventional chromatography, including gel-filtration, ion-exchange, and immunoaffinity chromatography, by high-performance liquid chromatography, such as reversed-phase high-performance liquid chromatography, ion-exchange high-performance liquid chromatography, size-exclusion high-performance liquid chromatography, high-performance chromatofocusing and hydrophobic interaction chromatography, etc., by electrophoretic separation, such as one-dimensional gel electrophoresis, two-dimensional gel electrophoresis, etc. Such methods are known in the art. See for example *Current Protocols in Molecular Biology*, Vols. 1 and 2, Ausubel et al. (eds.), John Wiley & Sons, NY (1988). Additionally, antibodies can be prepared against substantially pure preparations of the protein. See, for example, Radka et al. (1983) *J. Immunol.* 128:2804; and Radka et al. (1984) *Immunogenetics* 19:63. Any combination of methods may be utilized to purify protein having pesticidal properties. As-the protocol is being formulated, pesticidal activity is determined after each purification step.

Such purification steps will result in a substantially purified protein fraction. By "substantially purified" or "substantially pure" is intended protein which is substantially free of any compound normally associated with the protein in its natural state. "Substantially pure" preparations of protein can be assessed by the absence of other detectable protein bands following SDS-PAGE as determined visually or by densitometry scanning. Alternatively, the absence of other amino-terminal sequences or N-terminal residues in a purified preparation can indicate the level of purity. Purity can be verified by rechromatography of "pure" preparations showing the absence of other peaks by ion exchange, reverse phase or capillary electrophoresis. The terms "substantially pure" or "substantially purified" are not meant to exclude artificial or synthetic mixtures of the proteins with other compounds. The terms are also not meant to exclude the presence of minor impurities which do not interfere with the biological activity of the protein, and which may be present, for example, due to incomplete purification.

Once purified protein is isolated, the protein, or the polypeptides of which it is comprised, can be characterized and sequenced by standard methods known in the art. For example, the purified protein, or the polypeptides of which it is comprised, may be fragmented as with cyanogen bromide, or with proteases such as papain, chymotrypsin, trypsin, lysyl-C endopeptidase, etc. (Oike et al. (1982) *J. Biol. Chem.* 257:9751–9758; Liu et al. (1983) *Int. J. Pept. Protein Res.* 21:209–215). The resulting peptides are separated, preferably by HPLC, or by resolution of gels and electroblotting onto PVDF membranes, and subjected to amino acid sequencing. To accomplish this task, the peptides are preferably analyzed by automated sequenators. It is recognized that N-terminal, C-terminal, or internal amino acid sequences can be determined. From the amino acid sequence of the purified protein, a nucleotide sequence can be synthesized which can be used as a probe to aid in the isolation of the gene encoding the pesticidal protein.

It is recognized that the pesticidal proteins may be oligomeric and will vary in molecular weight, number of protomers, component peptides, activity against particular pests, and in other characteristics. However, by the methods set forth herein, proteins active against a variety of pests may be isolated and characterized.

Once the purified protein has been isolated and characterized it is recognized that it may be altered in various ways including amino acid substitutions, deletions, truncations, and insertions. Methods for such manipulations are generally known in the art. For example, amino acid sequence variants of the pesticidal proteins can be prepared by mutations in the DNA. Such variants will possess the desired pesticidal activity. Obviously, the mutations that will be made in the DNA encoding the variant must not place the sequence out of reading frame and preferably will not create complementary regions that could produce secondary mRNA structure. See, EP Patent Application Publication No. 75,444.

In this manner, the present invention encompasses the pesticidal proteins as well as components and fragments thereof. That is, it is recognized that component protomers, polypeptides or fragments of the proteins may be produced which retain pesticidal activity. These fragments include truncated sequences, as well as N-terminal, C-terminal, internal and internally deleted amino acid sequences of the proteins.

Most deletions, insertions, and substitutions of the protein sequence are not expected to produce radical changes in the characteristics of the pesticidal protein. However, when it is difficult to predict the exact effect of the substitution, deletion, or insertion in advance of doing so, one skilled in the art will appreciate that the effect will be evaluated by routine screening assays.

The proteins or other component polypeptides described herein may be used alone or in combination. That is, several proteins may be used to control different insect pests.

Some proteins are single polypeptide chains while many proteins consist of more than one polypeptide chain, i.e., they are oligomeric. Additionally, some VIPs are pesticidally active as oligomers. In these instances, additional protomers are utilized to enhance the pesticidal activity or to activate pesticidal proteins. Those protomers which enhance or activate are referred to as auxiliary proteins. Auxiliary proteins activate or enhance a pesticidal protein by interacting with the pesticidal protein to form an oligomeric protein having increased pesticidal activity compared to that observed in the absence of the auxiliary protein.

Auxiliary proteins activate or increase the activity of pesticidal proteins such as the VIP1 protein from AB78. Such auxiliary proteins are exemplified by, but not limited to, the VIP2 protein from AB78. As demonstrated in the Experimental section of the application, auxiliary proteins can activate a number of pesticidal proteins. Thus, in one embodiment of the invention, a plant, Parent 1, can be transformed with an auxiliary protein. This Parent 1 can be crossed with a number of Parent 2 plants transformed with one or more pesticidal proteins whose pesticidal activities are activated by the auxiliary protein.

The pesticidal proteins of the invention can be used in combination with Bt endotoxins or other insecticidal proteins to increase insect target range. Furthermore, the use of the VIPs of the present invention in combination with Bt δ-endotoxins or other insecticidal principles of a distinct nature has particular utility for the prevention and/or management of insect resistance. Other insecticidal principles include protease inhibitors (both serine and cysteine types), lectins, α-amylase and peroxidase. In one preferred embodiment, expression of VIPs in a transgenic plant is accompanied by the expression of one or more Bt δ-endotoxins. This co-expression of more than one insecticidal principle in the same transgenic plant can be achieved by genetically engineering a plant to contain and express all the genes necessary. Alternatively, a plant, Parent 1, can be genetically engineered for the expression of VIPs. A second plant, Parent 2, can be genetically engineered for the expression of Bt δ-endotoxin. By crossing Parent 1 with Parent 2, progeny plants are obtained which express all the genes introduced into Parents 1 and 2. Particularly preferred Bt δ-endotoxins are those disclosed in U.S. Pat. No. 5,625,136, herein incorporated by reference.

A substantial number of cytotoxic proteins, though not all, are binary in action. Binary toxins typically consist of two protein domains, one called the A domain and the other called the B domain (see *Sourcebook of Bacterial Protein Toxins*, J. E. Alouf and J. H. Freer eds.(1991) Academic Press). The A domain possesses a potent cytotoxic activity. The B domain binds an external cell surface receptor before being internalized. Typically, the cytotoxic A domain must be escorted to the cytoplasm by a translocation domain. Often the A and B domains are separate polypeptides or protomers, which are associated by a protein-protein interaction or a di-sulfide bond. However, the toxin can be a single polypeptide which is proteolytically processed within the cell into two domains as in the case for Pseudomonas exotoxin A. In summary binary toxins typically have three important domains, a cytotoxic A domain, a receptor binding B domain and a translocation domain. The A and B domain are often associated by protein-protein interacting domains.

The receptor binding domains of the present invention are useful for delivering any protein, toxin, enzyme, transcription factor, nucleic acid, chemical or any other factor into target insects having a receptor recognized by the receptor binding domain of the binary toxins described in this patent. Similarly, since binary toxins have translocation domains which penetrate phosopholipid bilayer membranes and escort cytotoxins across those membranes, such translocation domains may be useful in escorting any protein, toxin, enzyme, transcription factor, nucleic acid, chemical or any other factor across a phospholipid bilayer such as the plasma membrane or a vesicle membrane. The translocation domain may itself perforate membranes, thus having toxic or insecticidal properties. Further, all binary toxins have cytotoxic domains; such a cytotoxic domain may be useful as a lethal protein, either alone or when delivered into any target cell(s) by any means.

Finally, since binary toxins comprised of two polypeptides often form a complex, it is likely that there are protein-protein interacting regions within the components of the binary toxins of the invention. These protein-protein interacting domains may be useful in forming associations between any combination of toxins, enzymes, transcription factors, nucleic acids, antibodies, cell binding moieties, or any other chemicals, factors, proteins or protein domains.

Toxins, enzymes, transcription factors, antibodies, cell binding moieties or other protein domains can be fused to pesticidal or auxiliary proteins by producing in frame genetic fusions which, when translated by ribosomes, would produce a fusion protein with the combined attributes of the VIP and the other component used in the fusion. Furthermore, if the protein domain fused to the VIP has an affinity for another protein, nucleic acid, carbohydrate, lipid, or other chemical or factor, then a three-component complex can be formed. This complex will have the attributes of all of its components. A similar rationale can be used for producing four or more component complexes. These complexes are useful as insecticidal toxins, pharmaceuticals, laboratory reagents, and diagnostic reagents, etc. Examples where such complexes are currently used are fusion toxins for potential cancer therapies, reagents in ELISA assays and immunoblot analysis.

One strategy of altering pesticidal or auxiliary proteins is to fuse a 15-amino-acid "S-tag" to the protein without destroying the insect cell binding domain(s), translocation domains or protein-protein interacting domains of the proteins. The S-tag has a high affinity ($K_d=10^{-9}M$) for a ribonuclease S-protein, which, when bound to the S-tag, forms an active ribonuclease (See F. M. Richards and H. W. Wyckoff(1971) in "The Enzymes", Vol. IV (Boyer, P. D. ed.). pp. 647–806. Academic Press, New York). The fusion can be made in such a way as to destroy or remove the cytotoxic activity of the pesticidal or auxiliary protein, thereby replacing the VIP cytotoxic activity with a new cytotoxic ribonuclease activity. The final toxin would be comprised of the S-protein, a pesticidal protein and an auxiliary protein, where either the pesticidal protein or the auxiliary protein is produced as translational fusions with the S-tag. Similar strategies can be used to fuse other potential cytotoxins to pesticidal or auxiliary proteins including (but not limited to) ribosome inactivating proteins, insect hormones, hormone receptors, transcription factors, proteases, phosphatases, Pseudomonas exotoxin A, or any other protein or chemical factor that is lethal when delivered into cells. Similarly, proteins can be delivered into cells which are not lethal, but might alter cellular biochemistry or physiology.

The spectrum of toxicity toward different species can be altered by fusing domains to pesticidal or auxiliary proteins which recognize cell surface receptors from other species. Such domains might include (but are not limited to) antibodies, transferrin, hormones, or peptide sequences isolated from phage displayed affinity selectable libraries. Also, peptide sequences which are bound to nutrients, vitamins, hormones, or other chemicals that are transported into cells could be used to alter the spectrum of toxicity. Similarly, any other protein or chemical which binds a cell surface receptor or the membrane and could be internalized might be used to alter the spectrum of activity of VIP1 and VIP2.

The pesticidal proteins of the present invention are those proteins which confer a specific pesticidal property. Such proteins may vary in molecular weight, having component polypeptides at least a molecular weight of 30 kDa or greater, preferably about 50 kDa or greater.

The auxiliary proteins of the invention may vary in molecular weight, having at least a molecular weight of about 15 kDa or greater, preferably about 20 kDa or greater; more preferably, about 30 kDa or greater. The auxiliary proteins themselves may have component polypeptides.

It is possible that the pesticidal protein and the auxiliary protein may be components of a multimeric, insecticidal protein. Such a insecticidal protein which includes the auxiliary proteins as one or more of its component polypeptides may vary in molecular weight, having at least a molecular weight of 50 kDa up to at least 200 kDa, preferably about 100 kDa to 150 kDa.

An auxiliary protein may be used in combination with the pesticidal proteins of the invention to enhance activity or to activate the pesticidal protein. To determine whether the auxiliary protein will affect activity, the pesticidal protein can be expressed alone and in combination with the auxiliary protein and the respective activities compared in feeding assays for pesticidal activity.

It may be beneficial to screen strains for potential pesticidal activity by testing activity of the strain alone and in combination with the auxiliary protein. In some instances an auxiliary protein in combination with the native proteins of the strains yields pesticidal activity where none is seen in the absence of an auxiliary protein.

The auxiliary protein can be modified, as described above, by various methods known in the art. Therefore, for purposes of the invention, the term "Vegetative Insecticidal Protein" (VIP) encompasses those proteins produced during vegetative growth which alone or in combination can be used for pesticidal activity. This includes pesticidal proteins, auxiliary proteins and those proteins which demonstrate activity only in the presence of the auxiliary protein or the polypeptide components of these proteins.

It is recognized that there are alternative methods available to obtain the nucleotide and amino acid sequences of the present proteins. For example, to obtain the nucleotide sequence encoding the pesticidal protein, cosmid clones, which express the pesticidal protein, can be isolated from a genomic library. From larger active cosmid clones, smaller subclones can be made and tested for activity. In this manner, clones which express an active pesticidal protein can be sequenced to determine the nucleotide sequence of the gene. Then, an amino acid sequence can be deduced for the protein. For general molecular methods, see, for example, Molecular Cloning, A Laboratory Manual, Second Edition, Vols. 1–3, Sambrook et al. (eds.) Cold Spring Harbor Laboratory Press, Cold Spring Harbor, N.Y. (1989), and the references cited therein.

The present invention also encompasses nucleotide sequences from organisms other than Bacillus, where the nucleotide sequences are isolatable by hybridization with the Bacillus nucleotide sequences of the invention. Proteins encoded by such nucleotide sequences can be tested for pesticidal activity. The invention also encompasses the proteins encoded by the nucleotide sequences. Furthermore, the invention encompasses proteins obtained from organisms other than Bacillus wherein the protein cross-reacts with antibodies raised against the proteins of the invention. Again the isolated proteins can be assayed for pesticidal activity by the methods disclosed herein or others well-known in the art.

Once the nucleotide sequences encoding the pesticidal proteins of the invention have been isolated, they can be manipulated and used to express the protein in a variety of hosts including other organisms, including microorganisms and plants.

The pesticidal genes of the invention can be optimized for enhanced expression in plants. See, for example U.S. Pat. No. 5,625,136; EPA 0359472; EPA 0385962; WO 91/16432; Perlak et al. (1991) *Proc. Natl. Acad. Sci. USA* 88:3324–3328; and Murray et al. (1989) *Nucleic Acids Research* 17:477–498. In this manner, the genes can be synthesized utilizing plant preferred codons. That is the preferred codon for a particular host is the single codon which most frequently encodes that amino acid in that host.

The maize preferred codon, for example, for a particular amino acid may be derived from known gene sequences from maize. Maize codon usage for 28 genes from maize plants is found in Murray et al. (1989), *Nucleic Acids Research* 17:477–498, the disclosure of which is incorporated herein by reference. Synthetic genes can also be made based on the distribution of codons a particular host uses for a particular amino acid.

In this manner, the nucleotide sequences can be optimized for expression in any plant. It is recognized that all or any part of the gene sequence may be optimized or synthetic. That is, synthetic or partially optimized sequences may also be used.

In like manner, the nucleotide sequences can be optimized for expression in any microorganism. For Bacillus preferred codon usage, see, for example U.S. Pat. No. 5,024,837 and Johansen et al. (1988) *Gene* 65:293–304.

Methodologies for the construction of plant expression cassettes as well as the introduction of foreign DNA into plants are described in the art. Such expression cassettes may include promoters, terminators, enhancers, leader sequences, introns and other regulatory sequences operably linked to the pesticidal protein coding sequence. It is further recognized that promoters or terminators of the VIP genes can be used in expression cassettes.

Generally, for the introduction of foreign DNA into plants Ti plasmid vectors have been utilized for the delivery of foreign DNA as well as direct DNA uptake, liposomes, electroporation, micro-injection, and the use of microprojectiles. Such methods had been published in the art. See, for example, Guerche et al., (1987) *Plant Science* 52:111–116; Neuhause et al., (1987) *Theor. Appl. Genet.* 75:30–36; Klein et al., (1987) *Nature* 327:70–73; Howell et al., (1980) *Science* 208:1265; Horsch et al., (1985) *Science* 227:1229–1231; DeBlock et al., (1989) *Plant Physiology* 91:694–701; *Methods for Plant Molecular Biology* (Weissbach and Weissbach, eds.) Academic Press, Inc. (1988); and *Methods in Plant Molecular Biology* (Schuler and Zielinski, eds.) Academic Press, Inc. (1989). See also U.S. patent application Ser. No. 08/008,374 herein incorporated by reference. See also, EPA 0193259 and EPA 0451878A1. It is understood that the method of transformation will depend upon the plant cell to be transformed.

It is further recognized that the components of the expression cassette may be modified to increase expression. For example, truncated sequences, nucleotide substitutions or other modifications may be employed. See, for example Perlak et al. (1991) *Proc. Natl. Acad. Sci. USA* 88:3324–3328; Murray et al., (1989) *Nucleic Acids Research* 17:477–498; and WO 91/16432.

The construct may also include any other necessary regulators such as terminators, (Guerineau et al., (1991), *Mol. Gen. Genet.*, 226:141–144; Proudfoot, (1991), *Cell*, 64:671–674; Sanfacon et al., (1991), *Genes Dev.*, 5:141–149; Mogen et al., (1990), *Plant Cell*, 2:1261–1272; Munroe et al., (1990), *Gene*, 91:151–158; Ballas et al et al., (1989), *Nucleic Acids Res.*, 17:7891–7903; Joshi et al., (1987), *Nucleic Acid Res.*, 15:9627–9639); plant translational consensus sequences (Joshi, C. P., (1987), *Nucleic Acids Research*, 15:6643–6653), introns (Luehrsen and Walbot, (1991), *Mol. Gen. Genet.*, 225:81–93) and the like, operably linked to the nucleotide sequence. It may be beneficial to include 5' leader sequences in the expression cassette construct. Such leader sequences can act to enhance translation. Translational leaders are known in the art and include:

Picornavirus leaders, for example, EMCV leader (encephalomyocarditis 5' noncoding region) (Elroy-Stein, O., Fuerst, T. R., and Moss, B. (1989) *PNAS USA* 86:6126–6130);

Potyvirus leaders, for example, TEV leader (Tobacco Etch Virus) (Allison et al., (1986); MDMV leader (Maize Dwarf Mosaic Virus); *Virology*, 154:9–20), and Human immunoglobulin heavy-chain binding protein (BiP), (Macejak, D. G., and Sarnow, P., (1991), *Nature*, 353:90–94;

Untranslated leader from the coat protein mRNA of alfalfa mosaic virus (AMV RNA 4), (Jobling, S. A., and Gehrke, L., (1987), *Nature*, 325:622–625;

Tobacco mosaic virus leader (TMV), (Gallie, D. R. et al., (1989), *Molecular Biology of RNA*, pages 237–256; and Maize Chlorotic Mottle Virus leader (MCMV) (Lommel, S. A. et al., (1991), *Virology*, 81:382–385. See also, Della-Cioppa et al., (1987), *Plant Physiology*, 84:965–968.

A plant terminator may be utilized in the expression cassette. See, Rosenberg et al., (1987), *Gene*, 56:125; Guerineau et al., (1991), *Mol. Gen. Genet.*, 226:141–144; Proudfoot, (1991), *Cell*, 64:671–674; Sanfacon et al., (1991), *Genes Dev.*, 5:141–149; Mogen et al., (1990), *Plant Cell*, 2:1261–1272; Munroe et al., (1990), *Gene*, 91:151–158; Ballas et al., (1989), *Nucleic Acids Res.*, 17:7891–7903; Joshi et al., (1987), *Nucleic Acid Res.*, 15:9627–9639.

For tissue specific expression, the nucleotide sequences of the invention can be operably linked to tissue specific promoters. See, for example, U.S. Pat. No. 5,625,136 herein incorporated by reference.

It is recognized that the genes encoding the pesticidal proteins can be used to transform insect pathogenic organisms. Such organisms include Baculoviruses, fungi, protozoa, bacteria and nematodes.

The Bacillus strains of the invention may be used for protecting agricultural crops and products from pests. Alternatively, a gene encoding the pesticide may be introduced via a suitable vector into a microbial host, and said host applied to the environment or plants or animals. Microorganism hosts may be selected which are known to occupy the "phytosphere" (phylloplane, phyllosphere, rhizosphere, and/or rhizoplana) of one or more crops of interest. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

Such microorganisms include bacteria, algae, and fungi. Of particular interest are microorganisms, such as bacteria, e.g., Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter Azotobacter, Leuconostoc, and Alcaligenes; fungi, particularly yeast, e.g., Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum*, Agrobacteria, *Rhodopseudomonas spheroides, Xanthomonas campestris, Rhizobium melioti, Alcaligenes entrophus, Clavibacter xyli* and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae,* and *Aureobasidium pollulans*. Of particular interest are the pigmented microorganisms.

A number of ways are available for introducing a gene expressing the pesticidal protein into the microorganism host under conditions which allow for stable maintenance and expression of the gene. For example, expression cassettes can be constructed which include the DNA constructs of interest operably linked with the transcriptional and translational regulatory signals for expression of the DNA constructs, and a DNA sequence homologous with a sequence in the host organism, whereby integration will occur, and/or a replication system which is functional in the host, whereby integration or stable maintenance will occur.

Transcriptional and translational regulatory signals include but are not limited to promoter, transcriptional initiation start site, operators, activators, enhancers, other regulatory elements, ribosomal binding sites, an initiation codon, termination signals, and the like. See, for example, U.S. Pat. No. 5,039,523; U.S. Pat. No. 4,853,331; EPO 0480762A2; Sambrook et al. supra; Molecular Cloning, a Laboratory Manual, Maniatis et al. (eds) Cold Spring Harbor Laboratory, Cold Spring Harbor, N.Y. (1982); Advanced Bacterial Genetics, Davis et al. (eds.) Cold Spring Harbor Laboratory, Cold Spring Harbor, N.Y. (1980); and the references cited therein.

Suitable host cells, where the pesticide-containing cells will be treated to prolong the activity of the toxin in the cell when the then treated cell is applied to the environment of the target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such a Saccharomyces and Schizosaccharromyces; and Basidiomycetes yeast, such as Rhodotorula, Aureobasidium, Sporobolomyces, and the like.

Characteristics of particular interest in selecting a host cell for purposes of production include ease of introducing the protein gene into the host, availability of expression systems, efficiency of expression, stability of the protein in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, LactoBacillus sp., Bacillus sp., and the like. Specific organisms include *Pseudomonas aeurginosa, Pseudomonas fluorescens, Saccharomyces cerevisiae, Bacillus thuringiensis, Escherichia coli, Bacillus subtilis*, and the like.

VIP genes can be introduced into micro-organisms that multiply on plants (epiphytes) to deliver VIP proteins to potential target pests. Epiphytes can be gram-positive or gram-negative bacteria for example.

Root colonizing bacteria, for example, can be isolated from the plant of interest by methods known in the art. Specifically, a *Bacillus cereus* strain which colonizes roots could be isolated from roots of a plant (for example see J. Handelsman, S. Raffel, E. Mester, L. Wunderlich and C. Grau, *Appl. Environ. Microbiol.* 56:713–718, (1990)). VIP1 and/or VIP2 could be introduced into a root colonizing *Bacillus cereus* by standard methods known in the art.

Specifically, VIP1 and/or VIP2 derived from *Bacillus cereus* strain AB78 can be introduced into a root colonizing *Bacillus cereus* by means of conjugation using standard methods (J. Gonzalez, B. Brown and B. Carlton, *Proc. Natl. Acad. Sci.* 79:6951–6955, (1982)).

Also, VIP1 and/or VIP2 or other VIPs of the invention can be introduced into the root colonizing Bacillus by means of electro-transformation. Specifically, VIPs can be cloned into a shuttle vector, for example, pHT3101 (D. Lereclus et al., *FEMS Microbiol. Letts.,* 60:211–218 (1989)) as described in Example 10. The shuttle vector pHT3101 containing the coding sequence for the particular VIP can then be transformed into the root colonizing Bacillus by means of electroporation (D. Lereclus et al. 1989, *FEMS Microbiol. Letts.* 60:211–218).

Expression systems can be designed so that VIP proteins are secreted outside the cytoplasm of gram negative bacteria, *E. coli*, for example. Advantages of having VIP proteins secreted are (1) it avoids potential toxic effects of VIP proteins expressed within the cytoplasm and (2) it can increase the level of VIP protein expressed and (3) can aid in efficient purification of VIP protein.

VIP proteins can be made to be secreted in *E. coli*, for example, by fusing an appropriate *E. coli* signal peptide to the amino-terminal end of the VIP signal peptide or replacing the VIP signal peptide with the *E. coli* signal peptide. Signal peptides recognized by *E. coli* can be found in proteins already known to be secreted in *E. coli*, for example the OmpA protein (J. Ghrayeb, H. Kimura, M. Takahara, Y. Masui and M. Inouye, *EMBO J.,* 3:2437–2442 (1984)). OmpA is a major protein of the *E. coli* outer membrane and thus its signal peptide is thought to be efficient in the translocation process. Also, the OmpA signal peptide does not need to be modified before processing as may be the case for other signal peptides, for example lipoprotein signal peptide (G. Duffaud, P. March and M. Inouye, *Methods in Enzymology,* 153:492 (1987)).

Specifically, unique BamHI restriction sites can be introduced at the amino-terminal and carboxy-terminal ends of the VIP coding sequences using standard methods known in the art. These BamHI fragments can be cloned, in frame, into the vector pIN-III-ompA1, A2 or A3 (J. Ghrayeb, H. Kimura, M. Takahara, H. Hsiung, Y. Masui and M. Inouye, *EMBO J.,* 3:2437–2442 (1984)) thereby creating ompA:VIP fusion gene which is secreted into the periplasmic space. The other restriction sites in the polylinker of pIN-III-ompA can be eliminated by standard methods known in the art so that the VIP amino-terminal amino acid coding sequence is directly after the ompA signal peptide cleavage site. Thus, the secreted VIP sequence in E. coli would then be identical to the native VIP sequence.

When the VIP native signal peptide is not needed for proper folding of the mature protein, such signal sequences can be removed and replaced with the ompA signal sequence. Unique BamHI restriction sites can be introduced at the amino-termini of the proprotein coding sequences directly after the signal peptide coding sequences of VIP and at the carboxy-termini of VIP coding sequence. These BamHI fragments can then be cloned into the pIN-III-ompA vectors as described above.

General methods for employing the strains of the invention in pesticide control or in engineering other organisms as pesticidal agents are known in the art. See, for example U.S. Pat. No. 5,039,523 and EP 0480762A2.

VIPs can be fermented in a bacterial host and the resulting bacteria processed and used as a microbial spray in the same manner that Bacillus thuringiensis strains have been used as insecticidal sprays. In the case of a VIP(s) which is secreted from Bacillus, the secretion signal is removed or mutated using procedures known in the art. Such mutations and/or deletions prevent secretion of the VIP protein(s) into the growth medium during the fermentation process. The VIPs are retained within the cell and the cells are then processed to yield the encapsulated VIPs. Any suitable microorganism can be used for this purpose. Psuedomonas has been used to express Bacillus thuringiensis endotoxins as encapsulated proteins and the resulting cells processed and sprayed as an insecticide. (H. Gaertner et al. 1993, In Advanced Engineered Pesticides, L. Kim ed.)

Various strains of Bacillus thuringiensis are used in this manner. Such Bt strains produce endotoxin protein(s) as well as VIPs. Alternatively, such strains can produce only VIPs. A sporulation deficient strain of Bacillus subtilis has been shown to produce high levels of the CryIIIA endotoxin from Bacillus thuringiensis (Agaisse, H. and Lereclus, D., "Expression in Bacillus subtilis of the Bacillus thuringiensis CryIIIA toxin gene is not dependent on a sporulation-specific sigma factor and is increased in a spoOA mutant", J. Bacteriol. 176:4734–4741 (1994)). A similar spoOA mutant can be prepared in Bacillus thuringiensis and used to produce encapsulated VIPs which are not secreted into the medium but are retained within the cell.

To have VIPs maintained within the Bacillus cell the signal peptide can be disarmed so that it no longer functions as a secretion signal. Specifically, the putative signal peptide for VIP1 encompasses the first 31 amino acids of the protein with the putative consensus cleavage site, Ala-X-Ala, at the C-terminal portion of this sequence (G. von Heijne , J. Mol. Biol. 184:99–105 (1989)) and the putative signal peptide for VIP2 encompasses the first 40 amino acids of the protein with the putative cleavage site after Ala40. The cleavage sites in either VIP1 or VIP2 can be mutated with methods known in the art to replace the cleavage site consensus sequence with alternative amino acids that are not recognized by the signal peptidases.

Alternatively, the signal peptides of VIP1, VIP2 and/or other VIPs of the invention can be eliminated from the sequence thereby making them unrecognizable as secretion proteins in Bacillus. Specifically, a methionine start site can be engineered in front of the proprotein sequence in VIP1, starting at Asp32, or the proprotein sequence in VIP2, starting at Glu41 using methods known in the art.

VIP genes can be introduced into micro-organisms that multiply on plants (epiphytes) to deliver VIP proteins to potential target pests. Epiphytes can be gram-positive or gram-negative bacteria for example.

The Bacillus strains of the invention or the microorganisms which have been genetically altered to contain the pesticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticides are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein.

The active ingredients of the present invention are normally applied in the form of compositions and can be applied to the crop area or plant to be treated, simultaneously or in succession, with other compounds. These compounds can be both fertilizers or micronutrient donors or other preparations that influence plant-growth. They can also be selective herbicides, insecticides, fungicides, bactericides, nematicides, mollusicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

Preferred methods of applying an active ingredient of the present invention or an agrochemical composition of the present invention which contains at least one of the pesticidal proteins produced by the bacterial strains of the present invention are leaf application, seed coating and soil application. The number of applications and the rate of application depend on the intensity of infestation by the corresponding pest.

In one embodiment of the invention a Bacillus cereus microorganism has been isolated which is capable of killing Diabrotica virgifera virgifera, and Diabrotica longicornis barberi. The novel B. cereus strain AB78 has been deposited in the Agricultural Research Service, Patent Culture Collection (NRRL), Northern Regional Research Center, 1815 North University Street, Peoria, Ill. 61604, USA and given Accession No. NRRL B-21058.

A fraction protein has been substantially purified from the B. cereus strain. This purification of the protein has been verified by SDS-PAGE and biological activity. The protein has a molecular weight of about 60 to about 100 kDa, particularly about 70 to about 90 kDa, more particularly about 80 kDa, hereinafter VIP.

Amino-terminal sequencing has revealed the N-terminal amino-acid sequence to be: $NH_2$-Lys-Arg-Glu-Ile-Asp-Glu-Asp-Thr-Asp-Thr-Asx-Gly-Asp-Ser-Ile-Pro- (SEQ ID NO:8) where Asx represents either Asp or Asn. The entire amino acid sequence is given in SEQ ID NO:7. The DNA sequence which encodes the amino acid sequence of SEQ ID NO:7 is disclosed in SEQ ID NO:6.

An oligonucleotide probe for the region of the gene encoding amino acids 3–9 of the NH$_2$-terminus has been generated. The probe was synthesized based on the codon usage of a Bacillus thuringiensis (Bt) δ-endotoxin gene. The nucleotide sequence of the oligonucleotide probe used for Southern hybridizations was as follows:

5'-GAA ATT GAT CAA GAT ACN GAT-3' (SEQ ID NO:9) where N represents any base.

In addition, the DNA probe for the Bc AB78 VIP1 gene described herein, permits the screening of any Bacillus strain or other organisms to determine whether the VIP1 gene (or related gene) is naturally present or whether a particular transformed organism includes the VIP1 gene.

The invention now being generally described, the same will be better understood by reference to the following detailed examples that are provided for the purpose of illustration and are not to be considered limiting of the invention unless so specified.

A standard nomenclature has been developed based on the sequence identity of the proteins encompassed by the present invention. The gene and protein names for the detailed examples which follow and their relationship to the names used in the parent application are shown below.

| Gene/Protein Name under Standard Nomenclature | Gene/Protein Name in Parent | Description of Protein |
|---|---|---|
| VIP1A(a) | VIP1 | VIP1 from strain AB78 as disclosed in SEQ ID NO: 5. |
| VIP2A(a) | VIP2 | VIP2 from strain AB78 as disclosed in SEQ ID NO: 2. |
| VIP1A(b) | VIP1 homolog | VIP1 from Bacillus thuringiensis var. tenebrionis as disclosed in SEQ ID NO: 21. |
| VIP2A(b) | VIP2 homolog | VIP2 from Bacillus thuringiensis var. tenebrionis as disclosed in SEQ ID NO: 20. |
| VIP3A(a) | — | VIP from strain AB88 as disclosed in SEQ ID NO: 28 of the present application |
| VIP3A(b) | — | VIP from strain AB424 as disclosed in SEQ ID NO: 31 of the present application |

EXPERIMENTAL

EXAMPLE 1

AB78 ISOLATION AND CHARACTERIZATION

Bacillus cereus strain AB78 was isolated as a plate contaminant in the laboratory on T3 media (per liter: 3 g tryptone, 2 g tryptose, 1.5 g yeast extract, 0.05M sodium phosphate (pH 6.8), and 0.005 g MnCl$_2$; Travers, R. S. 1983). During log phase growth, AB78 gave significant activity against western corn rootworm. Antibiotic activity against gram-positive Bacillus spp. was also demonstrated (Table 12).

TABLE 12

Antibiotic activity of AB78 culture supernatant

| | Zone of inhibition (cm) | |
|---|---|---|
| Bacteria tested | AB78 | Streptomycin |
| E. coli | 0.0 | 3.0 |
| B. megaterium | 1.1 | 2.2 |

TABLE 12-continued

Antibiotic activity of AB78 culture supernatant

| | Zone of inhibition (cm) | |
|---|---|---|
| Bacteria tested | AB78 | Streptomycin |
| B. mycoides | 1.3 | 2.1 |
| B. cereus CB | 1.0 | 2.0 |
| B. cereus 11950 | 1.3 | 2.1 |
| B. cereus 14579 | 1.0 | 2.4 |
| B. cereus AB78 | 0.0 | 2.2 |
| Bt var. israelensis | 1.1 | 2.2 |
| Bt var. tenebrionis | 0.9 | 2.3 |

Morphological characteristics of AB78 are as follows:

Vegetative rods straight, 3.1–5.0 mm long and 0.5–2.0 mm wide. Cells with rounded ends, single in short chains. Single subterminal, cylindrical-oval, endospore formed per cell. No parasporal crystal formed. Colonies opaque, erose, lobate and flat. No pigments produced. Cells motile. Flagella present.

Growth characteristics of AB78 are as follows:

Facultative anaerobe with optimum growth temperature of 21°–30° C. Will grow at 15°, 20°, 25°, 30° and 37° C. Will not grow above 40° C. Grows in 5–7% NaCl.

Table 13 provides the biochemical profile of AB78.

TABLE 13

Biochemical characteristics of B. cereus strain AB78.

| Acid from L-arabinose | − | Methylene blue reoxidized | + |
|---|---|---|---|
| Gas from L-arabinose | − | Nitrate reduced | + |
| Acid from D-xylose | − | NO$_3$ reduced to NO$_2$ | + |
| Gas from D-xylose | − | VP | + |
| Acid from D-glucose | + | H$_2$O$_2$ decomposed | + |
| Gas from D-glucose | − | Indole | − |
| Acid from lactose | − | Tyrosine decomposed | + |
| Gas from lactose | − | Dihydroxiacetone | − |
| Acid from sucrose | − | Litmus milk acid | − |
| Gas from sucrose | − | Litmus milk coagulated | − |
| Acid from D-mannitol | − | Litmus milk alkaline | − |
| Gas from D-mannitol | − | Litmus milk peptonized | − |
| Proprionate utilization | + | Litmus milk reduced | − |
| Citrate utilization | + | Casein hydrolyzed | + |
| Hippurate hydrolysis | w | Starch hydrolyzed | + |
| Methylene blue reduced | + | Gelatin liquidified | + |
| | | Lecithinase produced | w | w = weak reaction

EXAMPLE 2

BACTERIAL CULTURE

A subculture of Bc strain AB78 was used to inoculate the following medium, known as TB broth:

| Tryptone | 12 g/l |
|---|---|
| Yeast Extract | 24 g/l |
| Glycerol | 4 ml/l |
| KH$_2$PO$_4$ | 2.1 g/l |
| K$_2$HPO$_4$ | 14.7 g/l |
| pH 7.4 | |

The potassium phosphate was added to the autoclaved broth after cooling. Flasks were incubated at 30° C. on a rotary shaker at 250 rpm for 24 h.–36 h, which represents an early to mid-log growth phase.

The above procedure can be readily scaled up to large fermentors by procedures well known in the art.

During vegetative growth, usually 24–36 h. after starting the culture, which represents an early to mid-log growth phase, AB78 bacteria were centrifuged from the culture supernatant. The culture supernatant containing the active protein was used in bioassays.

EXAMPLE 3

INSECT BIOASSAYS

B. cereus strain AB78 was tested against various insects as described below.

Western, Northern and Southern corn rootworm, *Diabrotica virgifera virgifera, D. longcornis barberi* and *D. undecempunctata howardi*, respectively: dilutions were made of AB78 culture supernatant grown 24–36 h., mixed with molten artificial diet (Marrone et al. (1985) *J. of Economic Entomology* 78:290–293) and allowed to solidify. Solidified diet was cut and placed in dishes. Neonate larvae were placed on the diet and held at 30° C. Mortality was recorded after 6 days.

*E. coli* clone bioassay: *E. coli* cells were grown overnight in broth containing 100 μg/ml ampicillin at 37° C. Ten ml culture was sonicated 3× for 20 sec each. 500 μl of sonicated culture was added to molten western corn rootworm diet.

Colorado potato beetle, *Leptinotarsa decemlineata*: dilutions in Triton X-100 (to give final concentration of 0.1% TX-100) were made of AB78 culture supernatant grown 24–36 h. Five cm² potato leaf pieces were dipped into these dilutions, air dried, and placed on moistened filter paper in plastic dishes. Neonate larvae were placed on the leaf pieces and held at 30° C. Mortality was recorded after 3–5 days.

Yellow mealworm, *Tenebrio molitor*: dilutions were made of AB78 culture supernatant grown 24–36 h., mixed with molten artificial diet (Bioserv #F9240) and allowed to solidify. Solidified diet was cut and placed in plastic dishes. Neonate larvae were placed on the diet and held at 30° C. Mortality was recorded after 6–8 days.

European corn borer, black cutworm, tobacco budworm, tobacco hornworm and beet armyworm; *Ostrinia nubilalis, Agrotis ipsilon, Heliothis virescens, Manduca sexta* and *Spodoptera exigua*, respectively: dilutions, in TX-100 (to give final concentration of 0.1% TX-100), were made of AB78 culture supernatant grown 24–36 hrs. 100 μl was pipetted onto the surface of 18 cm² of solidified artificial diet (Bioserv #F9240) and allowed to air dry. Neonate larvae were then placed onto the surface of the diet and held at 30° C. Mortality was recorded after 3–6 days.

Northern house mosquito, *Culex pipiens*:-dilutions were made of AB78 culture supernatant grown 24–36 h. 100 μl was pipetted into 10 ml water in a 30 ml plastic cup. Third instar larvae were added to the water and held at room temperature. Mortality was recorded after 24–48 hours. The spectrum of entomocidal activity of AB78 is given in Table 14.

TABLE 14

Activity of AB78 culture supernatant against various insect species

| Insect species tested to date | Order | Activity |
|---|---|---|
| Western corn rootworm (*Diabrotica virgifera virgifera*) | Col | +++ |
| Northern corn rootworm (*Diabrotica longicornis barberi*) | Col | +++ |
| Southern corn rootworm | Col | – |

TABLE 14-continued

Activity of AB78 culture supernatant against various insect species

| Insect species tested to date | Order | Activity |
|---|---|---|
| (*Diabrotica undecimpunctata howardi*) | | |
| Colorado potato beetle (*Leptinotarsa decemlineata*) | Col | – |
| Yellow mealworm (*Tenebrio molitor*) | Col | – |
| European corn borer (*Ostrinia nubilalis*) | Lep | – |
| Tobacco budworm (*Heliothis virescens*) | Lep | – |
| Tobacco hornworm (*Manduca sexta*) | Lep | – |
| Beet armyworm (*Spodoptera exigua*) | Lep | – |
| Black cutworm (*Agrotis ipsilon*) | Lep | – |
| Northern house mosquito (*Culex pipiens*) | Dip | – |

The newly discovered *B. cereus* strain AB78 showed a significantly different spectrum of insecticidal activity as compared to known coleopteran active δ-endotoxins from Bt. In particular, AB78 showed more selective activity against beetles than known coleopteran-active Bt strains in that it was specifically active against *Diabrotica* spp. More specifically, it was most active against *D. virgifera virgifera* and *D. longicornis barberi* but not *D. undecimpunctata howardi*.

A number of Bacillus strains were bioassayed for activity during vegetative growth (Table 15) against western corn rootworm. The results demonstrate that AB78 is unique in that activity against western corn rootworm is not a general phenomenon.

TABLE 15

Activity of culture supernatants from various Bacillus spp. against western corn rootworm

| Bacillus strain | Percent WCRW mortality |
|---|---|
| *B. cereus* AB78 (Bat.1) | 100 |
| *B. cereus* AB78 (Bat.2) | 100 |
| *B. cereus* (Carolina Bio.) | 12 |
| *B. cereus* ATCC 11950 | 12 |
| *B. cereus* ATCC 14579 | 8 |
| *B. mycoides* (Carolina Bio.) | 30 |
| *B. popilliae* | 28 |
| *B. thuringiensis* HD135 | 41 |
| *B. thuringiensis* HD191 | 9 |
| *B. thuringiensis* GC91 | 4 |
| *B. thuringiensis* isrealensis | 24 |
| Water Control | 4 |

Specific activity of AB78 against western corn rootworm is provided in Table 16.

TABLE 16

Activity of AB78 culture supernatant against neonate western corn rootworm

| Culture supernatant concentration (μl/ml) | Percent WCRW mortality |
|---|---|
| 100 | 100 |
| 25 | 87 |
| 10 | 80 |
| 5 | 40 |
| 2.5 | 20 |
| 1 | 6 |
| 0 | 0 |

The $LC_{50}$ was calculated to be 6.2 μl of culture supernatant per ml of western corn rootworm diet.

The cell pellet was also bioassayed and had no activity against WCRW. Thus, the presence of activity only in the supernatant indicates that this VIP is an exotoxin.

EXAMPLE 4

ISOLATION AND PURIFICATION OF CORN ROOTWORM ACTIVE PROTEINS FROM AB78

Culture media free of cells and debris was made to 70% saturation by the addition of solid ammonium sulfate (472 g/L). Dissolution was at room temperature followed by cooling in an ice bath and centrifugation at 10,000×g for thirty minutes to pellet the precipitated proteins. The supernatant was discarded and the pellet was dissolved in 1/10 the original volume of 20 mM TRIS-HCl at pH 7.5. The dissolved pellet was desalted either by dialysis in 20 mM TRIS-HCl pH 7.5, or passing through a desalting column.

The desalted material was titrated to pH 3.5 using 20 mM sodium citrate pH 2.5. Following a thirty minute room temperature incubation the solution was centrifuged at 3000×g for ten minutes. The supernatant at this stage contained the greatest amount of active protein.

Following neutralization of the pH to 7.0 the supernatant was applied to a Mono-Q, anion exchange, column equilibrated with 20 mM TRIS pH 7.5 at a flow rate of 300 mL/min. The column was developed with a stepwise and linear gradient employing 400 mM NaCl in 20 mM TRIS pH 7.5.

Bioassay of the column fractions and SDS-PAGE analysis were used to confirm the active fractions. SDS-PAGE analysis identified the biologically active protein as having components of a molecular weight in the range of about 80 kDa and 50 kDa.

EXAMPLE 5

SEQUENCE ANALYSIS OF THE CORN ROOTWORM ACTIVE PROTEIN

The 80 kDa component isolated by SDS-PAGE was transferred to PVDF membrane and was subjected to amino-terminal sequencing as performed by repetitive Edman cycles on an ABI 470 pulsed-liquid sequencer. Transfer was carried out in 10 mM CAPS buffer with 10% methanol pH 11.0 as follows:

Incubation of the gel following electrophoresis was done in transfer buffer for five minutes. ProBlott PVDF membrane was wetted with 100% MeOH briefly then equilibrated in transfer buffer. The sandwich was arranged between foam sponges and filter paper squares with the configuration of cathode-gel-membrane-anode.

Transfer was performed at 70 V constant voltage for 1 hour.

Following transfer, the membrane was rinsed with water and stained for two minutes with 0.25% Coomassie Blue R-250 in 50% MeOH.

Destaining was done with several rinses with 50% MeOH 40% water 10% acetic acid.

Following destaining the membrane was air dried prior to excision of the bands for sequence analysis. A BlottCartridge and appropriate cycles were utilized to achieve maximum efficiency and yield. Data analysis was performed using model 610 Sequence Analysis software for identifying and quantifying the PTH-amino acid derivatives for each sequential cycle.

The N-terminal sequence was determined to be: NH2-Lys-Arg-Glu-Ile-Asp-Glu-Asp-Thr-Asp-Thr-Asx-Gly-Asp-Ser-Ile-Pro- (SEQ ID NO:8) where Asx represents Asp or Asn. The complete amino acid sequence for the 80 kDa component is disclosed in SEQ ID NO:7. The DNA sequence which encodes SEQ ID NO:7 is disclosed in SEQ ID NO:6.

EXAMPLE 6

CONSTRUCTION OF DNA PROBE

An oligonucleotide probe for the region of the gene encoding amino acids 3–9 of the N-terminal sequence (Example 5) was generated. The probe was synthesized based on the codon usage of a *Bacillus thuringiensis* (Bt) δ-endotoxin gene. The nucleotide sequence 5'-GAA ATT GAT CAA GAT ACN GAT-3' (SEQ ID NO:9) was used as a probe in Southern hybridizations. The oligonucleotide was synthesized using standard procedures and equipment.

EXAMPLE 7

ISOELECTRIC POINT DETERMINATION OF THE CORN ROOTWORM ACTIVE PROTEIN

Purified protein from step 5 of the purification process was analyzed on a 3–9 pI isoelectric focusing gel using the Phastgel electrophoresis system (Pharmacia). Standard operating procedures for the unit were followed for both the separation and silver staining development procedures. The pI was approximated at about 4.9.

EXAMPLE 8

PCR DATA ON AB78

PCR analysis (See, for example U.S. patent application Ser. No. 08/008,006; and, Carozzi et al. (1991) *Appl. Environ. Microbiol.* 57(11):3057–3061, herein incorporated by reference.) was used to verify that the *B. cereus* strain AB78 did not contain any insecticidal crystal protein genes of *B. thuringiensis* or *B. sphaericus* (Table 17).

TABLE 17

| Bacillus insecticidal crystal protein gene primers tested by PCR against AB78 DNA. | |
|---|---|
| Primers Tested | Product Produced |
| 2 sets specific for CryIIIA | Negative |
| CryIIIB | Negative |
| 2 sets specific for CryIA | Negative |
| CryIA(a) | Negative |

TABLE 17-continued

Bacillus insecticidal crystal protein gene primers tested by PCR against AB78 DNA.

| Primers Tested | Product Produced |
| --- | --- |
| CryIA(b) specific | Negative |
| CryIB | Negative |
| CryIC specific | Negative |
| CryIE specific | Negative |
| 2 sets specific for B. sphaericus | Negative |
| 2 sets specific for CryIV | Negative |
| Bacillus control (PI-PLC) | Positive |

EXAMPLE 9

COSMID CLONING OF TOTAL DNA FROM B. CEREUS STRAIN AB78

The VIP1A(a) gene was cloned from total DNA prepared from strain AB78 as follows:

Isolation of AB78 DNA was as follows:
1. Grow bacteria in 10 ml L-broth overnight. (Use 50 ml sterile centrifuge tube)
2. Add 25 ml of fresh L-broth and ampicillin (30 µg/ml).
3. Grow cells 2–6 h. at 30° C. with shaking.
4. Spin cells in a 50 ml polypropylene orange cap tube in IEC benchtop clinical centrifuge at ¾ speed.
5. Resuspend cell pellet in 10 ml TES (TES=50 mM TRIS pH 8.0, 100 mM EDTA, 15 mM NaCl).
6. Add 30 mg lysozyme and incubate 2 hrs at 37° C.
7. Add 200 µl 20% SDS and 400 µl Proteinase K stock (20 mg/ml). Incubate at 37° C.
8. Add 200 µl fresh Proteinase K. Incubate 1 hr. at 55° C. Add 5 ml TES to make 15 ml final volume.
9. Phenol extract twice (10 ml phenol, spin at room temperature at ¾ speed in an IEC benchtop clinical centrifuge). Transfer supernatant (upper phase) to a clean tube using a wide bore pipette.
10. Extract once with 1:1 vol. phenol:chloroform/isoamyl alcohol (24:1 ratio).
11. Precipitate DNA with an equal volume of cold isopropanol; Centrifuge to pellet DNA.
12. Resuspend pellet in 5 ml TE.
13. Precipitate DNA with 0.5 ml 3M NaOAc pH 5.2 and 11 ml 95% ethanol. Place at −20° C. for 2 h.
14. "Hook" DNA from tube with a plastic loop, transfer to a microfuge tube, spin, pipette off excess ethanol, dry in vacuo.
15. Resuspend in 0.5 ml TE. Incubate 90 min. at 65° C. to help get DNA back into solution.
16. Determine concentration using standard procedures.

Cosmid Cloning of AB78

All procedures, unless indicated otherwise, were performed according to Stratagene Protocol, Supercos 1 Instruction Manual, Cat. No. 251301.

Generally, the steps were as follows:
A. Sau 3A partial digestion of the AB78 DNA.
B. Preparation of vector DNA
C. Ligation and packaging of DNA
D. Tittering the cosmid library
  1. Start a culture of HB101 cells by placing 50 ml of an overnight culture in 5 mls of TB with 0.2% maltose. Incubate 3.5 hrs. at 37° C.
  2. Spin out cells and resuspend in 0.5 ml 10 mM $MgSO_4$.
 3. Add together:
    100 µl cells
    100 µl diluted packaging mixture
    100 µl 10 mM $MgSO_4$
    30 µl TB
 4. Adsorb at room temperature for 30 minutes with no shaking.
 5. Add 1 ml TB and mix gently. Incubate 30 minutes at 37° C.
 6. Plate 200 µl onto L-amp plates. Incubate at 37° C. overnight.

At least 400 cosmid clones were selected at random and screened for activity against western corn rootworm as described in Example 3. DNA from 5 active clones and 5 non-active clones were used in Southern hybridizations. Results demonstrated that hybridization using the above described oligonucleotide probe correlated with western corn rootworm activity (Table 18).

Cosmid clones P3-12 and P5-4 have been deposited with the Agricultural Research Service Patent Culture Collection (NRRL) and given Accession Nos. NRRL B-21061 and NRRL B-21059 respectively.

TABLE 18

Activity of AB78 cosmid clones against western corn rootworm.

| Clone | Mean percent mortality (N = 4) |
| --- | --- |
| Clones which hybridize with probe | |
| P1-73 | 47 |
| P1-83 | 64 |
| P2-2 | 69 |
| P3-12 | 85 |
| P5-4 | 97 |
| Clones which do not hybridize with probe | |
| P1-2 | 5 |
| P3-8 | 4 |
| P3-9 | 12 |
| P3-18 | 0 |
| P4-6 | 9 |

EXAMPLE 10

IDENTIFICATION OF A 6 KB REGION ACTIVE AGAINST WESTERN CORN ROOTWORM

DNA from P3-12 was partially digested with restriction enzyme Sau 3A, and ligated into the E. coli vector pUC19 and transformed into E. coli. A DNA probe specific for the 80 kDa VIP1A(a) protein was synthesized by PCR amplification of a portion of P3-12 DNA. Oligonucleotides MK113 and MK117, which hybridize to portions of VIP1A (a), were synthesized using the partial amino acid sequence of the 80 kDa protein. Plasmid subclones were identified by colony hybridization to the PCR-generated probe, and tested for activity against western corn rootworm. One such clone, PL2, hybridized to the PCR-generated fragment, and was active against western corn rootworm in the assay previously described.

A 6 kb Cla I restriction fragment from pL2 was cloned into the Sma I site of the E. coli-Bacillus shuttle vector pHT 3101 (Lereclus, D. et al., FEMS Microbiology Letters 60:211–218 (1989)) to yield pCIB6201. This construct confers anti-western corn rootworm activity upon both Bacillus and E.coli strains, in either orientation. pCIB6022 contains this same 6 kb Cla I fragment in pBluescript SK(+)

(Stratagene), produces equivalent VIP1A(a) protein (by western blot), and is also active against western corn rootworm.

The nucleotide sequence of pCIB6022 was determined by the dideoxy termination method of Sanger et al., *Proc. Natl. Acad. Sci. USA*, 74:5463–5467 (1977), using PRISM Ready Reaction Dye Deoxy Terminator Cycle Sequencing Kits and PRISM Sequenase® Terminator Double-Stranded DNA Sequencing Kit and analyzed on an ABI 373 automatic sequencer. The sequence is given in SEQ ID NO:1. The 6 kb fragment encodes both VIP1A(a) and VIP2A(a), as indicated by the open reading frames described in SEQ ID NO:1. The sequence encoding VIP1A(a) is further disclosed in SEQ ID NO:4. The relationship between VIP1A(a) and VIP2A(a) within the 6 kb fragment found in pCIB6022 is depicted in FIG. 1. pCIB6022 was deposited with the Agricultural Research Service, Patent Culture Collection, (NRRL), Northern Regional Research Center, 1815 North University Street, Peoria, Ill. 61604, USA, and given the Accession No. NRRL B-21222.

EXAMPLE 11

FUNCTIONAL DISSECTION OF THE VIP1A(a) DNA REGION

To confirm that the VIP1A(a) open reading frame (ORF) is necessary for insecticidal activity a translational frameshift mutation was created in the gene. The restriction enzyme Bgl II recognizes a unique site located 857 bp into the coding region of VIP1A(a). pCIB6201 was digested with Bgl II, and the single-stranded ends filled-in with DNA polymerase (Klenow fragment) and dNTPS. The plasmid was re-ligated and transformed into *E. coli*. The resulting plasmid, pCIB6203, contains a four nucleotide insertion in the coding region of VIP1A(a). pCIB6203 does not confer WCRW insecticidal activity, confirming that VIP1A(a) is an essential component of western corn rootworm activity.

To further define the region necessary to encode VIP1A (a), subclones of the VIP1A(a) and VIP2A(a) (auxiliary protein) region were constructed and tested for their ability to complement the mutation in pCIB6203. pCIB6023 contains the 3.7 kb Xba I-EcoRV fragment in pBluescript SK(+) (Stratagene). Western blot analysis indicates that pCIB6023 produces VIP1A(a) protein of equal size and quantity as clones PL2 and pCIB6022. pCIB6023 contains the entire gene encoding the 80 kD protein. pCIB6023 was deposited with the Agricultural Research Service, Patent Culture Collection, (NRRL), Northern Regional Research Center, 1815 North University Street, Peoria, Ill. 61604, USA, and given the Accession No. NRRL B-21223N. pCIB6206 contains the 4.3 kb Xba I-Cla I fragment from pCIB6022 in pBluescript SK(+) (Stratagene). pCIB6206 was also deposited with the Agricultural Research Service, Patent Culture Collection, (NRRL), Northern Regional Research Center, 1815 North University Street, Peoria, Ill. 61604, USA, and given the Accession No. NRRL B-21321.

pCIB6023, pCIB6206, and pCIB6203 do not produce detectable western corn rootworm activity when tested individually. However, a mixture of cells containing pCIB6203 (VIP1A(a)-mutated, plus VIP2A(a)) and cells containing pCIB6023 (only VIP1A(a)) shows high activity against western corn rootworm. Similarly, a mixture of cells containing pCIB6206 and cells containing pCIB6203 shows high activity against western corn rootworm.

To further define the limits of VIP2A(a), we constructed pCIB6024, which contains the entirety of VIP2A(a), but lacks most of the VIP1A(a) coding region. pCIB6024 was constructed by gel purifying the 2.2 kb Cla I-Sca I restriction fragment from pCIB6022, filling in the single-stranded ends with DNA polymerase (Klenow fragment) and dNTPs, and ligating this fragment into pBluescript SK(+) vector (Stratagene) digested with the enzyme Eco RV. Cells containing pCIB6024 exhibit no activity against western corn rootworm. However, a mixture of cells containing pCIB6024 and cells containing pCIB6023 shows high activity against western corn rootworm. (See FIG. 1).

Thus, pCIB6023 and pCIB6206 must produce a functional VIP1A(a) gene product, while pCIB6203 and pCIB6024 must produce a functional VIP2A(a) gene product. These results suggest a requirement for a gene product (s) from the VIP2A(a) region, in combination with VIP1A (a), to confer maximal western corn rootworm activity. (See FIG. 1)

EXAMPLE 12

AB78 ANTIBODY PRODUCTION

Antibody production was initiated in 2 Lewis rats to allow for both the possibility of moving to production of hybridoma cell lines and also to produce enough serum for limited screening of genomic DNA library. Another factor was the very limited amount of antigen available and the fact that it could only be produced to purity by PAGE and subsequent electrotransfer to nitrocellulose.

Due to the limited availability of antigen on nitrocellulose, the nitrocellulose was emulsified in DMSO and injected into the hind footpads of the animals to elicit B-cell production in the popliteal lymph nodes just upstream. A strong reacting serum was produced as judged by western blot analysis with the first production bleed. Several subsequent injections and bleeds produced enough serum to accomplish all of the screening required.

Hybridoma production with one of the rats was then initiated. The popliteal lymph node was excised, macerated, and the resulting cells fused with mouse myeloma P3x63Ag8.653. Subsequent cell screening was accomplished as described below. Four initial wells were selected which gave the highest emulsified antigen reaction to be moved to limited dilution cloning. An additional 10 wells were chosen for expansion and cryoperservation.

Procedure to Emulsify AB78 on nitrocellulose in DMSO for ELISA screening

After electrotransfer of AB78 samples run on PAGE to nitrocellulose, the reversible strain Ponceau S is used to visualize all protein transferred. The band corresponding to AB78 toxin, previously identified and N-terminal sequenced, was identified and excised from nitrocellulose. Each band is approximately 1 mm×5 mm in size to minimize the amount of nitrocellulose emulsified. A single band is placed in a microfuge tube with 250 µl of DMSO and macerated using a plastic pestle (Kontes, Vineland, N.J.). To aid in emulsification, the DMSO mixture is heated for 2–3 minutes at 37° C.–45° C. Some further maceration might be necessary following heating; however, all of the nitrocellulose should be emulsified. Once the AB78 sample is emulsified, it is placed on ice. In preparation for microtiter plate coating with the emulsified antigen, the sample must be diluted in borate buffered saline as follows: 1:5, 1:10, 1:15, 1:20, 1:30, 1:50, 1:100, and 0. The coating antigen must be prepared fresh immediately prior to use.

ELISA protocol:

1. Coat with AB78/DMSO in BBS. Incubate overnight at 4° C.
2. Wash plate 3× with 1×ELISA wash buffer.
3. Block (1% BSA & 0.05% Tween 20 in PBS) for 30 minutes at Room Temperature.
4. Wash plate 3× with 1×ELISA wash buffer.
5. Add rat serum. Incubate 1.5 hours at 37° C.
6. Wash plate 3× with 1×ELISA wash buffer.
7. Add goat anti-rat at a concentration of 2 µg/ml in ELISA diluent. Incubate 1 hr. at 37° C.
8. Wash plate 3× with 1×ELISA wash buffer.
9. Add rabbit anti-goat alkaline phosphatase at 2 µg/ml in ELISA diluent. Incubate 1 hr. at 37° C.
10. Wash 3× with 1×ELISA wash buffer.
11. Add Substrate. Incubate 30 minutes at room temperature.
12. Stop with 3N NaOH after 30 minutes.

Preparation of VIP2A(a) Antisera

A partially purified AB78 culture supernatant was separated by discontinuous SDS PAGE (Novex) following manufacturer's instructions. Separated proteins were electrophoresed to nitrocellulose (S&S #21640) as described by Towbin et al., (1979). The nitrocellulose was stained with Ponceau S and the VIP2A(a) band identified. The VIP2A(a) band was excised and emulsified in DMSO immediately prior to injection. A rabbit was initially immunized with emulsified VIP2A(a) mixed approximately 1:1 with Freund's Complete adjuvant by intramuscular injection at four different sites. Subsequent immunizations occurred at four week intervals and were identical to the first, except for the use of Freund' Incomplete adjuvant. The first serum harvested following immunization reacted with VIP2A(a) protein. Western blot analysis of AB78 culture supernatant using this antisera identifies predominately full length VIP2A(a) protein.

EXAMPLE 13

ACTIVATION OF INSECTICIDAL ACTIVITY OF NON-ACTIVE BT STRAINS WITH AB78 VIP CLONES

Adding pCIB6203 together with a 24 h culture (early to mid-log phase) supernatant from Bt strain GC91 produces 100% mortality in *Diabrotica virgifera virgifera*. Neither pCIB6203 nor GC91 is active on *Diabrotica virgifera virgifera* by itself Data are shown below:

| Test material | Percent Diabrotica mortality |
| --- | --- |
| pCIB6203 | 0 |
| GC91 | 16 |
| pCIB6203 + GC91 | 100 |
| Control | 0 |

EXAMPLE 14

ISOLATION AND BIOLOGICAL ACTIVITY OF B. CEREUS AB81

A second *B. cereus* strain, designated AB81, was isolated from grain bin dust samples by standard methodologies. A subculture of AB81 was grown and prepared for bioassay as described in Example 2. Biological activity was evaluated as described in Example 3. The results are as follows:

| Insect species tested | Percent Mortality |
| --- | --- |
| Ostrinia nubilalis | 0 |
| Agrotis ipsilon | 0 |
| Diabrotica virgifera virgifera | 55 |

EXAMPLE 15

ISOLATION AND BIOLOGICAL ACTIVITY OF B. THURINGIENSIS AB6

A *B. thuringiensis* strain, designated AB6, was isolated from grain bin dust samples by standard methods known in the art. A subculture of AB6 was grown and prepared for bioassay as described in Example 2. Half of the sample was autoclaved 15 minutes to test for the presence of β-exotoxin.

Biological activity was evaluated as described in Example 3. The results are as follows:

| Insect species tested | Percent Mortality |
| --- | --- |
| Ostrinia nubilalis | 0 |
| Agrotis ipsilon | 100 |
| Agrotis ipsilon (autoclaved sample) | 0 |
| Diabrotica virgifera virgifera | 0 |

The reduction of insecticidal activity of the culture supernatant to insignificant levels by autoclaving indicates that the active principle is not β-exotoxin.

Strain AB6 has been deposited in the Agricultural Research Service, Patent Culture Collection (NRRL), Northern Regional Research Center, 1815 North University Street, Peoria, Ill. 61604, USA, and given Accession No. NRRL B-21060.

EXAMPLE 16

ISOLATION AND BIOLOGICAL CHARACTERIZATION OF B. THURINGIENSIS AB88

A Bt strain, designated AB88, was isolated from grain bin dust samples by standard methodologies. A subculture of AB88 was grown and prepared for bioassay as described in Example 2. Half of the sample was autoclaved 15 minutes to test for the presence of β-exotoxin. Biological activity was evaluated against a number of insect species as described in Example 3. The results are as follows:

| Insect species tested | Order | Percent mortality of culture supernatant | |
| --- | --- | --- | --- |
| | | Non-autoclaved | Autoclaved |
| Agrotis ipsilon | Lepidoptera | 100 | 5 |
| Ostrinia nubilalis | Lepidoptera | 100 | 0 |
| Spodoptera frugiperda | Lepidoptera | 100 | 4 |
| Helicoverpa zea | Lepidoptera | 100 | 12 |
| Heliothis virescens | Lepidoptera | 100 | 12 |
| Leptinotarsa decemlineata | Coleoptera | 0 | 0 |
| Diabrotica virgifera virgifera | Coleoptera | 0 | 5 |

The reduction of insecticidal activity of the culture supernatant to insignificant levels by autoclaving indicates that the active principle is not β-exotoxin.

Delta-endotoxin crystals were purified from strain AB88 by standard methodologies. No activity from pure crystals was observed when bioassayed against *Agrotis ipsilon*.

EXAMPLE 17

PURIFICATION OF VIPS FROM STRAIN AB88

Bacterial liquid culture was grown overnight at 30° C. in TB media. Cells were spun out and the supernatant retained. Proteins were precipitated with ammonium sulfate (70% saturation), centrifuged and the pellet retained. The pellet was resuspended in the original volume of 20 mM Tris pH 7.5 and dialyzed against the same buffer. AB88 dialysate was more turbid than comparable material from AB78. AB88 proteins have been separated by several different methods following clarification including isoelectric focusing (Rotofor, BioRad, Hercules, Calif.), precipitation at pH 4.5, ion-exchange chromotography, size exclusion chromatography and ultrafiltration.

European corn borer (ECB)-active protein remained in the pellet obtained by pH 4.5 precipitation of dialysate. When preparative IEF was done on the dialysate using pH 3–10 ampholytes, ECB insecticidal activity was found in all fractions with pH of 7 or greater. SDS-PAGE analysis of these fractions showed protein bands of MW ~60 kDa and ~80 kDa. The 60 kDa and 80 kDa bands were separated by anion exchange HPLC on a Poros-Q column (PerSeptive Biosystems, Cambridge, Mass.). N-terminal sequence was obtained from two fractions containing proteins of slightly differing MW, but both of approximately 60 kDa in size. The sequences obtained were similar to each other and to some δ-endotoxins.

| anion exchange fraction 23 (smaller): | xEPFVSAxxxQxxx (SEQ ID NO: 10) |
|---|---|
| anion exchange fraction 28 (larger): | xEYENVEPFVSAx (SEQ ID NO: 11) |

When the ECB-active pH 4.5 pellet was further separated by anion exchange on a Poros-Q column, activity was found only in fractions containing a major band of ~60 kDa.

Black cutworm-active protein also remained in the pellet when AB88 dialysate was brought down to pH 4.5. In preparative IEF using pH 3–10 ampholytes, activity was not found in the ECB-active IEF fractions; instead, it was highest in a fraction of pH 4.5–5.0. Its major components have molecular weights of ~35 and ~80 kDa.

The pH 4.5 pellet was separated by anion exchange HPLC to yield fractions containing only the 35 kDa material and fractions containing both 35 kDa and 80 kDa bands.

EXAMPLE 18

CHARACTERIZATION OF AB88 VIP

Fractions containing the various lepidopteran active vegetative proteins were generated as described in Example 17. Biological analysis of fractions demonstrated that different VIPs were responsible for the different lepidopteran species activity.

The *Agrotis ipsilon* activity is due to an 80 kDa and/or a 35 kDa protein, either delivered singly or in combination. These proteins are not related to any δ-endotoxins from Bt as evidenced by the lack of sequence homology of known Bt δ-endotoxin sequences. Also, these proteins are not found in the AB88 δ-endotoxin crystal. N-terminal sequences of the major δ-endotoxin proteins were compared with the N-terminal sequences of the 80 kDa and 35 kDa VIP and revealed no sequence homology. A summary of the results follows:

| Agrotis VIP N-terminal sequences | N-terminal sequence of major δ-endotoxin proteins |
|---|---|
|  | 130 kDa MDNNPNINE (SEQ ID NO: 14) |
| 80 kDa MNKNNTKLPTRALP (SEQ ID NO: 12) | 80 kDa MDNNPNINE (SEQ ID NO: 15) |
|  | 60 kDa MNVLNSGRTTI (SEQ ID NO: 16) |
| 35 kDa ALSENTGKDGGYIVP (SEQ ID NO: 13) |  |

The *Ostrinia nubilalis* activity is due to a 60 kDa VIP and the *Spodoptera frugiperda* activity is due to a VIP of unknown size.

*Bacillus thuringiensis* strain AB88 has been deposited in the Agricultural Research Service, Patent Culture Collection (NRRL), Northern Regional Research Center, 1815 North University Street, Peoria, Ill. 61604, USA and given the Accession No. NRRL B-21225.

EXAMPLE 18A

ISOLATION AND BIOLOGICAL ACTIVITY OF B. THURINGIENSIS AB424

A *B. thuringiensis* strain, designated AB424, was isolated from a moss covered pine cone sample by standard methods known in the art. A subculture of AB424 was grown and prepared for bioassay as described in Example 2.

Biological activity was evaluated as described in Example 3. The results are as follows:

| Insect species tested | Percent mortality |
|---|---|
| *Ostrinia nubilalis* | 100 |
| *Agrotis ipsilon* | 100 |
| *Diabrotica virgifera virgifera* | 0 |

Strain AB424 has been deposited in the Agricultural Research Service, Patent Culture Collection (NRRL), Northern Regional Research Center, 1815 North University Street, Peoria, Ill. 61604, USA, and given Accession No. NRRL B-21439.

EXAMPLE 18B

CLONING OF THE VIP3A(a) and VIP3A(b) GENES WHICH ENCODE PROTEINS ACTIVE AGAINST BLACK CUTWORM DNA from isolates AB88 and AB424 was digested with the restriction enzymes XbaI and EcoRI respectively, ligated into pBluescript vector previously linearized with the same enzymes and dephosphorylated, and transformed into *E. coli* DH5α strain. Recombinant clones were blotted onto nitrocellulose filters which were subsequently probed with a 33-bases long oligonucleotide corresponding to the 11-N terminal amino acids of the 80 kDa protein active against *Agrotis epsilon* (black cutworm). Four out of 400 recombinant clones were positive. Insect bioassays of the positive recombinants exhibited toxicity to black cutworm larvae comparable to that of AB88 or AB424 supernantants.

The nucleotide sequence of pCIB7104, a positive recombinant clone from AB88, and of pCIB7107, a positive recombinant clone from AB424, was determined by the dideoxy termination method of Sanger et al., *Proc. Natl. Acad. Sci.* USA, 74:5463–5467 (1977), using PRISM Ready Reaction Dye Deoxy Terminator Cycle Sequencing Kits and PRISM Sequenase® Terminator Double-Stranded DNA Sequencing Kit and analysed on an ABI 373 automatic sequencer.

The clone pCIB7104 contains the VIP3A(a) gene whose coding region is disclosed in SEQ ID NO:28 and the encoded protein sequence is disclosed in SEQ ID NO:29. A synthetic version of the coding region designed to be highly expressed in maize is given in SEQ ID NO:30. Any number of synthetic genes can be designed based on the amino acid sequence given in SEQ ID NO:29.

The clone pCIB7107 contains the VIP3A(b) gene whose coding region is disclosed in SEQ ID NO:31 and the encoded protein is disclosed in SEQ ID NO:32. Both pCIB7104 and pCIB7107 have been deposited with the Agricultural Research Service Patent Culture Collection (NRRL) and given Accession Nos. NRRL B-21422 and B-21423, respectively.

EXAMPLE 18C

IDENTIFICATION OF NOVEL VIP3-LIKE GENES BY HYBRIDIZATION

To identify Bacillus containing genes related to the VIP3A(a) from isolate AB88, a collection of Bacillus isolates was screened by hybridization. Cultures of 463 Bacillus strains were grown in microtiter wells until sporulation. A 96-pin colony stampel was used to transfer the cultures to 150 mm plates containing L-agar. Inoculated plates were kept at 30° C. for 10 hours, then at 4° C. overnight. Colonies were blotted onto nylon filters and probed with a 1.2 Kb HindIII VIP3A(a) derived fragment. Hybridization was performed overnight at 62° C. using hybridization conditions of Maniatis et al. *Molecular Cloning: A Laboratory Manual* (1982). Filters were washed with 2×SSC/0.1% SDS at 62° C. and exposed to X-ray film.

Of the 463 Bacillus strains screened, 60 contain VIP3-like genes that could detected by hybridization.

EXAMPLE 18D

CHARACTERIZATION OF A *B. thuringiensis* STRAIN M2194 CONTAINING A CRYPTIC VIP3-LIKE GENE A *B. thuringiensis* strain, designated M2194, was shown to contain VIP3-like gene(s) by colony hybridization as described in Example 18C. The M2194 VIP3 like gene is considered cryptic since no expression can be detected throughout the bacterial growth phases either by immunoblot analysis using polyclonal antibodies raised against the VIP3A(a) protein isolated from AB88 or by bioassay as described in Example 3.

The M2194 VIP3-like gene was cloned into pKS by following the protocol described in Example 9, which created pCIB7108. *E. coli* containing pCIB7108 which comprises the M2194 VIP3 gene were active against black cutworm demonstrating that the gene encodes a functional protein with insecticidal activity. The plasmid pCIB7108 has been deposited with the Agricultural Research Service Patent Culture Collection (NRRL) and given Accession No. NRRL B-21438.

EXAMPLE 19

ISOLATION AND BIOLOGICAL ACTIVITY OF OTHER BACILLUS SP.

Other Bacillus species have been isolated which produce proteins with insecticidal activity during vegetative growth. These strains were isolated from environmental samples by standard methodologies. Isolates were prepared for bioassay and assayed as described in Examples 2 and 3 respectively. Isolates which produced insecticidal proteins during vegetative growth with activity against *Agrotis ipsilon* in the bioassay are tabulated below. No correlation was observed between the presence of a δ-endotoxin crystal and vegetative insecticidal protein production.

| Bacillus isolate | Presence of δ-endotoxin crystal | Percent mortality |
| --- | --- | --- |
| AB6 | + | 100 |
| AB53 | − | 80 |
| AB88 | + | 100 |
| AB195 | − | 60 |
| AB211 | − | 70 |
| AB217 | − | 83 |
| AB272 | − | 80 |
| AB279 | − | 70 |
| AB289 | + | 100 |
| AB292 | + | 80 |
| AB294 | − | 100 |
| AB300 | − | 80 |
| AB359 | − | 100 |

Isolates AB289, AB294 and AB359 have been deposited in the Agricultural Research Service, Patent Culture Collection (NRRL), Northern Regional Research Center, 1815 North University Street, Peoria Ill. 61604, USA and given the Accession Numbers NRRL B-21227, NRRL B-21229, and NRRL B-21226 respectively.

Bacillus isolates which produce insecticidal proteins during vegetative growth with activity against *Diabrotica virgifera virgifera* are tabulated below.

| Bacillus isolate | Presence of δ-endotoxin crystal | Percent mortality |
| --- | --- | --- |
| AB52 | − | 50 |
| AB59 | − | 71 |
| AB68 | + | 60 |
| AB78 | − | 100 |
| AB122 | − | 57 |
| AB218 | − | 64 |
| AB256 | − | 64 |

Isolates AB59 and AB256 have been deposited in the Agricultural Research Service, Patent Culture Collection (NRRL), Northern Regional Research Center, 1815 North University Street, Peoria Ill. 61604, USA, and given the Accession Numbers NRRL B-21228 and NRRL B-21230, respectively.

EXAMPLE 20

IDENTIFICATION OF NOVEL VIP1/VIP2 LIKE GENES BY HYBRIDIZATION

To identify strains containing genes related to those found in the VIP1A(a)/VIP2A(a) region of AB78, a collection of Bacillus strains was screened by hybridization. Independent cultures of 463 Bacillus strains were grown in wells of 96 well microtiter dishes (five plates total) until the cultures sporulated. Of the strains tested, 288 were categorized as *Bacillus thuringiensis*, and 175 were categorized as other Bacillus species based on the presence or absence of δ-endotoxin crystals. For each microtiter dish, a 96-pin colony stamper was used to transfer approximately 10 μl of spore culture to two 150 mm plates containing L-agar. Inoculated plates were grown 4–8 hours at 30° C., then chilled to 4° C. Colonies were transferred to nylon filters, and the cells lysed by standard methods known in the art. The filters were hybridized to a DNA probe generated from DNA fragments containing both VIP1A(a) and VIP2A(a) DNA sequences. Hybridization was performed overnight at 65° C. using the hybridization conditions of Church and Gilbert (Church, G. M., and W. Gilbert, PNAS, 81:1991–1995 (1984)). Filters were washed with 2×SSC containing 0.1% SDS at 65° C. and exposed to X-Ray film.

Of the 463 Bacillus strains screened, 55 strains were identified that hybridized to the VIP1A(a)/VIP2A(a) probe. DNA was isolated from 22 of these strains, and analyzed using a Southern blot with VIP1A(a)/VIP2A(a) DNA as probes. These strains were grouped into 8 classes based on their Southern blot pattern. Each class differed in Southern blot pattern from AB78. One class had a pattern identical to that of the VIP1A(a)/VIP2A(a) homologs from *Bacillus thuringiensis var tenebrionis* (see below). Each of the 22 strains was tested for activity against western corn rootworm (WCRW). Three strains, AB433, AB434, and AB435 were found to be active on WCRW. Western blot analysis using VIP2A(a) antisera revealed that strains AB6, AB433, AB434, AB435, AB444, and AB445 produce a protein(s) of equivalent size to VIP2A(a).

Notable among the strains identified was *Bacillus thuringiensis* strain AB6, (NRRL B-21060) which produced a VIP active against black cutworm (*Agrotis ipsilon*) as described in Example 15. Western blot analysis with polyclonal antisera to VIP2A(a) and polyclonal antisera to VIP1A(a) suggests that AB6 produces proteins similar to VIP2A(a) and VIP1A(a). Thus, AB6 may contain VIPs similar to VIP1A(a) and VIP2A(a), but with a different spectrum of insecticidal activity.

EXAMPLE 21

CLONING OF A VIP1A(a)/VIP2A(a) HOMOLOG FROM *BACILLUS THURINGIENSIS VAR. TENEBRIONIS*

Several previously characterized Bacillus strains were tested for presence of DNA similar to VIP1A(a)/VIP2A(a) by Southern blot analysis. DNA from Bacillus strains AB78, AB88, GC91, HD-1 and ATCC 10876 was analyzed for presence of VIP1A(a)/VIP2A(a) like sequences. DNA from Bt strains GC91 and HD-1, and the Bc strain ATCC 10876 did not hybridize to VIP2A(a)/VIP1A(a) DNA, indicating they lack DNA sequences similar to VIP1A(a)/VIP2A(a) genes. Similarly, DNA from the insecticidal strain AB88 (Example 16) did not hybridize to VIP1A(a)/VIP2A(a) DNA region, suggesting that the VIP activity produced by this strain does not result from VIP1A(a)/VIP2A(a) homologs. In contrast, *Bacillus thuringiensis var. tenebrionis* (Btt) contained sequences that hybridized to the VIP1A(a)/VIP2A (a) region. Further analysis confirmed that Btt contains VIP1A(a)/VIP2A(a) like sequences.

To characterize the Btt homologs of VIP2A(a) and VIP1A (a), the genes encoding these proteins were cloned. Southern blot analysis identified a 9.5 kb Eco RI restriction fragment likely to contain the coding regions for the homologs. Genomic DNA was digested with Eco RI, and DNA fragments of approximately 9.5 kb in length were gel-purified. This DNA was ligated into pBluescript SK(+) digested with Eco RI, and transformed into *E. coli* to generate a plasmid library. Approximately 10,000 colonies were screened by colony hybridization for the presence of VIP2A(a) homologous sequences. Twenty eight positive colonies were identified. All twenty eight clones are identical, and contain VIP1A(a)VIP2A(a) homologs. Clone pCIB7100 has been deposited in the Agricultural Research Service, Patent Culture Collection (NRRL), Northern Regional Research Center, 1815 North University Street, Peoria Ill. 61604, USA, and given the Accession Number B-21322. Several subclones were constructed from pCIB7100. A 3.8 kb Xba I fragment from pCIB7100 was cloned into pBluescript SK(+) to yield pCIB7101. A 1.8 kb Hind III fragment and a 1.4 kb Hind III fragment from pCIB7100 were cloned into pBluescript SK(+) to yield pCIB7102 and pCIB7103, respectively. Subclones pCIB7101, pCIB7102 and pCIB7103 have been deposited in the Agricultural Research Service, Patent Culture Collection (NRRL), Northern Regional Research Center, 1815 North University Street, Peoria Ill. 61604, USA, and given the Accession Numbers B-21323, B-21324 and B-21325 respectively.

The DNA sequence of the region of pCIB7100 containing the VIP2A(a)/VIP1A(a) homologs was determined by the dideoxy chain termination method (Sanger et al., 1977, Proc. Natl. Acad. Sci. USA 74:5463–5467). Reactions were performed using PRISM Ready Reaction Dye Deoxy Terminator Cycle Sequencing Kits and PRISM Sequenase® Terminator Double-Stranded DNA Sequencing Kits, and analyzed on an ABI model 373 automated sequencer. Custom oligonucleotides were used as primers to determine the DNA sequence in certain regions. The DNA sequence of this region is shown in SEQ ID NO:19.

The 4 kb region shown in SEQ ID NO:19 contains two open readings frames (ORFs), which encode proteins with a high degree of similarity to VIP1A(a) and VIP2A(a) proteins from strain AB78. The amino acid sequence of the VIP2A(a) homolog, designated as VIP2A(b) using the standardized nomenclature, is found at SEQ ID NO:20 and the amino acid sequence of the VIP1A(a) homolog, designated as VIP1A(b) using the standardized nomenclature, is disclosed at SEQ ID NO:21. The VIP2A(b) protein exhibits 91% amino acid identity to VIP2A(a) from AB78. An alignment of the amino acid sequences of the two VIP2 proteins is provided in Table 19. The VIP1A(b) protein exhibits 77% amino acid identity to VIP1A(a) from AB78. An alignment of these two VIP1 proteins is provided in Table 20. The alignment shown in Table 21 discloses the similarity between VIP1A(b) and VIP1A(a) from AB78. This alignment reveals that the amino terminal regions of the two VIP1 proteins share higher amino acid identity in the amino-terminal region than in the carboxy terminal region. In fact, the amino terminal two thirds (up to aa 618 of the VIP1A(b) sequence shown in Table 20) of the two proteins exhibit 91% identity, while the carboxy-terminal third (from aa 619–833 of VIP1 A(b)) exhibit only 35% identity.

Western blot analysis indicated that *Bacillus thuringiensis var. tenebrionis* (Btt) produces both VIP1A(a) like and VIP2A(a) like proteins. However, these proteins do not appear to have activity against western corn rootworm. Bioassay for activity against western corn rootworm was performed using either a 24 h culture supernatant from Btt or *E. coli* clone pCIB7100 (which contains the entire region of the VIP1A(a)/VIP2A(a) homologs). No activity against western corn rootworm was detected in either case.

Given the similarity between the VIP2 proteins from Btt and AB78, the ability of VIP2A(b) from Btt to substitute for VIP2A(a) from AB78 was tested. Cells containing pCIB6206 (which produces AB78 VIP1A(a) but not VIP2A (a) protein) were mixed with Btt culture supernatant, and tested for activity against western corn rootworm. While neither Btt culture supernatant nor cells containing pCIB6206 had activity on WCRW, the mixture of Btt and pCIB6206 gave high activity against WCRW. Furthermore, additional bioassay showed that the Btt clone pCIB7100, which contains the Btt VIP1A(b)/VIP2A(b) genes in E. coli, also confers activity against WCRW when mixed with pCIB6206. Thus, the VIP2A(b) protein produced by Btt is functionally equivalent to the VIP2A(a) protein produced by AB78.

Thus, the ability to identify new strains with insecticidal activity by using VIP DNA as hybridization probes has been demonstrated. Furthermore, Bacillus strains that contain VIP1A(a)/VIP2A(a) like sequences, produce VIP1A(a)/VIP2A(a) like protein, yet demonstrate toxicity toward different insect pests. Similar methods can identify many more members of the VIP1/VIP2 family. Furthermore, use of similar methods can identify homologs of other varieties of VIPs (for example, the VIPs from AB88).

TABLE 19

Alignment of VIP2 Amino Acid Sequences from *Bacillus thuringienis* var. *tenebrionis* (VIP2A(b)) vs. AB78 (VIP2A(a))

```
Btt    1   M Q R M E G K L F V V S K T L Q V V T R T V L L S T V Y S I T L L N N V V I K A D Q L N I N S Q S K   50  SEQ ID NO: 20
           | . | | | | | | | | : | | | . | | | | | : | | | | | | | | : | | . | | | |   | | | | : | | | | | | | |
AB78   1   M K R M E G K L F M V S K K L Q V V T K T V L L S T V F S I S L L N N E V I K A E Q L N I N S Q S K   50  SEQ ID NO: 2

51  Y T N L Q N L K I P D N A E D F K E D K G K A K E W G K E K G E E W R P P A T E K G E M N N F L D N   100
           | | | | | | | | . | . . | | | | | | | : | | | | | | | | | | : . | | :   . | | | | . | | | | | | |
       51  Y T N L Q N L K I T D K V E D F K E D K E K A K E W G K E K E K E W K L T A T E K G K M N N F L D N   100

101 K N D I K T N Y K E I T F S M A G S C E D E I K D L E E I D K I F D K A N L S S S I I T Y K N V E P   150
           | | | |   | | | | | | | | | | | | | |   | | | | | | . | | | | : | | | . | | | . | | | | | | | | |
       101 K N D I X T N Y K E I T F S M A G S F E D E I K D L K E I D K M F D K T N L S N S I I T Y K N V E P   150

151 A T I G F N K S L T E G N T I N S D A M A Q F K E Q F L G K D M K F D S Y L D T H L T A Q Q V S S K   200
           . | | | | | | | | | | | | | | | | | | | | | | | | : : | : | | | | | | | | | | | | | | | | | | |
       151 T T I G F N K S L T E G N T I N S D A M A Q F K E Q F L D R D I K F D S Y L D T H L T A Q Q V S S K   200

201 K R V I L K V T V P S G K G S T T P T K A G V I L N N N E Y K M L I D N G Y V L H V D K V S K V V K   250
           . | | | | | | | | | | | | | | | | | | | | | | | | . | | | | | | | | | : : | | | | | | | | | |
       201 E R V I L K V T V P S G K G S T T P T K A G V I L N N S E Y K M L I D N G Y M V H V D K V S K V V K   250

251 K G M E C L Q V E G T L K K S L D F K N D I N A E A H S W G M K I Y E D W A K N L T A S Q R E A L D   300
           | | : | | | | : | | | | | | | | | | | | | | | | | | | | |   | | : | | | : | | . | | | | | | |
       251 K G V E C L Q I E G T L K K S L D F K N D I N A E A H S W G M K N Y E E W A K D L T D S Q R E A L D   300

301 G Y A R Q D Y K E I N N Y L R N Q G G S G N E K L D A Q L K N I S D A L G K K P I P E N I T V Y R W   350
           | | | | | | | | | | | | | | | | | | | | | | | | | : | | | | | | | | | | | | | | | | | | | | |
       301 G Y A R Q D Y K E I N N Y L R N Q G G S G N E K L D A Q I K N I S D A L G K K P I P E N I T V Y R W   350

351 C G M P E F G Y Q I S D P L P S L K D F E E Q F L N T I K E D K G Y M S T S L S S E R L A A F G S R   400
           | | | | | | | | | | | | | | | | | | | | | | | | | | | | | | | | | | | | | | | | | | | | | | |
       351 C G M P E F G Y Q I S D P L P S L K D F E E Q F L N T I K E D K G Y M S T S L S S E R L A A F G S R   400

401 K I I L R L Q V P K G S T G A Y L S A I G G F A S E K E I L L D K D S K Y H I D K A T E V I I K G V   450
           | | | | | | | | | | | | | | | | | | | | | | | | | | | | | | | | | | | | | . | | | | | | | |
       401 K I I L R L Q V P K G S T G A Y L S A I G G F A S E K E I L L D K D S K Y H I D K V T E V I I K G V   450

451 K R Y V V D A T L L T N   462
           | | | | | | | | | | | |
       451 K R Y V V D A T L L T N   462
```

TABLE 20

Alignment of VIP1 Amino Acid Sequenes from *Bacillus thuringiensis* var. *tenebrionis* (VIP1A(b)) vs. AB78(VIP1A(a))

```
Btt    1   M K N M K K K L A S V V T C M L L A P M F L N G N V N A V N A D S K I N Q I S T T Q E N Q Q K E M D   50  SEQ ID NO: 21
           | | | | | | | | | | | | | | | |   | | | | | | | | | | | | | | | | .   | | | | | | | .   | | | | | | |
Ab78   1   M K N M K K K L A S V V T C T L L A P M F L N G N V N A V Y A D S K T N Q I S T T Q K N Q Q K E M D   50  SEQ ID NO: 5

51  R K G L L G Y Y F K G K D F N N L T M F A P T R D N T L M Y D Q Q T A N A L L C K K Q Q E Y Q S I R   100
           | | | | | | | | | | | | | . | | | | | | | | | | . | | : | | | | | | | |   | | | | | | | | | | | |
       51  R K G L L G Y Y F K G K D F S N L T M F A P T R D S T L I Y D Q Q T A N K L L D K K Q Q E Y Q S I R   100

101 W I G L I Q R K E T G D F T F N L S K D E Q A I I E I D G K I I S N K G K E K Q V V H L E K E K L V   150
           | | | | | . | | | | | | | | | | . | | | | | | | | : | | | | | | | | | | | | | | | | | | : | | |
       101 W I G L I Q S K E T G D F T F N S L E D E Q A I I E I N G K I I S N K G K E D Q V V H L E K G K L V   150

151 P I K I E Y Q S D T K F N I D S K T F K E L K L F K I D S Q N Q S Q Q V Q . . . L R N P E F N K K E   197
           | | | | | | | | | | | | | | | | | | | | | | | | | | | | | | | | | . | | | |       | | | | | | | |
       151 P I K I E Y Q S D T K F N I D S K T F K E L K L F K I D S Q N Q P Q Q V Q Q D E L R N P E F N K K E   200
```

TABLE 20-continued

Alignment of VIP1 Amino Acid Sequenes from *Bacillus thuringiensis* var. *tenebrionis* (VIP1A(b)) vs. AB78(VIP1A(a))

```
198  S Q E F L A K A S K T N L F K Q K M K R D I D E D T D T D G D S I P D L W E E N G Y T I Q N K V A V  247
     | | | | | | | : | | . | | | . | | | | | : | | | | | | | | | | | | | | | | | | | | | | | | : : | |
201  S Q E F L A K P S K I N L F T Q K M K R E I D E D T D T D G D S I P D L W E E N G Y T I Q N R I A V  250

248  K W D D S L A S K G Y T K F V S N P L D S H T V G D P Y T D Y E K A A R D L D L S N A K E T F N P L  297
     | | | | | | | | | | | | | | | | | : | | | | | | | | | | | | | | | | | | | | | | | | | | | | | |
251  K W D D S L A S K G Y T K F V S N P L E S H T V G D P Y T D Y E K A A R D L D L S N A K E T F N P L  300

298  V A A F P S V N V S M E K V I L S P N E N L S N S V E S H S S T N W S Y T N T E G A S I E A G G G P  347
     | | | | | | | | | | | | | | | | | | | | | | | | | | | | | | | | | | | | | | | | | | | : | | |  | |
301  V A A F P S V N V S M E K V I L S P N E N L S N S V E S H S S T N W S Y T N T E G A S V E A G I G P  350

348  L G L S F G V S V T Y Q H S E T V A Q E W G T S T G N T S Q F N T A S A G Y L N A N V R Y N N V G T  397
     | : | | | | | | . | | | | | | | | | | | | | | | | | | | | | | | | | | | | | | | | | | | | | | |
351  K G I S F G V S V N Y Q H S E T V A Q E W G T S T G N T S Q F N T A S A G Y L N A N V R Y N N V G T  400

398  G A I Y D V K P T T S F V L N N N T I A T I T A K S N S T A L R I S P G D S Y P E I G E N A I A I T  447
     | | | | | | | | | | | | | | | : | | | | | | | | | | | | | | | . | | | | : | | | .   | : | : | | | |
401  G A I Y D V K P T T S F V L N N D T I A T I T A K S N S T A L N I S P G E S Y P K K G O N G I A I T  450

448  S M D D F N S H P I T L N K Q Q V N Q L I N N K P I M L E T D Q T D G V Y K I R D T H G N I V T G G  497
     | | | | | | | | | | | | . | | : . | : | | | | : | | | | : | | | | | | | | : | | | | | | | | | |
451  S M D D F N S H P I T L N K K Q V D N L L N N K P M M L E T N Q T D G V Y K I K D T H G N I V T G G  500

498  E W N G V T Q Q I K A K T A S I I V D D G K Q V A E K R V A A K D Y G H P E D K T P P L T L K D T L  547
     | | | | . | | | | | | | | | | | | | . . | | | | | | | | | | | | : : | | | | | | | . | | | | | . |
501  E W N G V I Q Q I K A K T A S I I V D D G E R V A E K R V A A K D Y E N P E D K T P S L T L K D A L  550

548  K L S Y P D E I K E T N G L L Y Y D D K P I Y E S S V M T Y L D E N T A K E V K K Q I N D T T G K F  597
     | | | | | | | | | . : | | | | | . : | | | | | | | | | | | | | | | | | | | | | . | | : | | | | | | |
551  K L S Y P D E I K E I E G L L Y Y K N K P I Y E S S V M T Y L D E N T A K E V T K Q L N D T T G K F  600

598  K D V N H L Y D V K L T P K M N F T I K M A S L Y D G A E N N H N S L G T W Y L T Y N V A G G N T G  647
     | | | . | | | | | | | | | | | | . | | | : .   | | | . | | . | . | | : | . |     |   | . | | | . |
601  K D V S H L Y D V K L T P K M N V T I K L S I L Y D N A E S N D N S I G K W T N T N I V S G G N N G  650

648  K R Q Y R S A H S C A H V A L S S E A K K K L N Q N A N Y Y L S M Y M K A D S T T E P T I E V A G E  697
     | : | | . | . :   | : : . | . . . | | | . |   : | | : | | | | | . . : | : : . |   : . | |
651  K K Q Y S S N N P D A N L T L N T D A Q E K L N K N R D Y Y I S L Y M K S E K N T Q C E I T I D G E  700

698  K S A I T S K K V K L N N Q N Y Q R V D I L V K N S E R N P M D K I Y I R G N G T T N V Y G D D V T  747
       : | | . | . | . : | | . | | | : . |   . . | : : . . | : . . . : . :     | | : .
701  I Y P I T T K T U N V N K D N Y K R L D I I A H N I K S N P I S S L H I K T N D E I T L F W D D I S  750

748  I P E V S A I N P A S L S D E E I Q E I F K D S T I E Y G N P S F V A D A V T F K . . . . . . . . . .  788
     | . : | . . | . | . . | . | : | : .   . |   . : . | . . . |   : : . . . . :
751  I T D V A S I K P E N L T D S E I K Q I Y S R Y G I K L E D G I L I D K K G G I H Y G E F I N E A S  800

789  . N I K P L Q N Y V K E Y E I Y H K . . . . . . . S H R Y E K K T V F D I M G V H Y E Y S I A R E Q  830
     | | . | | | | | | . . | :   . .               | . | . . . . . :     . : . : . : . .   . . .
801  F N I E P L Q N Y V T K Y K V T Y S S E L G Q N V S D T L E S D K I Y K D G T I K F D F T K U S K N  850

831  K K A  833
     . . :
851  E Q G  853
```

EXAMPLE 22

FUSION OF VIP PROTEINS TO MAKE A SINGLE POLYPEPTIDE

VIP proteins may occur in nature as single polypeptides, or as two or more interacting polypeptides. When an active VIP is comprised of two or more interacting protein chains, these protein chains can be produced as a single polypeptide chain from a gene resulting from the fusion of the two (or more) VIP coding regions. The genes encoding the two chains are fused by merging the coding regions of the genes to produce a single open reading frame encoding both VIP polypeptides. The composite polypeptides can be fused to produce the smaller polypeptide as the NH$_2$ terminus of the fusion protein, or they can be fused to produce the larger of the polypeptides as the NH$_2$ terminus of the fusion protein. A linker region can optionally be used between the two polypeptide domains. Such linkers are known in the art. This linker can optionally be designed to contain protease cleavage sites such that once the single fused polypeptide is ingested by the target insect it is cleaved in the linker region to liberate the two polypeptide components of the active VIP molecule.

VIP1A(a) and VIP2A(a) from *B. cereus* strain AB78 are fused to make a single polypeptide by fusing their coding regions. The resulting DNA has the sequence given in SEQ ID NO:22 with the encoded protein given in SEQ ID NO:23. In like manner, other fusion proteins may be produced.

The fusion of the genes encoding VIP1A(a) and VIP2A(a) is accomplished using standard techniques of molecular biology. The nucleotides deleted between the VIP1A(a) and VIP2A(a) coding regions are deleted using known mutagenesis techniques or, alternatively, the coding regions are fused using PCR techniques.

The fused VIP polypeptides can be expressed in other organisms using a synthetic gene, or partially synthetic gene, optimized for expression in the alternative host. For instance, to express the fused VIP polypeptide from above in maize, one makes a synthetic gene using the maize preferred codons for each amino acid, see for example U.S. Pat. No. 5,625,136 herein incorporated by reference. Synthetic DNA sequences created according to these methods are disclosed in SEQ ID NO:17 (maize optimized version of the 100 kDa VIP1A(a) coding sequence), SEQ ID NO:18 (maize optimized version of the 80 kDa VIP1A(a) coding sequence) and SEQ ID NO:24 (maize optimized version of the VIP2A(a) coding sequence).

Synthetic VIP1 and VIP2 genes optimized for expression in maize can be fused using PCR techniques, or the synthetic genes can be designed to be fused at a common restriction site. Alternatively, the synthetic fusion gene can be designed to encode a single polypeptide comprised of both VIP1 and VIP2 domains.

Addition of a peptide linker between the VIP1 and VIP2 domains of the fusion protein can be accomplished by PCR mutagenesis, use of a synthetic DNA linker encoding the linker peptide, or other methods known in the art.

The fused VIP polypeptides can be comprised of one or more binding domains. If more than one binding domain is used in the fusion, multiple target pests are controlled using such a fusion. The other binding domains can be obtained by using all or part of other VIPs; *Bacillus thuringiensis* endotoxins, or parts thereof; or other proteins capable of binding to the target pest or appropriate biding domains derived from such binding proteins.

One example of a fusion construction comprising a maize optimized DNA sequence encoding a single polypeptide chain fusion having VIP2A(a) at the N-terminal end and VIP1A(a) at the C-terminal end is provided by pCIB5531. A DNA sequence encoding a linker with the peptide sequence PSTPPTPSPSTPPTPS (SEQ ID NO:47) has been inserted between the two coding regions. The sequence encoding this linker and relevant cloning sites is 5'-CCC GGG CCT TCT ACT CCC CCA ACT CCC TCT CCT AGC ACG CCT CCG ACA CCT AGC GAT ATC GGA TC C-3' (SEQ ID NO:48). Oligonucleotides were synthesized to represent both the upper and lower strands and cloned into a pUC vector following hybridization and phosphorylation using standard procedures. The stop codon in VIP2A(a) was removed using PCR and replaced by the BglII restriction site with a Smal site. A translation fusion was made by ligating the Bam HI/PstI fragment of the VIP2A(a) gene from pCIB5522 (see Example 24), a PCR fragment containing the PstI-end fragment of the VIP2A(a) gene (identical to that used to construct pCIB5522), a synthetic linker having ends that would ligate with a blunt site at the 5' end and with BamHI at the 3' end and the modified synthetic VIP1A(a) gene from pCIB5526 described below (See SEQ ID NO:35). The fusion was obtained by a four way ligation that resulted in a plasmid containing the VIP2A(a) gene without a translation stop codon, with a linker and the VIP1A(a) coding region without the Bacillus secretion signal. The DNA sequence for this construction is disclosed in SEQ ID NO:49, which encodes the fusion protein disclosed in SEQ ID NO:50. A single polypeptide fusion where VIP1A(a) is at the N-terminal end and VIP2A(a) is at the C-terminal end can be made in a similar fashion. Furthermore, either one or both genes can be linked in a translation fusion with or without a linker at either the 5' or the 3' end to other molecules like toxin encoding genes or reporter genes.

EXAMPLE 23

TARGETING OF VIP2 TO PLANT ORGANELLES

Various mechanisms for targeting gene products are known to exist in plants and the sequences controlling the functioning of these mechanisms have been characterized in some detail. For example, the targeting of gene products to the chloroplast is controlled by a signal sequence found at the amino-terminal end of various proteins. This signal is cleaved during chloroplast import, yielding the mature protein (e.g. Comai et al. J. Biol. Chem. 263:15104–15109 (1988)). These signal sequences can be fused to heterologous gene products such as VIP2 to effect the import of those products into the chloroplast (van den Broeck et al. Nature 313:358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized.

Other gene products are localized to other organelles such as the mitochondrion and the peroxisome (e.g. Unger et al. Plant Molec. Biol. 13:411–418 (1989)). The cDNAs encoding these products can also be manipulated to effect the targeting of heterologous gene products such as VIP2 to these organelles. Examples of such sequences are the nuclear-encoded ATPases and specific aspartate amino transferase isoforms for mitochondria. Similarly, targeting to cellular protein bodies has been described by Rogers et al. (Proc. Natl. Acad. Sci. USA 82:6512–6516 (1985)).

By the fusion of the appropriate targeting sequences described above to coding sequences of interest such as VIP2 it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino-terminal ATG of the transgene. The signal sequence selected should include the known cleavage site and the fusion constructed should take into account any amino acids after the cleavage site which are required for cleavage. In some cases this requirement may be fulfilled by the addition of a small number of amino acids between the cleavage site and the start codon ATG, or alternatively replacement of some amino acids within the coding sequence. Fusions constructed for chloroplast import can be tested for efficacy of chloroplast uptake by in vitro translation of in vitro transcribed constructions followed by in vitro chloroplast uptake using techniques described by (Bartlett et al. In: Edelmann et al. (Eds.) Methods in Chloroplast Molecular Biology, Elsevier. pp 1081–1091 (1982); Wasmann et al. Mol. Gen. Genet. 205:446–453 (1986)). These construction techniques are well known in the art and are equally applicable to mitochondria and peroxisomes.

The above described mechanisms for cellular targeting can be utilized not only in conjunction with their cognate promoters, but also in conjunction with heterologous promoters so as to effect a specific cell targeting goal under the transcriptional regulation of a promoter which has an expression pattern different to that of the promoter from which the targeting signal derives.

A DNA sequence encoding a secretion signal is present in the native Bacillus VIP2 gene. This signal is not present in the mature protein which has the N-terminal sequence of LKITDKVEDF (amino acid residues 57 to 66 of SEQ ID NO:2). It is possible to engineer VIP2 to be secreted out of the plant cell or to be targeted to subcellular organelles such as the endoplasmic reticulum, vacuole, mitochondria or plastids including chloroplasts. Hybrid proteins made by fusion of a secretion signal peptide to a marker gene have been successfully targeted into the secretion pathway. (Itirriaga G. et al., *The Plant Cell,* 1:381–390 (1989), Denecke et al., *The Plant Cell,* 2:51–59 (1990). Amino-terminal sequences have been identified that are responsible for targeting to the ER, the apoplast, and extracellular secretion from aleurone cells (Koehler & Ho, Plant Cell 2:769–783 (1990)).

The presence of additional signals are required for the protein to be retained in the endoplasmic reticulum or the vacuole. The peptide sequence KDEL/HDEL at the carboxy-terminal of a protein is required for its retention in the endoplasmic reticulum (reviewed by Pelham, *Annual Review Cell Biol.,* 5:1–23 (1989). The signals for retention of proteins in the vacuole have also been characterized. Vacuolar targeting signals may be present either at the amino-terminal portion, (Holwerda et al., *The Plant* Cell, 4:307–318 (1992), Nakamura et al., *Plant Physiol.,* 101:1–5 (1993)), carboxy-terminal portion, or in the internal sequence of the targeted protein. (Tague et al., *The Plant Cell,* 4:307–318 (1992), Saalbach et al., *The Plant Cell,* 3:695–708 (1991)). Additionally, amino-terminal sequences in conjunction with carboxy-terminal sequences are responsible for vacuolar targeting of gene products (Shinshi et al. Plant Molec. Biol. 14:357–368 (1990)). Similarly, proteins may be targeted to the mitochondria or plastids using specific carboxy terminal signal peptide fusions (Heijne et al., *Eur. J. Biochem.,* 180:535–545 (1989), Archer and Keegstra, *Plant Molecular Biology,* 23:1105–1115 (1993)).

In order to target VIP2, either for secretion or to the various subcellular organelles, a maize optimized DNA sequence encoding a known signal peptide(s) may be designed to be at the 5' or the 3' end of the gene as required. To secrete VIP2 out of the cell, a DNA sequence encoding the eukaryotic secretion signal peptide MGWSWIFLFLLS-GAAGVHCL (SEQ ID NO:25) from U.S. patent application Ser. No. 08/267,641 or any other described in the literature (Itirriaga et al., *The Plant Cell,* 1:381–390 (1989), Denecke, et al., *The Plant Cell,* 2:51–59 (1990)) may be added to the 5' end of either the complete VIP2 gene sequence or to the sequence truncated to encode the mature protein or the gene truncated to nucleotide 286 or encoding a protein to start at amino acid residue 94 (methionine). To target VIP2 to be retained in the endoplasmic reticulum, a DNA sequence encoding the ER signal peptide KDEL/HDEL, in addition to the secretion signal, can be added to the 3' end of the gene. For vacuolar targeting a DNA sequence encoding the signal peptide SSSSFADSNPIRVTDRAAST (SEQ ID NO:3; Holwerda et al., *The Plant* Cell, 4:307–318 (1992)) can be designed to be adjacent to the secretion signal or a sequence encoding a carboxyl signal peptide as described by Dombrowski et al., *The Plant Cell,* 5:587–596 (1993) or a functional variation may be inserted at the 3' end of the gene. Similarly, VIP2 can be designed to be targeted to either the mitochondria or the plastids, including the chloroplasts, by inserting sequences in the VIP2 sequence described that would encode the required targeting signals. The bacterial secretion signal present in VIP2 may be retained or removed from the final construction.

One example of a construction which incorporates a eukaryotic secretion signal fused to a coding sequence for a VIP is provided by pCIB5528. Oligonucleotides corresponding to both the upper and lower strand of sequences encoding the secretion signal peptide of SEQ ID NO:25 was synthesized and has the sequence 5'-GGATCCACC ATG GGC TGG AGC TGG ATC TTC CTG TTC CTG CTG AGC GGC GCC GCG GGC GTG CAC TGC CTGCAG-3' (SEQ ID NO:41). When hybridized, the 5' end of the secretion signal resembled "sticky-ends" corresponding to restriction sites BamHI and PstI. The oligonucleotide was hybridized and phosphorylated and ligated into pCIB5527 (construction described in Example 23A) which had been digested with BamHI/PstI using standard procedures. The resulting maize optimized coding sequence is disclosed in SEQ ID NO:42 which encodes the protein disclosed in SEQ ID NO:43. This encoded protein comprises the eukaryotic secretion signal in place of the Bacillus secretion signal.

One example of a construction which incorporates a vacuolar targetting signal fused to a coding sequence for a VIP is provided by pCIB5533. Oligonucleotides corresponding to both the upper and lower strand of sequences encoding the vacuolar targetting peptide of SEQ ID NO:3 was synthesized and has the sequence 5'-CCG CGG GCG TGC ACT GCC TCA GCA GCA GCA GCT TCG CCG ACA GCA ACC CCA TCC GCG TGA CCG ACC GCG CCG CCA GCA CCC TGC AG-3' (SEQ ID NO:44). When hybridized, the 5' end of the vacuolar targetting signal resembled "sticky-ends" corresponding to restriction sites SacII and PstI. The oligonucleotide was hybridized and phosphorylated and ligated into pCIB5528 (construction described above) which had been digested with SacII/PstI using standard procedures. The resulting maize optimized coding sequence is disclosed in SEQ ID NO:45 which encodes the protein disclosed in SEQ ID NO:46. This encoded protein comprises the vacuolar targetting peptide in addition to the eukaryotic secretion signal.

The VIP1 gene can also be designed to be secreted or targeted to subcellular organelles by similar procedures.

EXAMPLE 23A

REMOVAL OF BACILLUS SECRETION SIGNAL FROM VIP1A(a) AND VIP2A(a)

VIP1A(a) and VIP2A(a) are secreted during the growth of strain AB78. The nature of peptide sequences that act as secretion signals has been described in the literature (Simonen and Palva, Microbiological reviews, pg. 109–137 (1993)). Following the information in the above publication, the putative secretion signal was identified in both genes. In VIP1A(a) this signal is composed of amino acids 1–33 (See SEQ ID NO:5). Processing of the secretion signal probably occurs after the serine at amino acid 33. The secretion signal in VIP2A(a) was identified as amino acids 1–49 (See SEQ ID NO:2). N-terminal peptide analysis of the secreted mature VIP2A(a) protein revealed the N-terminal sequence LKITDKVEDFKEDK. This sequence is found beginning at amino acid 57 in SEQ ID NO:2. The genes encoding these proteins have been modified by removal of the Bacillus secretion signals.

A maize optimized VIP1A(a) coding region was constructed which had the sequences encoding the first 33 amino acids, i.e., the secretion signal, removed from its 5' end. This modification was obtained by PCR using an forward primer that contained the sequence 5'-GGA TCC ACC ATG AAG ACC AAC CAG ATC AGC-3' (SEQ ID NO:33), which hybridizes with the maize optimized gene (SEQ ID NO:26) at nucleotide position 100, and added a BamHI restriction site and a eukaryotic translation start site consensus including a start codon. The reverse primer that contained the sequence 5'-AAG CTT CAG CTC CTT G-3' (SEQ ID NO:34) hybridizes on the complementary strand at nucelotide position 507. A 527 bp amplification product was obtained containing the restriction sites BamHI at the 5' end and HindIII site at the 3' end. The amplification product was cloned into a T-vector (described in Example 24, below) and sequenced to ensure the correct DNA sequence. The BamHI/HindIII fragment was then obtained by restriction digest and used to replace the BamHI/HindIII fragment of the maize optimized VIP1A(a) gene cloned in the root-preferred promoter cassette. The construct obtained was designated pCIB5526. The maize optimized coding region for VIP1A (a) with the Bacillus secretion signal removed is disclosed as SEQ ID NO:35 and the encoded protein is disclosed as SEQ ID NO:36.

The gene encoding the processed form of VIP2A(a), i.e., a coding region with the secretion signal removed, was constructed by a procedure similar to that described for that used to construct the processed form of VIP1A(a), above. The modification was obtained by PCR using the forward primer 5'-GGA TCC ACC ATG CTG CAG AAC CTG AAG ATC AC-3' (SEQ ID NO:37). This primer hybridizes at nucleotide position 150 of the maize optimized VIP2A(a) gene (SEQ ID NO:27). A silent mutation has been inserted at nucleotide position 15 of this primer to obtain a PstI restriction site. The reverse primer has the sequence 5'-AAG CTT CCA CTC CTT CTC-3' (SEQ ID NO:38). A 259 bp product was obtained with HindIII restriction site at the 3' end. The amplification product was cloned into a T-vector, sequenced and ligated to a BamHI/HindIII digested root-preferred promoter cassette containing the maize optimized VIP2A(a). The construct obtained was designated pCIB5527. The maize optimized coding region for VIP2A (a) with the Bacillus secretion signal removed is disclosed as SEQ ID NO:39 and the encoded protein is disclosed as SEQ ID NO:40.

EXAMPLE 24

CONSTRUCTION AND CLONING OF THE VIP1A(a) AND VIP2A(a) MAIZE OPTIMIZED GENES

Design

The maize optimized genes were designed by reverse translation of the native VIP1A(a) and VIP2A(a) protein sequences using codons that are used most often in maize (Murray et al., *Nucleic Acid Research*, 17:477–498 (1989)). To facilitate cloning, the DNA sequence was further modified to incorporate unique restriction sites at intervals of every 200–360 nucleotides. VIP1A(a) was designed to be cloned in 11 such fragments and VIP2A(a) was cloned in 5 fragments. Following cloning of the individual fragments, adjacent fragments were joined using the restriction sites common to both fragments, to obtain the complete gene. To clone each fragment, oligonucleotides (50–85 nucleotides) were designed to represent both the upper and the lower strand of the DNA. The upper oligo of the first oligo pair was designed to have a 15 bp single stranded region at the 3' end which was homologous to a similar single stranded region of the lower strand of the next oligo pair to direct the orientation and sequence of the various oligo pairs within a given fragment. The oligos are also designed such that when the all the oligos representing a fragment are hybridized, the ends have single stranded regions corresponding to the particular restriction site to be formed. The structure of each oligomer was examined for stable secondary structures such as hairpin loops using the OLIGO program from NBI Inc. Whenever necessary, nucleotides were changed to decrease the stability of the secondary structure without changing the amino acid sequence of the protein. A plant ribosomal binding site consensus sequence, TAAACA<u>ATG</u> (Joshi et al., *Nucleic Acid Res.*, 15:6643–6653 (1987)) or eukaryotic ribosomal binding site concensus sequence CCACC<u>ATG</u> (Kozak, *Nucleic Acid Research*, 12:857–872 (1984)) was inserted at the translational start codon of the gene.

Cloning

Oligos were synthesized by IDT Inc., and were supplied as lyophilized powders. They were resuspended at a concentration of 200 µM. To 30 µl of each oligo formamide was added a final concentration of 25–50% and the sample was boiled for two minutes before separation on a premade 10% polyacryamide/urea gel obtained from Novex. After electrophoresis, the oligo was detected by UV shadowing by placing the gel on a TLC plate containing a fluorescent indicator and exposing it to UV light. The region containing DNA of the correct size was excised and extracted from the polyacryamide by an overnight incubation of the minced gel fragment in a buffer containing 0.4M LiCl, 0.1 mM EDTA. The DNA was separated from the gel residue by centrifugation through a Millipore UFMC filter. The extracted DNA was ethanol precipitated by the addition of 2 volumes of absolute alcohol. After centrifugation, the precipitate was resuspended in $dH_2O$ at a concentration of 2.5 µM. Fragments were cloned either by hybridization of the oligos and ligation with the appropriate vector or by amplification of the hybridized fragment using a equimolar mixture of all the oligos for a particular fragment as a template and end-specific PCR primers.

Cloning by hybridization and ligation

Homologous double stranded oligo pairs were obtained by mixing 5 µl of the upper and of the lower oligo for each oligo pair with buffer containing 1×polynucleotide kinase (PNK) buffer (70 mM Tris-HCl (pH 7.6), 10 mM $MgCl_2$ 5 mM dithiothreitol (DTT)), 50 mM KCl, and 5% formamide in a final volume of 50 µl. The oligos were boiled for 10 minutes and slow cooled to 37° C. or room temperature. 10 µl was removed for analysis on a 4% agarose in a TAE buffer system (Metaphore®; FMC). Each hybridized oligo pair was kinased by the addition of ATP at a final concentration of 1 mM, BSA at a final concentration of 100 µg per ml and 200 units of polynucleotide kinase and 1 µl of 10×PNK buffer in a volume of 10 µl. Following hybridization and phosphorylation, the reaction was incubated at 37° C. for 2 hours to overnight. 10 µl of each of the oligo pairs for a particular fragment, were mixed in a final volume of 50 µl. The oligo pairs were hybridized by heating at 80° C. for 10 minutes and slow cooling to 37° C. 2 µl of oligos was mixed with about 100 ng an appropriate vector and ligated using a buffer containing 50 mM Tris-HCl (pH 7.8), 10 mM $MgCl_2$, 10 mM DTT, 1 mM ATP. The reaction was incubated at room temp. for 2 hours to overnight and transformed into DH5α strain of *E.coli*, plated on L-plates containing ampicillin at a concentration of 100 µg/ml using standard procedures. Positive clones were further characterized and confirmed by PCR miniscreen described in detail in U.S. Pat. No. 5,625,136 using the universal primers "Reverse" and M13 "–20" as primers. Positive clones were identified by digestion of DNA with appropriate enzymes followed by sequencing. Recombinants that had the expected DNA sequence were then selected for further work.

PCR Amplification and cloning into T-vector:

PCR amplification was carried out by using a mixture of all the oligomers that represented the upper and the lower strand of a particular fragment (final concentration 5 mM each) as template, specific end primers for the particular fragment (final concentration 2 µM) 200 µM of each dATP, dTTP, dCTP and dGTP, 10 mM Tris-HCl (pH 8.3), 50 mM KCl, 1.5 mM $MgCl_2$, 0.01% gelatin and 5 units of Taq polymerase in a final reaction volume of 50 µl. The amplification reaction was carried out in a Perkin Elmer thermocycler 9600 by incubation at 95° C. for 1 min (1 cycle ), followed by 20 cycles of 95° C. for 45 sec., 50° C. for 45 sec., 72° C. for 30 sec. Finally the reaction was incubated for 5 min at 72° C. before analyzing the product. 10 μl of the reaction was analyzed on a 2.5% Nusieve (FMC) agarose gel in a TAE buffer system. The correct size fragment was gel purified and used for cloning into a PCR cloning vector or T-vector. T-vector construction was as described by Marchuk et al., *Nucleic Acid Research,* 19:1154 (1991). pBluescriptsk+ (Stratagene®, Ca.) was used as the parent vector. Transformation and identification of the correct clone was carried out as described above.

Fragments 1, 3, 4, 5, 6, 8, and 9 of VIP1A(a) and fragments 2 and 4 of VIP2A(a) were obtained by cloning of PCR amplification products; whereas, fragments 2, 7, 10 and 11 of VIP1A(a) and fragments 1, 3, and 5 of VIP2A(a) were obtained by hybridization/ligation.

Once fragments with the desired sequence were obtained, the complete gene was assembled by cloning together adjacent fragments. The complete gene was resequenced and tested for activity against WCRW before moving it into plant expression vectors containing the root preferred promoter (disclosed in U.S. Pat. No. 5,466,785, herein incorporated by reference) and the rice actin promoter.

One such plant expression vector is pCIB5521. The maize optimized VIP1A(a) coding region (SEQ ID NO:26) was cloned in a plant expression vector containing the root preferred promoter at the 5' of the gene with the PEP Carboxylase intron #9 followed by the 35S terminator at the 3' end. The plasmid also contains sequences for ampicillin resistance from the plasmid pUC19. Another plant expression vector is pCIB5522, which contains the maize optimized VIP2A(a) coding region (SEQ ID NO:27) fused to the root preferred promoter at the 5' of the gene with the PEP Carboxylase intron #9 followed by the 35S terminator at the 3' end.

EXAMPLE 25

NAD AFFINITY CHROMATOGRAPHY

A purification strategy was used based on the affinity of VIP2 for the substrate NAD. The supernatant from the pH 3.5 sodium citrate buffer treatment described in Example 4 was dialyzed in 20 mM TRIS pH 7.5 overnight. The neutralized supernatant was added to an equal volume of washed NAD agarose and incubated with gentle rocking at 4° C. overnight. The resin and protein solution were added to a 10 ml disposable polypropylene column and the protein solution allowed to flow out. The column was washed with 5 column volumes of 20 mM TRIS pH 7.5 then washed with 2–5 column volumes of 20 mM TRIS pH 7.5, 100 mM NaCl, followed by 2–5 column volumes of 20 mM TRIS 7.5. The VIP proteins were eluted in 20 mM TRIS pH 7.5 supplemented with 5 mM NAD. Approximately 3 column volumes of the effluent were collected and concentrated in a Centricon–10. Yield is typically about 7–15 μg of protein per ml of resin.

When the purified proteins were analyzed by SDS-PAGE followed by silver staining, two polypeptides were visible, one with Mr of approximately 80,000 and one with Mr of approximately 45,000. N-terminal sequencing revealed that the Mr 80,000 protein corresponded to a proteolytically processed form of VIP1A(A) and the Mr 45,000 form corresponded to a proteolytically processed form of VIP2A (a). The co-purification of VIP1A(a) with VIP2A(a) indicates that the two proteins probably form a complex and have protein-protein interacting regions. VIP1A(a) and VIP2A(a) proteins purified in this manner were biologically active against western corn rootworm.

EXAMPLE 26

EXPRESSION OF MAIZE OPTIMIZED VIP1A(a) AND VIP2A(a)

*E. coli* strains containing different plasmids comprising VIP genes were assayed for expression of VIPs. *E. coli* strains harboring the individual plasmids were grown overnight in L-broth and expressed protein was extracted from the culture as described in Example 3, above. Protein expression was assayed by Western Blot analysis using antibodies developed using standard methods known in the art, similar to those described in Example 12, above. Also, insecticidal activity of the expressed proteins were tested against Western corn rootworm according to the method in Example 3, above. The results of the *E. coli* expression assays are described below.

Expression of VIPs in *E. coli*

| Extract of *E. coli* Strain Harboring Indicated Plasmid | Assay No. 1 % Mortality | Assay No. 2 % Mortality | Protein Detected |
|---|---|---|---|
| Control | 0 | 0 | no |
| pCIB5521 (maize optimized VIP1A(a)) | 47 | 27 | yes |
| pCIB5522 (maize optimized VIP2A(a)) | 7 | 7 | yes |
| pCIB6024 (native VIP2A(a)) | 13 | 13 | yes |
| pCIB6206 (native VIP1A(a)) | 27 | 40 | yes |
| Extracts pCIB5521 + pCIB5522 combined | 87 | 47 | |
| Extracts pCIB5521 + pCIB6024 combined | 93 | 100 | |
| Extracts pCIB5522 + pCIB6206 combined | 100 | 100 | |
| Extracts pCIB6024 + pCIB6206 combined | 100 | 100 | |

The DNA from these plasmids was used to transiently express the VIPs in a maize protoplast expression system. Protoplasts were isolated from maize 2717 Line 6 suspension cultures by digestion of the cell walls using Cellulase RS and Macerase R10 in appropriate buffer. Protoplasts were recovered by sieving and centrifugation. Protoplasts were transformed by a standard direct gene transfer method using approximately 75 μg plasmid DNA and PEG-40. Treated protoplasts were incubated overnight in the dark at room temperature. Analysis of VIP expression was accomplished on protoplast explants by Western blot analysis and insecticidal activity against Western corn rootworm as described above for the expression in *E. coli*. The results of the maize protoplast expression assays are described below.

Expression of VIPs in Plant Protoplasts

| Extract Tested | Assay No. 1 % Mortality | Assay No. 2 % Mortality | Protein Detected |
|---|---|---|---|
| No DNA Control | 27 | 10 | no |
| pCIB5521 (p) (maize optimized VIP1A(a)) | 20 (0) | 30 | yes |
| pCIB5522 (p) (maize optmizied VIP2A(a)) | 20 (0) | 20 | yes |
| Extracts pCIB5521 (p) + pCIB5522 (p) combined | 87 (82) | 90 | |
| Extracts pCIB5521 (p) + pCIB5522 (e) combined | 100 | — | |
| Extracts pCIB5522 (p) + PCIB5521 (e) combined | 53 (36) | — | |
| Extracts pCIB5521 (p) + pCIB6024 (e) combined | 100 | — | |
| Extracts pCIB5522 (p) + pCIB6206 (e) combined | 100 | — | |
| pCIB6024 (e) (native VIP2A(a)) | 0 | — | yes |
| pCIB6206 (e) (native VIP1A(a)) | 20 | — | yes |

Expression of VIPs in Plant Protoplasts

| Extract Tested | Assay No. 1 % Mortality | Assay No. 2 | Protein Detected |
|---|---|---|---|
| pCIB5521 + pCIB5522 (plasmids delivered by cotransformation) | 100 | 100 | yes |

(p) = extract of protoplast culture transformed with indicated plasmid
(e) = extract of *E. coli* strain harboring indicated plasmid The expression data obtained with both *E. coli* and maize protoplasts show that the maize optimized VIP1A(a) and VIP2A(a) genes make the same protein as the native VIP1A (a) and VIP2A(a) genes, respectively, and that the proteins encoded by the maize optimized genes are functionally equivalent to the proteins encoded by the native genes.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The following deposits have been made at Agricultural Research Service, Patent Culture Collection (NRRL), Northern Regional Research Center, 1815 North University Street, Peoria, Ill. 61604, USA:

| | |
|---|---|
| 1. *E. coli* PL2 | Accession No. NRRL B-21221N |
| 2. *E. coli* pCIB6022 | Accession No. NRRL B-21222 |
| 3. *E. coli* pCIB6023 | Accession No. NRRL B-21223N |
| 4. *Bacillus thuringiensis* HD73-78VIP | Accession No. NRRL B-21224 |
| 5. *Bacillus thuringiensis* AB88 | Accession No. NRRL B-21225 |
| 6. *Bacillus thuringiensis* AB359 | Accession No. NRRL B-21226 |
| 7. *Bacillus thuringiensis* AB289 | Accession No. NRRL B-21227 |
| 8. Bacillus sp. AB59 | Accession No. NRRL B-21228 |
| 9. Bacillus sp. AB294 | Accession No. NRRL B-21229 |
| 10. Bacillus sp. AB256 | Accession No. NRRL B-21230 |
| 11. *E. coli* P5-4 | Accession No. NRRL B-21059 |
| 12. *E. coli* P3-12 | Accession No. NRRL B-21061 |
| 13. *Bacillus cereus* AB78 | Accession No. NRRL B-21058 |
| 14. *Bacillus thuringiensis* AB6 | Accession No. NRRL B-21060 |
| 15. *E. coli* pCIB6202 | Accession No. NRRL B-21321 |
| 16. *E. coli* pCIB7100 | Accession No. NRRL B-21322 |
| 17. *E. coli* pCIB7101 | Accession No. NRRL B-21323 |
| 18. *E. coli* pCIB7102 | Accession No. NRRL B-21324 |
| 19. *E. coli* pCIB7102 | Accession No. NRRL B-21325 |
| 20. *E. coli* pCIB7104 | Accession No. NRRL B-21422 |
| 21. *E. coli* pCIB7107 | Accession No. NRRL B-21423 |
| 22. *E. coli* pCIB7108 | Accession No. NRRL B-21438 |
| 23. *Bacillus thuringiensis* AB424 | Accession No. NRRL B-21439 |

Although the foregoing invention has been described in some detail by way of illustration and example for purposes of clarity of understanding, it will be obvious that certain changes and modifications may be practiced within the scope of the appended claims.

SEQUENCE LISTING ( 1 ) GENERAL INFORMATION:

( i i i ) NUMBER OF SEQUENCES: 50

( 2 ) INFORMATION FOR SEQ ID NO:1:

( i ) SEQUENCE CHARACTERISTICS:
( A ) LENGTH: 6049 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Bacillus cereus
( B ) STRAIN: AB78
( C ) INDIVIDUAL ISOLATE: NRRL B- 21058

( i x ) FEATURE:
( A ) NAME/KEY: CDS
( B ) LOCATION: 1082..2467
( D ) OTHER INFORMATION: /product="VIP2A(a)"

( i x ) FEATURE:
( A ) NAME/KEY: misc_feature
( B ) LOCATION: 2475..5126
( D ) OTHER INFORMATION: /note= "Coding sequence for the 100 kd VIP1A(a) protein. This coding sequence is repeated in SEQ ID NO:4 and translated separately."

( x i ) SEQUENCE DESCRIPTION: SEQ ID NO:1:

ATCGATACAA TGTTGTTTTA CTTAGACCGG TAGTCTCTGT AATTTGTTTA ATGCTATATT 60

CTTTACTTTG ATACATTTTA ATAGCCATTT CAACCTTATC AGTATGTTTT TGTGGTCTTC 120

CTCCTTTTTT TCCACGAGCT CTAGCTGCGT TTAATCCTGT TTTGGTACGT TCGCTAATAA 180

| | |
|---|---|
| TATCTCTTTC TAATTCTGCA ATACTTGCCA TCATTCGAAA GAAGAATTTC CCCATAGCAT | 240 |
| TAGAGGTATC AATGTTGTCA TGAATAGAAA TAAAATCTAC ACCTAGCTCT TTGAATTTTT | 300 |
| CACTTAACTC AATTAGGTGT TTTGTAGAGC GAGAAATTCG ATCAAGTTTG TAAACAACTA | 360 |
| TCTTATCGCC TTTACGTAAT ACTTTTAGCA ACTCTTCGAG TTGAGGGCGC TCTTTTTTA | 420 |
| TTCCTGTTAT TTTCTCCTGA TATAGCCTTT CTACACCATA TTGTTGCAAA GCATCTATTT | 480 |
| GCATATCGAG ATTTGTTCT TCTGTGCTGA CACGAGCATA ACCAAAAATC AAATTGGTTT | 540 |
| CACTTCCTAT CTAAATATAT CTATTAAAAT AGCACCAAAA ACCTTATTAA ATTAAAATAA | 600 |
| GGAACTTTGT TTTTGGATAT GGATTTTGGT ACTCAATATG GATGAGTTTT TAACGCTTTT | 660 |
| GTTAAAAAAC AAACAAGTGC CATAAACGGT CGTTTTGGG ATGACATAAT AAATAATCTG | 720 |
| TTTGATTAAC CTAACCTTGT ATCCTTACAG CCCAGTTTTA TTTGTACTTC AACTGACTGA | 780 |
| ATATGAAAAC AACATGAAGG TTTCATAAAA TTTATATATT TTCCATAACG GATGCTCTAT | 840 |
| CTTTAGGTTA TAGTTAAATT ATAAGAAAAA AACAAACGGA GGGAGTGAAA AAAAGCATCT | 900 |
| TCTCTATAAT TTTACAGGCT CTTTAATAAG AAGGGGGGAG ATTAGATAAT AAATATGAAT | 960 |
| ATCTATCTAT AATTGTTTGC TTCTACAATA ACTTATCTAA CTTTCATATA CAACAACAAA | 1020 |
| ACAGACTAAA TCCAGATTGT ATATTCATTT TCAGTTGTTC CTTTATAAAA TAATTTCATA | 1080 |

| | |
|---|---|
| A ATG AAA AGA ATG GAG GGA AAG TTG TTT ATG GTG TCA AAA AAA TTA<br>Met Lys Arg Met Glu Gly Lys Leu Phe Met Val Ser Lys Lys Leu<br>1               5                   10                  15 | 1126 |
| CAA GTA GTT ACT AAA ACT GTA TTG CTT AGT ACA GTT TTC TCT ATA TCT<br>Gln Val Val Thr Lys Thr Val Leu Leu Ser Thr Val Phe Ser Ile Ser<br>        20                  25                  30 | 1174 |
| TTA TTA AAT AAT GAA GTG ATA AAA GCT GAA CAA TTA AAT ATA AAT TCT<br>Leu Leu Asn Asn Glu Val Ile Lys Ala Glu Gln Leu Asn Ile Asn Ser<br>            35                  40                  45 | 1222 |
| CAA AGT AAA TAT ACT AAC TTG CAA AAT CTA AAA ATC ACT GAC AAG GTA<br>Gln Ser Lys Tyr Thr Asn Leu Gln Asn Leu Lys Ile Thr Asp Lys Val<br>    50                  55                  60 | 1270 |
| GAG GAT TTT AAA GAA GAT AAG GAA AAA GCG AAA GAA TGG GGG AAA GAA<br>Glu Asp Phe Lys Glu Asp Lys Glu Lys Ala Lys Glu Trp Gly Lys Glu<br>65                  70                  75 | 1318 |
| AAA GAA AAA GAG TGG AAA CTA ACT GCT ACT GAA AAA GGA AAA ATG AAT<br>Lys Glu Lys Glu Trp Lys Leu Thr Ala Thr Glu Lys Gly Lys Met Asn<br>80                  85                  90                  95 | 1366 |
| AAT TTT TTA GAT AAT AAA AAT GAT ATA AAG ACA AAT TAT AAA GAA ATT<br>Asn Phe Leu Asp Asn Lys Asn Asp Ile Lys Thr Asn Tyr Lys Glu Ile<br>            100                 105                 110 | 1414 |
| ACT TTT TCT ATG GCA GGC TCA TTT GAA GAT GAA ATA AAA GAT TTA AAA<br>Thr Phe Ser Met Ala Gly Ser Phe Glu Asp Glu Ile Lys Asp Leu Lys<br>        115                 120                 125 | 1462 |
| GAA ATT GAT AAG ATG TTT GAT AAA ACC AAT CTA TCA AAT TCT ATT ATC<br>Glu Ile Asp Lys Met Phe Asp Lys Thr Asn Leu Ser Asn Ser Ile Ile<br>    130                 135                 140 | 1510 |
| ACC TAT AAA AAT GTG GAA CCG ACA ACA ATT GGA TTT AAT AAA TCT TTA<br>Thr Tyr Lys Asn Val Glu Pro Thr Thr Ile Gly Phe Asn Lys Ser Leu<br>145                 150                 155 | 1558 |
| ACA GAA GGT AAT ACG ATT AAT TCT GAT GCA ATG GCA CAG TTT AAA GAA<br>Thr Glu Gly Asn Thr Ile Asn Ser Asp Ala Met Ala Gln Phe Lys Glu<br>160                 165                 170                 175 | 1606 |
| CAA TTT TTA GAT AGG GAT ATT AAG TTT GAT AGT TAT CTA GAT ACG CAT<br>Gln Phe Leu Asp Arg Asp Ile Lys Phe Asp Ser Tyr Leu Asp Thr His<br>            180                 185                 190 | 1654 |
| TTA ACT GCT CAA CAA GTT TCC AGT AAA GAA AGA GTT ATT TTG AAG GTT<br>Leu Thr Ala Gln Gln Val Ser Ser Lys Glu Arg Val Ile Leu Lys Val | 1702 |

|  | 195 |  |  |  | 200 |  |  |  |  | 205 |  |  |  |  |  |
|---|---|---|---|---|---|---|---|---|---|---|---|---|---|---|---|
| ACG | GTT | CCG | AGT | GGG | AAA | GGT | TCT | ACT | ACT | CCA | ACA | AAA | GCA | GGT | GTC | 1750 |
| Thr | Val | Pro | Ser | Gly | Lys | Gly | Ser | Thr | Thr | Pro | Thr | Lys | Ala | Gly | Val |
|  |  | 210 |  |  |  | 215 |  |  |  |  | 220 |  |  |  |  |

```
ATT TTA AAT AAT AGT GAA TAC AAA ATG CTC ATT GAT AAT GGG TAT ATG      1798
Ile Leu Asn Asn Ser Glu Tyr Lys Met Leu Ile Asp Asn Gly Tyr Met
        225             230             235

GTC CAT GTA GAT AAG GTA TCA AAA GTG GTG AAA AAA GGG GTG GAG TGC      1846
Val His Val Asp Lys Val Ser Lys Val Val Lys Lys Gly Val Glu Cys
240             245             250             255

TTA CAA ATT GAA GGG ACT TTA AAA AAG AGT CTT GAC TTT AAA AAT GAT      1894
Leu Gln Ile Glu Gly Thr Leu Lys Lys Ser Leu Asp Phe Lys Asn Asp
                260             265             270

ATA AAT GCT GAA GCG CAT AGC TGG GGT ATG AAG AAT TAT GAA GAG TGG      1942
Ile Asn Ala Glu Ala His Ser Trp Gly Met Lys Asn Tyr Glu Glu Trp
            275             280             285

GCT AAA GAT TTA ACC GAT TCG CAA AGG GAA GCT TTA GAT GGG TAT GCT      1990
Ala Lys Asp Leu Thr Asp Ser Gln Arg Glu Ala Leu Asp Gly Tyr Ala
        290             295             300

AGG CAA GAT TAT AAA GAA ATC AAT AAT TAT TTA AGA AAT CAA GGC GGA      2038
Arg Gln Asp Tyr Lys Glu Ile Asn Asn Tyr Leu Arg Asn Gln Gly Gly
    305             310             315

AGT GGA AAT GAA AAA CTA GAT GCT CAA ATA AAA AAT ATT TCT GAT GCT      2086
Ser Gly Asn Glu Lys Leu Asp Ala Gln Ile Lys Asn Ile Ser Asp Ala
320             325             330             335

TTA GGG AAG AAA CCA ATA CCG GAA AAT ATT ACT GTG TAT AGA TGG TGT      2134
Leu Gly Lys Lys Pro Ile Pro Glu Asn Ile Thr Val Tyr Arg Trp Cys
                340             345             350

GGC ATG CCG GAA TTT GGT TAT CAA ATT AGT GAT CCG TTA CCT TCT TTA      2182
Gly Met Pro Glu Phe Gly Tyr Gln Ile Ser Asp Pro Leu Pro Ser Leu
            355             360             365

AAA GAT TTT GAA GAA CAA TTT TTA AAT ACA ATC AAA GAA GAC AAA GGA      2230
Lys Asp Phe Glu Glu Gln Phe Leu Asn Thr Ile Lys Glu Asp Lys Gly
        370             375             380

TAT ATG AGT ACA AGC TTA TCG AGT GAA CGT CTT GCA GCT TTT GGA TCT      2278
Tyr Met Ser Thr Ser Leu Ser Ser Glu Arg Leu Ala Ala Phe Gly Ser
    385             390             395

AGA AAA ATT ATA TTA CGA TTA CAA GTT CCG AAA GGA AGT ACG GGT GCG      2326
Arg Lys Ile Ile Leu Arg Leu Gln Val Pro Lys Gly Ser Thr Gly Ala
400             405             410             415

TAT TTA AGT GCC ATT GGT GGA TTT GCA AGT GAA AAA GAG ATC CTA CTT      2374
Tyr Leu Ser Ala Ile Gly Gly Phe Ala Ser Glu Lys Glu Ile Leu Leu
                420             425             430

GAT AAA GAT AGT AAA TAT CAT ATT GAT AAA GTA ACA GAG GTA ATT ATT      2422
Asp Lys Asp Ser Lys Tyr His Ile Asp Lys Val Thr Glu Val Ile Ile
            435             440             445

AAA GGT GTT AAG CGA TAT GTA GTG GAT GCA ACA TTA TTA ACA AAT          2467
Lys Gly Val Lys Arg Tyr Val Val Asp Ala Thr Leu Leu Thr Asn
        450             455             460
```

```
TAAGGAGATG AAAAATATGA AGAAAAAGTT AGCAAGTGTT GTAACGTGTA CGTTATTAGC    2527
TCCTATGTTT TTGAATGGAA ATGTGAATGC TGTTTACGCA GACAGCAAAA CAAATCAAAT    2587
TTCTACAACA CAGAAAAATC AACAGAAAGA GATGGACCGA AAAGGATTAC TTGGGTATTA    2647
TTTCAAAGGA AAAGATTTTA GTAATCTTAC TATGTTTGCA CCGACACGTG ATAGTACTCT    2707
TATTTATGAT CAACAAACAG CAAATAAACT ATTAGATAAA AAACAACAAG AATATCAGTC    2767
TATTCGTTGG ATTGGTTTGA TTCAGAGTAA AGAAACGGGA GATTTCACAT TTAACTTATC    2827
TGAGGATGAA CAGGCAATTA TAGAAATCAA TGGAAAATT ATTTCTAATA AAGGGAAAGA     2887
```

```
AAAGCAAGTT GTCCATTTAG AAAAAGGAAA ATTAGTTCCA ATCAAAATAG AGTATCAATC   2947
AGATACAAAA TTTAATATTG ACAGTAAAAC ATTTAAAGAA CTTAAATTAT TTAAAATAGA   3007
TAGTCAAAAC CAACCCCAGC AAGTCCAGCA AGATGAACTG AGAAATCCTG AATTTAACAA   3067
GAAAGAATCA CAGGAATTCT TAGCGAAACC ATCGAAAATA AATCTTTTCA CTCAAAAAAT   3127
GAAAGGGAA ATTGATGAAG ACACGGATAC GGATGGGGAC TCTATTCCTG ACCTTTGGGA    3187
AGAAAATGGG TATACGATTC ACAATAGAAT CGCTGTAAAG TGGGACGATT CTCTAGCAAG   3247
TAAAGGGTAT ACGAAATTTG TTTCAAATCC ACTAGAAAGT CACACAGTTG GTGATCCTTA   3307
TACAGATTAT GAAAAGGCAG CAAGAGATCT AGATTTGTCA AATGCAAAGG AAACGTTTAA   3367
CCCATTGGTA GCTGCTTTTC CAAGTGTGAA TGTTAGTATG GAAAGGTGA TATTATCACC    3427
AAATGAAAAT TTATCCAATA GTGTAGAGTC TCATTCATCC ACGAATTGGT CTTATACAAA   3487
TACAGAAGGT GCTTCTGTTG AAGCGGGGAT TGGACCAAAA GGTATTTCGT TCGGAGTTAG   3547
CGTAAACTAT CAACACTCTG AAACAGTTGC ACAAGAATGG GAACATCTA CAGGAAATAC    3607
TTCGCAATTC AATACGGCTT CAGCGGGATA TTTAAATGCA AATGTTCGAT ATAACAATGT   3667
AGGAACTGGT GCCATCTACG ATGTAAAACC TACAACAAGT TTTGTATTAA ATAACGATAC   3727
TATCGCAACT ATTACGGCGA AATCTAATTC TACAGCCTTA AATATATCTC CTGGAGAAAG   3787
TTACCCGAAA AAAGGACAAA ATGGAATCGC AATAACATCA ATGGATGATT TAATTCCCA    3847
TCCGATTACA TTAAATAAAA AACAAGTAGA TAATCTGCTA AATAATAAAC CTATGATGTT   3907
GGAAACAAAC CAAACAGATG GTGTTTATAA GATAAAAGAT ACACATGGAA ATATAGTAAC   3967
TGGCGGAGAA TGGAATGGTG TCATACAACA AATCAAGGCT AAAACAGCGT CTATTATTGT   4027
GGATGATGGG GAACGTGTAG CAGAAAAACG TGTAGCGGCA AAAGATTATG AAAATCCAGA   4087
AGATAAAACA CCGTCTTTAA CTTTAAAAGA TGCCCTGAAG CTTTCATATC CAGATGAAAT   4147
AAAAGAAATA GAGGGATTAT TATATTATAA AAACAAACCG ATATACGAAT CGAGCGTTAT   4207
GACTTACTTA GATGAAAATA CAGCAAAAGA AGTGACCAAA CAATTAAATG ATACCACTGG   4267
GAAATTTAAA GATGTAAGTC ATTTATATGA TGTAAAACTG ACTCCAAAAA TGAATGTTAC   4327
AATCAAATTG TCTATACTTT ATGATAATGC TGAGTCTAAT GATAACTCAA TTGGTAAATG   4387
GACAAACACA AATATTGTTT CAGGTGGAAA TAACGGAAAA AAACAATATT CTTCTAATAA   4447
TCCGGATGCT AATTTGACAT TAAATACAGA TGCTCAAGAA AAATTAAATA AAAATCGTGA   4507
CTATTATATA AGTTTATATA TGAAGTCAGA AAAAAACACA CAATGTGAGA TTACTATAGA   4567
TGGGGAGATT TATCCGATCA CTACAAAAAC AGTGAATGTG AATAAAGACA ATTACAAAAG   4627
ATTAGATATT ATAGCTCATA ATATAAAAG TAATCCAATT TCTTCACTTC ATATTAAAAC    4687
GAATGATGAA ATAACTTTAT TTTGGGATGA TATTTCTATA ACAGATGTAG CATCAATAAA   4747
ACCGGAAAAT TTAACAGATT CAGAAATTAA ACAGATTTAT AGTAGGTATG GTATTAAGTT   4807
AGAAGATGGA ATCCTTATTG ATAAAAAAGG TGGGATTCAT TATGGTGAAT TTATTAATGA   4867
AGCTAGTTTT AATATTGAAC CATTGCAAAA TTATGTGACC AAATATGAAG TTACTTATAG   4927
TAGTGAGTTA GGACCAAACG TGAGTGACAC ACTTGAAAGT GATAAAATTT ACAAGGATGG   4987
GACAATTAAA TTTGATTTTA CCAAATATAG TAAAAATGAA CAAGGATTAT TTTATGACAG   5047
TGGATTAAAT TGGGACTTTA AAATTAATGC TATTACTTAT GATGGTAAAG AGATGAATGT   5107
TTTTCATAGA TATAATAAAT AGTTATTATA TCTATGAAGC TGGTGCTAAA GATAGTGTAA   5167
AAGTTAATAT ACTGTAGGAT TGTAATAAAA GTAATGGAAT TGATATCGTA CTTTGGAGTG   5227
GGGGATACTT TGTAAATAGT TCTATCAGAA ACATTAGACT AAGAAAAGTT ACTACCCCCA   5287
```

-continued

```
CTTGAAAATG AAGATTCAAC TGATTACAAA CAACCTGTTA AATATTATAA GGTTTTAACA    5347

AAATATTAAA CTCTTTATGT TAATACTGTA ATATAAAGAG TTTAATTGTA TTCAAATGAA    5407

GCTTTCCCAC AAAATTAGAC TGATTATCTA ATGAAATAAT CAGTCTAATT TTGTAGAACA    5467

GGTCTGGTAT TATTGTACGT GGTCACTAAA AGATATCTAA TATTATTGGG CAAGGCGTTC    5527

CATGATTGAA TCCTCGAATG TCTTGCCCTT TTCATTTATT TAAGAAGGAT TGTGGAGAAA    5587

TTATGGTTTA GATAATGAAG AAAGACTTCA CTTCTAATTT TTGATGTTAA ATAAATCAAA    5647

ATTTGGCGAT TCACATTGTT TAATCCACTG ATAAACATA  CTGGAGTGTT CTTAAAAAT     5707

CAGCTTTTTT CTTTATAAAA TTTTGCTTAG CGTACGAAAT TCGTGTTTTG TTGGTGGGAC    5767

CCCATGCCCA TCAACTTAAG AGTAAATTAG TAATGAACTT TCGTTCATCT GGATTAAAAT    5827

AACCTCAAAT TAGGACATGT TTTTAAAAAT AAGCAGACCA AATAAGCCTA GAATAGGTAT    5887

CATTTTTAAA AATTATGCTG CTTTCTTTTG TTTTCCAAAT CCATTATACT CATAAGCAAC    5947

ACCCATAATG TCAAAGACTG TTTTTGTCTC ATATCGATAA GCTTGATATC GAATTCCTGC    6007

AGCCCGGGGG ATCCACTAGT TCTAGAGCGG CCGCCACCGC GG                       6049
```

( 2 ) INFORMATION FOR SEQ ID NO:2:

( i ) SEQUENCE CHARACTERISTICS:
        ( A ) LENGTH: 462 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Lys  Arg  Met  Glu  Gly  Lys  Leu  Phe  Met  Val  Ser  Lys  Lys  Leu  Gln
 1              5                        10                       15

Val  Val  Thr  Lys  Thr  Val  Leu  Leu  Ser  Thr  Val  Phe  Ser  Ile  Ser  Leu
            20                       25                       30

Leu  Asn  Asn  Glu  Val  Ile  Lys  Ala  Glu  Gln  Leu  Asn  Ile  Asn  Ser  Gln
         35                       40                       45

Ser  Lys  Tyr  Thr  Asn  Leu  Gln  Asn  Leu  Lys  Ile  Thr  Asp  Lys  Val  Glu
     50                       55                       60

Asp  Phe  Lys  Glu  Asp  Lys  Glu  Lys  Ala  Lys  Glu  Trp  Gly  Lys  Glu  Lys
 65                       70                       75                       80

Glu  Lys  Glu  Trp  Lys  Leu  Thr  Ala  Thr  Glu  Lys  Gly  Lys  Met  Asn  Asn
                     85                       90                       95

Phe  Leu  Asp  Asn  Lys  Asn  Asp  Ile  Lys  Thr  Asn  Tyr  Lys  Glu  Ile  Thr
               100                      105                      110

Phe  Ser  Met  Ala  Gly  Ser  Phe  Glu  Asp  Glu  Ile  Lys  Asp  Leu  Lys  Glu
          115                      120                      125

Ile  Asp  Lys  Met  Phe  Asp  Lys  Thr  Asn  Leu  Ser  Asn  Ser  Ile  Ile  Thr
     130                      135                      140

Tyr  Lys  Asn  Val  Glu  Pro  Thr  Thr  Ile  Gly  Phe  Asn  Lys  Ser  Leu  Thr
145                      150                      155                      160

Glu  Gly  Asn  Thr  Ile  Asn  Ser  Asp  Ala  Met  Ala  Gln  Phe  Lys  Glu  Gln
                    165                      170                      175

Phe  Leu  Asp  Arg  Asp  Ile  Lys  Phe  Asp  Ser  Tyr  Leu  Asp  Thr  His  Leu
               180                      185                      190

Thr  Ala  Gln  Gln  Val  Ser  Ser  Lys  Glu  Arg  Val  Ile  Leu  Lys  Val  Thr
          195                      200                      205

Val  Pro  Ser  Gly  Lys  Gly  Ser  Thr  Thr  Pro  Thr  Lys  Ala  Gly  Val  Ile
     210                      215                      220
```

```
Leu  Asn  Asn  Ser  Glu  Tyr  Lys  Met  Leu  Ile  Asp  Asn  Gly  Tyr  Met  Val
225            230                      235                 240

His  Val  Asp  Lys  Ser  Lys  Val  Val  Lys  Lys  Gly  Val  Glu  Cys  Leu
               245                 250                      255

Gln  Ile  Glu  Gly  Thr  Leu  Lys  Lys  Ser  Leu  Asp  Phe  Lys  Asn  Asp  Ile
               260                 265                      270

Asn  Ala  Glu  Ala  His  Ser  Trp  Gly  Met  Lys  Asn  Tyr  Glu  Glu  Trp  Ala
          275                      280                      285

Lys  Asp  Leu  Thr  Asp  Ser  Gln  Arg  Glu  Ala  Leu  Asp  Gly  Tyr  Ala  Arg
     290                 295                      300

Gln  Asp  Tyr  Lys  Glu  Ile  Asn  Asn  Tyr  Leu  Arg  Asn  Gln  Gly  Gly  Ser
305                      310                 315                           320

Gly  Asn  Glu  Lys  Leu  Asp  Ala  Gln  Ile  Lys  Asn  Ile  Ser  Asp  Ala  Leu
                    325                 330                      335

Gly  Lys  Lys  Pro  Ile  Pro  Glu  Asn  Ile  Thr  Val  Tyr  Arg  Trp  Cys  Gly
               340                 345                      350

Met  Pro  Glu  Phe  Gly  Tyr  Gln  Ile  Ser  Asp  Pro  Leu  Pro  Ser  Leu  Lys
          355                      360                      365

Asp  Phe  Glu  Glu  Gln  Phe  Leu  Asn  Thr  Ile  Lys  Glu  Asp  Lys  Gly  Tyr
     370                      375                 380

Met  Ser  Thr  Ser  Leu  Ser  Ser  Glu  Arg  Leu  Ala  Ala  Phe  Gly  Ser  Arg
385                 390                      395                           400

Lys  Ile  Ile  Leu  Arg  Leu  Gln  Val  Pro  Lys  Gly  Ser  Thr  Gly  Ala  Tyr
               405                      410                      415

Leu  Ser  Ala  Ile  Gly  Gly  Phe  Ala  Ser  Glu  Lys  Glu  Ile  Leu  Leu  Asp
               420                      425                      430

Lys  Asp  Ser  Lys  Tyr  His  Ile  Asp  Lys  Val  Thr  Glu  Val  Ile  Ile  Lys
          435                      440                 445

Gly  Val  Lys  Arg  Tyr  Val  Val  Asp  Ala  Thr  Leu  Leu  Thr  Asn
450                      455                 460
```

( 2 ) INFORMATION FOR SEQ ID NO:3:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..20
        ( D ) OTHER INFORMATION: /note= "Signal peptide for vacuolar
            targetting"

( x i ) SEQUENCE DESCRIPTION: SEQ ID NO:3:

```
Ser  Ser  Ser  Ser  Phe  Ala  Asp  Ser  Asn  Pro  Ile  Arg  Val  Thr  Asp  Arg
1              5                      10                      15

Ala  Ala  Ser  Thr
               20
```

( 2 ) INFORMATION FOR SEQ ID NO:4:

( i ) SEQUENCE CHARACTERISTICS:
        ( A ) LENGTH: 2655 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Bacillus cereus
    ( B ) STRAIN: AB78
    ( C ) INDIVIDUAL ISOLATE: NRRL B- 21058

( i x ) FEATURE:
    ( A ) NAME/KEY: CDS
    ( B ) LOCATION: 1..2652
    ( D ) OTHER INFORMATION: /product="100 kDa protein VIP1A(a)"
    / note= "This sequence is identical to the portion of
    SEQ ID NO:1 between and including nucleotide 2475
    to 5126."

( x i ) SEQUENCE DESCRIPTION: SEQ ID NO:4:

```
ATG  AAA  AAT  ATG  AAG  AAA  AAG  TTA  GCA  AGT  GTT  GTA  ACG  TGT  ACG  TTA         48
Met  Lys  Asn  Met  Lys  Lys  Lys  Leu  Ala  Ser  Val  Val  Thr  Cys  Thr  Leu
          465                      470                      475

TTA  GCT  CCT  ATG  TTT  TTG  AAT  GGA  AAT  GTG  AAT  GCT  GTT  TAC  GCA  GAC         96
Leu  Ala  Pro  Met  Phe  Leu  Asn  Gly  Asn  Val  Asn  Ala  Val  Tyr  Ala  Asp
     480                      485                      490

AGC  AAA  ACA  AAT  CAA  ATT  TCT  ACA  ACA  CAG  AAA  AAT  CAA  CAG  AAA  GAG        144
Ser  Lys  Thr  Asn  Gln  Ile  Ser  Thr  Thr  Gln  Lys  Asn  Gln  Gln  Lys  Glu
495                      500                      505                      510

ATG  GAC  CGA  AAA  GGA  TTA  CTT  GGG  TAT  TAT  TTC  AAA  GGA  AAA  GAT  TTT        192
Met  Asp  Arg  Lys  Gly  Leu  Leu  Gly  Tyr  Tyr  Phe  Lys  Gly  Lys  Asp  Phe
                    515                      520                      525

AGT  AAT  CTT  ACT  ATG  TTT  GCA  CCG  ACA  CGT  GAT  AGT  ACT  CTT  ATT  TAT        240
Ser  Asn  Leu  Thr  Met  Phe  Ala  Pro  Thr  Arg  Asp  Ser  Thr  Leu  Ile  Tyr
               530                      535                      540

GAT  CAA  CAA  ACA  GCA  AAT  AAA  CTA  TTA  GAT  AAA  AAA  CAA  CAA  GAA  TAT        288
Asp  Gln  Gln  Thr  Ala  Asn  Lys  Leu  Leu  Asp  Lys  Lys  Gln  Gln  Glu  Tyr
          545                      550                      555

CAG  TCT  ATT  CGT  TGG  ATT  GGT  TTG  ATT  CAG  AGT  AAA  GAA  ACG  GGA  GAT        336
Gln  Ser  Ile  Arg  Trp  Ile  Gly  Leu  Ile  Gln  Ser  Lys  Glu  Thr  Gly  Asp
     560                      565                      570

TTC  ACA  TTT  AAC  TTA  TCT  GAG  GAT  GAA  CAG  GCA  ATT  ATA  GAA  ATC  AAT        384
Phe  Thr  Phe  Asn  Leu  Ser  Glu  Asp  Glu  Gln  Ala  Ile  Ile  Glu  Ile  Asn
575                      580                      585                      590

GGG  AAA  ATT  ATT  TCT  AAT  AAA  GGG  AAA  GAA  AAG  CAA  GTT  GTC  CAT  TTA        432
Gly  Lys  Ile  Ile  Ser  Asn  Lys  Gly  Lys  Glu  Lys  Gln  Val  Val  His  Leu
                    595                      600                      605

GAA  AAA  GGA  AAA  TTA  GTT  CCA  ATC  AAA  ATA  GAG  TAT  CAA  TCA  GAT  ACA        480
Glu  Lys  Gly  Lys  Leu  Val  Pro  Ile  Lys  Ile  Glu  Tyr  Gln  Ser  Asp  Thr
               610                      615                      620

AAA  TTT  AAT  ATT  GAC  AGT  AAA  ACA  TTT  AAA  GAA  CTT  AAA  TTA  TTT  AAA        528
Lys  Phe  Asn  Ile  Asp  Ser  Lys  Thr  Phe  Lys  Glu  Leu  Lys  Leu  Phe  Lys
          625                      630                      635

ATA  GAT  AGT  CAA  AAC  CAA  CCC  CAG  CAA  GTC  CAG  CAA  GAT  GAA  CTG  AGA        576
Ile  Asp  Ser  Gln  Asn  Gln  Pro  Gln  Gln  Val  Gln  Gln  Asp  Glu  Leu  Arg
     640                      645                      650

AAT  CCT  GAA  TTT  AAC  AAG  AAA  GAA  TCA  CAG  GAA  TTC  TTA  GCG  AAA  CCA        624
Asn  Pro  Glu  Phe  Asn  Lys  Lys  Glu  Ser  Gln  Glu  Phe  Leu  Ala  Lys  Pro
655                      660                      665                      670

TCG  AAA  ATA  AAT  CTT  TTC  ACT  CAA  AAA  ATG  AAA  AGG  GAA  ATT  GAT  GAA        672
Ser  Lys  Ile  Asn  Leu  Phe  Thr  Gln  Lys  Met  Lys  Arg  Glu  Ile  Asp  Glu
                    675                      680                      685

GAC  ACG  GAT  ACG  GAT  GGG  GAC  TCT  ATT  CCT  GAC  CTT  TGG  GAA  GAA  AAT        720
Asp  Thr  Asp  Thr  Asp  Gly  Asp  Ser  Ile  Pro  Asp  Leu  Trp  Glu  Glu  Asn
               690                      695                      700
```

| | | | | | | | | | | | | | | | | |
|---|---|---|---|---|---|---|---|---|---|---|---|---|---|---|---|---|
| GGG | TAT | ACG | ATT | CAA | AAT | AGA | ATC | GCT | GTA | AAG | TGG | GAC | GAT | TCT | CTA | 768 |
| Gly | Tyr | Thr | Ile | Gln | Asn | Arg | Ile | Ala | Val | Lys | Trp | Asp | Asp | Ser | Leu | |
| | | 705 | | | | | 710 | | | | | 715 | | | | |
| GCA | AGT | AAA | GGG | TAT | ACG | AAA | TTT | GTT | TCA | AAT | CCA | CTA | GAA | AGT | CAC | 816 |
| Ala | Ser | Lys | Gly | Tyr | Thr | Lys | Phe | Val | Ser | Asn | Pro | Leu | Glu | Ser | His | |
| 720 | | | | | 725 | | | | | 730 | | | | | | |
| ACA | GTT | GGT | GAT | CCT | TAT | ACA | GAT | TAT | GAA | AAG | GCA | GCA | AGA | GAT | CTA | 864 |
| Thr | Val | Gly | Asp | Pro | Tyr | Thr | Asp | Tyr | Glu | Lys | Ala | Ala | Arg | Asp | Leu | |
| 735 | | | | | 740 | | | | | 745 | | | | | 750 | |
| GAT | TTG | TCA | AAT | GCA | AAG | GAA | ACG | TTT | AAC | CCA | TTG | GTA | GCT | GCT | TTT | 912 |
| Asp | Leu | Ser | Asn | Ala | Lys | Glu | Thr | Phe | Asn | Pro | Leu | Val | Ala | Ala | Phe | |
| | | | | 755 | | | | | 760 | | | | | 765 | | |
| CCA | AGT | GTG | AAT | GTT | AGT | ATG | GAA | AAG | GTG | ATA | TTA | TCA | CCA | AAT | GAA | 960 |
| Pro | Ser | Val | Asn | Val | Ser | Met | Glu | Lys | Val | Ile | Leu | Ser | Pro | Asn | Glu | |
| | | | 770 | | | | | 775 | | | | | 780 | | | |
| AAT | TTA | TCC | AAT | AGT | GTA | GAG | TCT | CAT | TCA | TCC | ACG | AAT | TGG | TCT | TAT | 1008 |
| Asn | Leu | Ser | Asn | Ser | Val | Glu | Ser | His | Ser | Ser | Thr | Asn | Trp | Ser | Tyr | |
| | | 785 | | | | | 790 | | | | | 795 | | | | |
| ACA | AAT | ACA | GAA | GGT | GCT | TCT | GTT | GAA | GCG | GGG | ATT | GGA | CCA | AAA | GGT | 1056 |
| Thr | Asn | Thr | Glu | Gly | Ala | Ser | Val | Glu | Ala | Gly | Ile | Gly | Pro | Lys | Gly | |
| 800 | | | | | 805 | | | | | 810 | | | | | | |
| ATT | TCG | TTC | GGA | GTT | AGC | GTA | AAC | TAT | CAA | CAC | TCT | GAA | ACA | GTT | GCA | 1104 |
| Ile | Ser | Phe | Gly | Val | Ser | Val | Asn | Tyr | Gln | His | Ser | Glu | Thr | Val | Ala | |
| 815 | | | | | 820 | | | | | 825 | | | | | 830 | |
| CAA | GAA | TGG | GGA | ACA | TCT | ACA | GGA | AAT | ACT | TCG | CAA | TTC | AAT | ACG | GCT | 1152 |
| Gln | Glu | Trp | Gly | Thr | Ser | Thr | Gly | Asn | Thr | Ser | Gln | Phe | Asn | Thr | Ala | |
| | | | | 835 | | | | | 840 | | | | | 845 | | |
| TCA | GCG | GGA | TAT | TTA | AAT | GCA | AAT | GTT | CGA | TAT | AAC | AAT | GTA | GGA | ACT | 1200 |
| Ser | Ala | Gly | Tyr | Leu | Asn | Ala | Asn | Val | Arg | Tyr | Asn | Asn | Val | Gly | Thr | |
| | | | 850 | | | | | 855 | | | | | 860 | | | |
| GGT | GCC | ATC | TAC | GAT | GTA | AAA | CCT | ACA | ACA | AGT | TTT | GTA | TTA | AAT | AAC | 1248 |
| Gly | Ala | Ile | Tyr | Asp | Val | Lys | Pro | Thr | Thr | Ser | Phe | Val | Leu | Asn | Asn | |
| | | 865 | | | | | 870 | | | | | 875 | | | | |
| GAT | ACT | ATC | GCA | ACT | ATT | ACG | GCG | AAA | TCT | AAT | TCT | ACA | GCC | TTA | AAT | 1296 |
| Asp | Thr | Ile | Ala | Thr | Ile | Thr | Ala | Lys | Ser | Asn | Ser | Thr | Ala | Leu | Asn | |
| 880 | | | | | 885 | | | | | 890 | | | | | | |
| ATA | TCT | CCT | GGA | GAA | AGT | TAC | CCG | AAA | AAA | GGA | CAA | AAT | GGA | ATC | GCA | 1344 |
| Ile | Ser | Pro | Gly | Glu | Ser | Tyr | Pro | Lys | Lys | Gly | Gln | Asn | Gly | Ile | Ala | |
| 895 | | | | | 900 | | | | | 905 | | | | | 910 | |
| ATA | ACA | TCA | ATG | GAT | GAT | TTT | AAT | TCC | CAT | CCG | ATT | ACA | TTA | AAT | AAA | 1392 |
| Ile | Thr | Ser | Met | Asp | Asp | Phe | Asn | Ser | His | Pro | Ile | Thr | Leu | Asn | Lys | |
| | | | | 915 | | | | | 920 | | | | | 925 | | |
| AAA | CAA | GTA | GAT | AAT | CTG | CTA | AAT | AAT | AAA | CCT | ATG | ATG | TTG | GAA | ACA | 1440 |
| Lys | Gln | Val | Asp | Asn | Leu | Leu | Asn | Asn | Lys | Pro | Met | Met | Leu | Glu | Thr | |
| | | | 930 | | | | | 935 | | | | | 940 | | | |
| AAC | CAA | ACA | GAT | GGT | GTT | TAT | AAG | ATA | AAA | GAT | ACA | CAT | GGA | AAT | ATA | 1488 |
| Asn | Gln | Thr | Asp | Gly | Val | Tyr | Lys | Ile | Lys | Asp | Thr | His | Gly | Asn | Ile | |
| | | 945 | | | | | 950 | | | | | 955 | | | | |
| GTA | ACT | GGC | GGA | GAA | TGG | AAT | GGT | GTC | ATA | CAA | CAA | ATC | AAG | GCT | AAA | 1536 |
| Val | Thr | Gly | Gly | Glu | Trp | Asn | Gly | Val | Ile | Gln | Gln | Ile | Lys | Ala | Lys | |
| | 960 | | | | | 965 | | | | | 970 | | | | | |
| ACA | GCG | TCT | ATT | ATT | GTG | GAT | GAT | GGG | GAA | CGT | GTA | GCA | GAA | AAA | CGT | 1584 |
| Thr | Ala | Ser | Ile | Ile | Val | Asp | Asp | Gly | Glu | Arg | Val | Ala | Glu | Lys | Arg | |
| 975 | | | | | 980 | | | | | 985 | | | | | 990 | |
| GTA | GCG | GCA | AAA | GAT | TAT | GAA | AAT | CCA | GAA | GAT | AAA | ACA | CCG | TCT | TTA | 1632 |
| Val | Ala | Ala | Lys | Asp | Tyr | Glu | Asn | Pro | Glu | Asp | Lys | Thr | Pro | Ser | Leu | |
| | | | | 995 | | | | | 1000 | | | | | 1005 | | |
| ACT | TTA | AAA | GAT | GCC | CTG | AAG | CTT | TCA | TAT | CCA | GAT | GAA | ATA | AAA | GAA | 1680 |
| Thr | Leu | Lys | Asp | Ala | Leu | Lys | Leu | Ser | Tyr | Pro | Asp | Glu | Ile | Lys | Glu | |
| | | | 1010 | | | | | 1015 | | | | | 1020 | | | |

```
ATA GAG GGA TTA TTA TAT TAT AAA AAC AAA CCG ATA TAC GAA TCG AGC      1728
Ile Glu Gly Leu Leu Tyr Tyr Lys Asn Lys Pro Ile Tyr Glu Ser Ser
        1025                    1030                    1035

GTT ATG ACT TAC TTA GAT GAA AAT ACA GCA AAA GAA GTG ACC AAA CAA      1776
Val Met Thr Tyr Leu Asp Glu Asn Thr Ala Lys Glu Val Thr Lys Gln
        1040                    1045                    1050

TTA AAT GAT ACC ACT GGG AAA TTT AAA GAT GTA AGT CAT TTA TAT GAT      1824
Leu Asn Asp Thr Thr Gly Lys Phe Lys Asp Val Ser His Leu Tyr Asp
1055                    1060                    1065           1070

GTA AAA CTG ACT CCA AAA ATG AAT GTT ACA ATC AAA TTG TCT ATA CTT      1872
Val Lys Leu Thr Pro Lys Met Asn Val Thr Ile Lys Leu Ser Ile Leu
        1075                    1080                    1085

TAT GAT AAT GCT GAG TCT AAT GAT AAC TCA ATT GGT AAA TGG ACA AAC      1920
Tyr Asp Asn Ala Glu Ser Asn Asp Asn Ser Ile Gly Lys Trp Thr Asn
        1090                    1095                    1100

ACA AAT ATT GTT TCA GGT GGA AAT AAC GGA AAA AAA CAA TAT TCT TCT      1968
Thr Asn Ile Val Ser Gly Gly Asn Asn Gly Lys Lys Gln Tyr Ser Ser
        1105                    1110                    1115

AAT AAT CCG GAT GCT AAT TTG ACA TTA AAT ACA GAT GCT CAA GAA AAA      2016
Asn Asn Pro Asp Ala Asn Leu Thr Leu Asn Thr Asp Ala Gln Glu Lys
        1120                    1125                    1130

TTA AAT AAA AAT CGT GAC TAT TAT ATA AGT TTA TAT ATG AAG TCA GAA      2064
Leu Asn Lys Asn Arg Asp Tyr Tyr Ile Ser Leu Tyr Met Lys Ser Glu
1135                    1140                    1145           1150

AAA AAC ACA CAA TGT GAG ATT ACT ATA GAT GGG GAG ATT TAT CCG ATC      2112
Lys Asn Thr Gln Cys Glu Ile Thr Ile Asp Gly Glu Ile Tyr Pro Ile
                1155                    1160                    1165

ACT ACA AAA ACA GTG AAT GTG AAT AAA GAC AAT TAC AAA AGA TTA GAT      2160
Thr Thr Lys Thr Val Asn Val Asn Lys Asp Asn Tyr Lys Arg Leu Asp
        1170                    1175                    1180

ATT ATA GCT CAT AAT ATA AAA AGT AAT CCA ATT TCT TCA CTT CAT ATT      2208
Ile Ile Ala His Asn Ile Lys Ser Asn Pro Ile Ser Ser Leu His Ile
        1185                    1190                    1195

AAA ACG AAT GAT GAA ATA ACT TTA TTT TGG GAT GAT ATT TCT ATA ACA      2256
Lys Thr Asn Asp Glu Ile Thr Leu Phe Trp Asp Asp Ile Ser Ile Thr
        1200                    1205                    1210

GAT GTA GCA TCA ATA AAA CCG GAA AAT TTA ACA GAT TCA GAA ATT AAA      2304
Asp Val Ala Ser Ile Lys Pro Glu Asn Leu Thr Asp Ser Glu Ile Lys
1215                    1220                    1225           1230

CAG ATT TAT AGT AGG TAT GGT ATT AAG TTA GAA GAT GGA ATC CTT ATT      2352
Gln Ile Tyr Ser Arg Tyr Gly Ile Lys Leu Glu Asp Gly Ile Leu Ile
                1235                    1240                    1245

GAT AAA AAA GGT GGG ATT CAT TAT GGT GAA TTT ATT AAT GAA GCT AGT      2400
Asp Lys Lys Gly Gly Ile His Tyr Gly Glu Phe Ile Asn Glu Ala Ser
        1250                    1255                    1260

TTT AAT ATT GAA CCA TTG CAA AAT TAT GTG ACC AAA TAT GAA GTT ACT      2448
Phe Asn Ile Glu Pro Leu Gln Asn Tyr Val Thr Lys Tyr Glu Val Thr
        1265                    1270                    1275

TAT AGT AGT GAG TTA GGA CCA AAC GTG AGT GAC ACA CTT GAA AGT GAT      2496
Tyr Ser Ser Glu Leu Gly Pro Asn Val Ser Asp Thr Leu Glu Ser Asp
        1280                    1285                    1290

AAA ATT TAC AAG GAT GGG ACA ATT AAA TTT GAT TTT ACC AAA TAT AGT      2544
Lys Ile Tyr Lys Asp Gly Thr Ile Lys Phe Asp Phe Thr Lys Tyr Ser
1295                    1300                    1305           1310

AAA AAT GAA CAA GGA TTA TTT TAT GAC AGT GGA TTA AAT TGG GAC TTT      2592
Lys Asn Glu Gln Gly Leu Phe Tyr Asp Ser Gly Leu Asn Trp Asp Phe
                1315                    1320                    1325

AAA ATT AAT GCT ATT ACT TAT GAT GGT AAA GAG ATG AAT GTT TTT CAT      2640
Lys Ile Asn Ala Ile Thr Tyr Asp Gly Lys Glu Met Asn Val Phe His
        1330                    1335                    1340
```

```
AGA TAT AAT AAA TAG                                                              2655
Arg Tyr Asn Lys
        1345
```

( 2 ) INFORMATION FOR SEQ ID NO:5:

( i ) SEQUENCE CHARACTERISTICS:
      ( A ) LENGTH: 884 amino acids
      ( B ) TYPE: amino acid
      ( D ) TOPOLOGY: linear ( i i ) MOLECULE TYPE: protein ( x i ) SEQUENCE DESCRIPTION: SEQ ID NO:5:

```
Met Lys Asn Met Lys Lys Leu Ala Ser Val Val Thr Cys Thr Leu
  1               5                  10                  15

Leu Ala Pro Met Phe Leu Asn Gly Asn Val Asn Ala Val Tyr Ala Asp
             20                  25                  30

Ser Lys Thr Asn Gln Ile Ser Thr Thr Gln Lys Asn Gln Gln Lys Glu
         35                  40                  45

Met Asp Arg Lys Gly Leu Leu Gly Tyr Tyr Phe Lys Gly Lys Asp Phe
     50                  55                  60

Ser Asn Leu Thr Met Phe Ala Pro Thr Arg Asp Ser Thr Leu Ile Tyr
 65                  70                  75                  80

Asp Gln Gln Thr Ala Asn Lys Leu Leu Asp Lys Lys Gln Gln Glu Tyr
                 85                  90                  95

Gln Ser Ile Arg Trp Ile Gly Leu Ile Gln Ser Lys Glu Thr Gly Asp
                100                 105                 110

Phe Thr Phe Asn Leu Ser Glu Asp Glu Gln Ala Ile Ile Glu Ile Asn
            115                 120                 125

Gly Lys Ile Ile Ser Asn Lys Gly Lys Glu Lys Gln Val Val His Leu
    130                 135                 140

Glu Lys Gly Lys Leu Val Pro Ile Lys Ile Glu Tyr Gln Ser Asp Thr
145                 150                 155                 160

Lys Phe Asn Ile Asp Ser Lys Thr Phe Lys Glu Leu Lys Leu Phe Lys
                165                 170                 175

Ile Asp Ser Gln Asn Gln Pro Gln Gln Val Gln Gln Asp Glu Leu Arg
            180                 185                 190

Asn Pro Glu Phe Asn Lys Lys Glu Ser Gln Glu Phe Leu Ala Lys Pro
            195                 200                 205

Ser Lys Ile Asn Leu Phe Thr Gln Lys Met Lys Arg Glu Ile Asp Glu
    210                 215                 220

Asp Thr Asp Thr Asp Gly Asp Ser Ile Pro Asp Leu Trp Glu Glu Asn
225                 230                 235                 240

Gly Tyr Thr Ile Gln Asn Arg Ile Ala Val Lys Trp Asp Asp Ser Leu
                245                 250                 255

Ala Ser Lys Gly Tyr Thr Lys Phe Val Ser Asn Pro Leu Glu Ser His
            260                 265                 270

Thr Val Gly Asp Pro Tyr Thr Asp Tyr Glu Lys Ala Ala Arg Asp Leu
            275                 280                 285

Asp Leu Ser Asn Ala Lys Glu Thr Phe Asn Pro Leu Val Ala Ala Phe
    290                 295                 300

Pro Ser Val Asn Val Ser Met Glu Lys Val Ile Leu Ser Pro Asn Glu
305                 310                 315                 320

Asn Leu Ser Asn Ser Val Glu Ser His Ser Ser Thr Asn Trp Ser Tyr
                325                 330                 335

Thr Asn Thr Glu Gly Ala Ser Val Glu Ala Gly Ile Gly Pro Lys Gly
```

-continued

|     |     |     |     |     | 340 |     |     |     |     | 345 |     |     |     |     | 350 |     |     |
|-----|-----|-----|-----|-----|-----|-----|-----|-----|-----|-----|-----|-----|-----|-----|-----|-----|-----|

Ile Ser Phe Gly Val Ser Val Asn Tyr Gln His Ser Glu Thr Val Ala
        355                          360                      365

Gln Glu Trp Gly Thr Ser Thr Gly Asn Thr Ser Gln Phe Asn Thr Ala
370                        375                      380

Ser Ala Gly Tyr Leu Asn Ala Asn Val Arg Tyr Asn Asn Val Gly Thr
385                      390                  395                  400

Gly Ala Ile Tyr Asp Val Lys Pro Thr Thr Ser Phe Val Leu Asn Asn
            405                  410                    415

Asp Thr Ile Ala Thr Ile Thr Ala Lys Ser Asn Ser Thr Ala Leu Asn
            420                425                430

Ile Ser Pro Gly Glu Ser Tyr Pro Lys Lys Gly Gln Asn Gly Ile Ala
        435                  440                  445

Ile Thr Ser Met Asp Asp Phe Asn Ser His Pro Ile Thr Leu Asn Lys
    450                455              460

Lys Gln Val Asp Asn Leu Asn Asn Lys Pro Met Met Leu Glu Thr
465                    470              475                  480

Asn Gln Thr Asp Gly Val Tyr Lys Ile Lys Asp Thr His Gly Asn Ile
                485              490                495

Val Thr Gly Gly Glu Trp Asn Gly Val Ile Gln Gln Ile Lys Ala Lys
            500                505                510

Thr Ala Ser Ile Ile Val Asp Asp Gly Glu Arg Val Ala Glu Lys Arg
        515                520              525

Val Ala Ala Lys Asp Tyr Glu Asn Pro Glu Asp Lys Thr Pro Ser Leu
530                    535              540

Thr Leu Lys Asp Ala Leu Lys Leu Ser Tyr Pro Asp Glu Ile Lys Glu
545                  550              555              560

Ile Glu Gly Leu Leu Tyr Tyr Lys Asn Lys Pro Ile Tyr Glu Ser Ser
            565                570                575

Val Met Thr Tyr Leu Asp Glu Asn Thr Ala Lys Glu Val Thr Lys Gln
        580                585                590

Leu Asn Asp Thr Thr Gly Lys Phe Lys Asp Val Ser His Leu Tyr Asp
        595                600                605

Val Lys Leu Thr Pro Lys Met Asn Val Thr Ile Lys Leu Ser Ile Leu
610                    615              620

Tyr Asp Asn Ala Glu Ser Asn Asp Asn Ser Ile Gly Lys Trp Thr Asn
625                    630              635              640

Thr Asn Ile Val Ser Gly Gly Asn Asn Gly Lys Lys Gln Tyr Ser Ser
            645                650                655

Asn Asn Pro Asp Ala Asn Leu Thr Leu Asn Thr Asp Ala Gln Glu Lys
        660                665                670

Leu Asn Lys Asn Arg Asp Tyr Tyr Ile Ser Leu Tyr Met Lys Ser Glu
        675                680                685

Lys Asn Thr Gln Cys Glu Ile Thr Ile Asp Gly Glu Ile Tyr Pro Ile
    690              695              700

Thr Thr Lys Thr Val Asn Val Asn Lys Asp Asn Tyr Lys Arg Leu Asp
705                    710              715              720

Ile Ile Ala His Asn Ile Lys Ser Asn Pro Ile Ser Ser Leu His Ile
            725              730                735

Lys Thr Asn Asp Glu Ile Thr Leu Phe Trp Asp Asp Ile Ser Ile Thr
        740                745                750

Asp Val Ala Ser Ile Lys Pro Glu Asn Leu Thr Asp Ser Glu Ile Lys
        755                760                765

```
Gln  Ile  Tyr  Ser  Arg  Tyr  Gly  Ile  Lys  Leu  Glu  Asp  Gly  Ile  Leu  Ile
     770                     775                    780

Asp  Lys  Lys  Gly  Gly  Ile  His  Tyr  Gly  Glu  Phe  Ile  Asn  Glu  Ala  Ser
785                          790                    795                         800

Phe  Asn  Ile  Glu  Pro  Leu  Gln  Asn  Tyr  Val  Thr  Lys  Tyr  Glu  Val  Thr
                    805                     810                         815

Tyr  Ser  Ser  Glu  Leu  Gly  Pro  Asn  Val  Ser  Asp  Thr  Leu  Glu  Ser  Asp
               820                      825                         830

Lys  Ile  Tyr  Lys  Asp  Gly  Thr  Ile  Lys  Phe  Asp  Phe  Thr  Lys  Tyr  Ser
          835                      840                    845

Lys  Asn  Glu  Gln  Gly  Leu  Phe  Tyr  Asp  Ser  Gly  Leu  Asn  Trp  Asp  Phe
     850                     855                         860

Lys  Ile  Asn  Ala  Ile  Thr  Tyr  Asp  Gly  Lys  Glu  Met  Asn  Val  Phe  His
865                      870                    875                         880

Arg  Tyr  Asn  Lys
```

( 2 ) INFORMATION FOR SEQ ID NO:6:

( i ) SEQUENCE CHARACTERISTICS:
        ( A ) LENGTH: 2004 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacillus cereus
        ( B ) STRAIN: AB78
        ( C ) INDIVIDUAL ISOLATE: NRRL B- 21058

( i x ) FEATURE:
        ( A ) NAME/KEY: CDS
        ( B ) LOCATION: 1..2001
        ( D ) OTHER INFORMATION: /product="80 kDa protein VIP1A(a)"
            / note= "This sequence is identical to that found in
            SEQ ID NO:1 between and including nucleotide positions
            3126 and 5126"

( x i ) SEQUENCE DESCRIPTION: SEQ ID NO:6:

```
ATG  AAA  AGG  GAA  ATT  GAT  GAA  GAC  ACG  GAT  ACG  GAT  GGG  GAC  TCT  ATT       48
Met  Lys  Arg  Glu  Ile  Asp  Glu  Asp  Thr  Asp  Thr  Asp  Gly  Asp  Ser  Ile
885                      890                    895                         900

CCT  GAC  CTT  TGG  GAA  GAA  AAT  GGG  TAT  ACG  ATT  CAA  AAT  AGA  ATC  GCT       96
Pro  Asp  Leu  Trp  Glu  Glu  Asn  Gly  Tyr  Thr  Ile  Gln  Asn  Arg  Ile  Ala
               905                      910                         915

GTA  AAG  TGG  GAC  GAT  TCT  CTA  GCA  AGT  AAA  GGG  TAT  ACG  AAA  TTT  GTT      144
Val  Lys  Trp  Asp  Asp  Ser  Leu  Ala  Ser  Lys  Gly  Tyr  Thr  Lys  Phe  Val
               920                      925                    930

TCA  AAT  CCA  CTA  GAA  AGT  CAC  ACA  GTT  GGT  GAT  CCT  TAT  ACA  GAT  TAT      192
Ser  Asn  Pro  Leu  Glu  Ser  His  Thr  Val  Gly  Asp  Pro  Tyr  Thr  Asp  Tyr
          935                      940                    945

GAA  AAG  GCA  GCA  AGA  GAT  CTA  GAT  TTG  TCA  AAT  GCA  AAG  GAA  ACG  TTT      240
Glu  Lys  Ala  Ala  Arg  Asp  Leu  Asp  Leu  Ser  Asn  Ala  Lys  Glu  Thr  Phe
     950                     955                         960

AAC  CCA  TTG  GTA  GCT  GCT  TTT  CCA  AGT  GTG  AAT  GTT  AGT  ATG  GAA  AAG      288
Asn  Pro  Leu  Val  Ala  Ala  Phe  Pro  Ser  Val  Asn  Val  Ser  Met  Glu  Lys
965                      970                    975                         980

GTG  ATA  TTA  TCA  CCA  AAT  GAA  AAT  TTA  TCC  AAT  AGT  GTA  GAG  TCT  CAT      336
Val  Ile  Leu  Ser  Pro  Asn  Glu  Asn  Leu  Ser  Asn  Ser  Val  Glu  Ser  His
               985                      990                         995
```

| | | | | | | | | | | | | | | | | |
|---|---|---|---|---|---|---|---|---|---|---|---|---|---|---|---|---|
| TCA | TCC | ACG | AAT | TGG | TCT | TAT | ACA | AAT | ACA | GAA | GGT | GCT | TCT | GTT | GAA | 384 |
| Ser | Ser | Thr | Asn | Trp | Ser | Tyr | Thr | Asn | Thr | Glu | Gly | Ala | Ser | Val | Glu | |
| | | | | 1000 | | | | 1005 | | | | | 1010 | | | |
| GCG | GGG | ATT | GGA | CCA | AAA | GGT | ATT | TCG | TTC | GGA | GTT | AGC | GTA | AAC | TAT | 432 |
| Ala | Gly | Ile | Gly | Pro | Lys | Gly | Ile | Ser | Phe | Gly | Val | Ser | Val | Asn | Tyr | |
| | | | | 1015 | | | | 1020 | | | | | 1025 | | | |
| CAA | CAC | TCT | GAA | ACA | GTT | GCA | CAA | GAA | TGG | GGA | ACA | TCT | ACA | GGA | AAT | 480 |
| Gln | His | Ser | Glu | Thr | Val | Ala | Gln | Glu | Trp | Gly | Thr | Ser | Thr | Gly | Asn | |
| | | | | 1030 | | | | 1035 | | | | | 1040 | | | |
| ACT | TCG | CAA | TTC | AAT | ACG | GCT | TCA | GCG | GGA | TAT | TTA | AAT | GCA | AAT | GTT | 528 |
| Thr | Ser | Gln | Phe | Asn | Thr | Ala | Ser | Ala | Gly | Tyr | Leu | Asn | Ala | Asn | Val | |
| | | | 1045 | | | | | 1050 | | | | | 1055 | | | 1060 |
| CGA | TAT | AAC | AAT | GTA | GGA | ACT | GGT | GCC | ATC | TAC | GAT | GTA | AAA | CCT | ACA | 576 |
| Arg | Tyr | Asn | Asn | Val | Gly | Thr | Gly | Ala | Ile | Tyr | Asp | Val | Lys | Pro | Thr | |
| | | | | 1065 | | | | 1070 | | | | | 1075 | | | |
| ACA | AGT | TTT | GTA | TTA | AAT | AAC | GAT | ACT | ATC | GCA | ACT | ATT | ACG | GCG | AAA | 624 |
| Thr | Ser | Phe | Val | Leu | Asn | Asn | Asp | Thr | Ile | Ala | Thr | Ile | Thr | Ala | Lys | |
| | | | | 1080 | | | | 1085 | | | | | 1090 | | | |
| TCT | AAT | TCT | ACA | GCC | TTA | AAT | ATA | TCT | CCT | GGA | GAA | AGT | TAC | CCG | AAA | 672 |
| Ser | Asn | Ser | Thr | Ala | Leu | Asn | Ile | Ser | Pro | Gly | Glu | Ser | Tyr | Pro | Lys | |
| | | | | 1095 | | | | 1100 | | | | | 1105 | | | |
| AAA | GGA | CAA | AAT | GGA | ATC | GCA | ATA | ACA | TCA | ATG | GAT | GAT | TTT | AAT | TCC | 720 |
| Lys | Gly | Gln | Asn | Gly | Ile | Ala | Ile | Thr | Ser | Met | Asp | Asp | Phe | Asn | Ser | |
| | | | | 1110 | | | | 1115 | | | | | 1120 | | | |
| CAT | CCG | ATT | ACA | TTA | AAT | AAA | AAA | CAA | GTA | GAT | AAT | CTG | CTA | AAT | AAT | 768 |
| His | Pro | Ile | Thr | Leu | Asn | Lys | Lys | Gln | Val | Asp | Asn | Leu | Leu | Asn | Asn | |
| 1125 | | | | | 1130 | | | | 1135 | | | | | 1140 | | |
| AAA | CCT | ATG | ATG | TTG | GAA | ACA | AAC | CAA | ACA | GAT | GGT | GTT | TAT | AAG | ATA | 816 |
| Lys | Pro | Met | Met | Leu | Glu | Thr | Asn | Gln | Thr | Asp | Gly | Val | Tyr | Lys | Ile | |
| | | | | 1145 | | | | 1150 | | | | | 1155 | | | |
| AAA | GAT | ACA | CAT | GGA | AAT | ATA | GTA | ACT | GGC | GGA | GAA | TGG | AAT | GGT | GTC | 864 |
| Lys | Asp | Thr | His | Gly | Asn | Ile | Val | Thr | Gly | Gly | Glu | Trp | Asn | Gly | Val | |
| | | | | 1160 | | | | 1165 | | | | | 1170 | | | |
| ATA | CAA | CAA | ATC | AAG | GCT | AAA | ACA | GCG | TCT | ATT | ATT | GTG | GAT | GAT | GGG | 912 |
| Ile | Gln | Gln | Ile | Lys | Ala | Lys | Thr | Ala | Ser | Ile | Ile | Val | Asp | Asp | Gly | |
| | | | | 1175 | | | | 1180 | | | | | 1185 | | | |
| GAA | CGT | GTA | GCA | GAA | AAA | CGT | GTA | GCG | GCA | AAA | GAT | TAT | GAA | AAT | CCA | 960 |
| Glu | Arg | Val | Ala | Glu | Lys | Arg | Val | Ala | Ala | Lys | Asp | Tyr | Glu | Asn | Pro | |
| | | | | 1190 | | | | 1195 | | | | | 1200 | | | |
| GAA | GAT | AAA | ACA | CCG | TCT | TTA | ACT | TTA | AAA | GAT | GCC | CTG | AAG | CTT | TCA | 1008 |
| Glu | Asp | Lys | Thr | Pro | Ser | Leu | Thr | Leu | Lys | Asp | Ala | Leu | Lys | Leu | Ser | |
| 1205 | | | | | 1210 | | | | 1215 | | | | | 1220 | | |
| TAT | CCA | GAT | GAA | ATA | AAA | GAA | ATA | GAG | GGA | TTA | TTA | TAT | TAT | AAA | AAC | 1056 |
| Tyr | Pro | Asp | Glu | Ile | Lys | Glu | Ile | Glu | Gly | Leu | Leu | Tyr | Tyr | Lys | Asn | |
| | | | | 1225 | | | | 1230 | | | | | 1235 | | | |
| AAA | CCG | ATA | TAC | GAA | TCG | AGC | GTT | ATG | ACT | TAC | TTA | GAT | GAA | AAT | ACA | 1104 |
| Lys | Pro | Ile | Tyr | Glu | Ser | Ser | Val | Met | Thr | Tyr | Leu | Asp | Glu | Asn | Thr | |
| | | | | 1240 | | | | 1245 | | | | | 1250 | | | |
| GCA | AAA | GAA | GTG | ACC | AAA | CAA | TTA | AAT | GAT | ACC | ACT | GGG | AAA | TTT | AAA | 1152 |
| Ala | Lys | Glu | Val | Thr | Lys | Gln | Leu | Asn | Asp | Thr | Thr | Gly | Lys | Phe | Lys | |
| | | | | 1255 | | | | 1260 | | | | | 1265 | | | |
| GAT | GTA | AGT | CAT | TTA | TAT | GAT | GTA | AAA | CTG | ACT | CCA | AAA | ATG | AAT | GTT | 1200 |
| Asp | Val | Ser | His | Leu | Tyr | Asp | Val | Lys | Leu | Thr | Pro | Lys | Met | Asn | Val | |
| | | | | 1270 | | | | 1275 | | | | | 1280 | | | |
| ACA | ATC | AAA | TTG | TCT | ATA | CTT | TAT | GAT | AAT | GCT | GAG | TCT | AAT | GAT | AAC | 1248 |
| Thr | Ile | Lys | Leu | Ser | Ile | Leu | Tyr | Asp | Asn | Ala | Glu | Ser | Asn | Asp | Asn | |
| 1285 | | | | | 1290 | | | | 1295 | | | | | 1300 | | |
| TCA | ATT | GGT | AAA | TGG | ACA | AAC | ACA | AAT | ATT | GTT | TCA | GGT | GGA | AAT | AAC | 1296 |
| Ser | Ile | Gly | Lys | Trp | Thr | Asn | Thr | Asn | Ile | Val | Ser | Gly | Gly | Asn | Asn | |
| | | | | 1305 | | | | 1310 | | | | | 1315 | | | |

```
GGA  AAA  AAA  CAA  TAT  TCT  TCT  AAT  AAT  CCG  GAT  GCT  AAT  TTG  ACA  TTA    1344
Gly  Lys  Lys  Gln  Tyr  Ser  Ser  Asn  Asn  Pro  Asp  Ala  Asn  Leu  Thr  Leu
          1320                    1325                    1330

AAT  ACA  GAT  GCT  CAA  GAA  AAA  TTA  AAT  AAA  AAT  CGT  GAC  TAT  TAT  ATA    1392
Asn  Thr  Asp  Ala  Gln  Glu  Lys  Leu  Asn  Lys  Asn  Arg  Asp  Tyr  Tyr  Ile
     1335                    1340                    1345

AGT  TTA  TAT  ATG  AAG  TCA  GAA  AAA  AAC  ACA  CAA  TGT  GAG  ATT  ACT  ATA    1440
Ser  Leu  Tyr  Met  Lys  Ser  Glu  Lys  Asn  Thr  Gln  Cys  Glu  Ile  Thr  Ile
     1350                    1355                    1360

GAT  GGG  GAG  ATT  TAT  CCG  ATC  ACT  ACA  AAA  ACA  GTG  AAT  GTG  AAT  AAA    1488
Asp  Gly  Glu  Ile  Tyr  Pro  Ile  Thr  Thr  Lys  Thr  Val  Asn  Val  Asn  Lys
1365                    1370                    1375                    1380

GAC  AAT  TAC  AAA  AGA  TTA  GAT  ATT  ATA  GCT  CAT  AAT  ATA  AAA  AGT  AAT    1536
Asp  Asn  Tyr  Lys  Arg  Leu  Asp  Ile  Ile  Ala  His  Asn  Ile  Lys  Ser  Asn
               1385                    1390                    1395

CCA  ATT  TCT  TCA  CTT  CAT  ATT  AAA  ACG  AAT  GAT  GAA  ATA  ACT  TTA  TTT    1584
Pro  Ile  Ser  Ser  Leu  His  Ile  Lys  Thr  Asn  Asp  Glu  Ile  Thr  Leu  Phe
          1400                    1405                    1410

TGG  GAT  GAT  ATT  TCT  ATA  ACA  GAT  GTA  GCA  TCA  ATA  AAA  CCG  GAA  AAT    1632
Trp  Asp  Asp  Ile  Ser  Ile  Thr  Asp  Val  Ala  Ser  Ile  Lys  Pro  Glu  Asn
     1415                    1420                    1425

TTA  ACA  GAT  TCA  GAA  ATT  AAA  CAG  ATT  TAT  AGT  AGG  TAT  GGT  ATT  AAG    1680
Leu  Thr  Asp  Ser  Glu  Ile  Lys  Gln  Ile  Tyr  Ser  Arg  Tyr  Gly  Ile  Lys
1430                    1435                    1440

TTA  GAA  GAT  GGA  ATC  CTT  ATT  GAT  AAA  AAA  GGT  GGG  ATT  CAT  TAT  GGT    1728
Leu  Glu  Asp  Gly  Ile  Leu  Ile  Asp  Lys  Lys  Gly  Gly  Ile  His  Tyr  Gly
1445                    1450                    1455                    1460

GAA  TTT  ATT  AAT  GAA  GCT  AGT  TTT  AAT  ATT  GAA  CCA  TTG  CCA  AAT  TAT    1776
Glu  Phe  Ile  Asn  Glu  Ala  Ser  Phe  Asn  Ile  Glu  Pro  Leu  Pro  Asn  Tyr
               1465                    1470                    1475

GTG  ACC  AAA  TAT  GAA  GTT  ACT  TAT  AGT  AGT  GAG  TTA  GGA  CCA  AAC  GTG    1824
Val  Thr  Lys  Tyr  Glu  Val  Thr  Tyr  Ser  Ser  Glu  Leu  Gly  Pro  Asn  Val
          1480                    1485                    1490

AGT  GAC  ACA  CTT  GAA  AGT  GAT  AAA  ATT  TAC  AAG  GAT  GGG  ACA  ATT  AAA    1872
Ser  Asp  Thr  Leu  Glu  Ser  Asp  Lys  Ile  Tyr  Lys  Asp  Gly  Thr  Ile  Lys
          1495                    1500                    1505

TTT  GAT  TTT  ACC  AAA  TAT  AGT  AAA  AAT  GAA  CAA  GGA  TTA  TTT  TAT  GAC    1920
Phe  Asp  Phe  Thr  Lys  Tyr  Ser  Lys  Asn  Glu  Gln  Gly  Leu  Phe  Tyr  Asp
     1510                    1515                    1520

AGT  GGA  TTA  AAT  TGG  GAC  TTT  AAA  ATT  AAT  GCT  ATT  ACT  TAT  GAT  GGT    1968
Ser  Gly  Leu  Asn  Trp  Asp  Phe  Lys  Ile  Asn  Ala  Ile  Thr  Tyr  Asp  Gly
1525                    1530                    1535                    1540

AAA  GAG  ATG  AAT  GTT  TTT  CAT  AGA  TAT  AAT  AAA  TAG                        2004
Lys  Glu  Met  Asn  Val  Phe  His  Arg  Tyr  Asn  Lys
               1545                    1550
```

( 2 ) INFORMATION FOR SEQ ID NO:7:

( i ) SEQUENCE CHARACTERISTICS:
        ( A ) LENGTH: 667 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met  Lys  Arg  Glu  Ile  Asp  Glu  Asp  Thr  Thr  Asp  Gly  Asp  Ser  Ile
 1                   5                   10                  15

Pro  Asp  Leu  Trp  Glu  Glu  Asn  Gly  Tyr  Thr  Ile  Gln  Asn  Arg  Ile  Ala
               20                  25                  30

Val  Lys  Trp  Asp  Asp  Ser  Leu  Ala  Ser  Lys  Gly  Tyr  Thr  Lys  Phe  Val
```

-continued

```
                    35                          40                         45

Ser  Asn  Pro  Leu  Glu  Ser  His  Thr  Val  Gly  Asp  Pro  Tyr  Thr  Asp  Tyr
          50                      55                      60

Glu  Lys  Ala  Ala  Arg  Asp  Leu  Asp  Leu  Ser  Asn  Ala  Lys  Glu  Thr  Phe
 65                      70                      75                           80

Asn  Pro  Leu  Val  Ala  Ala  Phe  Pro  Ser  Val  Asn  Val  Ser  Met  Glu  Lys
                         85                      90                     95

Val  Ile  Leu  Ser  Pro  Asn  Glu  Asn  Leu  Ser  Asn  Ser  Val  Glu  Ser  His
               100                     105                     110

Ser  Ser  Thr  Asn  Trp  Ser  Tyr  Thr  Asn  Thr  Glu  Gly  Ala  Ser  Val  Glu
          115                     120                          125

Ala  Gly  Ile  Gly  Pro  Lys  Gly  Ile  Ser  Phe  Gly  Val  Ser  Val  Asn  Tyr
          130                     135                     140

Gln  His  Ser  Glu  Thr  Val  Ala  Gln  Glu  Trp  Gly  Thr  Ser  Thr  Gly  Asn
145                          150                     155                     160

Thr  Ser  Gln  Phe  Asn  Thr  Ala  Ser  Ala  Gly  Tyr  Leu  Asn  Ala  Asn  Val
                    165                     170                     175

Arg  Tyr  Asn  Asn  Val  Gly  Thr  Gly  Ala  Ile  Tyr  Asp  Val  Lys  Pro  Thr
               180                     185                     190

Thr  Ser  Phe  Val  Leu  Asn  Asn  Asp  Thr  Ile  Ala  Thr  Ile  Thr  Ala  Lys
               195                     200                     205

Ser  Asn  Ser  Thr  Ala  Leu  Asn  Ile  Ser  Pro  Gly  Glu  Ser  Tyr  Pro  Lys
210                          215                     220

Lys  Gly  Gln  Asn  Gly  Ile  Ala  Ile  Thr  Ser  Met  Asp  Asp  Phe  Asn  Ser
225                     230                     235                          240

His  Pro  Ile  Thr  Leu  Asn  Lys  Lys  Gln  Val  Asp  Asn  Leu  Leu  Asn  Asn
                    245                     250                     255

Lys  Pro  Met  Met  Leu  Glu  Thr  Asn  Gln  Thr  Asp  Gly  Val  Tyr  Lys  Ile
               260                     265                     270

Lys  Asp  Thr  His  Gly  Asn  Ile  Val  Thr  Gly  Gly  Glu  Trp  Asn  Gly  Val
               275                     280                     285

Ile  Gln  Gln  Ile  Lys  Ala  Lys  Thr  Ala  Ser  Ile  Ile  Val  Asp  Asp  Gly
290                          295                     300

Glu  Arg  Val  Ala  Glu  Lys  Arg  Val  Ala  Ala  Lys  Asp  Tyr  Glu  Asn  Pro
305                     310                     315                          320

Glu  Asp  Lys  Thr  Pro  Ser  Leu  Thr  Leu  Lys  Asp  Ala  Leu  Lys  Leu  Ser
                    325                     330                     335

Tyr  Pro  Asp  Glu  Ile  Lys  Glu  Ile  Gly  Leu  Leu  Tyr  Tyr  Lys  Asn
               340                     345                     350

Lys  Pro  Ile  Tyr  Glu  Ser  Ser  Val  Met  Thr  Tyr  Leu  Asp  Glu  Asn  Thr
               355                     360                     365

Ala  Lys  Glu  Val  Thr  Lys  Gln  Leu  Asn  Asp  Thr  Thr  Gly  Lys  Phe  Lys
     370                     375                     380

Asp  Val  Ser  His  Leu  Tyr  Asp  Val  Lys  Leu  Thr  Pro  Lys  Met  Asn  Val
385                     390                     395                          400

Thr  Ile  Lys  Leu  Ser  Ile  Leu  Tyr  Asp  Asn  Ala  Glu  Ser  Asn  Asp  Asn
                    405                     410                     415

Ser  Ile  Gly  Lys  Trp  Thr  Asn  Thr  Asn  Ile  Val  Ser  Gly  Gly  Asn  Asn
               420                     425                     430

Gly  Lys  Lys  Gln  Tyr  Ser  Ser  Asn  Asn  Pro  Asp  Ala  Asn  Leu  Thr  Leu
          435                     440                     445

Asn  Thr  Asp  Ala  Gln  Glu  Lys  Leu  Asn  Lys  Asn  Arg  Asp  Tyr  Tyr  Ile
450                          455                     460
```

```
Ser  Leu  Tyr  Met  Lys  Ser  Glu  Lys  Asn  Thr  Gln  Cys  Glu  Ile  Thr  Ile
465                      470                 475                           480

Asp  Gly  Glu  Ile  Tyr  Pro  Ile  Thr  Thr  Lys  Thr  Val  Asn  Val  Asn  Lys
               485                      490                      495

Asp  Asn  Tyr  Lys  Arg  Leu  Asp  Ile  Ile  Ala  His  Asn  Ile  Lys  Ser  Asn
               500                 505                      510

Pro  Ile  Ser  Ser  Leu  His  Ile  Lys  Thr  Asn  Asp  Glu  Ile  Thr  Leu  Phe
          515                 520                      525

Trp  Asp  Asp  Ile  Ser  Ile  Thr  Asp  Val  Ala  Ser  Ile  Lys  Pro  Glu  Asn
     530                      535                 540

Leu  Thr  Asp  Ser  Glu  Ile  Lys  Gln  Ile  Tyr  Ser  Arg  Tyr  Gly  Ile  Lys
545                 550                      555                           560

Leu  Glu  Asp  Gly  Ile  Leu  Ile  Asp  Lys  Lys  Gly  Gly  Ile  His  Tyr  Gly
               565                      570                      575

Glu  Phe  Ile  Asn  Glu  Ala  Ser  Phe  Asn  Ile  Glu  Pro  Leu  Pro  Asn  Tyr
               580                 585                      590

Val  Thr  Lys  Tyr  Glu  Val  Thr  Tyr  Ser  Ser  Glu  Leu  Gly  Pro  Asn  Val
          595                      600                      605

Ser  Asp  Thr  Leu  Glu  Ser  Asp  Lys  Ile  Tyr  Lys  Asp  Gly  Thr  Ile  Lys
     610                      615                      620

Phe  Asp  Phe  Thr  Lys  Tyr  Ser  Lys  Asn  Glu  Gln  Gly  Leu  Phe  Tyr  Asp
625                      630                 635                           640

Ser  Gly  Leu  Asn  Trp  Asp  Phe  Lys  Ile  Asn  Ala  Ile  Thr  Tyr  Asp  Gly
               645                      650                      655

Lys  Glu  Met  Asn  Val  Phe  His  Arg  Tyr  Asn  Lys
               660                 665
```

( 2 ) INFORMATION FOR SEQ ID NO:8:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Bacillus cereus
        ( B ) STRAIN: AB78
( C ) INDIVIDUAL ISOLATE: NRRL B- 21058

( i x ) FEATURE:
( A ) NAME/KEY: Peptide
( B ) LOCATION: 1..16
( D ) OTHER INFORMATION: /note= "N-terminal sequence of protein purified from strain AB78"

( x i ) SEQUENCE DESCRIPTION: SEQ ID NO:8:

Lys Arg Glu Ile Asp Glu Asp Thr Asp Thr Asx Gly Asp Ser Ile Pro
1 5 10 15

( 2 ) INFORMATION FOR SEQ ID NO:9:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: misc_feature
    ( B ) LOCATION: 1..21
    ( D ) OTHER INFORMATION: /note= "Oligonucleotide probe based on amino acids 3 to 9 of SEQ ID NO:8, using codon usage of Bacillus thuringiensis"

( x i ) SEQUENCE DESCRIPTION: SEQ ID NO:9:

GAAATTGATC AAGATACNGA T 21

( 2 ) INFORMATION FOR SEQ ID NO:10:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
( A ) ORGANISM: Bacillus thuringiensis
( B ) STRAIN: AB88

( i x ) FEATURE:
( A ) NAME/KEY: Peptide
( B ) LOCATION: 1..14
( D ) OTHER INFORMATION: /note= "N-terminal amino acid sequence of protein known as anion exchange fraction 23 (smaller)"

( x i ) SEQUENCE DESCRIPTION: SEQ ID NO:10:

Xaa Glu Pro Phe Val Ser Ala Xaa Xaa Xaa Gln Xaa Xaa Xaa
1 5 10

( 2 ) INFORMATION FOR SEQ ID NO:11:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( v i ) ORIGINAL SOURCE:
( A ) ORGANISM: Bacillus thuringiensis ( x i ) SEQUENCE DESCRIPTION: SEQ ID NO:11:

Xaa Glu Tyr Glu Asn Val Glu Pro Phe Val Ser Ala Xaa
1 5 10

( 2 ) INFORMATION FOR SEQ ID NO:12:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( v i ) ORIGINAL SOURCE:
( A ) ORGANISM: Bacillus thurigiensis ( x i ) SEQUENCE DESCRIPTION: SEQ ID NO:12:

Met Asn Lys Asn Asn Thr Lys Leu Pro Thr Arg Ala Leu Pro
1 5 10

( 2 ) INFORMATION FOR SEQ ID NO:13:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Bacillus thuringiensis
        ( B ) STRAIN: AB88

( i x ) FEATURE:
        ( A ) NAME/KEY: Peptide
        ( B ) LOCATION: 1..15
        ( D ) OTHER INFORMATION: /note= "N-terminal amino acid
            sequence of 35 kDa VIP active against Agrotis ipsilon"

( x i ) SEQUENCE DESCRIPTION: SEQ ID NO:13:

```
Ala  Leu  Ser  Glu  Asn  Thr  Gly  Lys  Asp  Gly  Gly  Tyr  Ile  Val  Pro
1                  5                       10                       15
```

( 2 ) INFORMATION FOR SEQ ID NO:14:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( v i ) ORIGINAL SOURCE:
        ( A ) ORGANISM: Bacillus thuringiensis ( x i ) SEQUENCE DESCRIPTION: SEQ ID NO:14:

```
Met  Asp  Asn  Asn  Pro  Asn  Ile  Asn  Glu
1                  5
```

( 2 ) INFORMATION FOR SEQ ID NO:15:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( i x ) FEATURE:
        ( A ) NAME/KEY: Peptide
        ( B ) LOCATION: 1..9
        ( D ) OTHER INFORMATION: /note= "N-terminal sequence of 80
            kDa delta- endotoxin"

( x i ) SEQUENCE DESCRIPTION: SEQ ID NO:15:

```
Met  Asp  Asn  Asn  Pro  Asn  Ile  Asn  Glu
1                  5
```

( 2 ) INFORMATION FOR SEQ ID NO:16:

( i ) SEQUENCE CHARACTERISTICS:
        ( A ) LENGTH: 11 amino acids
        ( B ) TYPE: amino acid ( C ) STRANDEDNESS: single
( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
( A ) ORGANISM: Bacillus thuringiensis ( i x ) FEATURE:
( A ) NAME/KEY: Peptide
( B ) LOCATION: 1..11
( D ) OTHER INFORMATION: /note= "N-terminal sequence from 60 kDa delta- endotoxin"

( x i ) SEQUENCE DESCRIPTION: SEQ ID NO:16:

Met Asn Val Leu Asn Ser Gly Arg Thr Thr Ile
1 5 10

( 2 ) INFORMATION FOR SEQ ID NO:17:

( i ) SEQUENCE CHARACTERISTICS:
( A ) LENGTH: 2655 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
( A ) NAME/KEY: misc_feature
( B ) LOCATION: 1..2652
( D ) OTHER INFORMATION: /note= "Maize optimized DNA sequence for 100 kd VIP1A(a) protein from AB78"

( x i ) SEQUENCE DESCRIPTION: SEQ ID NO:17:

ATGAAGAACA TGAAGAAGAA GCTGGCCAGC GTGGTGACCT GCACCCTGCT GGCCCCCATG 60

TTCCTGAACG GCAACGTGAA CGCCGTGTAC GCCGACAGCA AGACCAACCA GATCAGCACC 120

ACCCAGAAGA ACCAGCAGAA GGAGATGGAC CGCAAGGGCC TGCTGGGCTA CTACTTCAAG 180

GGCAAGGACT TCAGCAACCT GACCATGTTC GCCCCCACGC GTGACAGCAC CCTGATCTAC 240

GACCAGCAGA CCGCCAACAA GCTGCTGGAC AAGAAGCAGC AGGAGTACCA GAGCATCCGC 300

TGGATCGGCC TGATCCAGAG CAAGGAGACC GGCGACTTCA CCTTCAACCT GAGCGAGGAC 360

GAGCAGGCCA TCATCGAGAT CAACGGCAAG ATCATCAGCA ACAAGGGCAA GGAGAAGCAG 420

GTGGTGCACC TGGAGAAGGG CAAGCTGGTG CCCATCAAGA TCGAGTACCA GAGCGACACC 480

AAGTTCAACA TCGACAGCAA GACCTTCAAG GAGCTGAAGC TTTTCAAGAT CGACAGCCAG 540

AACCAGCCCC AGCAGGTGCA GCAGGACGAG CTGCGCAACC CCGAGTTCAA CAAGAAGGAG 600

AGCCAGGAGT TCCTGGCCAA GCCCAGCAAG ATCAACCTGT TCACCCAGCA GATGAAGCGC 660

GAGATCGACG AGGACACCGA CACCGACGGC GACAGCATCC CCGACCTGTG GGAGGAGAAC 720

GGCTACACCA TCCAGAACCG CATCGCCGTG AAGTGGGACG ACAGCCTGGC TAGCAAGGGC 780

TACACCAAGT TCGTGAGCAA CCCCCTGGAG AGCCACACCG TGGGCGACCC CTACACCGAC 840

TACGAGAAGG CCGCCCGCGA CCTGGACCTG AGCAACGCCA AGGAGACCTT CAACCCCCTG 900

GTGGCCGCCT TCCCCAGCGT GAACGTGAGC ATGGAGAAGG TGATCCTGAG CCCCAACGAG 960

AACCTGAGCA ACAGCGTGGA GAGCCACTCG AGCACCAACT GGAGCTACAC CAACACCGAG 1020

| | | | | | | |
|---|---|---|---|---|---|---|
| GGCGCCAGCG | TGGAGGCCGG | CATCGGTCCC | AAGGGCATCA | GCTTCGGCGT | GAGCGTGAAC | 1080 |
| TACCAGCACA | GCGAGACCGT | GGCCCAGGAG | TGGGGCACCA | GCACCGGCAA | CACCAGCCAG | 1140 |
| TTCAACACCG | CCAGCGCCGG | CTACCTGAAC | GCCAACGTGC | GCTACAACAA | CGTGGGCACC | 1200 |
| GGCGCCATCT | ACGACGTGAA | GCCCACCACC | AGCTTCGTGC | TGAACAACGA | CACCATCGCC | 1260 |
| ACCATCACCG | CCAAGTCGAA | TTCCACCGCC | CTGAACATCA | GCCCCGGCGA | GAGCTACCCC | 1320 |
| AAGAAGGGCC | AGAACGGCAT | CGCCATCACC | AGCATGGACG | ACTTCAACAG | CCACCCCATC | 1380 |
| ACCCTGAACA | AGAAGCAGGT | GGACAACCTG | CTGAACAACA | AGCCCATGAT | GCTGGAGACC | 1440 |
| AACCAGACCG | ACGGCGTCTA | CAAGATCAAG | GACACCCACG | GCAACATCGT | GACCGGCGGC | 1500 |
| GAGTGGAACG | GCGTGATCCA | GCAGATCAAG | GCCAAGACCG | CCAGCATCAT | CGTCGACGAC | 1560 |
| GGCGAGCGCG | TGGCCGAGAA | GCGCGTGGCC | GCCAAGGACT | ACGAGAACCC | CGAGGACAAG | 1620 |
| ACCCCCAGCC | TGACCCTGAA | GGACGCCCTG | AAGCTGAGCT | ACCCCGACGA | GATCAAGGAG | 1680 |
| ATCGAGGGCC | TGCTGTACTA | CAAGAACAAG | CCCATCTACG | AGAGCAGCGT | GATGACCTAT | 1740 |
| CTAGACGAGA | ACACCGCCAA | GGAGGTGACC | AAGCAGCTGA | ACGACACCAC | CGGCAAGTTC | 1800 |
| AAGGACGTGA | GCCACCTGTA | CGACGTGAAG | CTGACCCCCA | AGATGAACGT | GACCATCAAG | 1860 |
| CTGAGCATCC | TGTACGACAA | CGCCGAGAGC | AACGACAACA | GCATCGGCAA | GTGGACCAAC | 1920 |
| ACCAACATCG | TGAGCGGCGG | CAACAACGGC | AAGAAGCAGT | ACAGCAGCAA | CAACCCCGAC | 1980 |
| GCCAACCTGA | CCCTGAACAC | CGACGCCCAG | GAGAAGCTGA | ACAAGAACCG | CGACTACTAC | 2040 |
| ATCAGCCTGT | ACATGAAGAG | CGAGAAGAAC | ACCCAGTGCG | AGATCACCAT | CGACGGCGAG | 2100 |
| ATATACCCCA | TCACCACCAA | GACCGTGAAC | GTGAACAAGG | ACAACTACAA | GCGCCTGGAC | 2160 |
| ATCATCGCCC | ACAACATCAA | GAGCAACCCC | ATCAGCAGCC | TGCACATCAA | GACCAACGAC | 2220 |
| GAGATCACCC | TGTTCTGGGA | CGACATATCG | ATTACCGACG | TCGCCAGCAT | CAAGCCCGAG | 2280 |
| AACCTGACCG | ACAGCGAGAT | CAAGCAGATA | TACAGTCGCT | ACGGCATCAA | GCTGGAGGAC | 2340 |
| GGCATCCTGA | TCGACAAGAA | GGGCGGCATC | CACTACGGCG | AGTTCATCAA | CGAGGCCAGC | 2400 |
| TTCAACATCG | AGCCCCTGCA | GAACTACGTG | ACCAAGTACG | AGGTGACCTA | CAGCAGCGAG | 2460 |
| CTGGGCCCCA | ACGTGAGCGA | CACCCTGGAG | AGCGACAAGA | TTTACAAGGA | CGGCACCATC | 2520 |
| AAGTTCGACT | TCACCAAGTA | CAGCAAGAAC | GAGCAGGGCC | TGTTCTACGA | CAGCGGCCTG | 2580 |
| AACTGGGACT | TCAAGATCAA | CGCCATCACC | TACGACGGCA | AGGAGATGAA | CGTGTTCCAC | 2640 |
| CGCTACAACA | AGTAG | | | | | 2655 |

( 2 ) INFORMATION FOR SEQ ID NO:18:

( i ) SEQUENCE CHARACTERISTICS:
    ( A ) LENGTH: 2004 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: misc_feature
    ( B ) LOCATION: 1..2004
    ( D ) OTHER INFORMATION: /note= "Maize optimized DNA
      sequence for VIP1A(a) 80 kd protein from AB78"

( x i ) SEQUENCE DESCRIPTION: SEQ ID NO:18:

| | | | | | | |
|---|---|---|---|---|---|---|
| ATGAAGCGCG | AGATCGACGA | GGACACCGAC | ACCGACGGCG | ACAGCATCCC | CGACCTGTGG | 60 |

```
GAGGAGAACG GCTACACCAT CCAGAACCGC ATCGCCGTGA AGTGGGACGA CAGCCTGGCT    120
AGCAAGGGCT ACACCAAGTT CGTGAGCAAC CCCCTGGAGA GCCACACCGT GGGCGACCCC    180
TACACCGACT ACGAGAAGGC CGCCCGCGAC CTGGACCTGA GCAACGCCAA GGAGACCTTC    240
AACCCCCTGG TGGCCGCCTT CCCCAGCGTG AACGTGAGCA TGGAGAAGGT GATCCTGAGC    300
CCCAACGAGA ACCTGAGCAA CAGCGTGGAG AGCCACTCGA GCACCAACTG GAGCTACACC    360
AACACCGAGG GCGCCAGCGT GGAGGCCGGC ATCGGTCCCA AGGGCATCAG CTTCGGCGTG    420
AGCGTGAACT ACCAGCACAG CGAGACCGTG GCCCAGGAGT GGGGCACCAG CACCGGCAAC    480
ACCAGCCAGT TCAACACCGC CAGCGCCGGC TACCTGAACG CCAACGTGCG CTACAACAAC    540
GTGGGCACCG GCGCCATCTA CGACGTGAAG CCCACCACCA GCTTCGTGCT GAACAACGAC    600
ACCATCGCCA CCATCACCGC CAAGTCGAAT TCCACCGCCC TGAACATCAG CCCCGGCGAG    660
AGCTACCCCA AGAAGGGCCA GAACGGCATC GCCATCACCA GCATGGACGA CTTCAACAGC    720
CACCCCATCA CCCTGAACAA GAAGCAGGTG GACAACCTGC TGAACAACAA GCCCATGATG    780
CTGGAGACCA ACCAGACCGA CGGCGTCTAC AAGATCAAGG ACACCCACGG CAACATCGTG    840
ACCGGCGGCG AGTGGAACGG CGTGATCCAG CAGATCAAGG CCAAGACCGC CAGCATCATC    900
GTCGACGACG GCGAGCGCGT GGCCGAGAAG CGCGTGGCCG CCAAGGACTA CGAGAACCCC    960
GAGGACAAGA CCCCCAGCCT GACCCTGAAG GACGCCCTGA AGCTGAGCTA CCCCGACGAG   1020
ATCAAGGAGA TCGAGGGCCT GCTGTACTAC AAGAACAAGC CCATCTACGA GAGCAGCGTG   1080
ATGACCTATC TAGACGAGAA CACCGCCAAG GAGGTGACCA AGCAGCTGAA CGACACCACC   1140
GGCAAGTTCA AGGACGTGAG CCACCTGTAC GACGTGAAGC TGACCCCCAA GATGAACGTG   1200
ACCATCAAGC TGAGCATCCT GTACGACAAC GCCGAGAGCA ACGACAACAG CATCGGCAAG   1260
TGGACCAACA CCAACATCGT GAGCGGCGGC AACAACGGCA AGAAGCAGTA CAGCAGCAAC   1320
AACCCCGACG CCAACCTGAC CCTGAACACC GACGCCCAGG AGAAGCTGAA CAAGAACCGC   1380
GACTACTACA TCAGCCTGTA CATGAAGAGC GAGAAGAACA CCCAGTGCGA GATCACCATC   1440
GACGGCGAGA TATACCCCAT CACCACCAAG ACCGTGAACG TGAACAAGGA CAACTACAAG   1500
CGCCTGGACA TCATCGCCCA CAACATCAAG AGCAACCCCA TCAGCAGCCT GCACATCAAG   1560
ACCAACGACG AGATCACCCT GTTCTGGGAC GACATATCGA TTACCGACGT CGCCAGCATC   1620
AAGCCCGAGA ACCTGACCGA CAGCGAGATC AAGCAGATAT ACAGTCGCTA CGGCATCAAG   1680
CTGGAGGACG GCATCCTGAT CGACAAGAAG GGCGGCATCC ACTACGGCGA GTTCATCAAC   1740
GAGGCCAGCT TCAACATCGA GCCCCTGCAG AACTACGTGA CCAAGTACGA GGTGACCTAC   1800
AGCAGCGAGC TGGGCCCCAA CGTGAGCGAC ACCCTGGAGA GCGACAAGAT TTACAAGGAC   1860
GGCACCATCA AGTTCGACTT CACCAAGTAC AGCAAGAACG AGCAGGGCCT GTTCTACGAC   1920
AGCGGCCTGA ACTGGGACTT CAAGATCAAC GCCATCACCT ACGACGGCAA GGAGATGAAC   1980
GTGTTCCACC GCTACAACAA GTAG                                         2004
```

( 2 ) INFORMATION FOR SEQ ID NO:19:

( i ) SEQUENCE CHARACTERISTICS:
        ( A ) LENGTH: 4074 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS ( B ) LOCATION: 1..1386
( D ) OTHER INFORMATION: /product="VIP2A(b) from Btt"

( i x ) FEATURE:
( A ) NAME/KEY: CDS
( B ) LOCATION: 1394..3895
( D ) OTHER INFORMATION: /product="VIP1A(b) from Btt"

( i x ) FEATURE:
( A ) NAME/KEY: misc_feature
( B ) LOCATION: 1..4074
( D ) OTHER INFORMATION: /note= "Cloned DNA sequence from Btt which contains the genes for both VIP1A(b) and VIP2A(b)"

( x i ) SEQUENCE DESCRIPTION: SEQ ID NO:19:

| ATG | CAA | AGA | ATG | GAG | GGA | AAG | TTG | TTT | GTG | GTG | TCA | AAA | ACA | TTA | CAA | 48 |
|---|---|---|---|---|---|---|---|---|---|---|---|---|---|---|---|---|
| Met | Gln | Arg | Met | Glu | Gly | Lys | Leu | Phe | Val | Val | Ser | Lys | Thr | Leu | Gln | |
| | | 670 | | | | 675 | | | | | 680 | | | | | |

| GTA | GTT | ACT | AGA | ACT | GTA | TTG | CTT | AGT | ACA | GTT | TAC | TCT | ATA | ACT | TTA | 96 |
|---|---|---|---|---|---|---|---|---|---|---|---|---|---|---|---|---|
| Val | Val | Thr | Arg | Thr | Val | Leu | Leu | Ser | Thr | Val | Tyr | Ser | Ile | Thr | Leu | |
| | | 685 | | | | 690 | | | | | 695 | | | | | |

| TTA | AAT | AAT | GTA | GTG | ATA | AAA | GCT | GAC | CAA | TTA | AAT | ATA | AAT | TCT | CAA | 144 |
|---|---|---|---|---|---|---|---|---|---|---|---|---|---|---|---|---|
| Leu | Asn | Asn | Val | Val | Ile | Lys | Ala | Asp | Gln | Leu | Asn | Ile | Asn | Ser | Gln | |
| 700 | | | | | 705 | | | | | 710 | | | | | 715 | |

| AGT | AAA | TAT | ACT | AAC | TTG | CAA | AAT | CTA | AAA | ATC | CCT | GAT | AAT | GCA | GAG | 192 |
|---|---|---|---|---|---|---|---|---|---|---|---|---|---|---|---|---|
| Ser | Lys | Tyr | Thr | Asn | Leu | Gln | Asn | Leu | Lys | Ile | Pro | Asp | Asn | Ala | Glu | |
| | | | | 720 | | | | | 725 | | | | | 730 | | |

| GAT | TTT | AAA | GAA | GAT | AAG | GGG | AAA | GCG | AAA | GAA | TGG | GGG | AAA | GAG | AAA | 240 |
|---|---|---|---|---|---|---|---|---|---|---|---|---|---|---|---|---|
| Asp | Phe | Lys | Glu | Asp | Lys | Gly | Lys | Ala | Lys | Glu | Trp | Gly | Lys | Glu | Lys | |
| | | | 735 | | | | | 740 | | | | | 745 | | | |

| GGG | GAA | GAG | TGG | AGG | CCT | CCT | GCT | ACT | GAG | AAA | GGA | GAA | ATG | AAT | AAT | 288 |
|---|---|---|---|---|---|---|---|---|---|---|---|---|---|---|---|---|
| Gly | Glu | Glu | Trp | Arg | Pro | Pro | Ala | Thr | Glu | Lys | Gly | Glu | Met | Asn | Asn | |
| | | 750 | | | | | 755 | | | | | 760 | | | | |

| TTT | TTA | GAT | AAT | AAA | AAT | GAT | ATA | AAG | ACC | AAT | TAT | AAA | GAA | ATT | ACT | 336 |
|---|---|---|---|---|---|---|---|---|---|---|---|---|---|---|---|---|
| Phe | Leu | Asp | Asn | Lys | Asn | Asp | Ile | Lys | Thr | Asn | Tyr | Lys | Glu | Ile | Thr | |
| | 765 | | | | | 770 | | | | | 775 | | | | | |

| TTT | TCT | ATG | GCA | GGT | TCA | TGT | GAA | GAT | GAA | ATA | AAA | GAT | TTA | GAA | GAA | 384 |
|---|---|---|---|---|---|---|---|---|---|---|---|---|---|---|---|---|
| Phe | Ser | Met | Ala | Gly | Ser | Cys | Glu | Asp | Glu | Ile | Lys | Asp | Leu | Glu | Glu | |
| 780 | | | | | 785 | | | | | 790 | | | | | 795 | |

| ATT | GAT | AAG | ATC | TTT | GAT | AAA | GCC | AAT | CTC | TCG | AGT | TCT | ATT | ATC | ACC | 432 |
|---|---|---|---|---|---|---|---|---|---|---|---|---|---|---|---|---|
| Ile | Asp | Lys | Ile | Phe | Asp | Lys | Ala | Asn | Leu | Ser | Ser | Ser | Ile | Ile | Thr | |
| | | | | 800 | | | | | 805 | | | | | 810 | | |

| TAT | AAA | AAT | GTG | GAA | CCA | GCA | ACA | ATT | GGA | TTT | AAT | AAA | TCT | TTA | ACA | 480 |
|---|---|---|---|---|---|---|---|---|---|---|---|---|---|---|---|---|
| Tyr | Lys | Asn | Val | Glu | Pro | Ala | Thr | Ile | Gly | Phe | Asn | Lys | Ser | Leu | Thr | |
| | | | 815 | | | | | 820 | | | | | 825 | | | |

| GAA | GGT | AAT | ACG | ATT | AAT | TCT | GAT | GCA | ATG | GCA | CAG | TTT | AAA | GAA | CAA | 528 |
|---|---|---|---|---|---|---|---|---|---|---|---|---|---|---|---|---|
| Glu | Gly | Asn | Thr | Ile | Asn | Ser | Asp | Ala | Met | Ala | Gln | Phe | Lys | Glu | Gln | |
| | | 830 | | | | | 835 | | | | | 840 | | | | |

| TTT | TTA | GGT | AAG | GAT | ATG | AAG | TTT | GAT | AGT | TAT | CTA | GAT | ACT | CAT | TTA | 576 |
|---|---|---|---|---|---|---|---|---|---|---|---|---|---|---|---|---|
| Phe | Leu | Gly | Lys | Asp | Met | Lys | Phe | Asp | Ser | Tyr | Leu | Asp | Thr | His | Leu | |
| | 845 | | | | | 850 | | | | | 855 | | | | | |

| ACT | GCT | CAA | CAA | GTT | TCC | AGT | AAA | AAA | AGA | GTT | ATT | TTG | AAG | GTT | ACG | 624 |
|---|---|---|---|---|---|---|---|---|---|---|---|---|---|---|---|---|
| Thr | Ala | Gln | Gln | Val | Ser | Ser | Lys | Lys | Arg | Val | Ile | Leu | Lys | Val | Thr | |
| 860 | | | | | 865 | | | | | 870 | | | | | 875 | |

| GTT | CCG | AGT | GGG | AAA | GGT | TCT | ACT | ACT | CCA | ACA | AAA | GCA | GGT | GTC | ATT | 672 |
|---|---|---|---|---|---|---|---|---|---|---|---|---|---|---|---|---|
| Val | Pro | Ser | Gly | Lys | Gly | Ser | Thr | Thr | Pro | Thr | Lys | Ala | Gly | Val | Ile | |
| | | | | 880 | | | | | 885 | | | | | 890 | | |

| TTA | AAC | AAT | AAT | GAA | TAC | AAA | ATG | CTC | ATT | GAT | AAT | GGG | TAT | GTG | CTC | 720 |
|---|---|---|---|---|---|---|---|---|---|---|---|---|---|---|---|---|
| Leu | Asn | Asn | Asn | Glu | Tyr | Lys | Met | Leu | Ile | Asp | Asn | Gly | Tyr | Val | Leu | |
| | | | 895 | | | | | 900 | | | | | 905 | | | |

| CAT | GTA | GAT | AAG | GTA | TCA | AAA | GTA | GTA | AAA | AAA | GGG | ATG | GAG | TGC | TTA | 768 |
|---|---|---|---|---|---|---|---|---|---|---|---|---|---|---|---|---|
| His | Val | Asp | Lys | Val | Ser | Lys | Val | Val | Lys | Lys | Gly | Met | Glu | Cys | Leu | |
| | | 910 | | | | | 915 | | | | | 920 | | | | |

| | | | | | | | | | | | | | | | | |
|---|---|---|---|---|---|---|---|---|---|---|---|---|---|---|---|---|
|CAA|GTT|GAA|GGG|ACT|TTA|AAA|AAG|AGT|CTC|GAC|TTT|AAA|AAT|GAT|ATA|816|
|Gln|Val|Glu|Gly|Thr|Leu|Lys|Lys|Ser|Leu|Asp|Phe|Lys|Asn|Asp|Ile| |
| |925| | | |930| | | |935| | | | | | | |

|AAT|GCT|GAA|GCG|CAT|AGC|TGG|GGG|ATG|AAA|ATT|TAT|GAA|GAC|TGG|GCT|864|
|---|---|---|---|---|---|---|---|---|---|---|---|---|---|---|---|---|
|Asn|Ala|Glu|Ala|His|Ser|Trp|Gly|Met|Lys|Ile|Tyr|Glu|Asp|Trp|Ala| |
|940| | | | |945| | | |950| | | | | |955| |

|AAA|AAT|TTA|ACC|GCT|TCG|CAA|AGG|GAA|GCT|TTA|GAT|GGG|TAT|GCT|AGG|912|
|---|---|---|---|---|---|---|---|---|---|---|---|---|---|---|---|---|
|Lys|Asn|Leu|Thr|Ala|Ser|Gln|Arg|Glu|Ala|Leu|Asp|Gly|Tyr|Ala|Arg| |
| | | | |960| | | | |965| | | | |970| | |

|CAA|GAT|TAT|AAA|GAA|ATC|AAT|AAT|TAT|TTG|CGC|AAT|CAA|GGC|GGG|AGT|960|
|---|---|---|---|---|---|---|---|---|---|---|---|---|---|---|---|---|
|Gln|Asp|Tyr|Lys|Glu|Ile|Asn|Asn|Tyr|Leu|Arg|Asn|Gln|Gly|Gly|Ser| |
| | | |975| | | | |980| | | | |985| | | |

|GGA|AAT|GAA|AAG|CTG|GAT|GCC|CAA|TTA|AAA|AAT|ATT|TCT|GAT|GCT|TTA|1008|
|---|---|---|---|---|---|---|---|---|---|---|---|---|---|---|---|---|
|Gly|Asn|Glu|Lys|Leu|Asp|Ala|Gln|Leu|Lys|Asn|Ile|Ser|Asp|Ala|Leu| |
| | |990| | | |995| | | | |1000| | | | | |

|GGG|AAG|AAA|CCC|ATA|CCA|GAA|AAT|ATT|ACC|GTG|TAT|AGA|TGG|TGT|GGC|1056|
|---|---|---|---|---|---|---|---|---|---|---|---|---|---|---|---|---|
|Gly|Lys|Lys|Pro|Ile|Pro|Glu|Asn|Ile|Thr|Val|Tyr|Arg|Trp|Cys|Gly| |
| |1005| | | | |1010| | | | |1015| | | | | |

|ATG|CCG|GAA|TTT|GGT|TAT|CAA|ATT|AGT|GAT|CCG|TTA|CCT|TCT|TTA|AAA|1104|
|---|---|---|---|---|---|---|---|---|---|---|---|---|---|---|---|---|
|Met|Pro|Glu|Phe|Gly|Tyr|Gln|Ile|Ser|Asp|Pro|Leu|Pro|Ser|Leu|Lys| |
|1020| | | | |1025| | | | |1030| | | | |1035| |

|GAT|TTT|GAA|GAA|CAA|TTT|TTA|AAT|ACA|ATT|AAA|GAA|GAC|AAA|GGG|TAT|1152|
|---|---|---|---|---|---|---|---|---|---|---|---|---|---|---|---|---|
|Asp|Phe|Glu|Glu|Gln|Phe|Leu|Asn|Thr|Ile|Lys|Glu|Asp|Lys|Gly|Tyr| |
| | | | |1040| | | | |1045| | | | |1050| | |

|ATG|AGT|ACA|AGC|TTA|TCG|AGT|GAA|CGT|CTT|GCA|GCT|TTT|GGA|TCT|AGA|1200|
|---|---|---|---|---|---|---|---|---|---|---|---|---|---|---|---|---|
|Met|Ser|Thr|Ser|Leu|Ser|Ser|Glu|Arg|Leu|Ala|Ala|Phe|Gly|Ser|Arg| |
| | | |1055| | | | |1060| | | | |1065| | | |

|AAA|ATT|ATA|TTA|CGC|TTA|CAA|GTT|CCG|AAA|GGA|AGT|ACG|GGG|GCG|TAT|1248|
|---|---|---|---|---|---|---|---|---|---|---|---|---|---|---|---|---|
|Lys|Ile|Ile|Leu|Arg|Leu|Gln|Val|Pro|Lys|Gly|Ser|Thr|Gly|Ala|Tyr| |
| | |1070| | | | |1075| | | | |1080| | | | |

|TTA|AGT|GCC|ATT|GGT|GGA|TTT|GCA|AGT|GAA|AAA|GAG|ATC|CTA|CTT|GAT|1296|
|---|---|---|---|---|---|---|---|---|---|---|---|---|---|---|---|---|
|Leu|Ser|Ala|Ile|Gly|Gly|Phe|Ala|Ser|Glu|Lys|Glu|Ile|Leu|Leu|Asp| |
| |1085| | | | |1090| | | | |1095| | | | | |

|AAA|GAT|AGT|AAA|TAT|CAT|ATT|GAT|AAA|GCA|ACA|GAG|GTA|ATC|ATT|AAA|1344|
|---|---|---|---|---|---|---|---|---|---|---|---|---|---|---|---|---|
|Lys|Asp|Ser|Lys|Tyr|His|Ile|Asp|Lys|Ala|Thr|Glu|Val|Ile|Ile|Lys| |
|1100| | | | |1105| | | | |1110| | | | |1115| |

|GGT|GTT|AAG|CGA|TAT|GTA|GTG|GAT|GCA|ACA|TTA|TTA|ACA|AAT| | |1386|
|---|---|---|---|---|---|---|---|---|---|---|---|---|---|---|---|---|
|Gly|Val|Lys|Arg|Tyr|Val|Val|Asp|Ala|Thr|Leu|Leu|Thr|Asn| | | |
| | | |1120| | | | |1125| | | | | | | | |

|TAAGGAG|ATG|AAA|AAT|ATG|AAG|AAA|AAG|TTA|GCA|AGT|GTT|GTA|ACC|TGT|1435|
|---|---|---|---|---|---|---|---|---|---|---|---|---|---|---|---|
| |Met|Lys|Asn|Met|Lys|Lys|Lys|Leu|Ala|Ser|Val|Val|Thr|Cys| |
| |1| | | |5| | | | |10| | | | | |

|ATG|TTA|TTA|GCT|CCT|ATG|TTT|TTG|AAT|GGA|AAT|GTG|AAT|GCT|GTT|AAC|1483|
|---|---|---|---|---|---|---|---|---|---|---|---|---|---|---|---|---|
|Met|Leu|Leu|Ala|Pro|Met|Phe|Leu|Asn|Gly|Asn|Val|Asn|Ala|Val|Asn| |
|15| | | | |20| | | | |25| | | | |30| |

|GCG|GAT|AGT|AAA|ATA|AAT|CAG|ATT|TCT|ACA|ACG|CAG|GAA|AAC|CAA|CAG|1531|
|---|---|---|---|---|---|---|---|---|---|---|---|---|---|---|---|---|
|Ala|Asp|Ser|Lys|Ile|Asn|Gln|Ile|Ser|Thr|Thr|Gln|Glu|Asn|Gln|Gln| |
| | | |35| | | | |40| | | | |45| | | |

|AAA|GAG|ATG|GAC|CGA|AAG|GGA|TTA|TTG|GGA|TAT|TAT|TTC|AAA|GGA|AAA|1579|
|---|---|---|---|---|---|---|---|---|---|---|---|---|---|---|---|---|
|Lys|Glu|Met|Asp|Arg|Lys|Gly|Leu|Leu|Gly|Tyr|Tyr|Phe|Lys|Gly|Lys| |
| | | |50| | | | |55| | | | |60| | | |

|GAT|TTT|AAT|AAT|CTT|ACT|ATG|TTT|GCA|CCG|ACA|CGT|GAT|AAT|ACC|CTT|1627|
|---|---|---|---|---|---|---|---|---|---|---|---|---|---|---|---|---|
|Asp|Phe|Asn|Asn|Leu|Thr|Met|Phe|Ala|Pro|Thr|Arg|Asp|Asn|Thr|Leu| |
| | |65| | | | |70| | | | |75| | | | |

|ATG|TAT|GAC|CAA|CAA|ACA|GCG|AAT|GCA|TTA|TTA|GAT|AAA|AAA|CAA|CAA|1675|
|---|---|---|---|---|---|---|---|---|---|---|---|---|---|---|---|---|
|Met|Tyr|Asp|Gln|Gln|Thr|Ala|Asn|Ala|Leu|Leu|Asp|Lys|Lys|Gln|Gln| |
| |80| | | | |85| | | | |90| | | | | |

|GAA|TAT|CAG|TCC|ATT|CGT|TGG|ATT|GGT|TTG|ATT|CAG|CGT|AAA|GAA|ACG|1723|
|---|---|---|---|---|---|---|---|---|---|---|---|---|---|---|---|---|
|Glu|Tyr|Gln|Ser|Ile|Arg|Trp|Ile|Gly|Leu|Ile|Gln|Arg|Lys|Glu|Thr| |
|95| | | | |100| | | | |105| | | | |110| |

| | | | | | | | | | | | | | | | | |
|---|---|---|---|---|---|---|---|---|---|---|---|---|---|---|---|---|
| GGC | GAT | TTC | ACA | TTT | AAC | TTA | TCA | AAG | GAT | GAA | CAG | GCA | ATT | ATA | GAA | 1771 |
| Gly | Asp | Phe | Thr | Phe | Asn | Leu | Ser | Lys | Asp | Glu | Gln | Ala | Ile | Ile | Glu | |
| | | | | 115 | | | | 120 | | | | | | 125 | | |
| ATC | GAT | GGG | AAA | ATC | ATT | TCT | AAT | AAA | GGG | AAA | GAA | AAG | CAA | GTT | GTC | 1819 |
| Ile | Asp | Gly | Lys | Ile | Ile | Ser | Asn | Lys | Gly | Lys | Glu | Lys | Gln | Val | Val | |
| | | | 130 | | | | | 135 | | | | | 140 | | | |
| CAT | TTA | GAA | AAA | GAA | AAA | TTA | GTT | CCA | ATC | AAA | ATA | GAG | TAT | CAA | TCA | 1867 |
| His | Leu | Glu | Lys | Glu | Lys | Leu | Val | Pro | Ile | Lys | Ile | Glu | Tyr | Gln | Ser | |
| | | | 145 | | | | | 150 | | | | | 155 | | | |
| GAT | ACG | AAA | TTT | AAT | ATT | GAT | AGT | AAA | ACA | TTT | AAA | GAA | CTT | AAA | TTA | 1915 |
| Asp | Thr | Lys | Phe | Asn | Ile | Asp | Ser | Lys | Thr | Phe | Lys | Glu | Leu | Lys | Leu | |
| | | 160 | | | | | 165 | | | | | 170 | | | | |
| TTT | AAA | ATA | GAT | AGT | CAA | AAC | CAA | TCT | CAA | CAA | GTT | CAA | CTG | AGA | AAC | 1963 |
| Phe | Lys | Ile | Asp | Ser | Gln | Asn | Gln | Ser | Gln | Gln | Val | Gln | Leu | Arg | Asn | |
| 175 | | | | | 180 | | | | | 185 | | | | | 190 | |
| CCT | GAA | TTT | AAC | AAA | AAA | GAA | TCA | CAG | GAA | TTT | TTA | GCA | AAA | GCA | TCA | 2011 |
| Pro | Glu | Phe | Asn | Lys | Lys | Glu | Ser | Gln | Glu | Phe | Leu | Ala | Lys | Ala | Ser | |
| | | | | 195 | | | | | 200 | | | | | 205 | | |
| AAA | ACA | AAC | CTT | TTT | AAG | CAA | AAA | ATG | AAA | AGA | GAT | ATT | GAT | GAA | GAT | 2059 |
| Lys | Thr | Asn | Leu | Phe | Lys | Gln | Lys | Met | Lys | Arg | Asp | Ile | Asp | Glu | Asp | |
| | | | 210 | | | | | 215 | | | | | 220 | | | |
| ACG | GAT | ACA | GAT | GGA | GAC | TCC | ATT | CCT | GAT | CTT | TGG | GAA | GAA | AAT | GGG | 2107 |
| Thr | Asp | Thr | Asp | Gly | Asp | Ser | Ile | Pro | Asp | Leu | Trp | Glu | Glu | Asn | Gly | |
| | | 225 | | | | | 230 | | | | | 235 | | | | |
| TAC | ACG | ATT | CAA | AAT | AAA | GTT | GCT | GTC | AAA | TGG | GAT | GAT | TCG | CTA | GCA | 2155 |
| Tyr | Thr | Ile | Gln | Asn | Lys | Val | Ala | Val | Lys | Trp | Asp | Asp | Ser | Leu | Ala | |
| | | 240 | | | | | 245 | | | | | 250 | | | | |
| AGT | AAG | GGA | TAT | ACA | AAA | TTT | GTT | TCG | AAT | CCA | TTA | GAC | AGC | CAC | ACA | 2203 |
| Ser | Lys | Gly | Tyr | Thr | Lys | Phe | Val | Ser | Asn | Pro | Leu | Asp | Ser | His | Thr | |
| 255 | | | | | 260 | | | | | 265 | | | | | 270 | |
| GTT | GGC | GAT | CCC | TAT | ACT | GAT | TAT | GAA | AAG | GCC | GCA | AGG | GAT | TTA | GAT | 2251 |
| Val | Gly | Asp | Pro | Tyr | Thr | Asp | Tyr | Glu | Lys | Ala | Ala | Arg | Asp | Leu | Asp | |
| | | | | 275 | | | | | 280 | | | | | 285 | | |
| TTA | TCA | AAT | GCA | AAG | GAA | ACG | TTC | AAC | CCA | TTG | GTA | GCT | GCT | TTT | CCA | 2299 |
| Leu | Ser | Asn | Ala | Lys | Glu | Thr | Phe | Asn | Pro | Leu | Val | Ala | Ala | Phe | Pro | |
| | | | 290 | | | | | 295 | | | | | 300 | | | |
| AGT | GTG | AAT | GTT | AGT | ATG | GAA | AAG | GTG | ATA | TTA | TCA | CCA | AAT | GAA | AAT | 2347 |
| Ser | Val | Asn | Val | Ser | Met | Glu | Lys | Val | Ile | Leu | Ser | Pro | Asn | Glu | Asn | |
| | | 305 | | | | | 310 | | | | | 315 | | | | |
| TTA | TCC | AAT | AGT | GTA | GAG | TCT | CAT | TCA | TCC | ACG | AAT | TGG | TCT | TAT | ACG | 2395 |
| Leu | Ser | Asn | Ser | Val | Glu | Ser | His | Ser | Ser | Thr | Asn | Trp | Ser | Tyr | Thr | |
| | 320 | | | | | 325 | | | | | 330 | | | | | |
| AAT | ACA | GAA | GGA | GCT | TCC | ATT | GAA | GCT | GGT | GGC | GGT | CCA | TTA | GGC | CTT | 2443 |
| Asn | Thr | Glu | Gly | Ala | Ser | Ile | Glu | Ala | Gly | Gly | Gly | Pro | Leu | Gly | Leu | |
| 335 | | | | | 340 | | | | | 345 | | | | | 350 | |
| TCT | TTT | GGC | GTG | AGT | GTT | ACT | TAT | CAA | CAC | TCT | GAA | ACA | GTT | GCA | CAA | 2491 |
| Ser | Phe | Gly | Val | Ser | Val | Thr | Tyr | Gln | His | Ser | Glu | Thr | Val | Ala | Gln | |
| | | | | 355 | | | | | 360 | | | | | 365 | | |
| GAA | TGG | GGA | ACA | TCT | ACA | GGA | AAT | ACT | TCA | CAA | TTC | AAT | ACG | GCT | TCA | 2539 |
| Glu | Trp | Gly | Thr | Ser | Thr | Gly | Asn | Thr | Ser | Gln | Phe | Asn | Thr | Ala | Ser | |
| | | | 370 | | | | | 375 | | | | | 380 | | | |
| GCG | GGA | TAT | TTA | AAT | GCA | AAT | GTT | CGG | TAT | AAC | AAT | GTA | GGG | ACT | GGT | 2587 |
| Ala | Gly | Tyr | Leu | Asn | Ala | Asn | Val | Arg | Tyr | Asn | Asn | Val | Gly | Thr | Gly | |
| | | 385 | | | | | 390 | | | | | 395 | | | | |
| GCC | ATC | TAT | GAT | GTA | AAA | CCT | ACA | ACA | AGT | TTT | GTA | TTA | AAT | AAC | AAT | 2635 |
| Ala | Ile | Tyr | Asp | Val | Lys | Pro | Thr | Thr | Ser | Phe | Val | Leu | Asn | Asn | Asn | |
| | | 400 | | | | | 405 | | | | | 410 | | | | |
| ACC | ATC | GCA | ACG | ATT | ACA | GCA | AAA | TCA | AAT | TCA | ACA | GCT | TTA | CGT | ATA | 2683 |
| Thr | Ile | Ala | Thr | Ile | Thr | Ala | Lys | Ser | Asn | Ser | Thr | Ala | Leu | Arg | Ile | |
| 415 | | | | | 420 | | | | | 425 | | | | | 430 | |

| | | | | | | | | | | | | | | | | |
|---|---|---|---|---|---|---|---|---|---|---|---|---|---|---|---|---|
| TCT | CCG | GGG | GAT | AGT | TAT | CCA | GAA | ATA | GGA | GAA | AAC | GCT | ATT | GCG | ATT | 2731 |
| Ser | Pro | Gly | Asp | Ser | Tyr | Pro | Glu | Ile | Gly | Glu | Asn | Ala | Ile | Ala | Ile | |
| | | | | 435 | | | | 440 | | | | | | 445 | | |
| ACA | TCT | ATG | GAT | GAT | TTT | AAT | TCT | CAT | CCA | ATT | ACA | TTA | AAT | AAA | CAA | 2779 |
| Thr | Ser | Met | Asp | Asp | Phe | Asn | Ser | His | Pro | Ile | Thr | Leu | Asn | Lys | Gln | |
| | | | 450 | | | | | 455 | | | | | 460 | | | |
| CAG | GTA | AAT | CAA | TTG | ATA | AAT | AAT | AAG | CCA | ATT | ATG | CTA | GAG | ACA | GAC | 2827 |
| Gln | Val | Asn | Gln | Leu | Ile | Asn | Asn | Lys | Pro | Ile | Met | Leu | Glu | Thr | Asp | |
| | | | 465 | | | | | 470 | | | | | 475 | | | |
| CAA | ACA | GAT | GGT | GTT | TAT | AAA | ATA | AGA | GAT | ACA | CAT | GGA | AAT | ATT | GTA | 2875 |
| Gln | Thr | Asp | Gly | Val | Tyr | Lys | Ile | Arg | Asp | Thr | His | Gly | Asn | Ile | Val | |
| | | 480 | | | | | 485 | | | | | 490 | | | | |
| ACT | GGT | GGA | GAA | TGG | AAT | GGT | GTA | ACA | CAA | CAA | ATT | AAA | GCA | AAA | ACA | 2923 |
| Thr | Gly | Gly | Glu | Trp | Asn | Gly | Val | Thr | Gln | Gln | Ile | Lys | Ala | Lys | Thr | |
| 495 | | | | | 500 | | | | | 505 | | | | | 510 | |
| GCG | TCT | ATT | ATT | GTG | GAT | GAC | GGG | AAA | CAG | GTA | GCA | GAA | AAA | CGT | GTG | 2971 |
| Ala | Ser | Ile | Ile | Val | Asp | Asp | Gly | Lys | Gln | Val | Ala | Glu | Lys | Arg | Val | |
| | | | | 515 | | | | | 520 | | | | | 525 | | |
| GCG | GCA | AAA | GAT | TAT | GGT | CAT | CCA | GAA | GAT | AAA | ACA | CCA | CCT | TTA | ACT | 3019 |
| Ala | Ala | Lys | Asp | Tyr | Gly | His | Pro | Glu | Asp | Lys | Thr | Pro | Pro | Leu | Thr | |
| | | | 530 | | | | | 535 | | | | | 540 | | | |
| TTA | AAA | GAT | ACC | CTG | AAG | CTT | TCA | TAC | CCA | GAT | GAA | ATA | AAA | GAA | ACT | 3067 |
| Leu | Lys | Asp | Thr | Leu | Lys | Leu | Ser | Tyr | Pro | Asp | Glu | Ile | Lys | Glu | Thr | |
| | | 545 | | | | | 550 | | | | | 555 | | | | |
| AAT | GGA | TTG | TTG | TAC | TAT | GAT | GAC | AAA | CCA | ATC | TAT | GAA | TCG | AGT | GTC | 3115 |
| Asn | Gly | Leu | Leu | Tyr | Tyr | Asp | Asp | Lys | Pro | Ile | Tyr | Glu | Ser | Ser | Val | |
| | 560 | | | | | 565 | | | | | 570 | | | | | |
| ATG | ACT | TAT | CTG | GAT | GAA | AAT | ACG | GCA | AAA | GAA | GTC | AAA | AAA | CAA | ATA | 3163 |
| Met | Thr | Tyr | Leu | Asp | Glu | Asn | Thr | Ala | Lys | Glu | Val | Lys | Lys | Gln | Ile | |
| 575 | | | | | 580 | | | | | 585 | | | | | 590 | |
| AAT | GAT | ACA | ACC | GGA | AAA | TTT | AAG | GAT | GTA | AAT | CAC | TTA | TAT | GAT | GTA | 3211 |
| Asn | Asp | Thr | Thr | Gly | Lys | Phe | Lys | Asp | Val | Asn | His | Leu | Tyr | Asp | Val | |
| | | | | 595 | | | | | 600 | | | | | 605 | | |
| AAA | CTG | ACT | CCA | AAA | ATG | AAT | TTT | ACG | ATT | AAA | ATG | GCT | TCC | TTG | TAT | 3259 |
| Lys | Leu | Thr | Pro | Lys | Met | Asn | Phe | Thr | Ile | Lys | Met | Ala | Ser | Leu | Tyr | |
| | | | 610 | | | | | 615 | | | | | 620 | | | |
| GAT | GGG | GCT | GAA | AAT | AAT | CAT | AAC | TCT | TTA | GGA | ACC | TGG | TAT | TTA | ACA | 3307 |
| Asp | Gly | Ala | Glu | Asn | Asn | His | Asn | Ser | Leu | Gly | Thr | Trp | Tyr | Leu | Thr | |
| | | 625 | | | | | 630 | | | | | 635 | | | | |
| TAT | AAT | GTT | GCT | GGT | GGA | AAT | ACT | GGG | AAG | AGA | CAA | TAT | CGT | TCA | GCT | 3355 |
| Tyr | Asn | Val | Ala | Gly | Gly | Asn | Thr | Gly | Lys | Arg | Gln | Tyr | Arg | Ser | Ala | |
| | 640 | | | | | 645 | | | | | 650 | | | | | |
| CAT | TCT | TGT | GCA | CAT | GTA | GCT | CTA | TCT | TCA | GAA | GCG | AAA | AAG | AAA | CTA | 3403 |
| His | Ser | Cys | Ala | His | Val | Ala | Leu | Ser | Ser | Glu | Ala | Lys | Lys | Lys | Leu | |
| 655 | | | | | 660 | | | | | 665 | | | | | 670 | |
| AAT | CAA | AAT | GCG | AAT | TAC | TAT | CTT | AGC | ATG | TAT | ATG | AAG | GCT | GAT | TCT | 3451 |
| Asn | Gln | Asn | Ala | Asn | Tyr | Tyr | Leu | Ser | Met | Tyr | Met | Lys | Ala | Asp | Ser | |
| | | | | 675 | | | | | 680 | | | | | 685 | | |
| ACT | ACG | GAA | CCT | ACA | ATA | GAA | GTA | GCT | GGG | GAA | AAA | TCT | GCA | ATA | ACA | 3499 |
| Thr | Thr | Glu | Pro | Thr | Ile | Glu | Val | Ala | Gly | Glu | Lys | Ser | Ala | Ile | Thr | |
| | | | 690 | | | | | 695 | | | | | 700 | | | |
| AGT | AAA | AAA | GTA | AAA | TTA | AAT | AAT | CAA | AAT | TAT | CAA | AGA | GTT | GAT | ATT | 3547 |
| Ser | Lys | Lys | Val | Lys | Leu | Asn | Asn | Gln | Asn | Tyr | Gln | Arg | Val | Asp | Ile | |
| | | 705 | | | | | 710 | | | | | 715 | | | | |
| TTA | GTG | AAA | AAT | TCT | GAA | AGA | AAT | CCA | ATG | GAT | AAA | ATA | TAT | ATA | AGA | 3595 |
| Leu | Val | Lys | Asn | Ser | Glu | Arg | Asn | Pro | Met | Asp | Lys | Ile | Tyr | Ile | Arg | |
| | 720 | | | | | 725 | | | | | 730 | | | | | |
| GGA | AAT | GGC | ACG | ACA | AAT | GTT | TAT | GGG | GAT | GAT | GTT | ACT | ATC | CCA | GAG | 3643 |
| Gly | Asn | Gly | Thr | Thr | Asn | Val | Tyr | Gly | Asp | Asp | Val | Thr | Ile | Pro | Glu | |
| 735 | | | | | 740 | | | | | 745 | | | | | 750 | |

```
GTA  TCA  GCT  ATA  AAT  CCG  GCT  AGT  CTA  TCA  GAT  GAA  GAA  ATT  CAA  GAA       3691
Val  Ser  Ala  Ile  Asn  Pro  Ala  Ser  Leu  Ser  Asp  Glu  Glu  Ile  Gln  Glu
               755                      760                         765

ATA  TTT  AAA  GAC  TCA  ACT  ATT  GAA  TAT  GGA  AAT  CCT  AGT  TTC  GTT  GCT       3739
Ile  Phe  Lys  Asp  Ser  Thr  Ile  Glu  Tyr  Gly  Asn  Pro  Ser  Phe  Val  Ala
               770                      775                         780

GAT  GCC  GTA  ACA  TTT  AAA  AAT  ATA  AAA  CCT  TTA  CAA  AAT  TAT  GTA  AAG       3787
Asp  Ala  Val  Thr  Phe  Lys  Asn  Ile  Lys  Pro  Leu  Gln  Asn  Tyr  Val  Lys
               785                      790                         795

GAA  TAT  GAA  ATA  TAT  CAT  AAA  TCT  CAT  CGA  TAT  GAA  AAG  AAA  ACG  GTC       3835
Glu  Tyr  Glu  Ile  Tyr  His  Lys  Ser  His  Arg  Tyr  Glu  Lys  Lys  Thr  Val
          800                 805                     810

TTT  GAT  ATC  ATG  GGT  GTT  CAT  TAT  GAG  TAT  AGT  ATA  GCT  AGG  GAA  CAA       3883
Phe  Asp  Ile  Met  Gly  Val  His  Tyr  Glu  Tyr  Ser  Ile  Ala  Arg  Glu  Gln
815                      820                 825                         830

AAG  AAA  GCC  GCA  TAATTTAAA  AATAAACTC  GTTAGAGTTT  ATTTAGCATG                     3935
Lys  Lys  Ala  Ala

GTATTTTTAA  GAATAATCAA  TATGTTGAAC  CGTTTGTAGC  TGTTTTGGAA  GGGAATTTCA               3995

TTTTATTTGG  TCTCTTAAGT  TGATGGGCAT  GGGATATGTT  CAGCATCCAA  GCGTTTNGGG               4055

GGTTANAAAA  TCCAATTTT                                                                4074
```

( 2 ) INFORMATION FOR SEQ ID NO:20:

( i ) SEQUENCE CHARACTERISTICS:
        ( A ) LENGTH: 462 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

```
Met  Gln  Arg  Met  Glu  Gly  Lys  Leu  Phe  Val  Val  Ser  Lys  Thr  Leu  Gln
 1                  5                   10                       15

Val  Val  Thr  Arg  Thr  Val  Leu  Leu  Ser  Thr  Val  Tyr  Ser  Ile  Thr  Leu
               20                  25                       30

Leu  Asn  Asn  Val  Val  Ile  Lys  Ala  Asp  Gln  Leu  Asn  Ile  Asn  Ser  Gln
          35                  40                       45

Ser  Lys  Tyr  Thr  Asn  Leu  Gln  Asn  Leu  Lys  Ile  Pro  Asp  Asn  Ala  Glu
     50                  55                       60

Asp  Phe  Lys  Glu  Asp  Lys  Gly  Lys  Ala  Lys  Glu  Trp  Gly  Lys  Glu  Lys
 65                  70                       75                            80

Gly  Glu  Glu  Trp  Arg  Pro  Pro  Ala  Thr  Glu  Lys  Gly  Glu  Met  Asn  Asn
               85                       90                       95

Phe  Leu  Asp  Asn  Lys  Asn  Asp  Ile  Lys  Thr  Asn  Tyr  Lys  Glu  Ile  Thr
                    100                 105                      110

Phe  Ser  Met  Ala  Gly  Ser  Cys  Glu  Asp  Glu  Ile  Lys  Asp  Leu  Glu  Glu
               115                 120                 125

Ile  Asp  Lys  Ile  Phe  Asp  Lys  Ala  Asn  Leu  Ser  Ser  Ser  Ile  Ile  Thr
     130                 135                      140

Tyr  Lys  Asn  Val  Glu  Pro  Ala  Thr  Ile  Gly  Phe  Asn  Lys  Ser  Leu  Thr
145                      150                      155                      160

Glu  Gly  Asn  Thr  Ile  Asn  Ser  Asp  Ala  Met  Ala  Gln  Phe  Lys  Glu  Gln
               165                      170                      175

Phe  Leu  Gly  Lys  Asp  Met  Lys  Phe  Asp  Ser  Tyr  Leu  Asp  Thr  His  Leu
               180                 185                      190

Thr  Ala  Gln  Gln  Val  Ser  Ser  Lys  Lys  Arg  Val  Ile  Leu  Lys  Val  Thr
               195                 200                      205
```

```
Val  Pro  Ser  Gly  Lys  Gly  Ser  Thr  Thr  Pro  Thr  Lys  Ala  Gly  Val  Ile
     210            215                      220

Leu  Asn  Asn  Asn  Glu  Tyr  Lys  Met  Leu  Ile  Asp  Asn  Gly  Tyr  Val  Leu
225                      230                 235                           240

His  Val  Asp  Lys  Val  Ser  Lys  Val  Val  Lys  Lys  Gly  Met  Glu  Cys  Leu
               245                           250                      255

Gln  Val  Glu  Gly  Thr  Leu  Lys  Lys  Ser  Leu  Asp  Phe  Lys  Asn  Asp  Ile
               260                      265                      270

Asn  Ala  Glu  Ala  His  Ser  Trp  Gly  Met  Lys  Ile  Tyr  Glu  Asp  Trp  Ala
          275                      280                      285

Lys  Asn  Leu  Thr  Ala  Ser  Gln  Arg  Glu  Ala  Leu  Asp  Gly  Tyr  Ala  Arg
     290                      295                      300

Gln  Asp  Tyr  Lys  Glu  Ile  Asn  Asn  Tyr  Leu  Arg  Asn  Gln  Gly  Gly  Ser
305                      310                      315                      320

Gly  Asn  Glu  Lys  Leu  Asp  Ala  Gln  Leu  Lys  Asn  Ile  Ser  Asp  Ala  Leu
                    325                      330                      335

Gly  Lys  Lys  Pro  Ile  Pro  Glu  Asn  Ile  Thr  Val  Tyr  Arg  Trp  Cys  Gly
               340                      345                      350

Met  Pro  Glu  Phe  Gly  Tyr  Gln  Ile  Ser  Asp  Pro  Leu  Pro  Ser  Leu  Lys
          355                      360                      365

Asp  Phe  Glu  Glu  Gln  Phe  Leu  Asn  Thr  Ile  Lys  Glu  Asp  Lys  Gly  Tyr
     370                      375                      380

Met  Ser  Thr  Ser  Leu  Ser  Ser  Glu  Arg  Leu  Ala  Ala  Phe  Gly  Ser  Arg
385                      390                      395                      400

Lys  Ile  Ile  Leu  Arg  Leu  Gln  Val  Pro  Lys  Gly  Ser  Thr  Gly  Ala  Tyr
               405                      410                      415

Leu  Ser  Ala  Ile  Gly  Gly  Phe  Ala  Ser  Glu  Lys  Glu  Ile  Leu  Leu  Asp
               420                      425                      430

Lys  Asp  Ser  Lys  Tyr  His  Ile  Asp  Lys  Ala  Thr  Glu  Val  Ile  Ile  Lys
               435                      440                      445

Gly  Val  Lys  Arg  Tyr  Val  Val  Asp  Ala  Thr  Leu  Leu  Thr  Asn
     450                      455                      460
```

( 2 ) INFORMATION FOR SEQ ID NO:21:

( i ) SEQUENCE CHARACTERISTICS:
        ( A ) LENGTH: 834 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

```
Met  Lys  Asn  Met  Lys  Lys  Lys  Leu  Ala  Ser  Val  Val  Thr  Cys  Met  Leu
1                   5                   10                      15

Leu  Ala  Pro  Met  Phe  Leu  Asn  Gly  Asn  Val  Asn  Ala  Val  Asn  Ala  Asp
               20                      25                      30

Ser  Lys  Ile  Asn  Gln  Ile  Ser  Thr  Thr  Gln  Glu  Asn  Gln  Gln  Lys  Glu
          35                      40                      45

Met  Asp  Arg  Lys  Gly  Leu  Leu  Gly  Tyr  Tyr  Phe  Lys  Gly  Lys  Asp  Phe
     50                      55                      60

Asn  Asn  Leu  Thr  Met  Phe  Ala  Pro  Thr  Arg  Asp  Asn  Thr  Leu  Met  Tyr
65                       70                      75                       80

Asp  Gln  Gln  Thr  Ala  Asn  Ala  Leu  Leu  Asp  Lys  Lys  Gln  Gln  Glu  Tyr
               85                      90                      95

Gln  Ser  Ile  Arg  Trp  Ile  Gly  Leu  Ile  Gln  Arg  Lys  Glu  Thr  Gly  Asp
```

-continued

```
                       100                         105                         110
Phe  Thr  Phe  Asn  Leu  Ser  Lys  Asp  Glu  Gln  Ala  Ile  Ile  Glu  Ile  Asp
               115                      120                      125

Gly  Lys  Ile  Ile  Ser  Asn  Lys  Gly  Lys  Glu  Lys  Gln  Val  Val  His  Leu
130                      135                      140

Glu  Lys  Glu  Lys  Leu  Val  Pro  Ile  Lys  Ile  Glu  Tyr  Gln  Ser  Asp  Thr
145                           150                     155                     160

Lys  Phe  Asn  Ile  Asp  Ser  Lys  Thr  Phe  Lys  Glu  Leu  Lys  Leu  Phe  Lys
                    165                      170                      175

Ile  Asp  Ser  Gln  Asn  Gln  Ser  Gln  Gln  Val  Gln  Leu  Arg  Asn  Pro  Glu
               180                      185                      190

Phe  Asn  Lys  Lys  Glu  Ser  Gln  Glu  Phe  Leu  Ala  Lys  Ala  Ser  Lys  Thr
          195                      200                      205

Asn  Leu  Phe  Lys  Gln  Lys  Met  Lys  Arg  Asp  Ile  Asp  Glu  Asp  Thr  Asp
     210                           215                      220

Thr  Asp  Gly  Asp  Ser  Ile  Pro  Asp  Leu  Trp  Glu  Glu  Asn  Gly  Tyr  Thr
225                           230                      235                     240

Ile  Gln  Asn  Lys  Val  Ala  Val  Lys  Trp  Asp  Asp  Ser  Leu  Ala  Ser  Lys
                    245                      250                      255

Gly  Tyr  Thr  Lys  Phe  Val  Ser  Asn  Pro  Leu  Asp  Ser  His  Thr  Val  Gly
               260                      265                      270

Asp  Pro  Tyr  Thr  Asp  Tyr  Glu  Lys  Ala  Ala  Arg  Asp  Leu  Asp  Leu  Ser
          275                      280                      285

Asn  Ala  Lys  Glu  Thr  Phe  Asn  Pro  Leu  Val  Ala  Ala  Phe  Pro  Ser  Val
     290                      295                      300

Asn  Val  Ser  Met  Glu  Lys  Val  Ile  Leu  Ser  Pro  Asn  Glu  Asn  Leu  Ser
305                      310                      315                          320

Asn  Ser  Val  Glu  Ser  His  Ser  Ser  Thr  Asn  Trp  Ser  Tyr  Thr  Asn  Thr
                    325                      330                      335

Glu  Gly  Ala  Ser  Ile  Glu  Ala  Gly  Gly  Pro  Leu  Gly  Leu  Ser  Phe
                    340                      345                      350

Gly  Val  Ser  Val  Thr  Tyr  Gln  His  Ser  Glu  Thr  Val  Ala  Gln  Glu  Trp
               355                      360                      365

Gly  Thr  Ser  Thr  Gly  Asn  Thr  Ser  Gln  Phe  Asn  Thr  Ala  Ser  Ala  Gly
     370                      375                      380

Tyr  Leu  Asn  Ala  Asn  Val  Arg  Tyr  Asn  Asn  Val  Gly  Thr  Gly  Ala  Ile
385                           390                      395                     400

Tyr  Asp  Val  Lys  Pro  Thr  Thr  Ser  Phe  Val  Leu  Asn  Asn  Asn  Thr  Ile
                    405                      410                      415

Ala  Thr  Ile  Thr  Ala  Lys  Ser  Asn  Ser  Thr  Ala  Leu  Arg  Ile  Ser  Pro
               420                      425                      430

Gly  Asp  Ser  Tyr  Pro  Glu  Ile  Gly  Glu  Asn  Ala  Ile  Ala  Ile  Thr  Ser
               435                      440                      445

Met  Asp  Asp  Phe  Asn  Ser  His  Pro  Ile  Thr  Leu  Asn  Lys  Gln  Gln  Val
     450                           455                      460

Asn  Gln  Leu  Ile  Asn  Asn  Lys  Pro  Ile  Met  Leu  Glu  Thr  Asp  Gln  Thr
465                           470                      475                     480

Asp  Gly  Val  Tyr  Lys  Ile  Arg  Asp  Thr  His  Gly  Asn  Ile  Val  Thr  Gly
                    485                      490                      495

Gly  Glu  Trp  Asn  Gly  Val  Thr  Gln  Gln  Ile  Lys  Ala  Lys  Thr  Ala  Ser
               500                      505                      510

Ile  Ile  Val  Asp  Asp  Gly  Lys  Gln  Val  Ala  Glu  Lys  Arg  Val  Ala  Ala
          515                      520                      525
```

-continued

Lys Asp Tyr Gly His Pro Glu Asp Lys Thr Pro Pro Leu Thr Leu Lys
530 535 540

Asp Thr Leu Lys Leu Ser Tyr Pro Asp Glu Ile Lys Glu Thr Asn Gly
545 550 555 560

Leu Leu Tyr Tyr Asp Asp Lys Pro Ile Tyr Glu Ser Ser Val Met Thr
565 570 575

Tyr Leu Asp Glu Asn Thr Ala Lys Glu Val Lys Lys Gln Ile Asn Asp
580 585 590

Thr Thr Gly Lys Phe Lys Asp Val Asn His Leu Tyr Asp Val Lys Leu
595 600 605

Thr Pro Lys Met Asn Phe Thr Ile Lys Met Ala Ser Leu Tyr Asp Gly
610 615 620

Ala Glu Asn Asn His Asn Ser Leu Gly Thr Trp Tyr Leu Thr Tyr Asn
625 630 635 640

Val Ala Gly Gly Asn Thr Gly Lys Arg Gln Tyr Arg Ser Ala His Ser
645 650 655

Cys Ala His Val Ala Leu Ser Ser Glu Ala Lys Lys Lys Leu Asn Gln
660 665 670

Asn Ala Asn Tyr Tyr Leu Ser Met Tyr Met Lys Ala Asp Ser Thr Thr
675 680 685

Glu Pro Thr Ile Glu Val Ala Gly Glu Lys Ser Ala Ile Thr Ser Lys
690 695 700

Lys Val Lys Leu Asn Asn Gln Asn Tyr Gln Arg Val Asp Ile Leu Val
705 710 715 720

Lys Asn Ser Glu Arg Asn Pro Met Asp Lys Ile Tyr Ile Arg Gly Asn
725 730 735

Gly Thr Thr Asn Val Tyr Gly Asp Asp Val Thr Ile Pro Glu Val Ser
740 745 750

Ala Ile Asn Pro Ala Ser Leu Ser Asp Glu Glu Ile Gln Glu Ile Phe
755 760 765

Lys Asp Ser Thr Ile Glu Tyr Gly Asn Pro Ser Phe Val Ala Asp Ala
770 775 780

Val Thr Phe Lys Asn Ile Lys Pro Leu Gln Asn Tyr Val Lys Glu Tyr
785 790 795 800

Glu Ile Tyr His Lys Ser His Arg Tyr Glu Lys Lys Thr Val Phe Asp
805 810 815

Ile Met Gly Val His Tyr Glu Tyr Ser Ile Ala Arg Glu Gln Lys Lys
820 825 830

Ala Ala ( 2 ) INFORMATION FOR SEQ ID NO:22:

( i ) SEQUENCE CHARACTERISTICS:
( A ) LENGTH: 4041 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..4038
( D ) OTHER INFORMATION: /product="VIP1A(a)/VIP2A(a) fusion product"

( x i ) SEQUENCE DESCRIPTION: SEQ ID NO:22:

ATG AAA AGA ATG GAG GGA AAG TTG TTT ATG GTG TCA AAA AAA TTA CAA 48
Met Lys Arg Met Glu Gly Lys Leu Phe Met Val Ser Lys Lys Leu Gln

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| 835 |     |     |     |     |     | 840 |     |     |     |     | 845 |     |     |     |     | 850 |
| GTA | GTT | ACT | AAA | ACT | GTA | TTG | CTT | AGT | ACA | GTT | TTC | TCT | ATA | TCT | TTA | 96  |
| Val | Val | Thr | Lys | Thr | Val | Leu | Leu | Ser | Thr | Val | Phe | Ser | Ile | Ser | Leu |     |
|     |     |     | 855 |     |     |     |     | 860 |     |     |     |     | 865 |     |     |     |
| TTA | AAT | AAT | GAA | GTG | ATA | AAA | GCT | GAA | CAA | TTA | AAT | ATA | AAT | TCT | CAA | 144 |
| Leu | Asn | Asn | Glu | Val | Ile | Lys | Ala | Glu | Gln | Leu | Asn | Ile | Asn | Ser | Gln |     |
|     |     |     | 870 |     |     |     | 875 |     |     |     |     | 880 |     |     |     |     |
| AGT | AAA | TAT | ACT | AAC | TTG | CAA | AAT | CTA | AAA | ATC | ACT | GAC | AAG | GTA | GAG | 192 |
| Ser | Lys | Tyr | Thr | Asn | Leu | Gln | Asn | Leu | Lys | Ile | Thr | Asp | Lys | Val | Glu |     |
|     |     | 885 |     |     |     |     | 890 |     |     |     |     | 895 |     |     |     |     |
| GAT | TTT | AAA | GAA | GAT | AAG | GAA | AAA | GCG | AAA | GAA | TGG | GGG | AAA | GAA | AAA | 240 |
| Asp | Phe | Lys | Glu | Asp | Lys | Glu | Lys | Ala | Lys | Glu | Trp | Gly | Lys | Glu | Lys |     |
|     | 900 |     |     |     | 905 |     |     |     |     | 910 |     |     |     |     |     |     |
| GAA | AAA | GAG | TGG | AAA | CTA | ACT | GCT | ACT | GAA | AAA | GGA | AAA | ATG | AAT | AAT | 288 |
| Glu | Lys | Glu | Trp | Lys | Leu | Thr | Ala | Thr | Glu | Lys | Gly | Lys | Met | Asn | Asn |     |
| 915 |     |     |     |     | 920 |     |     |     |     | 925 |     |     |     |     | 930 |     |
| TTT | TTA | GAT | AAT | AAA | AAT | GAT | ATA | AAG | ACA | AAT | TAT | AAA | GAA | ATT | ACT | 336 |
| Phe | Leu | Asp | Asn | Lys | Asn | Asp | Ile | Lys | Thr | Asn | Tyr | Lys | Glu | Ile | Thr |     |
|     |     |     |     | 935 |     |     |     |     | 940 |     |     |     |     | 945 |     |     |
| TTT | TCT | ATG | GCA | GGC | TCA | TTT | GAA | GAT | GAA | ATA | AAA | GAT | TTA | AAA | GAA | 384 |
| Phe | Ser | Met | Ala | Gly | Ser | Phe | Glu | Asp | Glu | Ile | Lys | Asp | Leu | Lys | Glu |     |
|     |     |     | 950 |     |     |     |     | 955 |     |     |     |     | 960 |     |     |     |
| ATT | GAT | AAG | ATG | TTT | GAT | AAA | ACC | AAT | CTA | TCA | AAT | TCT | ATT | ATC | ACC | 432 |
| Ile | Asp | Lys | Met | Phe | Asp | Lys | Thr | Asn | Leu | Ser | Asn | Ser | Ile | Ile | Thr |     |
|     |     | 965 |     |     |     |     | 970 |     |     |     |     | 975 |     |     |     |     |
| TAT | AAA | AAT | GTG | GAA | CCG | ACA | ACA | ATT | GGA | TTT | AAT | AAA | TCT | TTA | ACA | 480 |
| Tyr | Lys | Asn | Val | Glu | Pro | Thr | Thr | Ile | Gly | Phe | Asn | Lys | Ser | Leu | Thr |     |
|     |     | 980 |     |     |     |     | 985 |     |     |     |     | 990 |     |     |     |     |
| GAA | GGT | AAT | ACG | ATT | AAT | TCT | GAT | GCA | ATG | GCA | CAG | TTT | AAA | GAA | CAA | 528 |
| Glu | Gly | Asn | Thr | Ile | Asn | Ser | Asp | Ala | Met | Ala | Gln | Phe | Lys | Glu | Gln |     |
| 995 |     |     |     |     | 1000|     |     |     |     | 1005|     |     |     |     | 1010|     |
| TTT | TTA | GAT | AGG | GAT | ATT | AAG | TTT | GAT | AGT | TAT | CTA | GAT | ACG | CAT | TTA | 576 |
| Phe | Leu | Asp | Arg | Asp | Ile | Lys | Phe | Asp | Ser | Tyr | Leu | Asp | Thr | His | Leu |     |
|     |     |     |     | 1015|     |     |     |     | 1020|     |     |     |     | 1025|     |     |
| ACT | GCT | CAA | CAA | GTT | TCC | AGT | AAA | GAA | AGA | GTT | ATT | TTG | AAG | GTT | ACG | 624 |
| Thr | Ala | Gln | Gln | Val | Ser | Ser | Lys | Glu | Arg | Val | Ile | Leu | Lys | Val | Thr |     |
|     |     |     | 1030|     |     |     |     | 1035|     |     |     |     | 1040|     |     |     |
| GTT | CCG | AGT | GGG | AAA | GGT | TCT | ACT | ACT | CCA | ACA | AAA | GCA | GGT | GTC | ATT | 672 |
| Val | Pro | Ser | Gly | Lys | Gly | Ser | Thr | Thr | Pro | Thr | Lys | Ala | Gly | Val | Ile |     |
|     |     |     | 1045|     |     |     |     | 1050|     |     |     |     | 1055|     |     |     |
| TTA | AAT | AAT | AGT | GAA | TAC | AAA | ATG | CTC | ATT | GAT | AAT | GGG | TAT | ATG | GTC | 720 |
| Leu | Asn | Asn | Ser | Glu | Tyr | Lys | Met | Leu | Ile | Asp | Asn | Gly | Tyr | Met | Val |     |
|     |     |     | 1060|     |     |     | 1065|     |     |     |     | 1070|     |     |     |     |
| CAT | GTA | GAT | AAG | GTA | TCA | AAA | GTG | GTG | AAA | AAA | GGG | GTG | GAG | TGC | TTA | 768 |
| His | Val | Asp | Lys | Val | Ser | Lys | Val | Val | Lys | Lys | Gly | Val | Glu | Cys | Leu |     |
| 1075|     |     |     | 1080|     |     |     |     | 1085|     |     |     |     |     | 1090|     |
| CAA | ATT | GAA | GGG | ACT | TTA | AAA | AAG | AGT | CTT | GAC | TTT | AAA | AAT | GAT | ATA | 816 |
| Gln | Ile | Glu | Gly | Thr | Leu | Lys | Lys | Ser | Leu | Asp | Phe | Lys | Asn | Asp | Ile |     |
|     |     |     |     | 1095|     |     |     |     | 1100|     |     |     |     | 1105|     |     |
| AAT | GCT | GAA | GCG | CAT | AGC | TGG | GGT | ATG | AAG | AAT | TAT | GAA | GAG | TGG | GCT | 864 |
| Asn | Ala | Glu | Ala | His | Ser | Trp | Gly | Met | Lys | Asn | Tyr | Glu | Glu | Trp | Ala |     |
|     |     |     |     | 1110|     |     |     |     | 1115|     |     |     |     | 1120|     |     |
| AAA | GAT | TTA | ACC | GAT | TCG | CAA | AGG | GAA | GCT | TTA | GAT | GGG | TAT | GCT | AGG | 912 |
| Lys | Asp | Leu | Thr | Asp | Ser | Gln | Arg | Glu | Ala | Leu | Asp | Gly | Tyr | Ala | Arg |     |
|     |     |     | 1125|     |     |     |     | 1130|     |     |     |     | 1135|     |     |     |
| CAA | GAT | TAT | AAA | GAA | ATC | AAT | AAT | TAT | TTA | AGA | AAT | CAA | GGC | GGA | AGT | 960 |
| Gln | Asp | Tyr | Lys | Glu | Ile | Asn | Asn | Tyr | Leu | Arg | Asn | Gln | Gly | Gly | Ser |     |
|     |     | 1140|     |     |     |     | 1145|     |     |     |     | 1150|     |     |     |     |
| GGA | AAT | GAA | AAA | CTA | GAT | GCT | CAA | ATA | AAA | AAT | ATT | TCT | GAT | GCT | TTA | 1008|
| Gly | Asn | Glu | Lys | Leu | Asp | Ala | Gln | Ile | Lys | Asn | Ile | Ser | Asp | Ala | Leu |     |

```
              1155                  1160                 1165                 1170

GGG  AAG  AAA  CCA  ATA  CCG  GAA  AAT  ATT  ACT  GTG  TAT  AGA  TGG  TGT  GGC    1056
Gly  Lys  Lys  Pro  Ile  Pro  Glu  Asn  Ile  Thr  Val  Tyr  Arg  Trp  Cys  Gly
               1175                 1180                      1185

ATG  CCG  GAA  TTT  GGT  TAT  CAA  ATT  AGT  GAT  CCG  TTA  CCT  TCT  TTA  AAA    1104
Met  Pro  Glu  Phe  Gly  Tyr  Gln  Ile  Ser  Asp  Pro  Leu  Pro  Ser  Leu  Lys
               1190                 1195                      1200

GAT  TTT  GAA  GAA  CAA  TTT  TTA  AAT  ACA  ATC  AAA  GAA  GAC  AAA  GGA  TAT    1152
Asp  Phe  Glu  Glu  Gln  Phe  Leu  Asn  Thr  Ile  Lys  Glu  Asp  Lys  Gly  Tyr
               1205                 1210                      1215

ATG  AGT  ACA  AGC  TTA  TCG  AGT  GAA  CGT  CTT  GCA  GCT  TTT  GGA  TCT  AGA    1200
Met  Ser  Thr  Ser  Leu  Ser  Ser  Glu  Arg  Leu  Ala  Ala  Phe  Gly  Ser  Arg
               1220                 1225                      1230

AAA  ATT  ATA  TTA  CGA  TTA  CAA  GTT  CCG  AAA  GGA  AGT  ACG  GGT  GCG  TAT    1248
Lys  Ile  Ile  Leu  Arg  Leu  Gln  Val  Pro  Lys  Gly  Ser  Thr  Gly  Ala  Tyr
1235                 1240                 1245                      1250

TTA  AGT  GCC  ATT  GGT  GGA  TTT  GCA  AGT  GAA  AAA  GAG  ATC  CTA  CTT  GAT    1296
Leu  Ser  Ala  Ile  Gly  Gly  Phe  Ala  Ser  Glu  Lys  Glu  Ile  Leu  Leu  Asp
               1255                 1260                      1265

AAA  GAT  AGT  AAA  TAT  CAT  ATT  GAT  AAA  GTA  ACA  GAG  GTA  ATT  ATT  AAA    1344
Lys  Asp  Ser  Lys  Tyr  His  Ile  Asp  Lys  Val  Thr  Glu  Val  Ile  Ile  Lys
               1270                 1275                      1280

GGT  GTT  AAG  CGA  TAT  GTA  GTG  GAT  GCA  ACA  TTA  TTA  ACA  AAT  ATG  AAA    1392
Gly  Val  Lys  Arg  Tyr  Val  Val  Asp  Ala  Thr  Leu  Leu  Thr  Asn  Met  Lys
               1285                 1290                      1295

AAT  ATG  AAG  AAA  AAG  TTA  GCA  AGT  GTT  GTA  ACG  TGT  ACG  TTA  TTA  GCT    1440
Asn  Met  Lys  Lys  Lys  Leu  Ala  Ser  Val  Val  Thr  Cys  Thr  Leu  Leu  Ala
               1300                 1305                      1310

CCT  ATG  TTT  TTG  AAT  GGA  AAT  GTG  AAT  GCT  GTT  TAC  GCA  GAC  AGC  AAA    1488
Pro  Met  Phe  Leu  Asn  Gly  Asn  Val  Asn  Ala  Val  Tyr  Ala  Asp  Ser  Lys
1315                 1320                 1325                      1330

ACA  AAT  CAA  ATT  TCT  ACA  ACA  CAG  AAA  AAT  CAA  CAG  AAA  GAG  ATG  GAC    1536
Thr  Asn  Gln  Ile  Ser  Thr  Thr  Gln  Lys  Asn  Gln  Gln  Lys  Glu  Met  Asp
               1335                 1340                      1345

CGA  AAA  GGA  TTA  CTT  GGG  TAT  TAT  TTC  AAA  GGA  AAA  GAT  TTT  AGT  AAT    1584
Arg  Lys  Gly  Leu  Leu  Gly  Tyr  Tyr  Phe  Lys  Gly  Lys  Asp  Phe  Ser  Asn
               1350                 1355                      1360

CTT  ACT  ATG  TTT  GCA  CCG  ACA  CGT  GAT  AGT  ACT  CTT  ATT  TAT  GAT  CAA    1632
Leu  Thr  Met  Phe  Ala  Pro  Thr  Arg  Asp  Ser  Thr  Leu  Ile  Tyr  Asp  Gln
               1365                 1370                      1375

CAA  ACA  GCA  AAT  AAA  CTA  TTA  GAT  AAA  AAA  CAA  CAA  GAA  TAT  CAG  TCT    1680
Gln  Thr  Ala  Asn  Lys  Leu  Leu  Asp  Lys  Lys  Gln  Gln  Glu  Tyr  Gln  Ser
               1380                 1385                      1390

ATT  CGT  TGG  ATT  GGT  TTG  ATT  CAG  AGT  AAA  GAA  ACG  GGA  GAT  TTC  ACA    1728
Ile  Arg  Trp  Ile  Gly  Leu  Ile  Gln  Ser  Lys  Glu  Thr  Gly  Asp  Phe  Thr
1395                 1400                 1405                      1410

TTT  AAC  TTA  TCT  GAG  GAT  GAA  CAG  GCA  ATT  ATA  GAA  ATC  AAT  GGG  AAA    1776
Phe  Asn  Leu  Ser  Glu  Asp  Glu  Gln  Ala  Ile  Ile  Glu  Ile  Asn  Gly  Lys
               1415                 1420                      1425

ATT  ATT  TCT  AAT  AAA  GGG  AAA  GAA  AAG  CAA  GTT  GTC  CAT  TTA  GAA  AAA    1824
Ile  Ile  Ser  Asn  Lys  Gly  Lys  Glu  Lys  Gln  Val  Val  His  Leu  Glu  Lys
               1430                 1435                      1440

GGA  AAA  TTA  GTT  CCA  ATC  AAA  ATA  GAG  TAT  CAA  TCA  GAT  ACA  AAA  TTT    1872
Gly  Lys  Leu  Val  Pro  Ile  Lys  Ile  Glu  Tyr  Gln  Ser  Asp  Thr  Lys  Phe
1445                 1450                 1455

AAT  ATT  GAC  AGT  AAA  ACA  TTT  AAA  GAA  CTT  AAA  TTA  TTT  AAA  ATA  GAT    1920
Asn  Ile  Asp  Ser  Lys  Thr  Phe  Lys  Glu  Leu  Lys  Leu  Phe  Lys  Ile  Asp
1460                 1465                 1470

AGT  CAA  AAC  CAA  CCC  CAG  CAA  GTC  CAG  CAA  GAT  GAA  CTG  AGA  AAT  CCT    1968
Ser  Gln  Asn  Gln  Pro  Gln  Gln  Val  Gln  Gln  Asp  Glu  Leu  Arg  Asn  Pro
```

```
         1475                   1480                      1485                        1490

GAA  TTT  AAC  AAG  AAA  GAA  TCA  CAG  GAA  TTC  TTA  GCG  AAA  CCA  TCG  AAA       2016
Glu  Phe  Asn  Lys  Lys  Glu  Ser  Gln  Glu  Phe  Leu  Ala  Lys  Pro  Ser  Lys
               1495                     1500                     1505

ATA  AAT  CTT  TTC  ACT  CAA  AAA  ATG  AAA  AGG  GAA  ATT  GAT  GAA  GAC  ACG       2064
Ile  Asn  Leu  Phe  Thr  Gln  Lys  Met  Lys  Arg  Glu  Ile  Asp  Glu  Asp  Thr
               1510                     1515                     1520

GAT  ACG  GAT  GGG  GAC  TCT  ATT  CCT  GAC  CTT  TGG  GAA  GAA  AAT  GGG  TAT       2112
Asp  Thr  Asp  Gly  Asp  Ser  Ile  Pro  Asp  Leu  Trp  Glu  Glu  Asn  Gly  Tyr
               1525                     1530                     1535

ACG  ATT  CAA  AAT  AGA  ATC  GCT  GTA  AAG  TGG  GAC  GAT  TCT  CTA  GCA  AGT       2160
Thr  Ile  Gln  Asn  Arg  Ile  Ala  Val  Lys  Trp  Asp  Asp  Ser  Leu  Ala  Ser
               1540                     1545                     1550

AAA  GGG  TAT  ACG  AAA  TTT  GTT  TCA  AAT  CCA  CTA  GAA  AGT  CAC  ACA  GTT       2208
Lys  Gly  Tyr  Thr  Lys  Phe  Val  Ser  Asn  Pro  Leu  Glu  Ser  His  Thr  Val
1555                     1560                     1565                     1570

GGT  GAT  CCT  TAT  ACA  GAT  TAT  GAA  AAG  GCA  GCA  AGA  GAT  CTA  GAT  TTG       2256
Gly  Asp  Pro  Tyr  Thr  Asp  Tyr  Glu  Lys  Ala  Ala  Arg  Asp  Leu  Asp  Leu
               1575                     1580                     1585

TCA  AAT  GCA  AAG  GAA  ACG  TTT  AAC  CCA  TTG  GTA  GCT  GCT  TTT  CCA  AGT       2304
Ser  Asn  Ala  Lys  Glu  Thr  Phe  Asn  Pro  Leu  Val  Ala  Ala  Phe  Pro  Ser
               1590                     1595                     1600

GTG  AAT  GTT  AGT  ATG  GAA  AAG  GTG  ATA  TTA  TCA  CCA  AAT  GAA  AAT  TTA       2352
Val  Asn  Val  Ser  Met  Glu  Lys  Val  Ile  Leu  Ser  Pro  Asn  Glu  Asn  Leu
               1605                     1610                     1615

TCC  AAT  AGT  GTA  GAG  TCT  CAT  TCA  TCC  ACG  AAT  TGG  TCT  TAT  ACA  AAT       2400
Ser  Asn  Ser  Val  Glu  Ser  His  Ser  Ser  Thr  Asn  Trp  Ser  Tyr  Thr  Asn
               1620                     1625                     1630

ACA  GAA  GGT  GCT  TCT  GTT  GAA  GCG  GGG  ATT  GGA  CCA  AAA  GGT  ATT  TCG       2448
Thr  Glu  Gly  Ala  Ser  Val  Glu  Ala  Gly  Ile  Gly  Pro  Lys  Gly  Ile  Ser
1635                     1640                     1645                     1650

TTC  GGA  GTT  AGC  GTA  AAC  TAT  CAA  CAC  TCT  GAA  ACA  GTT  GCA  CAA  GAA       2496
Phe  Gly  Val  Ser  Val  Asn  Tyr  Gln  His  Ser  Glu  Thr  Val  Ala  Gln  Glu
               1655                     1660                     1665

TGG  GGA  ACA  TCT  ACA  GGA  AAT  ACT  TCG  CAA  TTC  AAT  ACG  GCT  TCA  GCG       2544
Trp  Gly  Thr  Ser  Thr  Gly  Asn  Thr  Ser  Gln  Phe  Asn  Thr  Ala  Ser  Ala
               1670                     1675                     1680

GGA  TAT  TTA  AAT  GCA  AAT  GTT  CGA  TAT  AAC  AAT  GTA  GGA  ACT  GGT  GCC       2592
Gly  Tyr  Leu  Asn  Ala  Asn  Val  Arg  Tyr  Asn  Asn  Val  Gly  Thr  Gly  Ala
               1685                     1690                     1695

ATC  TAC  GAT  GTA  AAA  CCT  ACA  ACA  AGT  TTT  GTA  TTA  AAT  AAC  GAT  ACT       2640
Ile  Tyr  Asp  Val  Lys  Pro  Thr  Thr  Ser  Phe  Val  Leu  Asn  Asn  Asp  Thr
               1700                     1705                     1710

ATC  GCA  ACT  ATT  ACG  GCG  AAA  TCT  AAT  TCT  ACA  GCC  TTA  AAT  ATA  TCT       2688
Ile  Ala  Thr  Ile  Thr  Ala  Lys  Ser  Asn  Ser  Thr  Ala  Leu  Asn  Ile  Ser
1715                     1720                     1725                     1730

CCT  GGA  GAA  AGT  TAC  CCG  AAA  AAA  GGA  CAA  AAT  GGA  ATC  GCA  ATA  ACA       2736
Pro  Gly  Glu  Ser  Tyr  Pro  Lys  Lys  Gly  Gln  Asn  Gly  Ile  Ala  Ile  Thr
               1735                     1740                     1745

TCA  ATG  GAT  GAT  TTT  AAT  TCC  CAT  CCG  ATT  ACA  TTA  AAT  AAA  AAA  CAA       2784
Ser  Met  Asp  Asp  Phe  Asn  Ser  His  Pro  Ile  Thr  Leu  Asn  Lys  Lys  Gln
               1750                     1755                     1760

GTA  GAT  AAT  CTG  CTA  AAT  AAT  AAA  CCT  ATG  ATG  TTG  GAA  ACA  AAC  CAA       2832
Val  Asp  Asn  Leu  Leu  Asn  Asn  Lys  Pro  Met  Met  Leu  Glu  Thr  Asn  Gln
               1765                     1770                     1775

ACA  GAT  GGT  GTT  TAT  AAG  ATA  AAA  GAT  ACA  CAT  GGA  AAT  ATA  GTA  ACT       2880
Thr  Asp  Gly  Val  Tyr  Lys  Ile  Lys  Asp  Thr  His  Gly  Asn  Ile  Val  Thr
               1780                     1785                     1790

GGC  GGA  GAA  TGG  AAT  GGT  GTC  ATA  CAA  CAA  ATC  AAG  GCT  AAA  ACA  GCG       2928
Gly  Gly  Glu  Trp  Asn  Gly  Val  Ile  Gln  Gln  Ile  Lys  Ala  Lys  Thr  Ala
```

|  |  |
|---|---|
| 1795 1800 1805 1810 | |
| TCT ATT ATT GTG GAT GAT GGG GAA CGT GTA GCA GAA AAA CGT GTA GCG<br>Ser Ile Ile Val Asp Asp Gly Glu Arg Val Ala Glu Lys Arg Val Ala<br>1815 1820 1825 | 2976 |
| GCA AAA GAT TAT GAA AAT CCA GAA GAT AAA ACA CCG TCT TTA ACT TTA<br>Ala Lys Asp Tyr Glu Asn Pro Glu Asp Lys Thr Pro Ser Leu Thr Leu<br>1830 1835 1840 | 3024 |
| AAA GAT GCC CTG AAG CTT TCA TAT CCA GAT GAA ATA AAA GAA ATA GAG<br>Lys Asp Ala Leu Lys Leu Ser Tyr Pro Asp Glu Ile Lys Glu Ile Glu<br>1845 1850 1855 | 3072 |
| GGA TTA TTA TAT TAT AAA AAC AAA CCG ATA TAC GAA TCG AGC GTT ATG<br>Gly Leu Leu Tyr Tyr Lys Asn Lys Pro Ile Tyr Glu Ser Ser Val Met<br>1860 1865 1870 | 3120 |
| ACT TAC TTA GAT GAA AAT ACA GCA AAA GAA GTG ACC AAA CAA TTA AAT<br>Thr Tyr Leu Asp Glu Asn Thr Ala Lys Glu Val Thr Lys Gln Leu Asn<br>1875 1880 1885 1890 | 3168 |
| GAT ACC ACT GGG AAA TTT AAA GAT GTA AGT CAT TTA TAT GAT GTA AAA<br>Asp Thr Thr Gly Lys Phe Lys Asp Val Ser His Leu Tyr Asp Val Lys<br>1895 1900 1905 | 3216 |
| CTG ACT CCA AAA ATG AAT GTT ACA ATC AAA TTG TCT ATA CTT TAT GAT<br>Leu Thr Pro Lys Met Asn Val Thr Ile Lys Leu Ser Ile Leu Tyr Asp<br>1910 1915 1920 | 3264 |
| AAT GCT GAG TCT AAT GAT AAC TCA ATT GGT AAA TGG ACA AAC ACA AAT<br>Asn Ala Glu Ser Asn Asp Asn Ser Ile Gly Lys Trp Thr Asn Thr Asn<br>1925 1930 1935 | 3312 |
| ATT GTT TCA GGT GGA AAT AAC GGA AAA AAA CAA TAT TCT TCT AAT AAT<br>Ile Val Ser Gly Gly Asn Asn Gly Lys Lys Gln Tyr Ser Ser Asn Asn<br>1940 1945 1950 | 3360 |
| CCG GAT GCT AAT TTG ACA TTA AAT ACA GAT GCT CAA GAA AAA TTA AAT<br>Pro Asp Ala Asn Leu Thr Leu Asn Thr Asp Ala Gln Glu Lys Leu Asn<br>1955 1960 1965 1970 | 3408 |
| AAA AAT CGT GAC TAT TAT ATA AGT TTA TAT ATG AAG TCA GAA AAA AAC<br>Lys Asn Arg Asp Tyr Tyr Ile Ser Leu Tyr Met Lys Ser Glu Lys Asn<br>1975 1980 1985 | 3456 |
| ACA CAA TGT GAG ATT ACT ATA GAT GGG GAG ATT TAT CCG ATC ACT ACA<br>Thr Gln Cys Glu Ile Thr Ile Asp Gly Glu Ile Tyr Pro Ile Thr Thr<br>1990 1995 2000 | 3504 |
| AAA ACA GTG AAT GTG AAT AAA GAC AAT TAC AAA AGA TTA GAT ATT ATA<br>Lys Thr Val Asn Val Asn Lys Asp Asn Tyr Lys Arg Leu Asp Ile Ile<br>2005 2010 2015 | 3552 |
| GCT CAT AAT ATA AAA AGT AAT CCA ATT TCT TCA CTT CAT ATT AAA ACG<br>Ala His Asn Ile Lys Ser Asn Pro Ile Ser Ser Leu His Ile Lys Thr<br>2020 2025 2030 | 3600 |
| AAT GAT GAA ATA ACT TTA TTT TGG GAT GAT ATT TCT ATA ACA GAT GTA<br>Asn Asp Glu Ile Thr Leu Phe Trp Asp Asp Ile Ser Ile Thr Asp Val<br>2035 2040 2045 2050 | 3648 |
| GCA TCA ATA AAA CCG GAA AAT TTA ACA GAT TCA GAA ATT AAA CAG ATT<br>Ala Ser Ile Lys Pro Glu Asn Leu Thr Asp Ser Glu Ile Lys Gln Ile<br>2055 2060 2065 | 3696 |
| TAT AGT AGG TAT GGT ATT AAG TTA GAA GAT GGA ATC CTT ATT GAT AAA<br>Tyr Ser Arg Tyr Gly Ile Lys Leu Glu Asp Gly Ile Leu Ile Asp Lys<br>2070 2075 2080 | 3744 |
| AAA GGT GGG ATT CAT TAT GGT GAA TTT ATT AAT GAA GCT AGT TTT AAT<br>Lys Gly Gly Ile His Tyr Gly Glu Phe Ile Asn Glu Ala Ser Phe Asn<br>2085 2090 2095 | 3792 |
| ATT GAA CCA TTG CAA AAT TAT GTG ACC AAA TAT GAA GTT ACT TAT AGT<br>Ile Glu Pro Leu Gln Asn Tyr Val Thr Lys Tyr Glu Val Thr Tyr Ser<br>2100 2105 2110 | 3840 |
| AGT GAG TTA GGA CCA AAC GTG AGT GAC ACA CTT GAA AGT GAT AAA ATT<br>Ser Glu Leu Gly Pro Asn Val Ser Asp Thr Leu Glu Ser Asp Lys Ile | 3888 |

-continued

```
                2115                        2120                        2125                        2130
TAC  AAG  GAT  GGG  ACA  ATT  AAA  TTT  GAT  TTT  ACC  AAA  TAT  AGT  AAA  AAT         3936
Tyr  Lys  Asp  Gly  Thr  Ile  Lys  Phe  Asp  Phe  Thr  Lys  Tyr  Ser  Lys  Asn
                         2135                     2140                    2145

GAA  CAA  GGA  TTA  TTT  TAT  GAC  AGT  GGA  TTA  AAT  TGG  GAC  TTT  AAA  ATT         3984
Glu  Gln  Gly  Leu  Phe  Tyr  Asp  Ser  Gly  Leu  Asn  Trp  Asp  Phe  Lys  Ile
                    2150                    2155                    2160

AAT  GCT  ATT  ACT  TAT  GAT  GGT  AAA  GAG  ATG  AAT  GTT  TTT  CAT  AGA  TAT         4032
Asn  Ala  Ile  Thr  Tyr  Asp  Gly  Lys  Glu  Met  Asn  Val  Phe  His  Arg  Tyr
               2165                    2170                    2175

AAT  AAA  TAG                                                                           4041
Asn  Lys
     2180
```

( 2 ) INFORMATION FOR SEQ ID NO:23:

( i ) SEQUENCE CHARACTERISTICS:
        ( A ) LENGTH: 1346 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

```
Met  Lys  Arg  Met  Glu  Gly  Lys  Leu  Phe  Met  Val  Ser  Lys  Lys  Leu  Gln
 1                  5                        10                       15

Val  Val  Thr  Lys  Thr  Val  Leu  Leu  Ser  Thr  Val  Phe  Ser  Ile  Ser  Leu
               20                       25                       30

Leu  Asn  Asn  Glu  Val  Ile  Lys  Ala  Glu  Gln  Leu  Asn  Ile  Asn  Ser  Gln
          35                       40                       45

Ser  Lys  Tyr  Thr  Asn  Leu  Gln  Asn  Leu  Lys  Ile  Thr  Asp  Lys  Val  Glu
     50                       55                       60

Asp  Phe  Lys  Glu  Asp  Lys  Glu  Lys  Ala  Lys  Glu  Trp  Gly  Lys  Glu  Lys
 65                      70                       75                       80

Glu  Lys  Glu  Trp  Lys  Leu  Thr  Ala  Thr  Glu  Lys  Gly  Lys  Met  Asn  Asn
                    85                       90                       95

Phe  Leu  Asp  Asn  Lys  Asn  Asp  Ile  Lys  Thr  Asn  Tyr  Lys  Glu  Ile  Thr
               100                      105                      110

Phe  Ser  Met  Ala  Gly  Ser  Phe  Glu  Asp  Glu  Ile  Lys  Asp  Leu  Lys  Glu
          115                      120                      125

Ile  Asp  Lys  Met  Phe  Asp  Lys  Thr  Asn  Leu  Ser  Asn  Ser  Ile  Ile  Thr
     130                      135                      140

Tyr  Lys  Asn  Val  Glu  Pro  Thr  Thr  Ile  Gly  Phe  Asn  Lys  Ser  Leu  Thr
145                      150                      155                      160

Glu  Gly  Asn  Thr  Ile  Asn  Ser  Asp  Ala  Met  Ala  Gln  Phe  Lys  Glu  Gln
                    165                      170                      175

Phe  Leu  Asp  Arg  Asp  Ile  Lys  Phe  Asp  Ser  Tyr  Leu  Asp  Thr  His  Leu
               180                      185                      190

Thr  Ala  Gln  Gln  Val  Ser  Ser  Lys  Glu  Arg  Val  Ile  Leu  Lys  Val  Thr
          195                      200                      205

Val  Pro  Ser  Gly  Lys  Gly  Ser  Thr  Thr  Pro  Thr  Lys  Ala  Gly  Val  Ile
     210                      215                      220

Leu  Asn  Asn  Ser  Glu  Tyr  Lys  Met  Leu  Ile  Asp  Asn  Gly  Tyr  Met  Val
225                      230                      235                      240

His  Val  Asp  Lys  Val  Ser  Lys  Val  Val  Lys  Lys  Gly  Val  Glu  Cys  Leu
                    245                      250                      255

Gln  Ile  Glu  Gly  Thr  Leu  Lys  Lys  Ser  Leu  Asp  Phe  Lys  Asn  Asp  Ile
               260                      265                      270
```

```
Asn Ala Glu Ala His Ser Trp Gly Met Lys Asn Tyr Glu Trp Ala
        275                 280                 285
Lys Asp Leu Thr Asp Ser Gln Arg Glu Ala Leu Asp Gly Tyr Ala Arg
        290                 295                 300
Gln Asp Tyr Lys Glu Ile Asn Asn Tyr Leu Arg Asn Gln Gly Gly Ser
305                 310                 315                 320
Gly Asn Glu Lys Leu Asp Ala Gln Ile Lys Asn Ile Ser Asp Ala Leu
                325                 330                 335
Gly Lys Lys Pro Ile Pro Glu Asn Ile Thr Val Tyr Arg Trp Cys Gly
                340                 345                 350
Met Pro Glu Phe Gly Tyr Gln Ile Ser Asp Pro Leu Pro Ser Leu Lys
                355                 360                 365
Asp Phe Glu Glu Gln Phe Leu Asn Thr Ile Lys Glu Asp Lys Gly Tyr
        370                 375                 380
Met Ser Thr Ser Leu Ser Ser Glu Arg Leu Ala Ala Phe Gly Ser Arg
385                 390                 395                 400
Lys Ile Ile Leu Arg Leu Gln Val Pro Lys Gly Ser Thr Gly Ala Tyr
                405                 410                 415
Leu Ser Ala Ile Gly Gly Phe Ala Ser Glu Lys Glu Ile Leu Leu Asp
                420                 425                 430
Lys Asp Ser Lys Tyr His Ile Asp Lys Val Thr Glu Val Ile Ile Lys
        435                 440                 445
Gly Val Lys Arg Tyr Val Val Asp Ala Thr Leu Leu Thr Asn Met Lys
        450                 455                 460
Asn Met Lys Lys Lys Leu Ala Ser Val Val Thr Cys Thr Leu Leu Ala
465                 470                 475                 480
Pro Met Phe Leu Asn Gly Asn Val Asn Ala Val Tyr Ala Asp Ser Lys
                485                 490                 495
Thr Asn Gln Ile Ser Thr Thr Gln Lys Asn Gln Lys Glu Met Asp
                500                 505                 510
Arg Lys Gly Leu Leu Gly Tyr Tyr Phe Lys Gly Lys Asp Phe Ser Asn
                515                 520                 525
Leu Thr Met Phe Ala Pro Thr Arg Asp Ser Thr Leu Ile Tyr Asp Gln
        530                 535                 540
Gln Thr Ala Asn Lys Leu Leu Asp Lys Lys Gln Glu Tyr Gln Ser
545                 550                 555                 560
Ile Arg Trp Ile Gly Leu Ile Gln Ser Lys Glu Thr Gly Asp Phe Thr
                565                 570                 575
Phe Asn Leu Ser Glu Asp Glu Gln Ala Ile Ile Glu Ile Asn Gly Lys
                580                 585                 590
Ile Ile Ser Asn Lys Gly Lys Glu Lys Gln Val Val His Leu Glu Lys
            595                 600                 605
Gly Lys Leu Val Pro Ile Lys Ile Glu Tyr Gln Ser Asp Thr Lys Phe
        610                 615                 620
Asn Ile Asp Ser Lys Thr Phe Lys Glu Leu Lys Leu Phe Lys Ile Asp
625                 630                 635                 640
Ser Gln Asn Gln Pro Gln Gln Val Gln Gln Asp Glu Leu Arg Asn Pro
                645                 650                 655
Glu Phe Asn Lys Lys Glu Ser Gln Glu Phe Leu Ala Lys Pro Ser Lys
                660                 665                 670
Ile Asn Leu Phe Thr Gln Lys Met Lys Arg Glu Ile Asp Glu Asp Thr
        675                 680                 685
Asp Thr Asp Gly Asp Ser Ile Pro Asp Leu Trp Glu Glu Asn Gly Tyr
```

|     |     |     |     |     |     |     |     |     |     |     |     |     |     |     |
| --- | --- | --- | --- | --- | --- | --- | --- | --- | --- | --- | --- | --- | --- | --- |
|     |     |     | 690 |     |     |     |     | 695 |     |     |     |     | 700 |     |
| Thr | Ile | Gln | Asn | Arg | Ile | Ala | Val | Lys | Trp | Asp | Asp | Ser | Leu | Ala | Ser |
| 705 |     |     |     |     | 710 |     |     |     |     | 715 |     |     |     |     | 720 |
| Lys | Gly | Tyr | Thr | Lys | Phe | Val | Ser | Asn | Pro | Leu | Glu | Ser | His | Thr | Val |
|     |     |     |     | 725 |     |     |     |     | 730 |     |     |     |     | 735 |     |
| Gly | Asp | Pro | Tyr | Thr | Asp | Tyr | Glu | Lys | Ala | Ala | Arg | Asp | Leu | Asp | Leu |
|     |     |     | 740 |     |     |     |     | 745 |     |     |     |     | 750 |     |     |
| Ser | Asn | Ala | Lys | Glu | Thr | Phe | Asn | Pro | Leu | Val | Ala | Ala | Phe | Pro | Ser |
|     |     | 755 |     |     |     |     | 760 |     |     |     |     | 765 |     |     |     |
| Val | Asn | Val | Ser | Met | Glu | Lys | Val | Ile | Leu | Ser | Pro | Asn | Glu | Asn | Leu |
|     | 770 |     |     |     |     | 775 |     |     |     |     | 780 |     |     |     |     |
| Ser | Asn | Ser | Val | Glu | Ser | His | Ser | Ser | Thr | Asn | Trp | Ser | Tyr | Thr | Asn |
| 785 |     |     |     |     | 790 |     |     |     |     | 795 |     |     |     |     | 800 |
| Thr | Glu | Gly | Ala | Ser | Val | Glu | Ala | Gly | Ile | Gly | Pro | Lys | Gly | Ile | Ser |
|     |     |     |     | 805 |     |     |     |     | 810 |     |     |     |     | 815 |     |
| Phe | Gly | Val | Ser | Val | Asn | Tyr | Gln | His | Ser | Glu | Thr | Val | Ala | Gln | Glu |
|     |     |     | 820 |     |     |     |     | 825 |     |     |     |     | 830 |     |     |
| Trp | Gly | Thr | Ser | Thr | Gly | Asn | Thr | Ser | Gln | Phe | Asn | Thr | Ala | Ser | Ala |
|     |     | 835 |     |     |     |     | 840 |     |     |     |     | 845 |     |     |     |
| Gly | Tyr | Leu | Asn | Ala | Asn | Val | Arg | Tyr | Asn | Asn | Val | Gly | Thr | Gly | Ala |
|     | 850 |     |     |     |     | 855 |     |     |     |     | 860 |     |     |     |     |
| Ile | Tyr | Asp | Val | Lys | Pro | Thr | Thr | Ser | Phe | Val | Leu | Asn | Asn | Asp | Thr |
| 865 |     |     |     |     | 870 |     |     |     |     | 875 |     |     |     |     | 880 |
| Ile | Ala | Thr | Ile | Thr | Ala | Lys | Ser | Asn | Ser | Thr | Ala | Leu | Asn | Ile | Ser |
|     |     |     |     | 885 |     |     |     |     | 890 |     |     |     |     | 895 |     |
| Pro | Gly | Glu | Ser | Tyr | Pro | Lys | Lys | Gly | Gln | Asn | Gly | Ile | Ala | Ile | Thr |
|     |     |     | 900 |     |     |     |     | 905 |     |     |     |     | 910 |     |     |
| Ser | Met | Asp | Asp | Phe | Asn | Ser | His | Pro | Ile | Thr | Leu | Asn | Lys | Lys | Gln |
|     |     | 915 |     |     |     |     | 920 |     |     |     |     | 925 |     |     |     |
| Val | Asp | Asn | Leu | Leu | Asn | Asn | Lys | Pro | Met | Met | Leu | Glu | Thr | Asn | Gln |
|     | 930 |     |     |     |     | 935 |     |     |     |     | 940 |     |     |     |     |
| Thr | Asp | Gly | Val | Tyr | Lys | Ile | Lys | Asp | Thr | His | Gly | Asn | Ile | Val | Thr |
| 945 |     |     |     |     | 950 |     |     |     |     | 955 |     |     |     |     | 960 |
| Gly | Gly | Glu | Trp | Asn | Gly | Val | Ile | Gln | Gln | Ile | Lys | Ala | Lys | Thr | Ala |
|     |     |     |     | 965 |     |     |     |     | 970 |     |     |     |     | 975 |     |
| Ser | Ile | Ile | Val | Asp | Asp | Gly | Glu | Arg | Val | Ala | Glu | Lys | Arg | Val | Ala |
|     |     |     | 980 |     |     |     |     | 985 |     |     |     |     | 990 |     |     |
| Ala | Lys | Asp | Tyr | Glu | Asn | Pro | Glu | Asp | Lys | Thr | Pro | Ser | Leu | Thr | Leu |
|     |     | 995 |     |     |     |     | 1000 |     |     |     |     | 1005 |     |     |     |
| Lys | Asp | Ala | Leu | Lys | Leu | Ser | Tyr | Pro | Asp | Glu | Ile | Lys | Glu | Ile | Glu |
|     | 1010 |     |     |     |     | 1015 |     |     |     |     | 1020 |     |     |     |     |
| Gly | Leu | Leu | Tyr | Tyr | Lys | Asn | Lys | Pro | Ile | Tyr | Glu | Ser | Ser | Val | Met |
| 1025 |     |     |     |     | 1030 |     |     |     |     | 1035 |     |     |     |     | 1040 |
| Thr | Tyr | Leu | Asp | Glu | Asn | Thr | Ala | Lys | Glu | Val | Thr | Lys | Gln | Leu | Asn |
|     |     |     |     | 1045 |     |     |     |     | 1050 |     |     |     |     | 1055 |     |
| Asp | Thr | Thr | Gly | Lys | Phe | Lys | Asp | Val | Ser | His | Leu | Tyr | Asp | Val | Lys |
|     |     |     | 1060 |     |     |     |     | 1065 |     |     |     |     | 1070 |     |     |
| Leu | Thr | Pro | Lys | Met | Asn | Val | Thr | Ile | Lys | Leu | Ser | Ile | Leu | Tyr | Asp |
|     |     | 1075 |     |     |     |     | 1080 |     |     |     |     | 1085 |     |     |     |
| Asn | Ala | Glu | Ser | Asn | Asp | Asn | Ser | Ile | Gly | Lys | Trp | Thr | Asn | Thr | Asn |
|     | 1090 |     |     |     |     | 1095 |     |     |     |     | 1100 |     |     |     |     |
| Ile | Val | Ser | Gly | Gly | Asn | Asn | Gly | Lys | Lys | Gln | Tyr | Ser | Ser | Asn | Asn |
| 1105 |     |     |     |     | 1110 |     |     |     |     | 1115 |     |     |     |     | 1120 |

| | | | | | | | | | | | | | |
|---|---|---|---|---|---|---|---|---|---|---|---|---|---|
|Pro|Asp|Ala|Asn|Leu|Thr|Leu|Asn|Thr|Asp|Ala|Gln|Glu|Lys|Leu|Asn|
| | | |1125| | | |1130| | | |1135| | |

Pro Asp Ala Asn Leu Thr Leu Asn Thr Asp Ala Gln Glu Lys Leu Asn
              1125                1130                1135

Lys Asn Arg Asp Tyr Tyr Ile Ser Leu Tyr Met Lys Ser Glu Lys Asn
             1140            1145            1150

Thr Gln Cys Glu Ile Thr Ile Asp Gly Glu Ile Tyr Pro Ile Thr Thr
         1155            1160            1165

Lys Thr Val Asn Val Asn Lys Asp Asn Tyr Lys Arg Leu Asp Ile Ile
     1170            1175            1180

Ala His Asn Ile Lys Ser Asn Pro Ile Ser Ser Leu His Ile Lys Thr
1185            1190            1195                 1200

Asn Asp Glu Ile Thr Leu Phe Trp Asp Ile Ser Ile Thr Asp Val
             1205            1210            1215

Ala Ser Ile Lys Pro Glu Asn Leu Thr Asp Ser Glu Ile Lys Gln Ile
         1220            1225            1230

Tyr Ser Arg Tyr Gly Ile Lys Leu Glu Asp Gly Ile Leu Ile Asp Lys
         1235            1240            1245

Lys Gly Gly Ile His Tyr Gly Glu Phe Ile Asn Glu Ala Ser Phe Asn
         1250            1255            1260

Ile Glu Pro Leu Gln Asn Tyr Val Thr Lys Tyr Glu Val Thr Tyr Ser
1265            1270            1275                 1280

Ser Glu Leu Gly Pro Asn Val Ser Asp Thr Leu Glu Ser Asp Lys Ile
             1285            1290            1295

Tyr Lys Asp Gly Thr Ile Lys Phe Asp Phe Thr Lys Tyr Ser Lys Asn
             1300            1305            1310

Glu Gln Gly Leu Phe Tyr Asp Ser Gly Leu Asn Trp Asp Phe Lys Ile
             1315            1320            1325

Asn Ala Ile Thr Tyr Asp Gly Lys Glu Met Asn Val Phe His Arg Tyr
         1330            1335            1340

Asn Lys
1345

(2) INFORMATION FOR SEQ ID NO:24:

(i) SEQUENCE CHARACTERISTICS:
        (A) LENGTH: 1399 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..1386
        (D) OTHER INFORMATION: /note= "Maize optimized DNA
         &nb -continued

| | | | | | | |
|---|---|---|---|---|---|---|
| GAGGGCAACA | CCATCAACAG | CGACGCCATG | GCCCAGTTCA | AGGAGCAGTT | CCTGGACCGC | 540 |
| GACATCAAGT | TCGACAGCTA | CCTGGACACC | CACCTGACCG | CCCAGCAGGT | GAGCAGCAAG | 600 |
| GAGCGCGTGA | TCCTGAAGGT | GACCGTCCCC | AGCGGCAAGG | GCAGCACCAC | CCCCACCAAG | 660 |
| GCCGGCGTGA | TCCTGAACAA | CAGCGAGTAC | AAGATGCTGA | TCGACAACGG | CTACATGGTG | 720 |
| CACGTGGACA | AGGTGAGCAA | GGTGGTGAAG | AAGGGCGTGG | AGTGCCTCCA | GATCGAGGGC | 780 |
| ACCCTGAAGA | AGAGTCTAGA | CTTCAAGAAC | GACATCAACG | CCGAGGCCCA | CAGCTGGGGC | 840 |
| ATGAAGAACT | ACGAGGAGTG | GGCCAAGGAC | CTGACCGACA | GCCAGCGCGA | GGCCCTGGAC | 900 |
| GGCTACGCCC | GCCAGGACTA | CAAGGAGATC | AACAACTACC | TGCGCAACCA | GGGCGGCAGC | 960 |
| GGCAACGAGA | AGCTGGACGC | CCAGATCAAG | AACATCAGCG | ACGCCCTGGG | CAAGAAGCCC | 1020 |
| ATCCCCGAGA | ACATCACCGT | GTACCGCTGG | TGCGGCATGC | CCGAGTTCGG | CTACCAGATC | 1080 |
| AGCGACCCCC | TGCCCAGCCT | GAAGGACTTC | GAGGAGCAGT | TCCTGAACAC | CATCAAGGAG | 1140 |
| GACAAGGGCT | ACATGAGCAC | CAGCCTGAGC | AGCGAGCGCC | TGGCCGCCTT | CGGCAGCCGC | 1200 |
| AAGATCATCC | TGCGCCTGCA | GGTGCCCAAG | GGCAGCACCG | GCGCCTACCT | GAGCGCCATC | 1260 |
| GGCGGCTTCG | CCAGCGAGAA | GGAGATCCTG | CTGGACAAGG | ACAGCAAGTA | CCACATCGAC | 1320 |
| AAGGTGACCG | AGGTGATCAT | CAAGGGCGTG | AAGCGCTACG | TGGTGGACGC | CACCCTGCTG | 1380 |
| ACCAACTAGA | TCTGAGCTC | | | | | 1399 |

( 2 ) INFORMATION FOR SEQ ID NO:25:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..19
( D ) OTHER INFORMATION: /note= "Secretion signal peptide to secrete VIP2 out of a cell"

( x i ) SEQUENCE DESCRIPTION: SEQ ID NO:25:

Gly Trp Ser Trp Ile Phe Leu Phe Leu Leu Ser Gly Ala Ala Gly Val
1 5 10 15

His Cys Leu ( 2 ) INFORMATION FOR SEQ ID NO:26:

( i ) SEQUENCE CHARACTERISTICS:
( A ) LENGTH: 2655 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Synthetic DNA"

( i i i ) HYPOTHETICAL: NO ( i x ) FEATURE:
( A ) NAME/KEY: misc_feature
( B ) LOCATION: 1..2655
( D ) OTHER INFORMATION: /note= "maize optimized DNA sequence encoding VIP1A(a)"

( x i ) SEQUENCE DESCRIPTION: SEQ ID NO:26:

| | | | | | | |
|---|---|---|---|---|---|---|
| ATGAAGAACA | TGAAGAAGAA | GCTGGCCAGC | GTGGTGACCT | GCACCCTGCT | GGCCCCCATG | 60 |

| | | | | | | |
|---|---|---|---|---|---|---|
| TTCCTGAACG | GCAACGTGAA | CGCCGTGTAC | GCCGACAGCA | AGACCAACCA | GATCAGCACC | 120 |
| ACCCAGAAGA | ACCAGCAGAA | GGAGATGGAC | CGCAAGGGCC | TGCTGGGCTA | CTACTTCAAG | 180 |
| GGCAAGGACT | TCAGCAACCT | GACCATGTTC | GCCCCCACGC | GTGACAGCAC | CCTGATCTAC | 240 |
| GACCAGCAGA | CCGCCAACAA | GCTGCTGGAC | AAGAAGCAGC | AGGAGTACCA | GAGCATCCGC | 300 |
| TGGATCGGCC | TGATCCAGAG | CAAGGAGACC | GGCGACTTCA | CCTTCAACCT | GAGCGAGGAC | 360 |
| GAGCAGGCCA | TCATCGAGAT | CAACGGCAAG | ATCATCAGCA | ACAAGGGCAA | GGAGAAGCAG | 420 |
| GTGGTGCACC | TGGAGAAGGG | CAAGCTGGTG | CCCATCAAGA | TCGAGTACCA | GAGCGACACC | 480 |
| AAGTTCAACA | TCGACAGCAA | GACCTTCAAG | GAGCTGAAGC | TTTTCAAGAT | CGACAGCCAG | 540 |
| AACCAGCCCC | AGCAGGTGCA | GCAGGACGAG | CTGCGCAACC | CCGAGTTCAA | CAAGAAGGAG | 600 |
| AGCCAGGAGT | TCCTGGCCAA | GCCCAGCAAG | ATCAACCTGT | TCACCCAGCA | GATGAAGCGC | 660 |
| GAGATCGACG | AGGACACCGA | CACCGACGGC | GACAGCATCC | CCGACCTGTG | GGAGGAGAAC | 720 |
| GGCTACACCA | TCCAGAACCG | CATCGCCGTG | AAGTGGGACG | ACAGCCTGGC | TAGCAAGGGC | 780 |
| TACACCAAGT | TCGTGAGCAA | CCCCCTGGAG | AGCCACACCG | TGGGCGACCC | CTACACCGAC | 840 |
| TACGAGAAGG | CCGCCCGCGA | CCTGGACCTG | AGCAACGCCA | AGGAGACCTT | CAACCCCCTG | 900 |
| GTGGCCGCCT | TCCCCAGCGT | GAACGTGAGC | ATGGAGAAGG | TGATCCTGAG | CCCCAACGAG | 960 |
| AACCTGAGCA | CAGCGTGGA | GAGCCACTCG | AGCACCAACT | GGAGCTACAC | CAACACCGAG | 1020 |
| GGCGCCAGCG | TGGAGGCCGG | CATCGGTCCC | AAGGGCATCA | GCTTCGGCGT | GAGCGTGAAC | 1080 |
| TACCAGCACA | GCGAGACCGT | GGCCCAGGAG | TGGGGCACCA | GCACCGGCAA | CACCAGCCAG | 1140 |
| TTCAACACCG | CCAGCGCCGG | CTACCTGAAC | GCCAACGTGC | GCTACAACAA | CGTGGGCACC | 1200 |
| GGCGCCATCT | ACGACGTGAA | GCCCACCACC | AGCTTCGTGC | TGAACAACGA | CACCATCGCC | 1260 |
| ACCATCACCG | CCAAGTCGAA | TTCCACCGCC | CTGAACATCA | GCCCCGGCGA | GAGCTACCCC | 1320 |
| AAGAAGGGCC | AGAACGGCAT | CGCCATCACC | AGCATGGACG | ACTTCAACAG | CCACCCCATC | 1380 |
| ACCCTGAACA | AGAAGCAGGT | GGACAACCTG | CTGAACAACA | AGCCCATGAT | GCTGGAGACC | 1440 |
| AACCAGACCG | ACGGCGTCTA | CAAGATCAAG | GACACCCACG | GCAACATCGT | GACGGGCGGC | 1500 |
| GAGTGGAACG | GCGTGATCCA | GCAGATCAAG | GCCAAGACCG | CCAGCATCAT | CGTCGACGAC | 1560 |
| GGCGAGCGCG | TGGCCGAGAA | GCGCGTGGCC | GCCAAGGACT | ACGAGAACCC | CGAGGACAAG | 1620 |
| ACCCCCAGCC | TGACCCTGAA | GGACGCCCTG | AAGCTGAGCT | ACCCCGACGA | GATCAAGGAG | 1680 |
| ATCGAGGGCT | TGCTGTACTA | CAAGAACAAG | CCCATCTACG | AGAGCAGCGT | GATGACCTAT | 1740 |
| CTAGACGAGA | ACACCGCCAA | GGAGGTGACC | AAGCAGCTGA | ACGACACCAC | CGGCAAGTTC | 1800 |
| AAGGACGTGA | GCCACCTGTA | CGACGTGAAG | CTGACCCCCA | AGATGAACGT | GACCATCAAG | 1860 |
| CTGAGCATCC | TGTACGACAA | CGCCGAGAGC | AACGACAACA | GCATCGGCAA | GTGGACCAAC | 1920 |
| ACCAACATCG | TGAGCGGCGG | CAACAACGGC | AAGAAGCAGT | ACAGCAGCAA | CAACCCCGAC | 1980 |
| GCCAACCTGA | CCCTGAACAC | CGACGCCCAG | GAGAAGCTGA | CAAGAACCG | CGACTACTAC | 2040 |
| ATCAGCCTGT | ACATGAAGAG | CGAGAAGAAC | ACCCAGTGCG | AGATCACCAT | CGACGGCGAG | 2100 |
| ATATACCCCA | TCACCACCAA | GACCGTGAAC | GTGAACAAGG | ACAACTACAA | GCGCCTGGAC | 2160 |
| ATCATCGCCC | ACAACATCAA | GAGCAACCCC | ATCAGCAGCC | TGCACATCAA | GACCAACGAC | 2220 |
| GAGATCACCC | TGTTCTGGGA | CGACATATCG | ATTACCGACG | TCGCCAGCAT | CAAGCCCGAG | 2280 |
| AACCTGACCG | ACAGCGAGAT | CAAGCAGATA | TACAGTCGCT | ACGGCATCAA | GCTGGAGGAC | 2340 |
| GGCATCCTGA | TCGACAAGAA | AGGCGGCATC | CACTACGGCG | AGTTCATCAA | CGAGGCCAGC | 2400 |
| TTCAACATCG | AGCCCCTGCA | GAACTACGTG | ACCAAGTACG | AGGTGACCTA | CAGCAGCGAG | 2460 |

-continued

```
CTGGGCCCCA ACGTGAGCGA CACCCTGGAG AGCGACAAGA TTTACAAGGA CGGCACCATC 2520
AAGTTCGACT TCACCAAGTA CAGCAAGAAC GAGCAGGGCC TGTTCTACGA CAGCGGCCTG 2580
AACTGGGACT TCAAGATCAA CGCCATCACC TACGACGGCA AGGAGATGAA CGTGTTCCAC 2640
CGCTACAACA AGTAG 2655
```

( 2 ) INFORMATION FOR SEQ ID NO:27:

( i ) SEQUENCE CHARACTERISTICS:
( A ) LENGTH: 1389 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Synthetic DNA"

( i i i ) HYPOTHETICAL: NO ( i x ) FEATURE:
( A ) NAME/KEY: misc_feature
( B ) LOCATION: 1..1389
( D ) OTHER INFORMATION: /note= "maize optimized DNA sequence encoding VIP2A(a)"

( x i ) SEQUENCE DESCRIPTION: SEQ ID NO:27:

```
ATGAAGCGCA TGGAGGGCAA GCTGTTCATG GTGAGCAAGA AGCTCCAGGT GGTGACCAAG 60
ACCGTGCTGC TGAGCACCGT GTTCAGCATC AGCCTGCTGA ACAACGAGGT GATCAAGGCC 120
GAGCAGCTGA ACATCAACAG CCAGAGCAAG TACACCAACC TCCAGAACCT GAAGATCACC 180
GACAAGGTGG AGGACTTCAA GGAGGACAAG GAGAAGGCCA AGGAGTGGGG CAAGGAGAAG 240
GAGAAGGAGT GGAAGCTTAC CGCCACCGAG AAGGGCAAGA TGAACAACTT CCTGGACAAC 300
AAGAACGACA TCAAGACCAA CTACAAGGAG ATCACCTTCA GCATAGCCGG CAGCTTCGAG 360
GACGAGATCA AGGACCTGAA GGAGATCGAC AAGATGTTCG ACAAGACCAA CCTGAGCAAC 420
AGCATCATCA CCTACAAGAA CGTGGAGCCC ACCACCATCG GCTTCAACAA GAGCCTGACC 480
GAGGGCAACA CCATCAACAG CGACGCCATG GCCCAGTTCA AGGAGCAGTT CCTGGACCGC 540
GACATCAAGT TCGACAGCTA CCTGGACACC CACCTGACCG CCCAGCAGGT GAGCAGCAAG 600
GAGCGCGTGA TCCTGAAGGT GACCGTCCCC AGCGGCAAGG GCAGCACCAC CCCCACCAAG 660
GCCGGCGTGA TCCTGAACAA CAGCGAGTAC AAGATGCTGA TCGACAACGG CTACATGGTG 720
CACGTGGACA AGGTGAGCAA GGTGGTGAAG AAGGGCGTGG AGTGCCTCCA GATCGAGGGC 780
ACCCTGAAGA AGAGTCTAGA CTTCAAGAAC GACATCAACG CCGAGGCCCA CAGCTGGGGC 840
ATGAAGAACT ACGAGGAGTG GGCCAAGGAC CTGACCGACA GCCAGCGCGA GGCCCTGGAC 900
GGCTACGCCC GCCAGGACTA CAAGGAGATC AACAACTACC TGCGCAACCA GGGCGGCAGC 960
GGCAACGAGA AGCTGGACGC CCAGATCAAG AACATCAGCG ACGCCCTGGG CAAGAAGCCC 1020
ATCCCCGAGA ACATCACCGT GTACCGCTGG TGCGGCATGC CCGAGTTCGG CTACCAGATC 1080
AGCGACCCCC TGCCCAGCCT GAAGGACTTC GAGGAGCAGT TCCTGAACAC CATCAAGGAG 1140
GACAAGGGCT ACATGAGCAC CAGCCTGAGC AGCGAGCGCC TGGCCGCCTT CGGCAGCCGC 1200
AAGATCATCC TGCGCCTGCA GGTGCCCAAG GGCAGCACTG GTGCCTACCT GAGCGCCATC 1260
GGCGGCTTCG CCAGCGAGAA GGAGATCCTG CTGGATAAGG ACAGCAAGTA CCACATCGAC 1320
AAGGTGACCG AGGTGATCAT CAAGGGCGTG AAGCGCTACG TGGTGGACGC CACCCTGCTG 1380
ACCAACTAG 1389
```

( 2 ) INFORMATION FOR SEQ ID NO:28:

( i ) SEQUENCE CHARACTERISTICS:
    ( A ) LENGTH: 2378 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i x ) FEATURE:
    ( A ) NAME/KEY: CDS
    ( B ) LOCATION: 9..2375
    ( D ) OTHER INFORMATION: /note= "Native DNA sequence encoding VIP3A(a) protein from AB88 as contained in pCIB7104"

( x i ) SEQUENCE DESCRIPTION: SEQ ID NO:28:

```
AGATGAAC ATG AAC AAG AAT AAT ACT AAA TTA AGC ACA AGA GCC TTA CCA     50
         Met Asn Lys Asn Asn Thr Lys Leu Ser Thr Arg Ala Leu Pro
           1               5                  10

AGT TTT ATT GAT TAT TTT AAT GGC ATT TAT GGA TTT GCC ACT GGT ATC      98
Ser Phe Ile Asp Tyr Phe Asn Gly Ile Tyr Gly Phe Ala Thr Gly Ile
 15                  20                  25                  30

AAA GAC ATT ATG AAC ATG ATT TTT AAA ACG GAT ACA GGT GGT GAT CTA     146
Lys Asp Ile Met Asn Met Ile Phe Lys Thr Asp Thr Gly Gly Asp Leu
                 35                  40                  45

ACC CTA GAC GAA ATT TTA AAG AAT CAG CAG TTA CTA AAT GAT ATT TCT     194
Thr Leu Asp Glu Ile Leu Lys Asn Gln Gln Leu Leu Asn Asp Ile Ser
             50                  55                  60

GGT AAA TTG GAT GGG GTG AAT GGA AGC TTA AAT GAT CTT ATC GCA CAG     242
Gly Lys Leu Asp Gly Val Asn Gly Ser Leu Asn Asp Leu Ile Ala Gln
         65                  70                  75

GGA AAC TTA AAT ACA GAA TTA TCT AAG GAA ATA TTA AAA ATT GCA AAT     290
Gly Asn Leu Asn Thr Glu Leu Ser Lys Glu Ile Leu Lys Ile Ala Asn
     80                  85                  90

GAA CAA AAT CAA GTT TTA AAT GAT GTT AAT AAC AAA CTC GAT GCG ATA     338
Glu Gln Asn Gln Val Leu Asn Asp Val Asn Asn Lys Leu Asp Ala Ile
 95                 100                 105                 110

AAT ACG ATG CTT CGG GTA TAT CTA CCT AAA ATT ACC TCT ATG TTG AGT     386
Asn Thr Met Leu Arg Val Tyr Leu Pro Lys Ile Thr Ser Met Leu Ser
                115                 120                 125

GAT GTA ATG AAA CAA AAT TAT GCG CTA AGT CTG CAA ATA GAA TAC TTA     434
Asp Val Met Lys Gln Asn Tyr Ala Leu Ser Leu Gln Ile Glu Tyr Leu
            130                 135                 140

AGT AAA CAA TTG CAA GAG ATT TCT GAT AAG TTG GAT ATT ATT AAT GTA     482
Ser Lys Gln Leu Gln Glu Ile Ser Asp Lys Leu Asp Ile Ile Asn Val
        145                 150                 155

AAT GTA CTT ATT AAC TCT ACA CTT ACT GAA ATT ACA CCT GCG TAT CAA     530
Asn Val Leu Ile Asn Ser Thr Leu Thr Glu Ile Thr Pro Ala Tyr Gln
    160                 165                 170

AGG ATT AAA TAT GTG AAC GAA AAA TTT GAG GAA TTA ACT TTT GCT ACA     578
Arg Ile Lys Tyr Val Asn Glu Lys Phe Glu Glu Leu Thr Phe Ala Thr
175                 180                 185                 190

GAA ACT AGT TCA AAA GTA AAA AAG GAT GGC TCT CCT GCA GAT ATT CTT     626
Glu Thr Ser Ser Lys Val Lys Lys Asp Gly Ser Pro Ala Asp Ile Leu
                195                 200                 205

GAT GAG TTA ACT GAG TTA ACT GAA CTA GCG AAA AGT GTA ACA AAA AAT     674
Asp Glu Leu Thr Glu Leu Thr Glu Leu Ala Lys Ser Val Thr Lys Asn
            210                 215                 220

GAT GTG GAT GGT TTT GAA TTT TAC CTT AAT ACA TTC CAC GAT GTA ATG     722
Asp Val Asp Gly Phe Glu Phe Tyr Leu Asn Thr Phe His Asp Val Met
        225                 230                 235
```

| | | | | | | | | | | | | | | | | |
|---|---|---|---|---|---|---|---|---|---|---|---|---|---|---|---|---|
| GTA | GGA | AAT | AAT | TTA | TTC | GGG | CGT | TCA | GCT | TTA | AAA | ACT | GCA | TCG | GAA | 770 |
| Val | Gly | Asn | Asn | Leu | Phe | Gly | Arg | Ser | Ala | Leu | Lys | Thr | Ala | Ser | Glu | |
| | 240 | | | | 245 | | | | | 250 | | | | | | |
| TTA | ATT | ACT | AAA | GAA | AAT | GTG | AAA | ACA | AGT | GGC | AGT | GAG | GTC | GGA | AAT | 818 |
| Leu | Ile | Thr | Lys | Glu | Asn | Val | Lys | Thr | Ser | Gly | Ser | Glu | Val | Gly | Asn | |
| 255 | | | | | 260 | | | | | 265 | | | | | 270 | |
| GTT | TAT | AAC | TTC | TTA | ATT | GTA | TTA | ACA | GCT | CTG | CAA | GCC | CAA | GCT | TTT | 866 |
| Val | Tyr | Asn | Phe | Leu | Ile | Val | Leu | Thr | Ala | Leu | Gln | Ala | Gln | Ala | Phe | |
| | | | | 275 | | | | | 280 | | | | | 285 | | |
| CTT | ACT | TTA | ACA | ACA | TGC | CGA | AAA | TTA | TTA | GGC | TTA | GCA | GAT | ATT | GAT | 914 |
| Leu | Thr | Leu | Thr | Thr | Cys | Arg | Lys | Leu | Leu | Gly | Leu | Ala | Asp | Ile | Asp | |
| | | | 290 | | | | | 295 | | | | | 300 | | | |
| TAT | ACT | TCT | ATT | ATG | AAT | GAA | CAT | TTA | AAT | AAG | GAA | AAA | GAG | GAA | TTT | 962 |
| Tyr | Thr | Ser | Ile | Met | Asn | Glu | His | Leu | Asn | Lys | Glu | Lys | Glu | Glu | Phe | |
| | | 305 | | | | | 310 | | | | | 315 | | | | |
| AGA | GTA | AAC | ATC | CTC | CCT | ACA | CTT | TCT | AAT | ACT | TTT | TCT | AAT | CCT | AAT | 1010 |
| Arg | Val | Asn | Ile | Leu | Pro | Thr | Leu | Ser | Asn | Thr | Phe | Ser | Asn | Pro | Asn | |
| | 320 | | | | | 325 | | | | | 330 | | | | | |
| TAT | GCA | AAA | GTT | AAA | GGA | AGT | GAT | GAA | GAT | GCA | AAG | ATG | ATT | GTG | GAA | 1058 |
| Tyr | Ala | Lys | Val | Lys | Gly | Ser | Asp | Glu | Asp | Ala | Lys | Met | Ile | Val | Glu | |
| 335 | | | | | 340 | | | | | 345 | | | | | 350 | |
| GCT | AAA | CCA | GGA | CAT | GCA | TTG | ATT | GGG | TTT | GAA | ATT | AGT | AAT | GAT | TCA | 1106 |
| Ala | Lys | Pro | Gly | His | Ala | Leu | Ile | Gly | Phe | Glu | Ile | Ser | Asn | Asp | Ser | |
| | | | | 355 | | | | | 360 | | | | | 365 | | |
| ATT | ACA | GTA | TTA | AAA | GTA | TAT | GAG | GCT | AAG | CTA | AAA | CAA | AAT | TAT | CAA | 1154 |
| Ile | Thr | Val | Leu | Lys | Val | Tyr | Glu | Ala | Lys | Leu | Lys | Gln | Asn | Tyr | Gln | |
| | | | 370 | | | | | 375 | | | | | 380 | | | |
| GTC | GAT | AAG | GAT | TCC | TTA | TCG | GAA | GTT | ATT | TAT | GGT | GAT | ATG | GAT | AAA | 1202 |
| Val | Asp | Lys | Asp | Ser | Leu | Ser | Glu | Val | Ile | Tyr | Gly | Asp | Met | Asp | Lys | |
| | | 385 | | | | | 390 | | | | | 395 | | | | |
| TTA | TTG | TGC | CCA | GAT | CAA | TCT | GAA | CAA | ATC | TAT | TAT | ACA | AAT | AAC | ATA | 1250 |
| Leu | Leu | Cys | Pro | Asp | Gln | Ser | Glu | Gln | Ile | Tyr | Tyr | Thr | Asn | Asn | Ile | |
| | 400 | | | | | 405 | | | | | 410 | | | | | |
| GTA | TTT | CCA | AAT | GAA | TAT | GTA | ATT | ACT | AAA | ATT | GAT | TTC | ACT | AAA | AAA | 1298 |
| Val | Phe | Pro | Asn | Glu | Tyr | Val | Ile | Thr | Lys | Ile | Asp | Phe | Thr | Lys | Lys | |
| 415 | | | | | 420 | | | | | 425 | | | | | 430 | |
| ATG | AAA | ACT | TTA | AGA | TAT | GAG | GTA | ACA | GCG | AAT | TTT | TAT | GAT | TCT | TCT | 1346 |
| Met | Lys | Thr | Leu | Arg | Tyr | Glu | Val | Thr | Ala | Asn | Phe | Tyr | Asp | Ser | Ser | |
| | | | | 435 | | | | | 440 | | | | | 445 | | |
| ACA | GGA | GAA | ATT | GAC | TTA | AAT | AAG | AAA | AAA | GTA | GAA | TCA | AGT | GAA | GCG | 1394 |
| Thr | Gly | Glu | Ile | Asp | Leu | Asn | Lys | Lys | Lys | Val | Glu | Ser | Ser | Glu | Ala | |
| | | | 450 | | | | | 455 | | | | | 460 | | | |
| GAG | TAT | AGA | ACG | TTA | AGT | GCT | AAT | GAT | GAT | GGG | GTG | TAT | ATG | CCG | TTA | 1442 |
| Glu | Tyr | Arg | Thr | Leu | Ser | Ala | Asn | Asp | Asp | Gly | Val | Tyr | Met | Pro | Leu | |
| | | 465 | | | | | 470 | | | | | 475 | | | | |
| GGT | GTC | ATC | AGT | GAA | ACA | TTT | TTG | ACT | CCG | ATT | AAT | GGG | TTT | GGC | CTC | 1490 |
| Gly | Val | Ile | Ser | Glu | Thr | Phe | Leu | Thr | Pro | Ile | Asn | Gly | Phe | Gly | Leu | |
| | 480 | | | | | 485 | | | | | 490 | | | | | |
| CAA | GCT | GAT | GAA | AAT | TCA | AGA | TTA | ATT | ACT | TTA | ACA | TGT | AAA | TCA | TAT | 1538 |
| Gln | Ala | Asp | Glu | Asn | Ser | Arg | Leu | Ile | Thr | Leu | Thr | Cys | Lys | Ser | Tyr | |
| 495 | | | | | 500 | | | | | 505 | | | | | 510 | |
| TTA | AGA | GAA | CTA | CTG | CTA | GCA | ACA | GAC | TTA | AGC | AAT | AAA | GAA | ACT | AAA | 1586 |
| Leu | Arg | Glu | Leu | Leu | Leu | Ala | Thr | Asp | Leu | Ser | Asn | Lys | Glu | Thr | Lys | |
| | | | | 515 | | | | | 520 | | | | | 525 | | |
| TTG | ATC | GTC | CCG | CCA | AGT | GGT | TTT | ATT | AGC | AAT | ATT | GTA | GAG | AAC | GGG | 1634 |
| Leu | Ile | Val | Pro | Pro | Ser | Gly | Phe | Ile | Ser | Asn | Ile | Val | Glu | Asn | Gly | |
| | | | 530 | | | | | 535 | | | | | 540 | | | |
| TCC | ATA | GAA | GAG | GAC | AAT | TTA | GAG | CCG | TGG | AAA | GCA | AAT | AAT | AAG | AAT | 1682 |
| Ser | Ile | Glu | Glu | Asp | Asn | Leu | Glu | Pro | Trp | Lys | Ala | Asn | Asn | Lys | Asn | |
| | | 545 | | | | | 550 | | | | | 555 | | | | |

| | | | | | | | | | | | | | | | | |
|---|---|---|---|---|---|---|---|---|---|---|---|---|---|---|---|---|
| GCG | TAT | GTA | GAT | CAT | ACA | GGC | GGA | GTG | AAT | GGA | ACT | AAA | GCT | TTA | TAT | 1730 |
| Ala | Tyr | Val | Asp | His | Thr | Gly | Gly | Val | Asn | Gly | Thr | Lys | Ala | Leu | Tyr | |
| | 560 | | | | | 565 | | | | | 570 | | | | | |
| GTT | CAT | AAG | GAC | GGA | GGA | ATT | TCA | CAA | TTT | ATT | GGA | GAT | AAG | TTA | AAA | 1778 |
| Val | His | Lys | Asp | Gly | Gly | Ile | Ser | Gln | Phe | Ile | Gly | Asp | Lys | Leu | Lys | |
| 575 | | | | 580 | | | | | 585 | | | | | | 590 | |
| CCG | AAA | ACT | GAG | TAT | GTA | ATC | CAA | TAT | ACT | GTT | AAA | GGA | AAA | CCT | TCT | 1826 |
| Pro | Lys | Thr | Glu | Tyr | Val | Ile | Gln | Tyr | Thr | Val | Lys | Gly | Lys | Pro | Ser | |
| | | | | 595 | | | | | 600 | | | | | 605 | | |
| ATT | CAT | TTA | AAA | GAT | GAA | AAT | ACT | GGA | TAT | ATT | CAT | TAT | GAA | GAT | ACA | 1874 |
| Ile | His | Leu | Lys | Asp | Glu | Asn | Thr | Gly | Tyr | Ile | His | Tyr | Glu | Asp | Thr | |
| | | | 610 | | | | | 615 | | | | | 620 | | | |
| AAT | AAT | AAT | TTA | GAA | GAT | TAT | CAA | ACT | ATT | AAT | AAA | CGT | TTT | ACT | ACA | 1922 |
| Asn | Asn | Asn | Leu | Glu | Asp | Tyr | Gln | Thr | Ile | Asn | Lys | Arg | Phe | Thr | Thr | |
| | | 625 | | | | | 630 | | | | | 635 | | | | |
| GGA | ACT | GAT | TTA | AAG | GGA | GTG | TAT | TTA | ATT | TTA | AAA | AGT | CAA | AAT | GGA | 1970 |
| Gly | Thr | Asp | Leu | Lys | Gly | Val | Tyr | Leu | Ile | Leu | Lys | Ser | Gln | Asn | Gly | |
| | 640 | | | | | 645 | | | | | 650 | | | | | |
| GAT | GAA | GCT | TGG | GGA | GAT | AAC | TTT | ATT | ATT | TTG | GAA | ATT | AGT | CCT | TCT | 2018 |
| Asp | Glu | Ala | Trp | Gly | Asp | Asn | Phe | Ile | Ile | Leu | Glu | Ile | Ser | Pro | Ser | |
| 655 | | | | | 660 | | | | | 665 | | | | | 670 | |
| GAA | AAG | TTA | TTA | AGT | CCA | GAA | TTA | ATT | AAT | ACA | AAT | AAT | TGG | ACG | AGT | 2066 |
| Glu | Lys | Leu | Leu | Ser | Pro | Glu | Leu | Ile | Asn | Thr | Asn | Asn | Trp | Thr | Ser | |
| | | | | 675 | | | | | 680 | | | | | 685 | | |
| ACG | GGA | TCA | ACT | AAT | ATT | AGC | GGT | AAT | ACA | CTC | ACT | CTT | TAT | CAG | GGA | 2114 |
| Thr | Gly | Ser | Thr | Asn | Ile | Ser | Gly | Asn | Thr | Leu | Thr | Leu | Tyr | Gln | Gly | |
| | | | 690 | | | | | 695 | | | | | 700 | | | |
| GGA | CGA | GGG | ATT | CTA | AAA | CAA | AAC | CTT | CAA | TTA | GAT | AGT | TTT | TCA | ACT | 2162 |
| Gly | Arg | Gly | Ile | Leu | Lys | Gln | Asn | Leu | Gln | Leu | Asp | Ser | Phe | Ser | Thr | |
| | | 705 | | | | | 710 | | | | | 715 | | | | |
| TAT | AGA | GTG | TAT | TTT | TCT | GTG | TCC | GGA | GAT | GCT | AAT | GTA | AGG | ATT | AGA | 2210 |
| Tyr | Arg | Val | Tyr | Phe | Ser | Val | Ser | Gly | Asp | Ala | Asn | Val | Arg | Ile | Arg | |
| | 720 | | | | | 725 | | | | | 730 | | | | | |
| AAT | TCT | AGG | GAA | GTG | TTA | TTT | GAA | AAA | AGA | TAT | ATG | AGC | GGT | GCT | AAA | 2258 |
| Asn | Ser | Arg | Glu | Val | Leu | Phe | Glu | Lys | Arg | Tyr | Met | Ser | Gly | Ala | Lys | |
| 735 | | | | | 740 | | | | | 745 | | | | | 750 | |
| GAT | GTT | TCT | GAA | ATG | TTC | ACT | ACA | AAA | TTT | GAG | AAA | GAT | AAC | TTT | TAT | 2306 |
| Asp | Val | Ser | Glu | Met | Phe | Thr | Thr | Lys | Phe | Glu | Lys | Asp | Asn | Phe | Tyr | |
| | | | | 755 | | | | | 760 | | | | | 765 | | |
| ATA | GAG | CTT | TCT | CAA | GGG | AAT | AAT | TTA | TAT | GGT | GGT | CCT | ATT | GTA | CAT | 2354 |
| Ile | Glu | Leu | Ser | Gln | Gly | Asn | Asn | Leu | Tyr | Gly | Gly | Pro | Ile | Val | His | |
| | | | 770 | | | | | 775 | | | | | 780 | | | |
| TTT | TAC | GAT | GTC | TCT | ATT | AAG | TAA | | | | | | | | | 2378 |
| Phe | Tyr | Asp | Val | Ser | Ile | Lys | | | | | | | | | | |
| | | 785 | | | | | | | | | | | | | | |

( 2 ) INFORMATION FOR SEQ ID NO:29:

( i ) SEQUENCE CHARACTERISTICS:
        ( A ) LENGTH: 789 amino acids
        ( B ) TYPE: amino acid
        ( D ) TOPOLOGY: linear ( i i ) MOLECULE TYPE: protein ( x i ) SEQUENCE DESCRIPTION: SEQ ID NO:29:

| | | | | | | | | | | | | | | | |
|---|---|---|---|---|---|---|---|---|---|---|---|---|---|---|---|
| Met | Asn | Lys | Asn | Asn | Thr | Lys | Leu | Ser | Thr | Arg | Ala | Leu | Pro | Ser | Phe |
| 1 | | | | 5 | | | | | 10 | | | | | 15 | |
| Ile | Asp | Tyr | Phe | Asn | Gly | Ile | Tyr | Gly | Phe | Ala | Thr | Gly | Ile | Lys | Asp |
| | | | 20 | | | | | 25 | | | | | 30 | | |
| Ile | Met | Asn | Met | Ile | Phe | Lys | Thr | Asp | Thr | Gly | Gly | Asp | Leu | Thr | Leu |
| | | 35 | | | | | 40 | | | | | 45 | | | |

```
Asp  Glu  Ile  Leu  Lys  Asn  Gln  Gln  Leu  Leu  Asn  Asp  Ile  Ser  Gly  Lys
         50                      55                      60

Leu  Asp  Gly  Val  Asn  Gly  Ser  Leu  Asn  Asp  Leu  Ile  Ala  Gln  Gly  Asn
 65                      70                      75                       80

Leu  Asn  Thr  Glu  Leu  Ser  Lys  Glu  Ile  Leu  Lys  Ile  Ala  Asn  Glu  Gln
                         85                      90                       95

Asn  Gln  Val  Leu  Asn  Asp  Val  Asn  Asn  Lys  Leu  Asp  Ala  Ile  Asn  Thr
               100                     105                    110

Met  Leu  Arg  Val  Tyr  Leu  Pro  Lys  Ile  Thr  Ser  Met  Leu  Ser  Asp  Val
          115                    120                    125

Met  Lys  Gln  Asn  Tyr  Ala  Leu  Ser  Leu  Gln  Ile  Glu  Tyr  Leu  Ser  Lys
          130                    135                    140

Gln  Leu  Gln  Glu  Ile  Ser  Asp  Lys  Leu  Asp  Ile  Ile  Asn  Val  Asn  Val
145                      150                    155                        160

Leu  Ile  Asn  Ser  Thr  Leu  Thr  Glu  Ile  Thr  Pro  Ala  Tyr  Gln  Arg  Ile
                    165                    170                    175

Lys  Tyr  Val  Asn  Glu  Lys  Phe  Glu  Glu  Leu  Thr  Phe  Ala  Thr  Glu  Thr
               180                    185                    190

Ser  Ser  Lys  Val  Lys  Lys  Asp  Gly  Ser  Pro  Ala  Asp  Ile  Leu  Asp  Glu
          195                    200                    205

Leu  Thr  Glu  Leu  Thr  Glu  Leu  Ala  Lys  Ser  Val  Thr  Lys  Asn  Asp  Val
     210                    215                    220

Asp  Gly  Phe  Glu  Phe  Tyr  Leu  Asn  Thr  Phe  His  Asp  Val  Met  Val  Gly
225                      230                    235                        240

Asn  Asn  Leu  Phe  Gly  Arg  Ser  Ala  Leu  Lys  Thr  Ala  Ser  Glu  Leu  Ile
                    245                    250                    255

Thr  Lys  Glu  Asn  Val  Lys  Thr  Ser  Gly  Ser  Glu  Val  Gly  Asn  Val  Tyr
               260                    265                    270

Asn  Phe  Leu  Ile  Val  Leu  Thr  Ala  Leu  Gln  Ala  Gln  Ala  Phe  Leu  Thr
          275                    280                    285

Leu  Thr  Thr  Cys  Arg  Lys  Leu  Leu  Gly  Leu  Ala  Asp  Ile  Asp  Tyr  Thr
     290                    295                    300

Ser  Ile  Met  Asn  Glu  His  Leu  Asn  Lys  Glu  Lys  Glu  Glu  Phe  Arg  Val
305                      310                    315                        320

Asn  Ile  Leu  Pro  Thr  Leu  Ser  Asn  Thr  Phe  Ser  Asn  Pro  Asn  Tyr  Ala
                    325                    330                    335

Lys  Val  Lys  Gly  Ser  Asp  Glu  Asp  Ala  Lys  Met  Ile  Val  Glu  Ala  Lys
               340                    345                    350

Pro  Gly  His  Ala  Leu  Ile  Gly  Phe  Glu  Ile  Ser  Asn  Asp  Ser  Ile  Thr
          355                    360                    365

Val  Leu  Lys  Val  Tyr  Glu  Ala  Lys  Leu  Lys  Gln  Asn  Tyr  Gln  Val  Asp
     370                    375                    380

Lys  Asp  Ser  Leu  Ser  Glu  Val  Ile  Tyr  Gly  Asp  Met  Asp  Lys  Leu  Leu
385                      390                    395                        400

Cys  Pro  Asp  Gln  Ser  Glu  Gln  Ile  Tyr  Tyr  Thr  Asn  Asn  Ile  Val  Phe
                    405                    410                    415

Pro  Asn  Glu  Tyr  Val  Ile  Thr  Lys  Ile  Asp  Phe  Thr  Lys  Lys  Met  Lys
               420                    425                    430

Thr  Leu  Arg  Tyr  Glu  Val  Thr  Ala  Asn  Phe  Tyr  Asp  Ser  Ser  Thr  Gly
          435                    440                    445

Glu  Ile  Asp  Leu  Asn  Lys  Lys  Lys  Val  Glu  Ser  Ser  Glu  Ala  Glu  Tyr
     450                    455                    460

Arg  Thr  Leu  Ser  Ala  Asn  Asp  Asp  Gly  Val  Tyr  Met  Pro  Leu  Gly  Val
```

|     |     |     |     | 465 |     |     |     |     | 470 |     |     |     |     | 475 |     |     |     |     | 480 |
| --- | --- | --- | --- | --- | --- | --- | --- | --- | --- | --- | --- | --- | --- | --- | --- | --- | --- | --- | --- |

Ile Ser Glu Thr Phe Leu Thr Pro Ile Asn Gly Phe Gly Leu Gln Ala
             485                 490                 495

Asp Glu Asn Ser Arg Leu Ile Thr Leu Thr Cys Lys Ser Tyr Leu Arg
         500                 505                 510

Glu Leu Leu Leu Ala Thr Asp Leu Ser Asn Lys Glu Thr Lys Leu Ile
         515                 520                 525

Val Pro Pro Ser Gly Phe Ile Ser Asn Ile Val Glu Asn Gly Ser Ile
    530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
             565                 570                 575

Lys Asp Gly Gly Ile Ser Gln Phe Ile Gly Asp Lys Leu Lys Pro Lys
             580                 585                 590

Thr Glu Tyr Val Ile Gln Tyr Thr Val Lys Gly Lys Pro Ser Ile His
         595                 600                 605

Leu Lys Asp Glu Asn Thr Gly Tyr Ile His Tyr Glu Asp Thr Asn Asn
    610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
             645                 650                 655

Ala Trp Gly Asp Asn Phe Ile Ile Leu Glu Ile Ser Pro Ser Glu Lys
             660                 665                 670

Leu Leu Ser Pro Glu Leu Ile Asn Thr Asn Asn Trp Thr Ser Thr Gly
         675                 680                 685

Ser Thr Asn Ile Ser Gly Asn Thr Leu Thr Leu Tyr Gln Gly Gly Arg
    690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
             725                 730                 735

Arg Glu Val Leu Phe Glu Lys Arg Tyr Met Ser Gly Ala Lys Asp Val
             740                 745                 750

Ser Glu Met Phe Thr Thr Lys Phe Glu Lys Asp Asn Phe Tyr Ile Glu
         755                 760                 765

Leu Ser Gln Gly Asn Asn Leu Tyr Gly Gly Pro Ile Val His Phe Tyr
    770                 775                 780

Asp Val Ser Ile Lys
785

( 2 ) INFORMATION FOR SEQ ID NO:30:

( i ) SEQUENCE CHARACTERISTICS:
        ( A ) LENGTH: 2403 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: misc_feature
        ( B ) LOCATION: 11..2389
        ( D ) OTHER INFORMATION: /note= "maize optimized DNA sequence encoding VIP3A(a)"

( x i ) SEQUENCE DESCRIPTION: SEQ ID NO:30:

| | | | | | | |
|---|---|---|---|---|---|---|
| GGATCCACCA | ATGAACATGA | ACAAGAACAA | CACCAAGCTG | AGCACCCGCG | CCCTGCCGAG | 60 |
| CTTCATCGAC | TACTTCAACG | GCATCTACGG | CTTCGCCACC | GGCATCAAGG | ACATCATGAA | 120 |
| CATGATCTTC | AAGACCGACA | CCGGCGGCGA | CCTGACCCTG | GACGAGATCC | TGAAGAACCA | 180 |
| GCAGCTGCTG | AACGACATCA | GCGGCAAGCT | GGACGGCGTG | AACGGCAGCC | TGAACGACCT | 240 |
| GATCGCCCAG | GGCAACCTGA | ACACCGAGCT | GAGCAAGGAG | ATCCTTAAGA | TCGCCAACGA | 300 |
| GCAGAACCAG | GTGCTGAACG | ACGTGAACAA | CAAGCTGGAC | GCCATCAACA | CCATGCTGCG | 360 |
| CGTGTACCTG | CCGAAGATCA | CCAGCATGCT | GAGCGACGTG | ATGAAGCAGA | ACTACGCCCT | 420 |
| GAGCCTGCAG | ATCGAGTACC | TGAGCAAGCA | GCTGCAGGAG | ATCAGCGACA | AGCTGGACAT | 480 |
| CATCAACGTG | AACGTCCTGA | TCAACAGCAC | CCTGACCGAG | ATCACCCCGG | CCTACCAGCG | 540 |
| CATCAAGTAC | GTGAACGAGA | AGTTCGAAGA | GCTGACCTTC | GCCACCGAGA | CCAGCAGCAA | 600 |
| GGTGAAGAAG | GACGGCAGCC | CGGCCGACAT | CCTGGACGAG | CTGACCGAGC | TGACCGAGCT | 660 |
| GGCCAAGAGC | GTGACCAAGA | ACGACGTGGA | CGGCTTCGAG | TTCTACCTGA | ACACCTTCCA | 720 |
| CGACGTGATG | GTGGGCAACA | ACCTGTTCGG | CCGCAGCGCC | CTGAAGACCG | CCAGCGAGCT | 780 |
| GATCACCAAG | GAGAACGTGA | AGACCAGCGG | CAGCGAGGTG | GGCAACGTGT | ACAACTTCCT | 840 |
| GATCGTGCTG | ACCGCCCTGC | AGGCCCAGGC | CTTCCTGACC | CTGACCACCT | GTCGCAAGCT | 900 |
| GCTGGGCCTG | GCCGACATCG | ACTACACCAG | CATCATGAAC | GAGCACTTGA | CAAGGAGAA | 960 |
| GGAGGAGTTC | CGCGTGAACA | TCCTGCCGAC | CCTGAGCAAC | ACCTTCAGCA | ACCCGAACTA | 1020 |
| CGCCAAGGTG | AAGGGCAGCG | ACGAGGACGC | CAAGATGATC | GTGGAGGCTA | AGCCGGGCCA | 1080 |
| CGCGTTGATC | GGCTTCGAGA | TCAGCAACGA | CAGCATCACC | GTGCTGAAGG | TGTACGAGGC | 1140 |
| CAAGCTGAAG | CAGAACTACC | AGGTGGACAA | GGACAGCTTG | AGCGAGGTGA | TCTACGGCGA | 1200 |
| CATGGACAAG | CTGCTGTGTC | CGGACCAGAG | CGAGCAAATC | TACTACACCA | ACAACATCGT | 1260 |
| GTTCCCGAAC | GAGTACGTGA | TCACCAAGAT | CGACTTCACC | AAGAAGATGA | AGACCCTGCG | 1320 |
| CTACGAGGTG | ACCGCCAACT | TCTACGACAG | CAGCACCGGC | GAGATCGACC | TGAACAAGAA | 1380 |
| GAAGGTGGAG | AGCAGCGAGG | CCGAGTACCG | CACCCTGAGC | GCGAACGACG | ACGGCGTCTA | 1440 |
| CATGCCACTG | GGCGTGATCA | GCGAGACCTT | CCTGACCCCG | ATCAACGGCT | TTGGCCTGCA | 1500 |
| GGCCGACGAG | AACAGCCGCC | TGATCACCCT | GACCTGTAAG | AGCTACCTGC | GCGAGCTGCT | 1560 |
| GCTAGCCACC | GACCTGAGCA | ACAAGGAGAC | CAAGCTGATC | GTGCCACCGA | GCGGCTTCAT | 1620 |
| CAGCAACATC | GTGGAGAACG | GCAGCATCGA | GGAGGACAAC | CTGGAGCCGT | GGAAGGCCAA | 1680 |
| CAACAAGAAC | GCCTACGTGG | ACCACACCGG | CGGCGTGAAC | GGCACCAAGG | CCCTGTACGT | 1740 |
| GCACAAGGAC | GGCGGCATCA | GCCAGTTCAT | CGGCGACAAG | CTGAAGCCGA | AGACCGAGTA | 1800 |
| CGTGATCCAG | TACACCGTGA | AGGGCAAGCC | ATCGATTCAC | CTGAAGGACG | AGAACACCGG | 1860 |
| CTACATCCAC | TACGAGGACA | CCAACAACAA | CCTGGAGGAC | TACCAGACCA | TCAACAAGCG | 1920 |
| CTTCACCACC | GGCACCGACC | TGAAGGGCGT | GTACCTGATC | CTGAAGAGCC | AGAACGGCGA | 1980 |
| CGAGGCCTGG | GGCGACAACT | TCATCATCCT | GGAGATCAGC | CCGAGCGAGA | AGCTGCTGAG | 2040 |
| CCCGGAGCTG | ATCAACACCA | ACAACTGGAC | CAGCACCGGC | AGCACCAACA | TCAGCGGCAA | 2100 |
| CACCCTGACC | CTGTACCAGG | GCGGCCGCGG | CATCCTGAAG | CAGAACCTGC | AGCTGGACAG | 2160 |
| CTTCAGCACC | TACCGCGTGT | ACTTCAGCGT | GAGCGGCGAC | GCCAACGTGC | GCATCCGCAA | 2220 |
| CAGCCGCGAG | GTGCTGTTCG | AGAAGAGGTA | CATGAGCGGC | GCCAAGGACG | TGAGCGAGAT | 2280 |

-continued

```
GTTCACCACC AAGTTCGAGA AGGACAACTT CTACATCGAG CTGAGCCAGG GCAACAACCT    2340

GTACGGCGGC CCGATCGTGC ACTTCTACGA CGTGAGCATC AAGTTAACGT AGAGCTCAGA    2400

TCT                                                                  2403
```

( 2 ) INFORMATION FOR SEQ ID NO:31:

( i ) SEQUENCE CHARACTERISTICS:
( A ) LENGTH: 2612 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i x ) FEATURE:
( A ) NAME/KEY: CDS
( B ) LOCATION: 118..2484
( D ) OTHER INFORMATION: /note= "Native DNA sequence encoding VIP3A(b) from AB424"

( x i ) SEQUENCE DESCRIPTION: SEQ ID NO:31:

```
ATTGAAATTG ATAAAAAGTT ATGAGTGTTT AATAATCAGT AATTACCAAT AAAGAATTAA      60

GAATACAAGT TTACAAGAAA TAAGTGTTAC AAAAAATAGC TGAAAAGGAA GATGAAC        117

ATG AAC AAG AAT AAT ACT AAA TTA AGC ACA AGA GCC TTA CCA AGT TTT       165
Met Asn Lys Asn Asn Thr Lys Leu Ser Thr Arg Ala Leu Pro Ser Phe
790                 795                 800                 805

ATT GAT TAT TTC AAT GGC ATT TAT GGA TTT GCC ACT GGT ATC AAA GAC       213
Ile Asp Tyr Phe Asn Gly Ile Tyr Gly Phe Ala Thr Gly Ile Lys Asp
                810                 815                 820

ATT ATG AAC ATG ATT TTT AAA ACG GAT ACA GGT GGT GAT CTA ACC CTA       261
Ile Met Asn Met Ile Phe Lys Thr Asp Thr Gly Gly Asp Leu Thr Leu
            825                 830                 835

GAC GAA ATT TTA AAG AAT CAG CAG CTA CTA AAT GAT ATT TCT GGT AAA       309
Asp Glu Ile Leu Lys Asn Gln Gln Leu Leu Asn Asp Ile Ser Gly Lys
        840                 845                 850

TTG GAT GGG GTG AAT GGA AGC TTA AAT GAT CTT ATC GCA CAG GGA AAC       357
Leu Asp Gly Val Asn Gly Ser Leu Asn Asp Leu Ile Ala Gln Gly Asn
    855                 860                 865

TTA AAT ACA GAA TTA TCT AAG GAA ATA TTA AAA ATT GCA AAT GAA CAA       405
Leu Asn Thr Glu Leu Ser Lys Glu Ile Leu Lys Ile Ala Asn Glu Gln
870                 875                 880                 885

AAT CAA GTT TTA AAT GAT GTT AAT AAC AAA CTC GAT GCG ATA AAT ACG       453
Asn Gln Val Leu Asn Asp Val Asn Asn Lys Leu Asp Ala Ile Asn Thr
                890                 895                 900

ATG CTT CGG GTA TAT CTA CCT AAA ATT ACC TCT ATG TTG AGT GAT GTA       501
Met Leu Arg Val Tyr Leu Pro Lys Ile Thr Ser Met Leu Ser Asp Val
            905                 910                 915

ATG AAA CAA AAT TAT GCG CTA AGT CTG CAA ATA GAA TAC TTA AGT AAA       549
Met Lys Gln Asn Tyr Ala Leu Ser Leu Gln Ile Glu Tyr Leu Ser Lys
        920                 925                 930

CAA TTG CAA GAG ATT TCT GAT AAG TTG GAT ATT ATT AAT GTA AAT GTA       597
Gln Leu Gln Glu Ile Ser Asp Lys Leu Asp Ile Ile Asn Val Asn Val
    935                 940                 945

CTT ATT AAC TCT ACA CTT ACT GAA ATT ACA CCT GCG TAT CAA AGG ATT       645
Leu Ile Asn Ser Thr Leu Thr Glu Ile Thr Pro Ala Tyr Gln Arg Ile
950                 955                 960                 965

AAA TAT GTG AAC GAA AAA TTT GAG GAA TTA ACT TTT GCT ACA GAA ACT       693
Lys Tyr Val Asn Glu Lys Phe Glu Glu Leu Thr Phe Ala Thr Glu Thr
                970                 975                 980

AGT TCA AAA GTA AAA AAG GAT GGC TCT CCT GCA GAT ATT CGT GAT GAG       741
```

-continued

```
          Ser  Ser  Lys  Val  Lys  Lys  Asp  Gly  Ser  Pro  Ala  Asp  Ile  Arg  Asp  Glu
                         985                      990                      995

TTA  ACT  GAG  TTA  ACT  GAA  CTA  GCG  AAA  AGT  GTA  ACA  AAA  AAT  GAT  GTG         789
Leu  Thr  Glu  Leu  Thr  Glu  Leu  Ala  Lys  Ser  Val  Thr  Lys  Asn  Asp  Val
              1000                     1005                     1010

GAT  GGT  TTT  GAA  TTT  TAC  CTT  AAT  ACA  TTC  CAC  GAT  GTA  ATG  GTA  GGA         837
Asp  Gly  Phe  Glu  Phe  Tyr  Leu  Asn  Thr  Phe  His  Asp  Val  Met  Val  Gly
              1015                     1020                     1025

AAT  AAT  TTA  TTC  GGG  CGT  TCA  GCT  TTA  AAA  ACT  GCA  TCG  GAA  TTA  ATT         885
Asn  Asn  Leu  Phe  Gly  Arg  Ser  Ala  Leu  Lys  Thr  Ala  Ser  Glu  Leu  Ile
1030                     1035                     1040                     1045

ACT  AAA  GAA  AAT  GTG  AAA  ACA  AGT  GGC  AGT  GAG  GTC  GGA  AAT  GTT  TAT         933
Thr  Lys  Glu  Asn  Val  Lys  Thr  Ser  Gly  Ser  Glu  Val  Gly  Asn  Val  Tyr
                         1050                     1055                     1060

AAC  TTC  CTA  ATT  GTA  TTA  ACA  GCT  CTG  CAA  GCA  AAA  GCT  TTT  CTT  ACT         981
Asn  Phe  Leu  Ile  Val  Leu  Thr  Ala  Leu  Gln  Ala  Lys  Ala  Phe  Leu  Thr
              1065                     1070                     1075

TTA  ACA  CCA  TGC  CGA  AAA  TTA  TTA  GGC  TTA  GCA  GAT  ATT  GAT  TAT  ACT        1029
Leu  Thr  Pro  Cys  Arg  Lys  Leu  Leu  Gly  Leu  Ala  Asp  Ile  Asp  Tyr  Thr
              1080                     1085                     1090

TCT  ATT  ATG  AAT  GAA  CAT  TTA  AAT  AAG  GAA  AAA  GAG  GAA  TTT  AGA  GTA        1077
Ser  Ile  Met  Asn  Glu  His  Leu  Asn  Lys  Glu  Lys  Glu  Glu  Phe  Arg  Val
              1095                     1100                     1105

AAC  ATC  CTC  CCT  ACA  CTT  TCT  AAT  ACT  TTT  TCT  AAT  CCT  AAT  TAT  GCA        1125
Asn  Ile  Leu  Pro  Thr  Leu  Ser  Asn  Thr  Phe  Ser  Asn  Pro  Asn  Tyr  Ala
1110                     1115                     1120                     1125

AAA  GTT  AAA  GGA  AGT  GAT  GAA  GAT  GCA  AAG  ATG  ATT  GTG  GAA  GCT  AAA        1173
Lys  Val  Lys  Gly  Ser  Asp  Glu  Asp  Ala  Lys  Met  Ile  Val  Glu  Ala  Lys
                         1130                     1135                     1140

CCA  GGA  CAT  GCA  TTG  ATT  GGG  TTT  GAA  ATT  AGT  AAT  GAT  TCA  ATT  ACA        1221
Pro  Gly  His  Ala  Leu  Ile  Gly  Phe  Glu  Ile  Ser  Asn  Asp  Ser  Ile  Thr
              1145                     1150                     1155

GTA  TTA  AAA  GTA  TAT  GAG  GCT  AAG  CTA  AAA  CAA  AAT  TAT  CAA  GTC  GAT        1269
Val  Leu  Lys  Val  Tyr  Glu  Ala  Lys  Leu  Lys  Gln  Asn  Tyr  Gln  Val  Asp
              1160                     1165                     1170

AAG  GAT  TCC  TTA  TCG  GAA  GTT  ATT  TAT  GGC  GAT  ATG  GAT  AAA  TTA  TTG        1317
Lys  Asp  Ser  Leu  Ser  Glu  Val  Ile  Tyr  Gly  Asp  Met  Asp  Lys  Leu  Leu
              1175                     1180                     1185

TGC  CCA  GAT  CAA  TCT  GGA  CAA  ATC  TAT  TAT  ACA  AAT  AAC  ATA  GTA  TTT        1365
Cys  Pro  Asp  Gln  Ser  Gly  Gln  Ile  Tyr  Tyr  Thr  Asn  Asn  Ile  Val  Phe
1190                     1195                     1200                     1205

CCA  AAT  GAA  TAT  GTA  ATT  ACT  AAA  ATT  GAT  TTC  ACT  AAA  AAA  ATG  AAA        1413
Pro  Asn  Glu  Tyr  Val  Ile  Thr  Lys  Ile  Asp  Phe  Thr  Lys  Lys  Met  Lys
                         1210                     1215                     1220

ACT  TTA  AGA  TAT  GAG  GTA  ACA  GCG  AAT  TTT  TAT  GAT  TCT  TCT  ACA  GGA        1461
Thr  Leu  Arg  Tyr  Glu  Val  Thr  Ala  Asn  Phe  Tyr  Asp  Ser  Ser  Thr  Gly
              1225                     1230                     1235

GAA  ATT  GAC  TTA  AAT  AAG  AAA  AAA  GTA  GAA  TCA  GTT  GAA  GCG  GAG  TAT        1509
Glu  Ile  Asp  Leu  Asn  Lys  Lys  Lys  Val  Glu  Ser  Ser  Glu  Ala  Glu  Tyr
              1240                     1245                     1250

AGA  ACG  TTA  AGT  GCT  AAT  GAT  GAT  GGG  GTG  TAT  ATG  CCG  TTA  GGT  GTC        1557
Arg  Thr  Leu  Ser  Ala  Asn  Asp  Asp  Gly  Val  Tyr  Met  Pro  Leu  Gly  Val
              1255                     1260                     1265

ATC  AGT  GAA  ACA  TTT  TTG  ACT  CCG  ATT  AAT  GGG  TTT  GGC  CTC  CAA  GCT        1605
Ile  Ser  Glu  Thr  Phe  Leu  Thr  Pro  Ile  Asn  Gly  Phe  Gly  Leu  Gln  Ala
1270                     1275                     1280                     1285

GAT  GAA  AAT  TCA  AGA  TTA  ATT  ACT  TTA  ACA  TGT  AAA  TCA  TAT  TTA  AGA        1653
Asp  Glu  Asn  Ser  Arg  Leu  Ile  Thr  Leu  Thr  Cys  Lys  Ser  Tyr  Leu  Arg
              1290                     1295                     1300

GAA  CTA  CTG  CTA  GCA  ACA  GAC  TTA  AGC  AAT  AAA  GAA  ACT  AAA  TTG  ATC        1701
```

```
       Glu  Leu  Leu  Leu  Ala  Thr  Asp  Leu  Ser  Asn  Lys  Glu  Thr  Lys  Leu  Ile
                      1305                     1310                     1315

GTC CCG CCA AGT GGT TTT ATT AGC AAT ATT GTA GAG AAC GGG TCC ATA                    1749
Val Pro Pro Ser Gly Phe Ile Ser Asn Ile Val Glu Asn Gly Ser Ile
            1320                     1325                     1330

GAA GAG GAC AAT TTA GAG CCG TGG AAA GCA AAT AAT AAG AAT GCG TAT                    1797
Glu Glu Asp Asn Leu Glu Pro Trp Lys Ala Asn Asn Lys Asn Ala Tyr
            1335                     1340                     1345

GTA GAT CAT ACA GGC GGA GTG AAT GGA ACT AAA GCT TTA TAT GTT CAT                    1845
Val Asp His Thr Gly Gly Val Asn Gly Thr Lys Ala Leu Tyr Val His
1350                     1355                     1360                     1365

AAG GAC GGA GGA ATT TCA CAA TTT ATT GGA GAT AAG TTA AAA CCG AAA                    1893
Lys Asp Gly Gly Ile Ser Gln Phe Ile Gly Asp Lys Leu Lys Pro Lys
                1370                     1375                     1380

ACT GAG TAT GTA ATC CAA TAT ACT GTT AAA GGA AAA CCT TCT ATT CAT                    1941
Thr Glu Tyr Val Ile Gln Tyr Thr Val Lys Gly Lys Pro Ser Ile His
                    1385                     1390                     1395

TTA AAA GAT GAA AAT ACT GGA TAT ATT CAT TAT GAA GAT ACA AAT AAT                    1989
Leu Lys Asp Glu Asn Thr Gly Tyr Ile His Tyr Glu Asp Thr Asn Asn
            1400                     1405                     1410

AAT TTA GAA GAT TAT CAA ACT ATT AAT AAA CGT TTT ACT ACA GGA ACT                    2037
Asn Leu Glu Asp Tyr Gln Thr Ile Asn Lys Arg Phe Thr Thr Gly Thr
            1415                     1420                     1425

GAT TTA AAG GGA GTG TAT TTA ATT TTA AAA AGT CAA AAT GGA GAT GAA                    2085
Asp Leu Lys Gly Val Tyr Leu Ile Leu Lys Ser Gln Asn Gly Asp Glu
1430                     1435                     1440                     1445

GCT TGG GGA GAT AAC TTT ATT ATT TTG GAA ATT AGT CCT TCT GAA AAG                    2133
Ala Trp Gly Asp Asn Phe Ile Ile Leu Glu Ile Ser Pro Ser Glu Lys
                1450                     1455                     1460

TTA TTA AGT CCA GAA TTA ATT AAT ACA AAT AAT TGG ACG AGT ACG GGA                    2181
Leu Leu Ser Pro Glu Leu Ile Asn Thr Asn Asn Trp Thr Ser Thr Gly
            1465                     1470                     1475

TCA ACT AAT ATT AGC GGT AAT ACA CTC ACT CTT TAT CAG GGA GGA CGA                    2229
Ser Thr Asn Ile Ser Gly Asn Thr Leu Thr Leu Tyr Gln Gly Gly Arg
            1480                     1485                     1490

GGG ATT CTA AAA CAA AAC CTT CAA TTA GAT AGT TTT TCA ACT TAT AGA                    2277
Gly Ile Leu Lys Gln Asn Leu Gln Leu Asp Ser Phe Ser Thr Tyr Arg
    1495                     1500                     1505

GTG TAT TTC TCT GTG TCC GGA GAT GCT AAT GTA AGG ATT AGA AAT TCT                    2325
Val Tyr Phe Ser Val Ser Gly Asp Ala Asn Val Arg Ile Arg Asn Ser
1510                     1515                     1520                     1525

AGG GAA GTG TTA TTT GAA AAA AGA TAT ATG AGC GGT GCT AAA GAT GTT                    2373
Arg Glu Val Leu Phe Glu Lys Arg Tyr Met Ser Gly Ala Lys Asp Val
                    1530                     1535                     1540

TCT GAA ATG TTC ACT ACA AAA TTT GAG AAA GAT AAC TTC TAT ATA GAG                    2421
Ser Glu Met Phe Thr Thr Lys Phe Glu Lys Asp Asn Phe Tyr Ile Glu
                1545                     1550                     1555

CTT TCT CAA GGG AAT AAT TTA TAT GGT GGT CCT ATT GTA CAT TTT TAC                    2469
Leu Ser Gln Gly Asn Asn Leu Tyr Gly Gly Pro Ile Val His Phe Tyr
            1560                     1565                     1570

GAT GTC TCT ATT AAG TAAGATCGGG ATCTAATATT AACAGTTTTT AGAAGCTAAT                    2524
Asp Val Ser Ile Lys
            1575

TCTTGTATAA TGTCCTTGAT TATGGAAAAA CACAATTTTG TTTGCTAAGA TGTATATATA                  2584

GCTCACTCAT TAAAAGGCAA TCAAGCTT                                                     2612
```

( 2 ) INFORMATION FOR SEQ ID NO:32:

( i ) SEQUENCE CHARACTERISTICS:
        ( A ) LENGTH: 789 amino acids ( B ) TYPE: amino acid
( D ) TOPOLOGY: linear ( i i ) MOLECULE TYPE: protein ( x i ) SEQUENCE DESCRIPTION: SEQ ID NO:32:

```
Met  Asn  Lys  Asn  Asn  Thr  Lys  Leu  Ser  Thr  Arg  Ala  Leu  Pro  Ser  Phe
 1              5                      10                      15

Ile  Asp  Tyr  Phe  Asn  Gly  Ile  Tyr  Gly  Phe  Ala  Thr  Gly  Ile  Lys  Asp
              20                      25                      30

Ile  Met  Asn  Met  Ile  Phe  Lys  Thr  Asp  Thr  Gly  Gly  Asp  Leu  Thr  Leu
              35                      40                      45

Asp  Glu  Ile  Leu  Lys  Asn  Gln  Gln  Leu  Leu  Asn  Asp  Ile  Ser  Gly  Lys
       50                      55                      60

Leu  Asp  Gly  Val  Asn  Gly  Ser  Leu  Asn  Asp  Leu  Ile  Ala  Gln  Gly  Asn
65                      70                      75                      80

Leu  Asn  Thr  Glu  Leu  Ser  Lys  Glu  Ile  Leu  Lys  Ile  Ala  Asn  Glu  Gln
                      85                      90                      95

Asn  Gln  Val  Leu  Asn  Asp  Val  Asn  Asn  Lys  Leu  Asp  Ala  Ile  Asn  Thr
                     100                     105                     110

Met  Leu  Arg  Val  Tyr  Leu  Pro  Lys  Ile  Thr  Ser  Met  Leu  Ser  Asp  Val
           115                     120                     125

Met  Lys  Gln  Asn  Tyr  Ala  Leu  Ser  Leu  Gln  Ile  Glu  Tyr  Leu  Ser  Lys
           130                     135                     140

Gln  Leu  Gln  Glu  Ile  Ser  Asp  Lys  Leu  Asp  Ile  Ile  Asn  Val  Asn  Val
145                     150                     155                     160

Leu  Ile  Asn  Ser  Thr  Leu  Thr  Glu  Ile  Thr  Pro  Ala  Tyr  Gln  Arg  Ile
                     165                     170                     175

Lys  Tyr  Val  Asn  Glu  Lys  Phe  Glu  Glu  Leu  Thr  Phe  Ala  Thr  Glu  Thr
                180                     185                     190

Ser  Ser  Lys  Val  Lys  Lys  Asp  Gly  Ser  Pro  Ala  Asp  Ile  Arg  Asp  Glu
           195                     200                     205

Leu  Thr  Glu  Leu  Thr  Glu  Leu  Ala  Lys  Ser  Val  Thr  Lys  Asn  Asp  Val
     210                     215                     220

Asp  Gly  Phe  Glu  Phe  Tyr  Leu  Asn  Thr  Phe  His  Asp  Val  Met  Val  Gly
225                     230                     235                     240

Asn  Asn  Leu  Phe  Gly  Arg  Ser  Ala  Leu  Lys  Thr  Ala  Ser  Glu  Leu  Ile
                245                     250                     255

Thr  Lys  Glu  Asn  Val  Lys  Thr  Ser  Gly  Ser  Glu  Val  Gly  Asn  Val  Tyr
                260                     265                     270

Asn  Phe  Leu  Ile  Val  Leu  Thr  Ala  Leu  Gln  Ala  Lys  Ala  Phe  Leu  Thr
           275                     280                     285

Leu  Thr  Pro  Cys  Arg  Lys  Leu  Leu  Gly  Leu  Ala  Asp  Ile  Asp  Tyr  Thr
     290                     295                     300

Ser  Ile  Met  Asn  Glu  His  Leu  Asn  Lys  Glu  Lys  Glu  Glu  Phe  Arg  Val
305                     310                     315                     320

Asn  Ile  Leu  Pro  Thr  Leu  Ser  Asn  Thr  Phe  Ser  Asn  Pro  Asn  Tyr  Ala
                325                     330                     335

Lys  Val  Lys  Gly  Ser  Asp  Glu  Asp  Ala  Lys  Met  Ile  Val  Glu  Ala  Lys
                340                     345                     350

Pro  Gly  His  Ala  Leu  Ile  Gly  Phe  Glu  Ile  Ser  Asn  Asp  Ser  Ile  Thr
           355                     360                     365

Val  Leu  Lys  Val  Tyr  Glu  Ala  Lys  Leu  Lys  Gln  Asn  Tyr  Gln  Val  Asp
     370                     375                     380

Lys  Asp  Ser  Leu  Ser  Glu  Val  Ile  Tyr  Gly  Asp  Met  Asp  Lys  Leu  Leu
```

```
385                      390                      395                      400
Cys Pro Asp Gln Ser Gly Gln Ile Tyr Tyr Thr Asn Asn Ile Val Phe
            405                      410                      415

Pro Asn Glu Tyr Val Ile Thr Lys Ile Asp Phe Thr Lys Lys Met Lys
            420                      425                      430

Thr Leu Arg Tyr Glu Val Thr Ala Asn Phe Tyr Asp Ser Ser Thr Gly
            435                      440                      445

Glu Ile Asp Leu Asn Lys Lys Lys Val Glu Ser Ser Glu Ala Glu Tyr
            450                      455                      460

Arg Thr Leu Ser Ala Asn Asp Asp Gly Val Tyr Met Pro Leu Gly Val
465                      470                      475                      480

Ile Ser Glu Thr Phe Leu Thr Pro Ile Asn Gly Phe Gly Leu Gln Ala
            485                      490                      495

Asp Glu Asn Ser Arg Leu Ile Thr Leu Thr Cys Lys Ser Tyr Leu Arg
            500                      505                      510

Glu Leu Leu Leu Ala Thr Asp Leu Ser Asn Lys Glu Thr Lys Leu Ile
            515                      520                      525

Val Pro Pro Ser Gly Phe Ile Ser Asn Ile Val Glu Asn Gly Ser Ile
            530                      535                      540

Glu Glu Asp Asn Leu Glu Pro Trp Lys Ala Asn Asn Lys Asn Ala Tyr
545                      550                      555                      560

Val Asp His Thr Gly Gly Val Asn Gly Thr Lys Ala Leu Tyr Val His
            565                      570                      575

Lys Asp Gly Gly Ile Ser Gln Phe Ile Gly Asp Lys Leu Lys Pro Lys
            580                      585                      590

Thr Glu Tyr Val Ile Gln Tyr Thr Val Lys Gly Lys Pro Ser Ile His
            595                      600                      605

Leu Lys Asp Glu Asn Thr Gly Tyr Ile His Tyr Glu Asp Thr Asn Asn
610                      615                      620

Asn Leu Glu Asp Tyr Gln Thr Ile Asn Lys Arg Phe Thr Thr Gly Thr
625                      630                      635                      640

Asp Leu Lys Gly Val Tyr Leu Ile Leu Lys Ser Gln Asn Gly Asp Glu
            645                      650                      655

Ala Trp Gly Asp Asn Phe Ile Ile Leu Glu Ile Ser Pro Ser Glu Lys
            660                      665                      670

Leu Leu Ser Pro Glu Leu Ile Asn Thr Asn Asn Trp Thr Ser Thr Gly
            675                      680                      685

Ser Thr Asn Ile Ser Gly Asn Thr Leu Thr Leu Tyr Gln Gly Gly Arg
            690                      695                      700

Gly Ile Leu Lys Gln Asn Leu Gln Leu Asp Ser Phe Ser Thr Tyr Arg
705                      710                      715                      720

Val Tyr Phe Ser Val Ser Gly Asp Ala Asn Val Arg Ile Arg Asn Ser
            725                      730                      735

Arg Glu Val Leu Phe Glu Lys Arg Tyr Met Ser Gly Ala Lys Asp Val
            740                      745                      750

Ser Glu Met Phe Thr Thr Lys Phe Glu Lys Asp Asn Phe Tyr Ile Glu
            755                      760                      765

Leu Ser Gln Gly Asn Asn Leu Tyr Gly Gly Pro Ile Val His Phe Tyr
            770                      775                      780

Asp Val Ser Ile Lys
785
```

( 2 ) INFORMATION FOR SEQ ID NO:33:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "forward primer used to make pCIB5526"

(iii) HYPOTHETICAL: NO (xi) SEQUENCE DESCRIPTION: SEQ ID NO:33:

```
GGATCCACCA TGAAGACCAA CCAGATCAGC                                    30
```

(2) INFORMATION FOR SEQ ID NO:34:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "reverse primer used to make pCIB5526"

(iii) HYPOTHETICAL: NO (xi) SEQUENCE DESCRIPTION: SEQ ID NO:34:

```
AAGCTTCAGC TCCTT                                                    15
```

(2) INFORMATION FOR SEQ ID NO:35:

(i) SEQUENCE CHARACTERISTICS:
    (A) LENGTH: 2576 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "Synthetic DNA"

(iii) HYPOTHETICAL: NO (ix) FEATURE:
    (A) NAME/KEY: CDS
    (B) LOCATION: 9..2564
    (D) OTHER INFORMATION: /note= "Maize optimized sequence encoding VIP1A(a) with the Bacillus secretion signal removed as contained in pCIB5526"

(xi) SEQUENCE DESCRIPTION: SEQ ID NO:35:

```
GATCCACC ATG AAG ACC AAC CAG ATC AGC ACC ACC CAG AAG AAC CAG CAG    50
         Met Lys Thr Asn Gln Ile Ser Thr Thr Gln Lys Asn Gln Gln
             825                 830                 835

AAG GAG ATG GAC CGC AAG GGC CTG CTG GGC TAC TAC TTC AAG GGC AAG     98
Lys Glu Met Asp Arg Lys Gly Leu Leu Gly Tyr Tyr Phe Lys Gly Lys
            840                 845                 850

GAC TTC AGC AAC CTG ACC ATG TTC GCC CCC ACG CGT GAC AGC ACC CTG    146
Asp Phe Ser Asn Leu Thr Met Phe Ala Pro Thr Arg Asp Ser Thr Leu
            855                 860                 865

ATC TAC GAC CAG CAG ACC GCC AAC AAG CTG CTG GAC AAG AAG CAG CAG    194
Ile Tyr Asp Gln Gln Thr Ala Asn Lys Leu Leu Asp Lys Lys Gln Gln
        870                 875                 880

GAG TAC CAG AGC ATC CGC TGG ATC GGC CTG ATC CAG AGC AAG GAG ACC    242
Glu Tyr Gln Ser Ile Arg Trp Ile Gly Leu Ile Gln Ser Lys Glu Thr
        885                 890                 895

GGC GAC TTC ACC TTC AAC CTG AGC GAG GAC GAG CAG GCC ATC ATC GAG    290
Gly Asp Phe Thr Phe Asn Leu Ser Glu Asp Glu Gln Ala Ile Ile Glu
```

-continued

```
                900                     905                     910                     915
ATC  AAC  GGC  AAG  ATC  ATC  AGC  AAC  AAG  GGC  AAG  GAG  AAG  CAG  GTG  GTG          338
Ile  Asn  Gly  Lys  Ile  Ile  Ser  Asn  Lys  Gly  Lys  Glu  Lys  Gln  Val  Val
               920                     925                     930

CAC  CTG  GAG  AAG  GGC  AAG  CTG  GTG  CCC  ATC  AAG  ATC  GAG  TAC  CAG  AGC          386
His  Leu  Glu  Lys  Gly  Lys  Leu  Val  Pro  Ile  Lys  Ile  Glu  Tyr  Gln  Ser
               935                     940                     945

GAC  ACC  AAG  TTC  AAC  ATC  GAC  AGC  AAG  ACC  TTC  AAG  GAG  CTG  AAG  CTT          434
Asp  Thr  Lys  Phe  Asn  Ile  Asp  Ser  Lys  Thr  Phe  Lys  Glu  Leu  Lys  Leu
               950                     955                     960

TTC  AAG  ATC  GAC  AGC  CAG  AAC  CAG  CCC  CAG  CAG  GTG  CAG  CAG  GAC  GAG          482
Phe  Lys  Ile  Asp  Ser  Gln  Asn  Gln  Pro  Gln  Gln  Val  Gln  Gln  Asp  Glu
          965                     970                     975

CTG  CGC  AAC  CCC  GAG  TTC  AAC  AAG  AAG  GAG  AGC  CAG  GAG  TTC  CTG  GCC          530
Leu  Arg  Asn  Pro  Glu  Phe  Asn  Lys  Lys  Glu  Ser  Gln  Glu  Phe  Leu  Ala
980                      985                     990                     995

AAG  CCC  AGC  AAG  ATC  AAC  CTG  TTC  ACC  CAG  CAG  ATG  AAG  CGC  GAG  ATC          578
Lys  Pro  Ser  Lys  Ile  Asn  Leu  Phe  Thr  Gln  Gln  Met  Lys  Arg  Glu  Ile
                    1000                    1005                    1010

GAC  GAG  GAC  ACC  GAC  ACC  GAC  GGC  GAC  AGC  ATC  CCC  GAC  CTG  TGG  GAG          626
Asp  Glu  Asp  Thr  Asp  Thr  Asp  Gly  Asp  Ser  Ile  Pro  Asp  Leu  Trp  Glu
               1015                    1020                    1025

GAG  AAC  GGC  TAC  ACC  ATC  CAG  AAC  CGC  ATC  GCC  GTG  AAG  TGG  GAC  GAC          674
Glu  Asn  Gly  Tyr  Thr  Ile  Gln  Asn  Arg  Ile  Ala  Val  Lys  Trp  Asp  Asp
               1030                    1035                    1040

AGC  CTG  GCT  AGC  AAG  GGC  TAC  ACC  AAG  TTC  GTG  AGC  AAC  CCC  CTG  GAG          722
Ser  Leu  Ala  Ser  Lys  Gly  Tyr  Thr  Lys  Phe  Val  Ser  Asn  Pro  Leu  Glu
               1045                    1050                    1055

AGC  CAC  ACC  GTG  GGC  GAC  CCC  TAC  ACC  GAC  TAC  GAG  AAG  GCC  GCC  CGC          770
Ser  His  Thr  Val  Gly  Asp  Pro  Tyr  Thr  Asp  Tyr  Glu  Lys  Ala  Ala  Arg
1060                     1065                    1070                    1075

GAC  CTG  GAC  CTG  AGC  AAC  GCC  AAG  GAG  ACC  TTC  AAC  CCC  CTG  GTG  GCC          818
Asp  Leu  Asp  Leu  Ser  Asn  Ala  Lys  Glu  Thr  Phe  Asn  Pro  Leu  Val  Ala
               1080                    1085                    1090

GCC  TTC  CCC  AGC  GTG  AAC  GTG  AGC  ATG  GAG  AAG  GTG  ATC  CTG  AGC  CCC          866
Ala  Phe  Pro  Ser  Val  Asn  Val  Ser  Met  Glu  Lys  Val  Ile  Leu  Ser  Pro
               1095                    1100                    1105

AAC  GAG  AAC  CTG  AGC  AAC  AGC  GTG  GAG  AGC  CAC  TCG  AGC  ACC  AAC  TGG          914
Asn  Glu  Asn  Leu  Ser  Asn  Ser  Val  Glu  Ser  His  Ser  Ser  Thr  Asn  Trp
               1110                    1115                    1120

AGC  TAC  ACC  AAC  ACC  GAG  GGC  GCC  AGC  GTG  GAG  GCC  GGC  ATC  GGT  CCC          962
Ser  Tyr  Thr  Asn  Thr  Glu  Gly  Ala  Ser  Val  Glu  Ala  Gly  Ile  Gly  Pro
               1125                    1130                    1135

AAG  GGC  ATC  AGC  TTC  GGC  GTG  AGC  GTG  AAC  TAC  CAG  CAC  AGC  GAG  ACC         1010
Lys  Gly  Ile  Ser  Phe  Gly  Val  Ser  Val  Asn  Tyr  Gln  His  Ser  Glu  Thr
1140                     1145                    1150                    1155

GTG  GCC  CAG  GAG  TGG  GGC  ACC  AGC  ACC  GGC  AAC  ACC  AGC  CAG  TTC  AAC         1058
Val  Ala  Gln  Glu  Trp  Gly  Thr  Ser  Thr  Gly  Asn  Thr  Ser  Gln  Phe  Asn
               1160                    1165                    1170

ACC  GCC  AGC  GCC  GGC  TAC  CTG  AAC  GCC  AAC  GTG  CGC  TAC  AAC  AAC  GTG         1106
Thr  Ala  Ser  Ala  Gly  Tyr  Leu  Asn  Ala  Asn  Val  Arg  Tyr  Asn  Asn  Val
               1175                    1180                    1185

GGC  ACC  GGC  GCC  ATC  TAC  GAC  GTG  AAG  CCC  ACC  ACC  AGC  TTC  GTG  CTG         1154
Gly  Thr  Gly  Ala  Ile  Tyr  Asp  Val  Lys  Pro  Thr  Thr  Ser  Phe  Val  Leu
               1190                    1195                    1200

AAC  AAC  GAC  ACC  ATC  GCC  ACC  ATC  ACC  GCC  AAG  TCG  AAT  TCC  ACC  GCC         1202
Asn  Asn  Asp  Thr  Ile  Ala  Thr  Ile  Thr  Ala  Lys  Ser  Asn  Ser  Thr  Ala
1205                     1210                    1215

CTG  AAC  ATC  AGC  CCC  GGC  GAG  AGC  TAC  CCC  AAG  AAG  GGC  CAG  AAC  GGC         1250
Leu  Asn  Ile  Ser  Pro  Gly  Glu  Ser  Tyr  Pro  Lys  Lys  Gly  Gln  Asn  Gly
```

```
                1220              1225                    1230                    1235
ATC GCC ATC ACC AGC ATG GAC GAC TTC AAC AGC CAC CCC ATC ACC CTG        1298
Ile Ala Ile Thr Ser Met Asp Asp Phe Asn Ser His Pro Ile Thr Leu
                    1240                        1245                    1250

AAC AAG AAG CAG GTG GAC AAC CTG CTG AAC AAC AAG CCC ATG ATG CTG        1346
Asn Lys Lys Gln Val Asp Asn Leu Leu Asn Asn Lys Pro Met Met Leu
            1255                        1260                    1265

GAG ACC AAC CAG ACC GAC GGC GTC TAC AAG ATC AAG GAC ACC CAC GGC        1394
Glu Thr Asn Gln Thr Asp Gly Val Tyr Lys Ile Lys Asp Thr His Gly
            1270                        1275                    1280

AAC ATC GTG ACG GGC GGC GAG TGG AAC GGC GTG ATC CAG CAG ATC AAG        1442
Asn Ile Val Thr Gly Gly Glu Trp Asn Gly Val Ile Gln Gln Ile Lys
    1285                        1290                    1295

GCC AAG ACC GCC AGC ATC ATC GTC GAC GAC GGC GAG CGC GTG GCC GAG        1490
Ala Lys Thr Ala Ser Ile Ile Val Asp Asp Gly Glu Arg Val Ala Glu
1300                        1305                    1310                    1315

AAG CGC GTG GCC GCC AAG GAC TAC GAG AAC CCC GAG GAC AAG ACC CCC        1538
Lys Arg Val Ala Ala Lys Asp Tyr Glu Asn Pro Glu Asp Lys Thr Pro
                1320                        1325                    1330

AGC CTG ACC CTG AAG GAC GCC CTG AAG CTG AGC TAC CCC GAC GAG ATC        1586
Ser Leu Thr Leu Lys Asp Ala Leu Lys Leu Ser Tyr Pro Asp Glu Ile
            1335                        1340                    1345

AAG GAG ATC GAG GGC TTG CTG TAC TAC AAG AAC AAG CCC ATC TAC GAG        1634
Lys Glu Ile Glu Gly Leu Leu Tyr Tyr Lys Asn Lys Pro Ile Tyr Glu
            1350                        1355                    1360

AGC AGC GTG ATG ACC TAT CTA GAC GAG AAC ACC GCC AAG GAG GTG ACC        1682
Ser Ser Val Met Thr Tyr Leu Asp Glu Asn Thr Ala Lys Glu Val Thr
            1365                        1370                    1375

AAG CAG CTG AAC GAC ACC ACC GGC AAG TTC AAG GAC GTG AGC CAC CTG        1730
Lys Gln Leu Asn Asp Thr Thr Gly Lys Phe Lys Asp Val Ser His Leu
1380                        1385                    1390                    1395

TAC GAC GTG AAG CTG ACC CCC AAG ATG AAC GTG ACC ATC AAG CTG AGC        1778
Tyr Asp Val Lys Leu Thr Pro Lys Met Asn Val Thr Ile Lys Leu Ser
                1400                        1405                    1410

ATC CTG TAC GAC AAC GCC GAG AGC AAC GAC AAC AGC ATC GGC AAG TGG        1826
Ile Leu Tyr Asp Asn Ala Glu Ser Asn Asp Asn Ser Ile Gly Lys Trp
            1415                        1420                    1425

ACC AAC ACC AAC ATC GTG AGC GGC GGC AAC AAC GGC AAG AAG CAG TAC        1874
Thr Asn Thr Asn Ile Val Ser Gly Gly Asn Asn Gly Lys Lys Gln Tyr
            1430                        1435                    1440

AGC AGC AAC AAC CCC GAC GCC AAC CTG ACC CTG AAC ACC GAC GCC CAG        1922
Ser Ser Asn Asn Pro Asp Ala Asn Leu Thr Leu Asn Thr Asp Ala Gln
            1445                        1450                    1455

GAG AAG CTG AAC AAG AAC CGC GAC TAC TAC ATC AGC CTG TAC ATG AAG        1970
Glu Lys Leu Asn Lys Asn Arg Asp Tyr Tyr Ile Ser Leu Tyr Met Lys
1460                        1465                    1470                    1475

AGC GAG AAG AAC ACC CAG TGC GAG ATC ACC ATC GAC GGC GAG ATA TAC        2018
Ser Glu Lys Asn Thr Gln Cys Glu Ile Thr Ile Asp Gly Glu Ile Tyr
                1480                        1485                    1490

CCC ATC ACC ACC AAG ACC GTG AAC GTG AAC AAG GAC AAC TAC AAG CGC        2066
Pro Ile Thr Thr Lys Thr Val Asn Val Asn Lys Asp Asn Tyr Lys Arg
            1495                        1500                    1505

CTG GAC ATC ATC GCC CAC AAC ATC AAG AGC AAC CCC ATC AGC AGC CTG        2114
Leu Asp Ile Ile Ala His Asn Ile Lys Ser Asn Pro Ile Ser Ser Leu
            1510                        1515                    1520

CAC ATC AAG ACC AAC GAC GAG ATC ACC CTG TTC TGG GAC GAC ATA TCG        2162
His Ile Lys Thr Asn Asp Glu Ile Thr Leu Phe Trp Asp Asp Ile Ser
    1525                        1530                    1535

ATT ACC GAC GTC GCC AGC ATC AAG CCC GAG AAC CTG ACC GAC AGC GAG        2210
Ile Thr Asp Val Ala Ser Ile Lys Pro Glu Asn Leu Thr Asp Ser Glu
```

-continued

```
        1540                  1545                  1550                  1555
ATC  AAG  CAG  ATA  TAC  AGT  CGC  TAC  GGC  ATC  AAG  CTG  GAG  GAC  GGC  ATC         2258
Ile  Lys  Gln  Ile  Tyr  Ser  Arg  Tyr  Gly  Ile  Lys  Leu  Glu  Asp  Gly  Ile
               1560                       1565                       1570

CTG  ATC  GAC  AAG  AAA  GGC  GGC  ATC  CAC  TAC  GGC  GAG  TTC  ATC  AAC  GAG         2306
Leu  Ile  Asp  Lys  Lys  Gly  Gly  Ile  His  Tyr  Gly  Glu  Phe  Ile  Asn  Glu
               1575                       1580                       1585

GCC  AGC  TTC  AAC  ATC  GAG  CCC  CTG  CAG  AAC  TAC  GTG  ACC  AAG  TAC  GAG         2354
Ala  Ser  Phe  Asn  Ile  Glu  Pro  Leu  Gln  Asn  Tyr  Val  Thr  Lys  Tyr  Glu
               1590                       1595                       1600

GTG  ACC  TAC  AGC  AGC  GAG  CTG  GGC  CCC  AAC  GTG  AGC  GAC  ACC  CTG  GAG         2402
Val  Thr  Tyr  Ser  Ser  Glu  Leu  Gly  Pro  Asn  Val  Ser  Asp  Thr  Leu  Glu
               1605                       1610                       1615

AGC  GAC  AAG  ATT  TAC  AAG  GAC  GGC  ACC  ATC  AAG  TTC  GAC  TTC  ACC  AAG         2450
Ser  Asp  Lys  Ile  Tyr  Lys  Asp  Gly  Thr  Ile  Lys  Phe  Asp  Phe  Thr  Lys
1620                1625                       1630                       1635

TAC  AGC  AAG  AAC  GAG  CAG  GGC  CTG  TTC  TAC  GAC  AGC  GGC  CTG  AAC  TGG         2498
Tyr  Ser  Lys  Asn  Glu  Gln  Gly  Leu  Phe  Tyr  Asp  Ser  Gly  Leu  Asn  Trp
               1640                       1645                       1650

GAC  TTC  AAG  ATC  AAC  GCC  ATC  ACC  TAC  GAC  GGC  AAG  GAG  ATG  AAC  GTG         2546
Asp  Phe  Lys  Ile  Asn  Ala  Ile  Thr  Tyr  Asp  Gly  Lys  Glu  Met  Asn  Val
               1655                       1660                       1665

TTC  CAC  CGC  TAC  AAC  AAG  TAGATCTGAG  CT                                            2576
Phe  His  Arg  Tyr  Asn  Lys
               1670
```

( 2 ) INFORMATION FOR SEQ ID NO:36:

( i ) SEQUENCE CHARACTERISTICS:
        ( A ) LENGTH: 852 amino acids
        ( B ) TYPE: amino acid
        ( D ) TOPOLOGY: linear ( i i ) MOLECULE TYPE: protein ( x i ) SEQUENCE DESCRIPTION: SEQ ID NO:36:

```
Met  Lys  Thr  Asn  Gln  Ile  Ser  Thr  Thr  Gln  Lys  Asn  Gln  Gln  Lys  Glu
  1                   5                       10                      15

Met  Asp  Arg  Lys  Gly  Leu  Leu  Gly  Tyr  Tyr  Phe  Lys  Gly  Lys  Asp  Phe
               20                       25                      30

Ser  Asn  Leu  Thr  Met  Phe  Ala  Pro  Thr  Arg  Asp  Ser  Thr  Leu  Ile  Tyr
               35                       40                       45

Asp  Gln  Gln  Thr  Ala  Asn  Lys  Leu  Leu  Asp  Lys  Lys  Gln  Gln  Glu  Tyr
          50                       55                       60

Gln  Ser  Ile  Arg  Trp  Ile  Gly  Leu  Ile  Gln  Ser  Lys  Glu  Thr  Gly  Asp
 65                       70                       75                       80

Phe  Thr  Phe  Asn  Leu  Ser  Glu  Asp  Glu  Gln  Ala  Ile  Ile  Glu  Ile  Asn
                    85                       90                       95

Gly  Lys  Ile  Ile  Ser  Asn  Lys  Gly  Lys  Glu  Lys  Gln  Val  Val  His  Leu
               100                      105                      110

Glu  Lys  Gly  Lys  Leu  Val  Pro  Ile  Lys  Ile  Glu  Tyr  Gln  Ser  Asp  Thr
               115                      120                      125

Lys  Phe  Asn  Ile  Asp  Ser  Lys  Thr  Phe  Lys  Glu  Leu  Lys  Leu  Phe  Lys
          130                      135                      140

Ile  Asp  Ser  Gln  Asn  Gln  Pro  Gln  Val  Gln  Gln  Asp  Glu  Leu  Arg
145                      150                      155                      160

Asn  Pro  Glu  Phe  Asn  Lys  Lys  Glu  Ser  Gln  Glu  Phe  Leu  Ala  Lys  Pro
                    165                      170                      175

Ser  Lys  Ile  Asn  Leu  Phe  Thr  Gln  Gln  Met  Lys  Arg  Glu  Ile  Asp  Glu
```

-continued

```
                        180                           185                           190
Asp  Thr  Asp  Thr  Asp  Gly  Asp  Ser  Ile  Pro  Asp  Leu  Trp  Glu  Glu  Asn
          195                      200                      205

Gly  Tyr  Thr  Ile  Gln  Asn  Arg  Ile  Ala  Val  Lys  Trp  Asp  Asp  Ser  Leu
     210                      215                      220

Ala  Ser  Lys  Gly  Tyr  Thr  Lys  Phe  Val  Ser  Asn  Pro  Leu  Glu  Ser  His
225                      230                      235                          240

Thr  Val  Gly  Asp  Pro  Tyr  Thr  Asp  Tyr  Glu  Lys  Ala  Ala  Arg  Asp  Leu
                    245                      250                      255

Asp  Leu  Ser  Asn  Ala  Lys  Glu  Thr  Phe  Asn  Pro  Leu  Val  Ala  Ala  Phe
               260                      265                      270

Pro  Ser  Val  Asn  Val  Ser  Met  Glu  Lys  Val  Ile  Leu  Ser  Pro  Asn  Glu
          275                      280                      285

Asn  Leu  Ser  Asn  Ser  Val  Glu  Ser  His  Ser  Ser  Thr  Asn  Trp  Ser  Tyr
          290                      295                      300

Thr  Asn  Thr  Glu  Gly  Ala  Ser  Val  Glu  Ala  Gly  Ile  Gly  Pro  Lys  Gly
305                      310                      315                          320

Ile  Ser  Phe  Gly  Val  Ser  Val  Asn  Tyr  Gln  His  Ser  Glu  Thr  Val  Ala
                    325                      330                      335

Gln  Glu  Trp  Gly  Thr  Ser  Thr  Gly  Asn  Thr  Ser  Gln  Phe  Asn  Thr  Ala
               340                      345                      350

Ser  Ala  Gly  Tyr  Leu  Asn  Ala  Asn  Val  Arg  Tyr  Asn  Asn  Val  Gly  Thr
          355                      360                      365

Gly  Ala  Ile  Tyr  Asp  Val  Lys  Pro  Thr  Thr  Ser  Phe  Val  Leu  Asn  Asn
          370                      375                      380

Asp  Thr  Ile  Ala  Thr  Ile  Thr  Ala  Lys  Ser  Asn  Ser  Thr  Ala  Leu  Asn
385                      390                      395                          400

Ile  Ser  Pro  Gly  Glu  Ser  Tyr  Pro  Lys  Lys  Gly  Gln  Asn  Gly  Ile  Ala
                    405                      410                      415

Ile  Thr  Ser  Met  Asp  Asp  Phe  Asn  Ser  His  Pro  Ile  Thr  Leu  Asn  Lys
               420                      425                      430

Lys  Gln  Val  Asp  Asn  Leu  Leu  Asn  Asn  Lys  Pro  Met  Met  Leu  Glu  Thr
          435                      440                      445

Asn  Gln  Thr  Asp  Gly  Val  Tyr  Lys  Ile  Lys  Asp  Thr  His  Gly  Asn  Ile
          450                      455                      460

Val  Thr  Gly  Gly  Glu  Trp  Asn  Gly  Val  Ile  Gln  Gln  Ile  Lys  Ala  Lys
465                      470                      475                          480

Thr  Ala  Ser  Ile  Ile  Val  Asp  Asp  Gly  Glu  Arg  Val  Ala  Glu  Lys  Arg
                    485                      490                      495

Val  Ala  Ala  Lys  Asp  Tyr  Glu  Asn  Pro  Glu  Asp  Lys  Thr  Pro  Ser  Leu
               500                      505                      510

Thr  Leu  Lys  Asp  Ala  Leu  Lys  Leu  Ser  Tyr  Pro  Asp  Glu  Ile  Lys  Glu
          515                      520                      525

Ile  Glu  Gly  Leu  Leu  Tyr  Tyr  Lys  Asn  Lys  Pro  Ile  Tyr  Glu  Ser  Ser
          530                      535                      540

Val  Met  Thr  Tyr  Leu  Asp  Glu  Asn  Thr  Ala  Lys  Glu  Val  Thr  Lys  Gln
545                      550                      555                          560

Leu  Asn  Asp  Thr  Thr  Gly  Lys  Phe  Lys  Asp  Val  Ser  His  Leu  Tyr  Asp
                    565                      570                      575

Val  Lys  Leu  Thr  Pro  Lys  Met  Asn  Val  Thr  Ile  Lys  Leu  Ser  Ile  Leu
               580                      585                      590

Tyr  Asp  Asn  Ala  Glu  Ser  Asn  Asp  Asn  Ser  Ile  Gly  Lys  Trp  Thr  Asn
          595                      600                      605
```

| | | | | | | | | | | | | | | |
|---|---|---|---|---|---|---|---|---|---|---|---|---|---|---|
| Thr | Asn | Ile | Val | Ser | Gly | Gly | Asn | Asn | Gly | Lys | Lys | Gln | Tyr | Ser | Ser |
| 610 | | | | | 615 | | | | | 620 | | | | | |
| Asn | Asn | Pro | Asp | Ala | Asn | Leu | Thr | Leu | Asn | Thr | Asp | Ala | Gln | Glu | Lys |
| 625 | | | | | 630 | | | | | 635 | | | | | 640 |
| Leu | Asn | Lys | Asn | Arg | Asp | Tyr | Tyr | Ile | Ser | Leu | Tyr | Met | Lys | Ser | Glu |
| | | | | 645 | | | | | 650 | | | | | 655 | |
| Lys | Asn | Thr | Gln | Cys | Glu | Ile | Thr | Ile | Asp | Gly | Glu | Ile | Tyr | Pro | Ile |
| | | | 660 | | | | | 665 | | | | | 670 | | |
| Thr | Thr | Lys | Thr | Val | Asn | Val | Asn | Lys | Asp | Asn | Tyr | Lys | Arg | Leu | Asp |
| | | 675 | | | | | 680 | | | | | 685 | | | |
| Ile | Ile | Ala | His | Asn | Ile | Lys | Ser | Asn | Pro | Ile | Ser | Ser | Leu | His | Ile |
| | 690 | | | | | 695 | | | | | 700 | | | | |
| Lys | Thr | Asn | Asp | Glu | Ile | Thr | Leu | Phe | Trp | Asp | Asp | Ile | Ser | Ile | Thr |
| 705 | | | | | 710 | | | | | 715 | | | | | 720 |
| Asp | Val | Ala | Ser | Ile | Lys | Pro | Glu | Asn | Leu | Thr | Asp | Ser | Glu | Ile | Lys |
| | | | | 725 | | | | | 730 | | | | | 735 | |
| Gln | Ile | Tyr | Ser | Arg | Tyr | Gly | Ile | Lys | Leu | Glu | Asp | Gly | Ile | Leu | Ile |
| | | | 740 | | | | | 745 | | | | | 750 | | |
| Asp | Lys | Lys | Gly | Gly | Ile | His | Tyr | Gly | Glu | Phe | Ile | Asn | Glu | Ala | Ser |
| | | 755 | | | | | 760 | | | | | 765 | | | |
| Phe | Asn | Ile | Glu | Pro | Leu | Gln | Asn | Tyr | Val | Thr | Lys | Tyr | Glu | Val | Thr |
| | 770 | | | | | 775 | | | | | 780 | | | | |
| Tyr | Ser | Ser | Glu | Leu | Gly | Pro | Asn | Val | Ser | Asp | Thr | Leu | Glu | Ser | Asp |
| 785 | | | | | 790 | | | | | 795 | | | | | 800 |
| Lys | Ile | Tyr | Lys | Asp | Gly | Thr | Ile | Lys | Phe | Asp | Phe | Thr | Lys | Tyr | Ser |
| | | | | 805 | | | | | 810 | | | | | 815 | |
| Lys | Asn | Glu | Gln | Gly | Leu | Phe | Tyr | Asp | Ser | Gly | Leu | Asn | Trp | Asp | Phe |
| | | | 820 | | | | | 825 | | | | | 830 | | |
| Lys | Ile | Asn | Ala | Ile | Thr | Tyr | Asp | Gly | Lys | Glu | Met | Asn | Val | Phe | His |
| | | 835 | | | | | 840 | | | | | 845 | | | |
| Arg | Tyr | Asn | Lys | | | | | | | | | | | | |
| | | | 850 | | | | | | | | | | | | |

( 2 ) INFORMATION FOR SEQ ID NO:37:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "forward primer used to make pCIB5527"

( i i i ) HYPOTHETICAL: NO ( x i ) SEQUENCE DESCRIPTION: SEQ ID NO:37:

GGATCCACCA TGCTGCAGAA CCTGAAGATC AC    32

( 2 ) INFORMATION FOR SEQ ID NO:38:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "reverse primer used to make pCIB5527"

5,840,868

163 164

-continued ( i i i ) HYPOTHETICAL: NO ( x i ) SEQUENCE DESCRIPTION: SEQ ID NO:38:

```
AAGCTTCCAC TCCTTCTC                                                    18
```

( 2 ) INFORMATION FOR SEQ ID NO:39:

( i ) SEQUENCE CHARACTERISTICS:
        ( A ) LENGTH: 1241 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: CDS
        ( B ) LOCATION: 9..1238
        ( D ) OTHER INFORMATION: /note= "Maize optimized DNA
            sequence encoding VIP2A(a) with the Bacillus secretion
            signal removed as contained in pCIB5527"

( x i ) SEQUENCE DESCRIPTION: SEQ ID NO:39:

```
GATCCACC ATG CTG CAG AAC CTG AAG ATC ACC GAC AAG GTG GAG GAC TTC          50
         Met Leu Gln Asn Leu Lys Ile Thr Asp Lys Val Glu Asp Phe
             855             860                 865

AAG GAG GAC AAG GAG AAG GCC AAG GAG TGG GGC AAG GAG AAG GAG AAG           98
Lys Glu Asp Lys Glu Lys Ala Lys Glu Trp Gly Lys Glu Lys Glu Lys
                870             875                 880

GAG TGG AAG CTT ACC GCC ACC GAG AAG GGC AAG ATG AAC AAC TTC CTG          146
Glu Trp Lys Leu Thr Ala Thr Glu Lys Gly Lys Met Asn Asn Phe Leu
        885             890                 895

GAC AAC AAG AAC GAC ATC AAG ACC AAC TAC AAG GAG ATC ACC TTC AGC          194
Asp Asn Lys Asn Asp Ile Lys Thr Asn Tyr Lys Glu Ile Thr Phe Ser
    900             905                 910

ATA GCC GGC AGC TTC GAG GAC GAG ATC AAG GAC CTG AAG GAG ATC GAC          242
Ile Ala Gly Ser Phe Glu Asp Glu Ile Lys Asp Leu Lys Glu Ile Asp
915             920                 925                 930

AAG ATG TTC GAC AAG ACC AAC CTG AGC AAC AGC ATC ATC ACC TAC AAG          290
Lys Met Phe Asp Lys Thr Asn Leu Ser Asn Ser Ile Ile Thr Tyr Lys
                935             940                 945

AAC GTG GAG CCC ACC ACC ATC GGC TTC AAC AAG AGC CTG ACC GAG GGC          338
Asn Val Glu Pro Thr Thr Ile Gly Phe Asn Lys Ser Leu Thr Glu Gly
            950             955                 960

AAC ACC ATC AAC AGC GAC GCC ATG GCC CAG TTC AAG GAG CAG TTC CTG          386
Asn Thr Ile Asn Ser Asp Ala Met Ala Gln Phe Lys Glu Gln Phe Leu
        965             970                 975

GAC CGC GAC ATC AAG TTC GAC AGC TAC CTG GAC ACC CAC CTG ACC GCC          434
Asp Arg Asp Ile Lys Phe Asp Ser Tyr Leu Asp Thr His Leu Thr Ala
    980             985                 990

CAG CAG GTG AGC AGC AAG GAG CGC GTG ATC CTG AAG GTG ACC GTC CCC          482
Gln Gln Val Ser Ser Lys Glu Arg Val Ile Leu Lys Val Thr Val Pro
995             1000                1005                1010

AGC GGC AAG GGC AGC ACC ACC CCC ACC AAG GCC GGC GTG ATC CTG AAC          530
Ser Gly Lys Gly Ser Thr Thr Pro Thr Lys Ala Gly Val Ile Leu Asn
                1015            1020                1025

AAC AGC GAG TAC AAG ATG CTG ATC GAC AAC GGC TAC ATG GTG CAC GTG          578
Asn Ser Glu Tyr Lys Met Leu Ile Asp Asn Gly Tyr Met Val His Val
            1030            1035                1040

GAC AAG GTG AGC AAG GTG GTG AAG AAG GGC GTG GAG TGC CTC CAG ATC          626
Asp Lys Val Ser Lys Val Val Lys Lys Gly Val Glu Cys Leu Gln Ile
        1045            1050                1055
```

```
GAG GGC ACC CTG AAG AAG AGT CTA GAC TTC AAG AAC GAC ATC AAC GCC      674
Glu Gly Thr Leu Lys Lys Ser Leu Asp Phe Lys Asn Asp Ile Asn Ala
            1060            1065            1070

GAG GCC CAC AGC TGG GGC ATG AAG AAC TAC GAG GAG TGG GCC AAG GAC      722
Glu Ala His Ser Trp Gly Met Lys Asn Tyr Glu Glu Trp Ala Lys Asp
1075            1080            1085            1090

CTG ACC GAC AGC CAG CGC GAG GCC CTG GAC GGC TAC GCC CGC CAG GAC      770
Leu Thr Asp Ser Gln Arg Glu Ala Leu Asp Gly Tyr Ala Arg Gln Asp
            1095            1100            1105

TAC AAG GAG ATC AAC AAC TAC CTG CGC AAC CAG GGC GGC AGC GGC AAC      818
Tyr Lys Glu Ile Asn Asn Tyr Leu Arg Asn Gln Gly Gly Ser Gly Asn
            1110            1115            1120

GAG AAG CTG GAC GCC CAG ATC AAG AAC ATC AGC GAC GCC CTG GGC AAG      866
Glu Lys Leu Asp Ala Gln Ile Lys Asn Ile Ser Asp Ala Leu Gly Lys
            1125            1130            1135

AAG CCC ATC CCC GAG AAC ATC ACC GTG TAC CGC TGG TGC GGC ATG CCC      914
Lys Pro Ile Pro Glu Asn Ile Thr Val Tyr Arg Trp Cys Gly Met Pro
            1140            1145            1150

GAG TTC GGC TAC CAG ATC AGC GAC CCC CTG CCC AGC CTG AAG GAC TTC      962
Glu Phe Gly Tyr Gln Ile Ser Asp Pro Leu Pro Ser Leu Lys Asp Phe
1155            1160            1165            1170

GAG GAG CAG TTC CTG AAC ACC ATC AAG GAG GAC AAG GGC TAC ATG AGC     1010
Glu Glu Gln Phe Leu Asn Thr Ile Lys Glu Asp Lys Gly Tyr Met Ser
            1175            1180            1185

ACC AGC CTG AGC AGC GAG CGC CTG GCC GCC TTC GGC AGC CGC AAG ATC     1058
Thr Ser Leu Ser Ser Glu Arg Leu Ala Ala Phe Gly Ser Arg Lys Ile
            1190            1195            1200

ATC CTG CGC CTG CAG GTG CCC AAG GGC AGC ACT GGT GCC TAC CTG AGC     1106
Ile Leu Arg Leu Gln Val Pro Lys Gly Ser Thr Gly Ala Tyr Leu Ser
            1205            1210            1215

GCC ATC GGC GGC TTC GCC AGC GAG AAG GAG ATC CTG CTG GAT AAG GAC     1154
Ala Ile Gly Gly Phe Ala Ser Glu Lys Glu Ile Leu Leu Asp Lys Asp
1220            1225            1230

AGC AAG TAC CAC ATC GAC AAG GTG ACC GAG GTG ATC ATC AAG GGC GTG     1202
Ser Lys Tyr His Ile Asp Lys Val Thr Glu Val Ile Ile Lys Gly Val
1235            1240            1245            1250

AAG CGC TAC GTG GTG GAC GCC ACC CTG CTG ACC AAC TAG                 1241
Lys Arg Tyr Val Val Asp Ala Thr Leu Leu Thr Asn
            1255            1260
```

( 2 ) INFORMATION FOR SEQ ID NO:40:

( i ) SEQUENCE CHARACTERISTICS:
        ( A ) LENGTH: 410 amino acids
        ( B ) TYPE: amino acid
        ( D ) TOPOLOGY: linear ( i i ) MOLECULE TYPE: protein ( x i ) SEQUENCE DESCRIPTION: SEQ ID NO:40:

```
Met Leu Gln Asn Leu Lys Ile Thr Asp Lys Val Glu Asp Phe Lys Glu
1               5                   10                  15

Asp Lys Glu Lys Ala Lys Glu Trp Gly Lys Glu Lys Glu Lys Glu Trp
            20                  25                  30

Lys Leu Thr Ala Thr Glu Lys Gly Lys Met Asn Asn Phe Leu Asp Asn
            35                  40                  45

Lys Asn Asp Ile Lys Thr Asn Tyr Lys Glu Ile Thr Phe Ser Ile Ala
            50                  55                  60

Gly Ser Phe Glu Asp Gly Ile Lys Asp Leu Lys Glu Ile Asp Lys Met
65                  70                  75                  80
```

```
Phe  Asp  Lys  Thr  Asn  Leu  Ser  Asn  Ser  Ile  Ile  Thr  Tyr  Lys  Asn  Val
               85                       90                            95

Glu  Pro  Thr  Thr  Ile  Gly  Phe  Asn  Lys  Ser  Leu  Thr  Glu  Gly  Asn  Thr
               100                      105                 110

Ile  Asn  Ser  Asp  Ala  Met  Ala  Gln  Phe  Lys  Glu  Gln  Phe  Leu  Asp  Arg
          115                      120                      125

Asp  Ile  Lys  Phe  Asp  Ser  Tyr  Leu  Asp  Thr  His  Leu  Thr  Ala  Gln  Gln
     130                      135                      140

Val  Ser  Ser  Lys  Glu  Arg  Val  Ile  Leu  Lys  Val  Thr  Val  Pro  Ser  Gly
145                      150                      155                      160

Lys  Gly  Ser  Thr  Thr  Pro  Thr  Lys  Ala  Gly  Val  Ile  Leu  Asn  Asn  Ser
                    165                      170                      175

Glu  Tyr  Lys  Met  Leu  Ile  Asp  Asn  Gly  Tyr  Met  Val  His  Val  Asp  Lys
               180                      185                           190

Val  Ser  Lys  Val  Val  Lys  Lys  Gly  Val  Glu  Cys  Leu  Gln  Ile  Glu  Gly
          195                      200                      205

Thr  Leu  Lys  Lys  Ser  Leu  Asp  Phe  Lys  Asn  Asp  Ile  Asn  Ala  Glu  Ala
     210                      215                      220

His  Ser  Trp  Gly  Met  Lys  Asn  Tyr  Glu  Glu  Trp  Ala  Lys  Asp  Leu  Thr
225                      230                      235                      240

Asp  Ser  Gln  Arg  Glu  Ala  Leu  Asp  Gly  Tyr  Ala  Arg  Gln  Asp  Tyr  Lys
               245                      250                      255

Glu  Ile  Asn  Asn  Tyr  Leu  Arg  Asn  Gln  Gly  Gly  Ser  Gly  Asn  Glu  Lys
               260                      265                      270

Leu  Asp  Ala  Gln  Ile  Lys  Asn  Ile  Ser  Asp  Ala  Leu  Gly  Lys  Lys  Pro
          275                      280                      285

Ile  Pro  Glu  Asn  Ile  Thr  Val  Tyr  Arg  Trp  Cys  Gly  Met  Pro  Glu  Phe
     290                      295                      300

Gly  Tyr  Gln  Ile  Ser  Asp  Pro  Leu  Pro  Ser  Leu  Lys  Asp  Phe  Glu  Glu
305                      310                      315                      320

Gln  Phe  Leu  Asn  Thr  Ile  Lys  Glu  Asp  Lys  Gly  Tyr  Met  Ser  Thr  Ser
                    325                      330                      335

Leu  Ser  Ser  Glu  Arg  Leu  Ala  Ala  Phe  Gly  Ser  Arg  Lys  Ile  Ile  Leu
               340                      345                      350

Arg  Leu  Gln  Val  Pro  Lys  Gly  Ser  Thr  Gly  Ala  Tyr  Leu  Ser  Ala  Ile
          355                      360                      365

Gly  Gly  Phe  Ala  Ser  Glu  Lys  Glu  Ile  Leu  Leu  Asp  Lys  Asp  Ser  Lys
     370                      375                      380

Tyr  His  Ile  Asp  Lys  Val  Thr  Glu  Val  Ile  Ile  Lys  Gly  Val  Lys  Arg
385                      390                      395                      400

Tyr  Val  Val  Asp  Ala  Thr  Leu  Leu  Thr  Asn
                    405                      410
```

( 2 ) INFORMATION FOR SEQ ID NO:41:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide encoding
            eukaryotic secretion signal used to construct pCIB5527"

( i i i ) HYPOTHETICAL: NO ( x i ) SEQUENCE DESCRIPTION: SEQ ID NO:41:

-continued

| GGATCCACCA | TGGGCTGGAG | CTGGATCTTC | CTGTTCCTGC | TGAGCGGCGC | CGCGGGCGTG | 60 |
| CACTGCCTGC | AG | | | | | 72 |

( 2 ) INFORMATION FOR SEQ ID NO:42:

( i ) SEQUENCE CHARACTERISTICS:
        ( A ) LENGTH: 1241 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: CDS
        ( B ) LOCATION: 9..1238
        ( D ) OTHER INFORMATION: /note= "Maize optimized DNA
            sequence encoding VIP2A(a) with the Bacillus secretion signal removed and the eukaryotic secretion signal inserted as contained in pCIB5528"

( x i ) SEQUENCE DESCRIPTION: SEQ ID NO:42:

```
GATCCACC ATG CTG CAG AAC CTG AAG ATC ACC GAC AAG GTG GAG GAC TTC     50
         Met Leu Gln Asn Leu Lys Ile Thr Asp Lys Val Glu Asp Phe
                         415                     420

AAG GAG GAC AAG GAG AAG GCC AAG GAG TGG GGC AAG GAG AAG GAG AAG      98
Lys Glu Asp Lys Glu Lys Ala Lys Glu Trp Gly Lys Glu Lys Glu Lys
425                 430                 435                 440

GAG TGG AAG CTT ACC GCC ACC GAG AAG GGC AAG ATG AAC AAC TTC CTG     146
Glu Trp Lys Leu Thr Ala Thr Glu Lys Gly Lys Met Asn Asn Phe Leu
                445                 450                 455

GAC AAC AAG AAC GAC ATC AAG ACC AAC TAC AAG GAG ATC ACC TTC AGC     194
Asp Asn Lys Asn Asp Ile Lys Thr Asn Tyr Lys Glu Ile Thr Phe Ser
            460                 465                 470

ATA GCC GGC AGC TTC GAG GAC GAG ATC AAG GAC CTG AAG GAG ATC GAC     242
Ile Ala Gly Ser Phe Glu Asp Glu Ile Lys Asp Leu Lys Glu Ile Asp
        475                 480                 485

AAG ATG TTC GAC AAG ACC AAC CTG AGC AAC AGC ATC ATC ACC TAC AAG     290
Lys Met Phe Asp Lys Thr Asn Leu Ser Asn Ser Ile Ile Thr Tyr Lys
    490                 495                 500

AAC GTG GAG CCC ACC ACC ATC GGC TTC AAC AAG AGC CTG ACC GAG GGC     338
Asn Val Glu Pro Thr Thr Ile Gly Phe Asn Lys Ser Leu Thr Glu Gly
505                 510                 515                 520

AAC ACC ATC AAC AGC GAC GCC ATG GCC CAG TTC AAG GAG CAG TTC CTG     386
Asn Thr Ile Asn Ser Asp Ala Met Ala Gln Phe Lys Glu Gln Phe Leu
                525                 530                 535

GAC CGC GAC ATC AAG TTC GAC AGC TAC CTG GAC ACC CAC CTG ACC GCC     434
Asp Arg Asp Ile Lys Phe Asp Ser Tyr Leu Asp Thr His Leu Thr Ala
            540                 545                 550

CAG CAG GTG AGC AGC AAG GAG CGC GTG ATC CTG AAG GTG ACC GTC CCC     482
Gln Gln Val Ser Ser Lys Glu Arg Val Ile Leu Lys Val Thr Val Pro
        555                 560                 565

AGC GGC AAG GGC AGC ACC ACC CCC ACC AAG GCC GGC GTG ATC CTG AAC     530
Ser Gly Lys Gly Ser Thr Thr Pro Thr Lys Ala Gly Val Ile Leu Asn
    570                 575                 580

AAC AGC GAG TAC AAG ATG CTG ATC GAC AAC GGC TAC ATG GTG CAC GTG     578
Asn Ser Glu Tyr Lys Met Leu Ile Asp Asn Gly Tyr Met Val His Val
585                 590                 595                 600

GAC AAG GTG AGC AAG GTG GTG AAG AAG GGC GTG GAG TGC CTC CAG ATC     626
Asp Lys Val Ser Lys Val Val Lys Lys Gly Val Glu Cys Leu Gln Ile
                605                 610                 615
```

| | | | | | | | | | | | | | | | | |
|---|---|---|---|---|---|---|---|---|---|---|---|---|---|---|---|---|
| GAG | GGC | ACC | CTG | AAG | AAG | AGT | CTA | GAC | TTC | AAG | AAC | GAC | ATC | AAC | GCC | 674 |
| Glu | Gly | Thr | Leu | Lys | Lys | Ser | Leu | Asp | Phe | Lys | Asn | Asp | Ile | Asn | Ala | |
| | | | 620 | | | | | 625 | | | | | 630 | | | |
| GAG | GCC | CAC | AGC | TGG | GGC | ATG | AAG | AAC | TAC | GAG | GAG | TGG | GCC | AAG | GAC | 722 |
| Glu | Ala | His | Ser | Trp | Gly | Met | Lys | Asn | Tyr | Glu | Glu | Trp | Ala | Lys | Asp | |
| | | 635 | | | | 640 | | | | | 645 | | | | | |
| CTG | ACC | GAC | AGC | CAG | CGC | GAG | GCC | CTG | GAC | GGC | TAC | GCC | CGC | CAG | GAC | 770 |
| Leu | Thr | Asp | Ser | Gln | Arg | Glu | Ala | Leu | Asp | Gly | Tyr | Ala | Arg | Gln | Asp | |
| | 650 | | | | | 655 | | | | 660 | | | | | | |
| TAC | AAG | GAG | ATC | AAC | AAC | TAC | CTG | CGC | AAC | CAG | GGC | GGC | AGC | GGC | AAC | 818 |
| Tyr | Lys | Glu | Ile | Asn | Asn | Tyr | Leu | Arg | Asn | Gln | Gly | Gly | Ser | Gly | Asn | |
| 665 | | | | | 670 | | | | | 675 | | | | | 680 | |
| GAG | AAG | CTG | GAC | GCC | CAG | ATC | AAG | AAC | ATC | AGC | GAC | GCC | CTG | GGC | AAG | 866 |
| Glu | Lys | Leu | Asp | Ala | Gln | Ile | Lys | Asn | Ile | Ser | Asp | Ala | Leu | Gly | Lys | |
| | | | | 685 | | | | | 690 | | | | | 695 | | |
| AAG | CCC | ATC | CCC | GAG | AAC | ATC | ACC | GTG | TAC | CGC | TGG | TGC | GGC | ATG | CCC | 914 |
| Lys | Pro | Ile | Pro | Glu | Asn | Ile | Thr | Val | Tyr | Arg | Trp | Cys | Gly | Met | Pro | |
| | | | 700 | | | | | 705 | | | | | 710 | | | |
| GAG | TTC | GGC | TAC | CAG | ATC | AGC | GAC | CCC | CTG | CCC | AGC | CTG | AAG | GAC | TTC | 962 |
| Glu | Phe | Gly | Tyr | Gln | Ile | Ser | Asp | Pro | Leu | Pro | Ser | Leu | Lys | Asp | Phe | |
| | | 715 | | | | 720 | | | | | 725 | | | | | |
| GAG | GAG | CAG | TTC | CTG | AAC | ACC | ATC | AAG | GAG | GAC | AAG | GGC | TAC | ATG | AGC | 1010 |
| Glu | Glu | Gln | Phe | Leu | Asn | Thr | Ile | Lys | Glu | Asp | Lys | Gly | Tyr | Met | Ser | |
| | 730 | | | | | 735 | | | | 740 | | | | | | |
| ACC | AGC | CTG | AGC | AGC | GAG | CGC | CTG | GCC | GCC | TTC | GGC | AGC | CGC | AAG | ATC | 1058 |
| Thr | Ser | Leu | Ser | Ser | Glu | Arg | Leu | Ala | Ala | Phe | Gly | Ser | Arg | Lys | Ile | |
| 745 | | | | | 750 | | | | | 755 | | | | | 760 | |
| ATC | CTG | CGC | CTG | CAG | GTG | CCC | AAG | GGC | AGC | ACT | GGT | GCC | TAC | CTG | AGC | 1106 |
| Ile | Leu | Arg | Leu | Gln | Val | Pro | Lys | Gly | Ser | Thr | Gly | Ala | Tyr | Leu | Ser | |
| | | | | 765 | | | | | 770 | | | | | 775 | | |
| GCC | ATC | GGC | GGC | TTC | GCC | AGC | GAG | AAG | GAG | ATC | CTG | CTG | GAT | AAG | GAC | 1154 |
| Ala | Ile | Gly | Gly | Phe | Ala | Ser | Glu | Lys | Glu | Ile | Leu | Leu | Asp | Lys | Asp | |
| | | | 780 | | | | | 785 | | | | | 790 | | | |
| AGC | AAG | TAC | CAC | ATC | GAC | AAG | GTG | ACC | GAG | GTG | ATC | ATC | AAG | GGC | GTG | 1202 |
| Ser | Lys | Tyr | His | Ile | Asp | Lys | Val | Thr | Glu | Val | Ile | Ile | Lys | Gly | Val | |
| | | 795 | | | | 800 | | | | | 805 | | | | | |
| AAG | CGC | TAC | GTG | GTG | GAC | GCC | ACC | CTG | CTG | ACC | AAC | TAG | | | | 1241 |
| Lys | Arg | Tyr | Val | Val | Asp | Ala | Thr | Leu | Leu | Thr | Asn | | | | | |
| | 810 | | | | | 815 | | | | | 820 | | | | | |

( 2 ) INFORMATION FOR SEQ ID NO:43:

( i ) SEQUENCE CHARACTERISTICS:
        ( A ) LENGTH: 410 amino acids
        ( B ) TYPE: amino acid
        ( D ) TOPOLOGY: linear ( i i ) MOLECULE TYPE: protein ( x i ) SEQUENCE DESCRIPTION: SEQ ID NO:43:

| | | | | | | | | | | | | | | | |
|---|---|---|---|---|---|---|---|---|---|---|---|---|---|---|---|
| Met | Leu | Gln | Asn | Leu | Lys | Ile | Thr | Asp | Lys | Val | Glu | Asp | Phe | Lys | Glu |
| 1 | | | | 5 | | | | | 10 | | | | | 15 | |
| Asp | Lys | Glu | Lys | Ala | Lys | Glu | Trp | Gly | Lys | Glu | Lys | Glu | Lys | Glu | Trp |
| | | | 20 | | | | | 25 | | | | | 30 | | |
| Lys | Leu | Thr | Ala | Thr | Glu | Lys | Gly | Lys | Met | Asn | Asn | Phe | Leu | Asp | Asn |
| | | | 35 | | | | | 40 | | | | | 45 | | |
| Lys | Asn | Asp | Ile | Lys | Thr | Asn | Tyr | Lys | Glu | Ile | Thr | Phe | Ser | Ile | Ala |
| | | 50 | | | | | 55 | | | | | 60 | | | |
| Gly | Ser | Phe | Glu | Asp | Glu | Ile | Lys | Asp | Leu | Lys | Glu | Ile | Asp | Lys | Met |
| 65 | | | | | 70 | | | | | 75 | | | | | 80 |
| Phe | Asp | Lys | Thr | Asn | Leu | Ser | Asn | Ser | Ile | Ile | Thr | Tyr | Lys | Asn | Val |

|  |  |  |  |  |  |  |  | 85 |  |  |  |  |  |  |  | 90 |  |  |  |  |  |  |  | 95 |  |  |  |
|---|---|---|---|---|---|---|---|---|---|---|---|---|---|---|---|---|---|---|---|---|---|---|---|---|---|---|---|

Glu Pro Thr Thr Ile Gly Phe Asn Lys Ser Leu Thr Glu Gly Asn Thr
                100                     105                 110

Ile Asn Ser Asp Ala Met Ala Gln Phe Lys Glu Gln Phe Leu Asp Arg
        115                     120                 125

Asp Ile Lys Phe Asp Ser Tyr Leu Asp Thr His Leu Thr Ala Gln Gln
        130                     135                 140

Val Ser Ser Lys Glu Arg Val Ile Leu Lys Val Thr Val Pro Ser Gly
145                     150                     155                 160

Lys Gly Ser Thr Thr Pro Thr Lys Ala Gly Val Ile Leu Asn Asn Ser
                165                     170                 175

Glu Tyr Lys Met Leu Ile Asp Asn Gly Tyr Met Val His Val Asp Lys
                180                     185                 190

Val Ser Lys Val Val Lys Lys Gly Val Glu Cys Leu Gln Ile Glu Gly
        195                     200                 205

Thr Leu Lys Lys Ser Leu Asp Phe Lys Asn Asp Ile Asn Ala Glu Ala
        210                     215                 220

His Ser Trp Gly Met Lys Asn Tyr Glu Glu Trp Ala Lys Asp Leu Thr
225                     230                     235                 240

Asp Ser Gln Arg Glu Ala Leu Asp Gly Tyr Ala Arg Gln Asp Tyr Lys
                245                     250                 255

Glu Ile Asn Asn Tyr Leu Arg Asn Gln Gly Gly Ser Gly Asn Glu Lys
                260                     265                 270

Leu Asp Ala Gln Ile Lys Asn Ile Ser Asp Ala Leu Gly Lys Lys Pro
        275                     280                 285

Ile Pro Glu Asn Ile Thr Val Tyr Arg Trp Cys Gly Met Pro Glu Phe
        290                     295                 300

Gly Tyr Gln Ile Ser Asp Pro Leu Pro Ser Leu Lys Asp Phe Glu Glu
305                     310                     315                 320

Gln Phe Leu Asn Thr Ile Lys Glu Asp Lys Gly Tyr Met Ser Thr Ser
                325                     330                 335

Leu Ser Ser Glu Arg Leu Ala Ala Phe Gly Ser Arg Lys Ile Ile Leu
                340                     345                 350

Arg Leu Gln Val Pro Lys Gly Ser Thr Gly Ala Tyr Leu Ser Ala Ile
        355                     360                 365

Gly Gly Phe Ala Ser Glu Lys Glu Ile Leu Leu Asp Lys Asp Ser Lys
370                     375                     380

Tyr His Ile Asp Lys Val Thr Glu Val Ile Ile Lys Gly Val Lys Arg
385                     390                     395                 400

Tyr Val Val Asp Ala Thr Leu Leu Thr Asn
                405                     410

(2) INFORMATION FOR SEQ ID NO:44:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide encoding vacuolar targetting peptide used to construct pCIB5533"

(iii) HYPOTHETICAL: NO (xi) SEQUENCE DESCRIPTION: SEQ ID NO:44:

CCGCGGGCGT GCACTGCCTC AGCAGCAGCA GCTTCGCCGA CAGCAACCCC ATCCGCGTGA   60

CCGACCGCGC CGCCAGCACC CTGCAG                                                86

(2) INFORMATION FOR SEQ ID NO:45:

(i) SEQUENCE CHARACTERISTICS:
        (A) LENGTH: 1358 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (ix) FEATURE:
        (A) NAME/KEY: CDS
        (B) LOCATION: 9..1355
        (D) OTHER INFORMATION: /note= "Maize optimized VIP2A(a)
   &nbs

```
Lys Ala Gly Val Ile Leu Asn Asn Ser Glu Tyr Lys Met Leu Ile Asp
            620                 625                 630

AAC GGC TAC ATG GTG CAC GTG GAC AAG GTG AGC AAG GTG GTG AAG AAG    722
Asn Gly Tyr Met Val His Val Asp Lys Val Ser Lys Val Val Lys Lys
            635                 640                 645

GGC GTG GAG TGC CTC CAG ATC GAG GGC ACC CTG AAG AAG AGT CTA GAC    770
Gly Val Glu Cys Leu Gln Ile Glu Gly Thr Leu Lys Lys Ser Leu Asp
            650                 655                 660

TTC AAG AAC GAC ATC AAC GCC GAG GCC CAC AGC TGG GGC ATG AAG AAC    818
Phe Lys Asn Asp Ile Asn Ala Glu Ala His Ser Trp Gly Met Lys Asn
665                 670                 675                 680

TAC GAG GAG TGG GCC AAG GAC CTG ACC GAC AGC CAG CGC GAG GCC CTG    866
Tyr Glu Glu Trp Ala Lys Asp Leu Thr Asp Ser Gln Arg Glu Ala Leu
                685                 690                 695

GAC GGC TAC GCC CGC CAG GAC TAC AAG GAG ATC AAC AAC TAC CTG CGC    914
Asp Gly Tyr Ala Arg Gln Asp Tyr Lys Glu Ile Asn Asn Tyr Leu Arg
            700                 705                 710

AAC CAG GGC GGC AGC GGC AAC GAG AAG CTG GAC GCC CAG ATC AAG AAC    962
Asn Gln Gly Gly Ser Gly Asn Glu Lys Leu Asp Ala Gln Ile Lys Asn
            715                 720                 725

ATC AGC GAC GCC CTG GGC AAG AAG CCC ATC CCC GAG AAC ATC ACC GTG   1010
Ile Ser Asp Ala Leu Gly Lys Lys Pro Ile Pro Glu Asn Ile Thr Val
    730                 735                 740

TAC CGC TGG TGC GGC ATG CCC GAG TTC GGC TAC CAG ATC AGC GAC CCC   1058
Tyr Arg Trp Cys Gly Met Pro Glu Phe Gly Tyr Gln Ile Ser Asp Pro
745                 750                 755                 760

CTG CCC AGC CTG AAG GAC TTC GAG GAG CAG TTC CTG AAC ACC ATC AAG   1106
Leu Pro Ser Leu Lys Asp Phe Glu Glu Gln Phe Leu Asn Thr Ile Lys
                765                 770                 775

GAG GAC AAG GGC TAC ATG AGC ACC AGC CTG AGC AGC GAG CGC CTG GCC   1154
Glu Asp Lys Gly Tyr Met Ser Thr Ser Leu Ser Ser Glu Arg Leu Ala
            780                 785                 790

GCC TTC GGC AGC CGC AAG ATC ATC CTG CGC CTG CAG GTG CCC AAG GGC   1202
Ala Phe Gly Ser Arg Lys Ile Ile Leu Arg Leu Gln Val Pro Lys Gly
            795                 800                 805

AGC ACT GGT GCC TAC CTG AGC GCC ATC GGC GGC TTC GCC AGC GAG AAG   1250
Ser Thr Gly Ala Tyr Leu Ser Ala Ile Gly Gly Phe Ala Ser Glu Lys
    810                 815                 820

GAG ATC CTG CTG GAT AAG GAC AGC AAG TAC CAC ATC GAC AAG GTG ACC   1298
Glu Ile Leu Leu Asp Lys Asp Ser Lys Tyr His Ile Asp Lys Val Thr
825                 830                 835                 840

GAG GTG ATC ATC AAG GGC GTG AAG CGC TAC GTG GTG GAC GCC ACC CTG   1346
Glu Val Ile Ile Lys Gly Val Lys Arg Tyr Val Val Asp Ala Thr Leu
                845                 850                 855

CTG ACC AAC TAG                                                    1358
Leu Thr Asn
```

( 2 ) INFORMATION FOR SEQ ID NO:46:

( i ) SEQUENCE CHARACTERISTICS:
        ( A ) LENGTH: 449 amino acids
        ( B ) TYPE: amino acid
        ( D ) TOPOLOGY: linear ( i i ) MOLECULE TYPE: protein ( x i ) SEQUENCE DESCRIPTION: SEQ ID NO:46:

```
Met Gly Trp Ser Trp Ile Phe Leu Phe Leu Leu Ser Gly Ala Ala Gly
 1               5                   10                  15

Val His Cys Leu Ser Ser Ser Ser Phe Ala Asp Ser Asn Pro Ile Arg
                20                  25                  30
```

-continued

| | | | | | | | | | | | | | | |
|---|---|---|---|---|---|---|---|---|---|---|---|---|---|---|
|Val|Thr|Asp|Arg|Ala|Ala|Ser|Thr|Leu|Gln|Asn|Leu|Lys|Ile|Thr|Asp|
| | |35| | | |40| | | | |45| | | |
|Lys|Val|Glu|Asp|Phe|Lys|Glu|Asp|Lys|Glu|Lys|Ala|Lys|Glu|Trp|Gly|
| |50| | | |55| | | |60| | | | | |
|Lys|Glu|Lys|Glu|Lys|Glu|Trp|Lys|Leu|Thr|Ala|Thr|Glu|Lys|Gly|Lys|
|65| | | |70| | | |75| | | | | |80|
|Met|Asn|Asn|Phe|Leu|Asp|Asn|Lys|Asn|Asp|Ile|Lys|Thr|Asn|Tyr|Lys|
| | | |85| | | | |90| | | | |95| |
|Glu|Ile|Thr|Phe|Ser|Ile|Ala|Gly|Ser|Phe|Glu|Asp|Glu|Ile|Lys|Asp|
| | |100| | | |105| | | |110| | | | |
|Leu|Lys|Glu|Ile|Asp|Lys|Met|Phe|Asp|Lys|Thr|Asn|Leu|Ser|Asn|Ser|
| |115| | | |120| | | |125| | | | | |
|Ile|Ile|Thr|Tyr|Lys|Asn|Val|Glu|Pro|Thr|Thr|Ile|Gly|Phe|Asn|Lys|
| |130| | | |135| | | |140| | | | | |
|Ser|Leu|Thr|Glu|Gly|Asn|Thr|Ile|Asn|Ser|Asp|Ala|Met|Ala|Gln|Phe|
|145| | | |150| | | |155| | | | |160| |
|Lys|Glu|Gln|Phe|Leu|Asp|Arg|Asp|Ile|Lys|Phe|Asp|Ser|Tyr|Leu|Asp|
| | | |165| | | |170| | | |175| | | |
|Thr|His|Leu|Thr|Ala|Gln|Gln|Val|Ser|Lys|Glu|Arg|Val|Ile|Leu|
| | |180| | | |185| | | |190| | | | |
|Lys|Val|Thr|Val|Pro|Ser|Gly|Lys|Gly|Ser|Thr|Thr|Pro|Thr|Lys|Ala|
| |195| | | |200| | | |205| | | | | |
|Gly|Val|Ile|Leu|Asn|Asn|Ser|Glu|Tyr|Lys|Met|Leu|Ile|Asp|Asn|Gly|
| |210| | | |215| | | |220| | | | | |
|Tyr|Met|Val|His|Val|Asp|Lys|Val|Ser|Lys|Val|Val|Lys|Lys|Gly|Val|
|225| | | |230| | | |235| | | | |240| |
|Glu|Cys|Leu|Gln|Ile|Glu|Gly|Thr|Leu|Lys|Lys|Ser|Leu|Asp|Phe|Lys|
| | | |245| | | |250| | | |255| | | |
|Asn|Asp|Ile|Asn|Ala|Glu|Ala|His|Ser|Trp|Gly|Met|Lys|Asn|Tyr|Glu|
| | |260| | | |265| | | |270| | | | |
|Glu|Trp|Ala|Lys|Asp|Leu|Thr|Asp|Ser|Gln|Arg|Glu|Ala|Leu|Asp|Gly|
| |275| | | |280| | | |285| | | | | |
|Tyr|Ala|Arg|Gln|Asp|Tyr|Lys|Glu|Ile|Asn|Asn|Tyr|Leu|Arg|Asn|Gln|
| |290| | | |295| | | |300| | | | | |
|Gly|Gly|Ser|Gly|Asn|Glu|Lys|Leu|Asp|Ala|Gln|Ile|Lys|Asn|Ile|Ser|
|305| | | |310| | | |315| | | | |320| |
|Asp|Ala|Leu|Gly|Lys|Lys|Pro|Ile|Pro|Glu|Asn|Ile|Thr|Val|Tyr|Arg|
| | | |325| | | |330| | | |335| | | |
|Trp|Cys|Gly|Met|Pro|Glu|Phe|Gly|Tyr|Gln|Ile|Ser|Asp|Pro|Leu|Pro|
| | |340| | | |345| | | |350| | | | |
|Ser|Leu|Lys|Asp|Phe|Glu|Glu|Gln|Phe|Leu|Asn|Thr|Ile|Lys|Glu|Asp|
| |355| | | |360| | | |365| | | | | |
|Lys|Gly|Tyr|Met|Ser|Thr|Ser|Leu|Ser|Ser|Glu|Arg|Leu|Ala|Ala|Phe|
| |370| | | |375| | | |380| | | | | |
|Gly|Ser|Arg|Lys|Ile|Ile|Leu|Arg|Leu|Gln|Val|Pro|Lys|Gly|Ser|Thr|
|385| | | |390| | | |395| | | | |400| |
|Gly|Ala|Tyr|Leu|Ser|Ala|Ile|Gly|Gly|Phe|Ala|Ser|Glu|Lys|Glu|Ile|
| | | |405| | | |410| | | |415| | | |
|Leu|Leu|Asp|Lys|Asp|Ser|Lys|Tyr|His|Ile|Asp|Lys|Val|Thr|Glu|Val|
| | |420| | | |425| | | |430| | | | |
|Ile|Ile|Lys|Gly|Val|Lys|Arg|Tyr|Val|Val|Asp|Ala|Thr|Leu|Leu|Thr|
| |435| | | |440| | | |445| | | | | |
|Asn| | | | | | | | | | | | | | | |

( 2 ) INFORMATION FOR SEQ ID NO:47:

( i ) SEQUENCE CHARACTERISTICS:
  ( A ) LENGTH: 16 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i x ) FEATURE:
  ( A ) NAME/KEY: Peptide
  ( B ) LOCATION: 1..16
  ( D ) OTHER INFORMATION: /note= "linker peptide for fusion
   of VIP1A(a) and VIP2A(a) used to construct pCIB5533"

( x i ) SEQUENCE DESCRIPTION: SEQ ID NO:47:

```
Pro  Ser  Thr  Pro  Pro  Thr  Pro  Ser  Pro  Ser  Thr  Pro  Pro  Thr  Pro  Ser
1                   5                        10                      15
```

( 2 ) INFORMATION FOR SEQ ID NO:48:

( i ) SEQUENCE CHARACTERISTICS:
  ( A ) LENGTH: 66 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "DNA encoding linker peptide
   used to construct pCIB5533"

( i i i ) HYPOTHETICAL: NO ( x i ) SEQUENCE DESCRIPTION: SEQ ID NO:48:

```
CCCGGGCCTT  CTACTCCCCC  AACTCCCTCT  CCTAGCACGC  CTCCGACACC  TAGCGATATC     60

GGATCC                                                                    66
```

( 2 ) INFORMATION FOR SEQ ID NO:49:

( i ) SEQUENCE CHARACTERISTICS:
  ( A ) LENGTH: 4031 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "Synthetic DNA"

( i i i ) HYPOTHETICAL: NO ( i x ) FEATURE:
  ( A ) NAME/KEY: CDS
  ( B ) LOCATION: 6..4019
  ( D ) OTHER INFORMATION: /note= "Maize optimized DNA
   sequence encoding a VIP2A(a) - VIP1A(a) fusion protein as
   contained in pCIB5531"

( x i ) SEQUENCE DESCRIPTION: SEQ ID NO:49:

```
GATCC  ATG  AAG  CGC  ATG  GAG  GGC  AAG  CTG  TTC  ATG  GTG  AGC  AAG  AAG      47
       Met  Lys  Arg  Met  Glu  Gly  Lys  Leu  Phe  Met  Val  Ser  Lys  Lys
       450                      455                     460

CTC  CAG  GTG  GTG  ACC  AAG  ACC  GTG  CTG  CTG  AGC  ACC  GTG  TTC  AGC  ATC   95
Leu  Gln  Val  Val  Thr  Lys  Thr  Val  Leu  Leu  Ser  Thr  Val  Phe  Ser  Ile
465                     470                     475

AGC  CTG  CTG  AAC  AAC  GAG  GTG  ATC  AAG  GCC  GAG  CAG  CTG  AAC  ATC  AAC   143
Ser  Leu  Leu  Asn  Asn  Glu  Val  Ile  Lys  Ala  Glu  Gln  Leu  Asn  Ile  Asn
480                     485                     490                     495
```

| | | | | | | | | | | | | | | | | |
|---|---|---|---|---|---|---|---|---|---|---|---|---|---|---|---|---|
| AGC | CAG | AGC | AAG | TAC | ACC | AAC | CTC | CAG | AAC | CTG | AAG | ATC | ACC | GAC | AAG | 191 |
| Ser | Gln | Ser | Lys | Tyr 500 | Thr | Asn | Leu | Gln 505 | Asn | Leu | Lys | Ile | Thr 510 | Asp | Lys | |
| GTG | GAG | GAC | TTC | AAG | GAG | GAC | AAG | GAG | AAG | GCC | AAG | GAG | TGG | GGC | AAG | 239 |
| Val | Glu | Asp | Phe 515 | Lys | Glu | Asp | Lys | Glu 520 | Lys | Ala | Lys | Glu | Trp 525 | Gly | Lys | |
| GAG | AAG | GAG | AAG | GAG | TGG | AAG | CTT | ACC | GCC | ACC | GAG | AAG | GGC | AAG | ATG | 287 |
| Glu | Lys | Glu 530 | Lys | Glu | Trp | Lys | Leu | Thr 535 | Ala | Thr | Glu | Lys | Gly 540 | Lys | Met | |
| AAC | AAC | TTC | CTG | GAC | AAC | AAG | AAC | GAC | ATC | AAG | ACC | AAC | TAC | AAG | GAG | 335 |
| Asn | Asn 545 | Phe | Leu | Asp | Asn | Lys 550 | Asn | Asp | Ile | Lys | Thr 555 | Asn | Tyr | Lys | Glu | |
| ATC | ACC | TTC | AGC | ATA | GCC | GGC | AGC | TTC | GAG | GAC | GAG | ATC | AAG | GAC | CTG | 383 |
| Ile 560 | Thr | Phe | Ser | Ile | Ala 565 | Gly | Ser | Phe | Glu | Asp 570 | Glu | Ile | Lys | Asp | Leu 575 | |
| AAG | GAG | ATC | GAC | AAG | ATG | TTC | GAC | AAG | ACC | AAC | CTG | AGC | AAC | AGC | ATC | 431 |
| Lys | Glu | Ile | Asp | Lys 580 | Met | Phe | Asp | Lys | Thr 585 | Asn | Leu | Ser | Asn | Ser 590 | Ile | |
| ATC | ACC | TAC | AAG | AAC | GTG | GAG | CCC | ACC | ACC | ATC | GGC | TTC | AAC | AAG | AGC | 479 |
| Ile | Thr | Tyr | Lys 595 | Asn | Val | Glu | Pro | Thr 600 | Thr | Ile | Gly | Phe | Asn 605 | Lys | Ser | |
| CTG | ACC | GAG | GGC | AAC | ACC | ATC | AAC | AGC | GAC | GCC | ATG | GCC | CAG | TTC | AAG | 527 |
| Leu | Thr | Glu 610 | Gly | Asn | Thr | Ile | Asn 615 | Ser | Asp | Ala | Met | Ala 620 | Gln | Phe | Lys | |
| GAG | CAG | TTC | CTG | GAC | CGC | GAC | ATC | AAG | TTC | GAC | AGC | TAC | CTG | GAC | ACC | 575 |
| Glu | Gln 625 | Phe | Leu | Asp | Arg | Asp 630 | Ile | Lys | Phe | Asp | Ser 635 | Tyr | Leu | Asp | Thr | |
| CAC | CTG | ACC | GCC | CAG | CAG | GTG | AGC | AGC | AAG | GAG | CGC | GTG | ATC | CTG | AAG | 623 |
| His 640 | Leu | Thr | Ala | Gln | Gln 645 | Val | Ser | Ser | Lys | Glu 650 | Arg | Val | Ile | Leu | Lys 655 | |
| GTG | ACC | GTC | CCC | AGC | GGC | AAG | GGC | AGC | ACC | ACC | CCC | ACC | AAG | GCC | GGC | 671 |
| Val | Thr | Val | Pro | Ser 660 | Gly | Lys | Gly | Ser | Thr 665 | Thr | Pro | Thr | Lys | Ala 670 | Gly | |
| GTG | ATC | CTG | AAC | AAC | AGC | GAG | TAC | AAG | ATG | CTG | ATC | GAC | AAC | GGC | TAC | 719 |
| Val | Ile | Leu | Asn | Asn 675 | Ser | Glu | Tyr | Lys | Met 680 | Leu | Ile | Asp | Asn | Gly 685 | Tyr | |
| ATG | GTG | CAC | GTG | GAC | AAG | GTG | AGC | AAG | GTG | GTG | AAG | AAG | GGC | GTG | GAG | 767 |
| Met | Val | His 690 | Val | Asp | Lys | Val | Ser 695 | Lys | Val | Val | Lys | Lys 700 | Gly | Val | Glu | |
| TGC | CTC | CAG | ATC | GAG | GGC | ACC | CTG | AAG | AAG | AGT | CTA | GAC | TTC | AAG | AAC | 815 |
| Cys | Leu 705 | Gln | Ile | Glu | Gly | Thr 710 | Leu | Lys | Lys | Ser | Leu 715 | Asp | Phe | Lys | Asn | |
| GAC | ATC | AAC | GCC | GAG | GCC | CAC | AGC | TGG | GGC | ATG | AAG | AAC | TAC | GAG | GAG | 863 |
| Asp | Ile | Asn | Ala 720 | Glu | Ala | His | Ser | Trp 725 | Gly | Met | Lys | Asn | Tyr 730 | Glu | Glu 735 | |
| TGG | GCC | AAG | GAC | CTG | ACC | GAC | AGC | CAG | CGC | GAG | GCC | CTG | GAC | GGC | TAC | 911 |
| Trp | Ala | Lys | Asp | Leu 740 | Thr | Asp | Ser | Gln | Arg 745 | Glu | Ala | Leu | Asp | Gly 750 | Tyr | |
| GCC | CGC | CAG | GAC | TAC | AAG | GAG | ATC | AAC | AAC | TAC | CTG | CGC | AAC | CAG | GGC | 959 |
| Ala | Arg | Gln | Asp | Tyr 755 | Lys | Glu | Ile | Asn | Asn 760 | Tyr | Leu | Arg | Asn | Gln 765 | Gly | |
| GGC | AGC | GGC | AAC | GAG | AAG | CTG | GAC | GCC | CAG | ATC | AAG | AAC | ATC | AGC | GAC | 1007 |
| Gly | Ser | Gly | Asn 770 | Glu | Lys | Leu | Asp | Ala 775 | Gln | Ile | Lys | Asn | Ile 780 | Ser | Asp | |
| GCC | CTG | GGC | AAG | AAG | CCC | ATC | CCC | GAG | AAC | ATC | ACC | GTG | TAC | CGC | TGG | 1055 |
| Ala | Leu | Gly | Lys 785 | Lys | Pro | Ile | Pro | Glu 790 | Asn | Ile | Thr | Val | Tyr 795 | Arg | Trp | |
| TGC | GGC | ATG | CCC | GAG | TTC | GGC | TAC | CAG | ATC | AGC | GAC | CCC | CTG | CCC | AGC | 1103 |
| Cys | Gly | Met | Pro 800 | Glu | Phe | Gly | Tyr | Gln 805 | Ile | Ser | Asp | Pro | Leu 810 | Pro | Ser 815 | |

| | | | | | | | | | | | | | | | | |
|---|---|---|---|---|---|---|---|---|---|---|---|---|---|---|---|---|
| CTG | AAG | GAC | TTC | GAG | GAG | CAG | TTC | CTG | AAC | ACC | ATC | AAG | GAG | GAC | AAG | 1151 |
| Leu | Lys | Asp | Phe | Glu | Glu | Gln | Phe | Leu | Asn | Thr | Ile | Lys | Glu | Asp | Lys | |
| | | | 820 | | | | | 825 | | | | | 830 | | | |
| GGC | TAC | ATG | AGC | ACC | AGC | CTG | AGC | AGC | GAG | CGC | CTG | GCC | GCC | TTC | GGC | 1199 |
| Gly | Tyr | Met | Ser | Thr | Ser | Leu | Ser | Ser | Glu | Arg | Leu | Ala | Ala | Phe | Gly | |
| | | | 835 | | | | | 840 | | | | | 845 | | | |
| AGC | CGC | AAG | ATC | ATC | CTG | CGC | CTG | CAG | GTG | CCC | AAG | GGC | AGC | ACT | GGT | 1247 |
| Ser | Arg | Lys | Ile | Ile | Leu | Arg | Leu | Gln | Val | Pro | Lys | Gly | Ser | Thr | Gly | |
| | | 850 | | | | | 855 | | | | | 860 | | | | |
| GCC | TAC | CTG | AGC | GCC | ATC | GGC | GGC | TTC | GCC | AGC | GAG | AAG | GAG | ATC | CTG | 1295 |
| Ala | Tyr | Leu | Ser | Ala | Ile | Gly | Gly | Phe | Ala | Ser | Glu | Lys | Glu | Ile | Leu | |
| | 865 | | | | | 870 | | | | | 875 | | | | | |
| CTG | GAT | AAG | GAC | AGC | AAG | TAC | CAC | ATC | GAC | AAG | GTG | ACC | GAG | GTG | ATC | 1343 |
| Leu | Asp | Lys | Asp | Ser | Lys | Tyr | His | Ile | Asp | Lys | Val | Thr | Glu | Val | Ile | |
| 880 | | | | | 885 | | | | | 890 | | | | | 895 | |
| ATC | AAG | GGC | GTG | AAG | CGC | TAC | GTG | GTG | GAC | GCC | ACC | CTG | CTG | ACC | AAC | 1391 |
| Ile | Lys | Gly | Val | Lys | Arg | Tyr | Val | Val | Asp | Ala | Thr | Leu | Leu | Thr | Asn | |
| | | | | 900 | | | | | 905 | | | | | 910 | | |
| TCC | CGG | GGG | CCT | TCT | ACT | CCC | CCA | ACT | CCC | TCT | CCT | AGC | ACG | CCT | CCG | 1439 |
| Ser | Arg | Gly | Pro | Ser | Thr | Pro | Pro | Thr | Pro | Ser | Pro | Ser | Thr | Pro | Pro | |
| | | | 915 | | | | 920 | | | | | 925 | | | | |
| ACA | CCT | AGC | GAT | ATC | GGA | TCC | ACC | ATG | AAG | ACC | AAC | CAG | ATC | AGC | ACC | 1487 |
| Thr | Pro | Ser | Asp | Ile | Gly | Ser | Thr | Met | Lys | Thr | Asn | Gln | Ile | Ser | Thr | |
| | | 930 | | | | | 935 | | | | | 940 | | | | |
| ACC | CAG | AAG | AAC | CAG | CAG | AAG | GAG | ATG | GAC | CGC | AAG | GGC | CTG | CTG | GGC | 1535 |
| Thr | Gln | Lys | Asn | Gln | Gln | Lys | Glu | Met | Asp | Arg | Lys | Gly | Leu | Leu | Gly | |
| | 945 | | | | | 950 | | | | | 955 | | | | | |
| TAC | TAC | TTC | AAG | GGC | AAG | GAC | TTC | AGC | AAC | CTG | ACC | ATG | TTC | GCC | CCC | 1583 |
| Tyr | Tyr | Phe | Lys | Gly | Lys | Asp | Phe | Ser | Asn | Leu | Thr | Met | Phe | Ala | Pro | |
| 960 | | | | | 965 | | | | | 970 | | | | | 975 | |
| ACG | CGT | GAC | AGC | ACC | CTG | ATC | TAC | GAC | CAG | CAG | ACC | GCC | AAC | AAG | CTG | 1631 |
| Thr | Arg | Asp | Ser | Thr | Leu | Ile | Tyr | Asp | Gln | Gln | Thr | Ala | Asn | Lys | Leu | |
| | | | | 980 | | | | | 985 | | | | | 990 | | |
| CTG | GAC | AAG | AAG | CAG | CAG | GAG | TAC | CAG | AGC | ATC | CGC | TGG | ATC | GGC | CTG | 1679 |
| Leu | Asp | Lys | Lys | Gln | Gln | Glu | Tyr | Gln | Ser | Ile | Arg | Trp | Ile | Gly | Leu | |
| | | | 995 | | | | | 1000 | | | | | 1005 | | | |
| ATC | CAG | AGC | AAG | GAG | ACC | GGC | GAC | TTC | ACC | TTC | AAC | CTG | AGC | GAG | GAC | 1727 |
| Ile | Gln | Ser | Lys | Glu | Thr | Gly | Asp | Phe | Thr | Phe | Asn | Leu | Ser | Glu | Asp | |
| | | | 1010 | | | | | 1015 | | | | | 1020 | | | |
| GAG | CAG | GCC | ATC | ATC | GAG | ATC | AAC | GGC | AAG | ATC | ATC | AGC | AAC | AAG | GGC | 1775 |
| Glu | Gln | Ala | Ile | Ile | Glu | Ile | Asn | Gly | Lys | Ile | Ile | Ser | Asn | Lys | Gly | |
| | | | 1025 | | | | | 1030 | | | | | 1035 | | | |
| AAG | GAG | AAG | CAG | GTG | GTG | CAC | CTG | GAG | AAG | GGC | AAG | CTG | GTG | CCC | ATC | 1823 |
| Lys | Glu | Lys | Gln | Val | Val | His | Leu | Glu | Lys | Gly | Lys | Leu | Val | Pro | Ile | |
| 1040 | | | | | 1045 | | | | | 1050 | | | | | 1055 | |
| AAG | ATC | GAG | TAC | CAG | AGC | GAC | ACC | AAG | TTC | AAC | ATC | GAC | AGC | AAG | ACC | 1871 |
| Lys | Ile | Glu | Tyr | Gln | Ser | Asp | Thr | Lys | Phe | Asn | Ile | Asp | Ser | Lys | Thr | |
| | | | | 1060 | | | | | 1065 | | | | | 1070 | | |
| TTC | AAG | GAG | CTG | AAG | CTT | TTC | AAG | ATC | GAC | AGC | AG | AAC | CAG | CCC | CAG | 1919 |
| Phe | Lys | Glu | Leu | Lys | Leu | Phe | Lys | Ile | Asp | Ser | Gln | Asn | Gln | Pro | Gln | |
| | | | 1075 | | | | | 1080 | | | | | 1085 | | | |
| CAG | GTG | CAG | CAG | GAC | GAG | CTG | CGC | AAC | CCC | GAG | TTC | AAC | AAG | AAG | GAG | 1967 |
| Gln | Val | Gln | Gln | Asp | Glu | Leu | Arg | Asn | Pro | Glu | Phe | Asn | Lys | Lys | Glu | |
| | | | 1090 | | | | | 1095 | | | | | 1100 | | | |
| AGC | CAG | GAG | TTC | CTG | GCC | AAG | CCC | AGC | AAG | ATC | AAC | CTG | TTC | ACC | CAG | 2015 |
| Ser | Gln | Glu | Phe | Leu | Ala | Lys | Pro | Ser | Lys | Ile | Asn | Leu | Phe | Thr | Gln | |
| | | | 1105 | | | | | 1110 | | | | | 1115 | | | |
| CAG | ATG | AAG | CGC | GAG | ATC | GAC | GAG | GAC | ACC | GAC | ACC | GAC | GGC | GAC | AGC | 2063 |
| Gln | Met | Lys | Arg | Glu | Ile | Asp | Glu | Asp | Thr | Asp | Thr | Asp | Gly | Asp | Ser | |
| | | 1120 | | | | | 1125 | | | | | 1130 | | | | 1135 |

```
ATC  CCC  GAC  CTG  TGG  GAG  GAG  AAC  GGC  TAC  ACC  ATC  CAG  AAC  CGC  ATC     2111
Ile  Pro  Asp  Leu  Trp  Glu  Glu  Asn  Gly  Tyr  Thr  Ile  Gln  Asn  Arg  Ile
               1140                     1145                    1150

GCC  GTG  AAG  TGG  GAC  GAC  AGC  CTG  GCT  AGC  AAG  GGC  TAC  ACC  AAG  TTC     2159
Ala  Val  Lys  Trp  Asp  Asp  Ser  Leu  Ala  Ser  Lys  Gly  Tyr  Thr  Lys  Phe
          1155                     1160                         1165

GTG  AGC  AAC  CCC  CTG  GAG  AGC  CAC  ACC  GTG  GGC  GAC  CCC  TAC  ACC  GAC     2207
Val  Ser  Asn  Pro  Leu  Glu  Ser  His  Thr  Val  Gly  Asp  Pro  Tyr  Thr  Asp
     1170                     1175                          1180

TAC  GAG  AAG  GCC  GCC  CGC  GAC  CTG  GAC  CTG  AGC  AAC  GCC  AAG  GAG  ACC     2255
Tyr  Glu  Lys  Ala  Ala  Arg  Asp  Leu  Asp  Leu  Ser  Asn  Ala  Lys  Glu  Thr
          1185                     1190                         1195

TTC  AAC  CCC  CTG  GTG  GCC  GCC  TTC  CCC  AGC  GTG  AAC  GTG  AGC  ATG  GAG     2303
Phe  Asn  Pro  Leu  Val  Ala  Ala  Phe  Pro  Ser  Val  Asn  Val  Ser  Met  Glu
1200                     1205                    1210                     1215

AAG  GTG  ATC  CTG  AGC  CCC  AAC  GAG  AAC  CTG  AGC  AAC  AGC  GTG  GAG  AGC     2351
Lys  Val  Ile  Leu  Ser  Pro  Asn  Glu  Asn  Leu  Ser  Asn  Ser  Val  Glu  Ser
               1220                     1225                    1230

CAC  TCG  AGC  ACC  AAC  TGG  AGC  TAC  ACC  AAC  ACC  GAG  GGC  GCC  AGC  GTG     2399
His  Ser  Ser  Thr  Asn  Trp  Ser  Tyr  Thr  Asn  Thr  Glu  Gly  Ala  Ser  Val
               1235                     1240                         1245

GAG  GCC  GGC  ATC  GGT  CCC  AAG  GGC  ATC  AGC  TTC  GGC  GTG  AGC  GTG  AAC     2447
Glu  Ala  Gly  Ile  Gly  Pro  Lys  Gly  Ile  Ser  Phe  Gly  Val  Ser  Val  Asn
          1250                     1255                    1260

TAC  CAG  CAC  AGC  GAG  ACC  GTG  GCC  CAG  GAG  TGG  GGC  ACC  AGC  ACC  GGC     2495
Tyr  Gln  His  Ser  Glu  Thr  Val  Ala  Gln  Glu  Trp  Gly  Thr  Ser  Thr  Gly
     1265                     1270                         1275

AAC  ACC  AGC  CAG  TTC  AAC  ACC  GCC  AGC  GCC  GGC  TAC  CTG  AAC  GCC  AAC     2543
Asn  Thr  Ser  Gln  Phe  Asn  Thr  Ala  Ser  Ala  Gly  Tyr  Leu  Asn  Ala  Asn
1280                     1285                    1290                     1295

GTG  CGC  TAC  AAC  AAC  GTG  GGC  ACC  GGC  GCC  ATC  TAC  GAC  GTG  AAG  CCC     2591
Val  Arg  Tyr  Asn  Asn  Val  Gly  Thr  Gly  Ala  Ile  Tyr  Asp  Val  Lys  Pro
               1300                     1305                    1310

ACC  ACC  AGC  TTC  GTG  CTG  AAC  AAC  GAC  ACC  ATC  GCC  ACC  ATC  ACC  GCC     2639
Thr  Thr  Ser  Phe  Val  Leu  Asn  Asn  Asp  Thr  Ile  Ala  Thr  Ile  Thr  Ala
               1315                     1320                    1325

AAG  TCG  AAT  TCC  ACC  GCC  CTG  AAC  ATC  AGC  CCC  GGC  GAG  AGC  TAC  CCC     2687
Lys  Ser  Asn  Ser  Thr  Ala  Leu  Asn  Ile  Ser  Pro  Gly  Glu  Ser  Tyr  Pro
          1330                     1335                         1340

AAG  AAG  GGC  CAG  AAC  GGC  ATC  GCC  ATC  ACC  AGC  ATG  GAC  GAC  TTC  AAC     2735
Lys  Lys  Gly  Gln  Asn  Gly  Ile  Ala  Ile  Thr  Ser  Met  Asp  Asp  Phe  Asn
          1345                     1350                    1355

AGC  CAC  CCC  ATC  ACC  CTG  AAC  AAG  AAG  CAG  GTG  GAC  AAC  CTG  CTG  AAC     2783
Ser  His  Pro  Ile  Thr  Leu  Asn  Lys  Lys  Gln  Val  Asp  Asn  Leu  Leu  Asn
1360                     1365                    1370                     1375

AAC  AAG  CCC  ATG  ATG  CTG  GAG  ACC  AAC  CAG  ACC  GAC  GGC  GTC  TAC  AAG     2831
Asn  Lys  Pro  Met  Met  Leu  Glu  Thr  Asn  Gln  Thr  Asp  Gly  Val  Tyr  Lys
               1380                     1385                    1390

ATC  AAG  GAC  ACC  CAC  GGC  AAC  ATC  GTG  ACG  GGC  GGC  GAG  TGG  AAC  GGC     2879
Ile  Lys  Asp  Thr  His  Gly  Asn  Ile  Val  Thr  Gly  Gly  Glu  Trp  Asn  Gly
          1395                     1400                         1405

GTG  ATC  CAG  CAG  ATC  AAG  GCC  AAG  ACC  GCC  AGC  ATC  ATC  GTC  GAC  GAC     2927
Val  Ile  Gln  Gln  Ile  Lys  Ala  Lys  Thr  Ala  Ser  Ile  Ile  Val  Asp  Asp
     1410                     1415                         1420

GGC  GAG  CGC  GTG  GCC  GAG  AAG  CGC  GTG  GCC  GCC  AAG  GAC  TAC  GAG  AAC     2975
Gly  Glu  Arg  Val  Ala  Glu  Lys  Arg  Val  Ala  Ala  Lys  Asp  Tyr  Glu  Asn
     1425                     1430                         1435

CCC  GAG  GAC  AAG  ACC  CCC  AGC  CTG  ACC  CTG  AAG  GAC  GCC  CTG  AAG  CTG     3023
Pro  Glu  Asp  Lys  Thr  Pro  Ser  Leu  Thr  Leu  Lys  Asp  Ala  Leu  Lys  Leu
1440                     1445                    1450                     1455
```

```
AGC  TAC  CCC  GAC  GAG  ATC  AAG  GAG  ATC  GAG  GGC  TTG  CTG  TAC  TAC  AAG   3071
Ser  Tyr  Pro  Asp  Glu  Ile  Lys  Glu  Ile  Glu  Gly  Leu  Leu  Tyr  Tyr  Lys
               1460                1465                          1470

AAC  AAG  CCC  ATC  TAC  GAG  AGC  AGC  GTG  ATG  ACC  TAT  CTA  GAC  GAG  AAC   3119
Asn  Lys  Pro  Ile  Tyr  Glu  Ser  Ser  Val  Met  Thr  Tyr  Leu  Asp  Glu  Asn
          1475                     1480                          1485

ACC  GCC  AAG  GAG  GTG  ACC  AAG  CAG  CTG  AAC  GAC  ACC  ACC  GGC  AAG  TTC   3167
Thr  Ala  Lys  Glu  Val  Thr  Lys  Gln  Leu  Asn  Asp  Thr  Thr  Gly  Lys  Phe
     1490                          1495                          1500

AAG  GAC  GTG  AGC  CAC  CTG  TAC  GAC  GTG  AAG  CTG  ACC  CCC  AAG  ATG  AAC   3215
Lys  Asp  Val  Ser  His  Leu  Tyr  Asp  Val  Lys  Leu  Thr  Pro  Lys  Met  Asn
1505                     1510                          1515

GTG  ACC  ATC  AAG  CTG  AGC  ATC  CTG  TAC  GAC  AAC  GCC  GAG  AGC  AAC  GAC   3263
Val  Thr  Ile  Lys  Leu  Ser  Ile  Leu  Tyr  Asp  Asn  Ala  Glu  Ser  Asn  Asp
1520                     1525                          1530                    1535

AAC  AGC  ATC  GGC  AAG  TGG  ACC  AAC  ACC  AAC  ATC  GTG  AGC  GGC  GGC  AAC   3311
Asn  Ser  Ile  Gly  Lys  Trp  Thr  Asn  Thr  Asn  Ile  Val  Ser  Gly  Gly  Asn
               1540                     1545                     1550

AAC  GGC  AAG  AAG  CAG  TAC  AGC  AGC  AAC  AAC  CCC  GAC  GCC  AAC  CTG  ACC   3359
Asn  Gly  Lys  Lys  Gln  Tyr  Ser  Ser  Asn  Asn  Pro  Asp  Ala  Asn  Leu  Thr
                    1555                     1560                     1565

CTG  AAC  ACC  GAC  GCC  CAG  GAG  AAG  CTG  AAC  AAG  AAC  CGC  GAC  TAC  TAC   3407
Leu  Asn  Thr  Asp  Ala  Gln  Glu  Lys  Leu  Asn  Lys  Asn  Arg  Asp  Tyr  Tyr
          1570                          1575                     1580

ATC  AGC  CTG  TAC  ATG  AAG  AGC  GAG  AAG  AAC  ACC  CAG  TGC  GAG  ATC  ACC   3455
Ile  Ser  Leu  Tyr  Met  Lys  Ser  Glu  Lys  Asn  Thr  Gln  Cys  Glu  Ile  Thr
     1585                          1590                     1595

ATC  GAC  GGC  GAG  ATA  TAC  CCC  ATC  ACC  ACC  AAG  ACC  GTG  AAC  GTG  AAC   3503
Ile  Asp  Gly  Glu  Ile  Tyr  Pro  Ile  Thr  Thr  Lys  Thr  Val  Asn  Val  Asn
1600                     1605                          1610                    1615

AAG  GAC  AAC  TAC  AAG  CGC  CTG  GAC  ATC  ATC  GCC  CAC  AAC  ATC  AAG  AGC   3551
Lys  Asp  Asn  Tyr  Lys  Arg  Leu  Asp  Ile  Ile  Ala  His  Asn  Ile  Lys  Ser
                    1620                     1625                     1630

AAC  CCC  ATC  AGC  AGC  CTG  CAC  ATC  AAG  ACC  AAC  GAC  GAG  ATC  ACC  CTG   3599
Asn  Pro  Ile  Ser  Ser  Leu  His  Ile  Lys  Thr  Asn  Asp  Glu  Ile  Thr  Leu
               1635                     1640                     1645

TTC  TGG  GAC  GAC  ATA  TCG  ATT  ACC  GAC  GTC  GCC  AGC  ATC  AAG  CCC  GAG   3647
Phe  Trp  Asp  Asp  Ile  Ser  Ile  Thr  Asp  Val  Ala  Ser  Ile  Lys  Pro  Glu
                    1650                     1655                     1660

AAC  CTG  ACC  GAC  AGC  GAG  ATC  AAG  CAG  ATA  TAC  AGT  CGC  TAC  GGC  ATC   3695
Asn  Leu  Thr  Asp  Ser  Glu  Ile  Lys  Gln  Ile  Tyr  Ser  Arg  Tyr  Gly  Ile
     1665                          1670                     1675

AAG  CTG  GAG  GAC  GGC  ATC  CTG  ATC  GAC  AAG  AAA  GGC  GGC  ATC  CAC  TAC   3743
Lys  Leu  Glu  Asp  Gly  Ile  Leu  Ile  Asp  Lys  Lys  Gly  Gly  Ile  His  Tyr
1680                     1685                          1690                    1695

GGC  GAG  TTC  ATC  AAC  GAG  GCC  AGC  TTC  AAC  ATC  GAG  CCC  CTG  CAG  AAC   3791
Gly  Glu  Phe  Ile  Asn  Glu  Ala  Ser  Phe  Asn  Ile  Glu  Pro  Leu  Gln  Asn
                    1700                     1705                     1710

TAC  GTG  ACC  AAG  TAC  GAG  GTG  ACC  TAC  AGC  AGC  GAG  CTG  GGC  CCC  AAC   3839
Tyr  Val  Thr  Lys  Tyr  Glu  Val  Thr  Tyr  Ser  Ser  Glu  Leu  Gly  Pro  Asn
               1715                     1720                     1725

GTG  AGC  GAC  ACC  CTG  GAG  AGC  GAC  AAG  ATT  TAC  AAG  GAC  GGC  ACC  ATC   3887
Val  Ser  Asp  Thr  Leu  Glu  Ser  Asp  Lys  Ile  Tyr  Lys  Asp  Gly  Thr  Ile
          1730                     1735                     1740

AAG  TTC  GAC  TTC  ACC  AAG  TAC  AGC  AAG  AAC  GAG  CAG  GGC  CTG  TTC  TAC   3935
Lys  Phe  Asp  Phe  Thr  Lys  Tyr  Ser  Lys  Asn  Glu  Gln  Gly  Leu  Phe  Tyr
     1745                          1750                     1755

GAC  AGC  GGC  CTG  AAC  TGG  GAC  TTC  AAG  ATC  AAC  GCC  ATC  ACC  TAC  GAC   3983
Asp  Ser  Gly  Leu  Asn  Trp  Asp  Phe  Lys  Ile  Asn  Ala  Ile  Thr  Tyr  Asp
1760                     1765                     1770                     1775
```

| | | | | | | | | | | | | | | |
|---|---|---|---|---|---|---|---|---|---|---|---|---|---|---|
| GGC | AAG | GAG | ATG | AAC | GTG | TTC | CAC | CGC | TAC | AAC | AAG | TAGATCTGAG | | 4029 |
| Gly | Lys | Glu | Met | Asn | Val | Phe | His | Arg | Tyr | Asn | Lys | | | |
| | | | 1780 | | | | | 1785 | | | | | | |

CT 4031

(2) INFORMATION FOR SEQ ID NO:50:

(i) SEQUENCE CHARACTERISTICS:
        (A) LENGTH: 1338 amino acids
        (B) TYPE: amino acid
        (D) TOPOLOGY: linear (ii) MOLECULE TYPE: protein (xi) SEQUENCE DESCRIPTION: SEQ ID NO:50:

```
Met  Lys  Arg  Met  Glu  Gly  Lys  Leu  Phe  Met  Val  Ser  Lys  Lys  Leu  Gln
 1                  5                    10                       15

Val  Val  Thr  Lys  Thr  Val  Leu  Leu  Ser  Thr  Val  Phe  Ser  Ile  Ser  Leu
               20                    25                       30

Leu  Asn  Asn  Glu  Val  Ile  Lys  Ala  Glu  Gln  Leu  Asn  Ile  Asn  Ser  Gln
          35                         40                       45

Ser  Lys  Tyr  Thr  Asn  Leu  Gln  Asn  Leu  Lys  Ile  Thr  Asp  Lys  Val  Glu
     50                         55                       60

Asp  Phe  Lys  Glu  Asp  Lys  Glu  Lys  Ala  Lys  Glu  Trp  Gly  Lys  Glu  Lys
 65                      70                       75                       80

Glu  Lys  Glu  Trp  Lys  Leu  Thr  Ala  Thr  Glu  Lys  Gly  Lys  Met  Asn  Asn
                    85                         90                   95

Phe  Leu  Asp  Asn  Lys  Asn  Asp  Ile  Lys  Thr  Asn  Tyr  Lys  Glu  Ile  Thr
               100                      105                      110

Phe  Ser  Ile  Ala  Gly  Ser  Phe  Glu  Asp  Glu  Ile  Lys  Asp  Leu  Lys  Glu
               115                      120                      125

Ile  Asp  Lys  Met  Phe  Asp  Lys  Thr  Asn  Leu  Ser  Asn  Ser  Ile  Ile  Thr
 130                      135                      140

Tyr  Lys  Asn  Val  Glu  Pro  Thr  Thr  Ile  Gly  Phe  Asn  Lys  Ser  Leu  Thr
 145                      150                      155                      160

Glu  Gly  Asn  Thr  Ile  Asn  Ser  Asp  Ala  Met  Ala  Gln  Phe  Lys  Glu  Gln
               165                      170                      175

Phe  Leu  Asp  Arg  Asp  Ile  Lys  Phe  Asp  Ser  Tyr  Leu  Asp  Thr  His  Leu
               180                      185                      190

Thr  Ala  Gln  Gln  Val  Ser  Ser  Lys  Glu  Arg  Val  Ile  Leu  Lys  Val  Thr
               195                      200                      205

Val  Pro  Ser  Gly  Lys  Gly  Ser  Thr  Thr  Pro  Thr  Lys  Ala  Gly  Val  Ile
     210                      215                      220

Leu  Asn  Asn  Ser  Glu  Tyr  Lys  Met  Leu  Ile  Asp  Asn  Gly  Tyr  Met  Val
 225                      230                      235                      240

His  Val  Asp  Lys  Val  Ser  Lys  Val  Val  Lys  Lys  Gly  Val  Glu  Cys  Leu
               245                      250                      255

Gln  Ile  Glu  Gly  Thr  Leu  Lys  Lys  Ser  Leu  Asp  Phe  Lys  Asn  Asp  Ile
               260                      265                      270

Asn  Ala  Glu  Ala  His  Ser  Trp  Gly  Met  Lys  Asn  Tyr  Glu  Glu  Trp  Ala
               275                      280                      285

Lys  Asp  Leu  Thr  Asp  Ser  Gln  Arg  Glu  Ala  Leu  Asp  Gly  Tyr  Ala  Arg
               290                      295                      300

Gln  Asp  Tyr  Lys  Glu  Ile  Asn  Asn  Tyr  Leu  Arg  Asn  Gln  Gly  Gly  Ser
 305                      310                      315                      320

Gly  Asn  Glu  Lys  Leu  Asp  Ala  Gln  Ile  Lys  Asn  Ile  Ser  Asp  Ala  Leu
               325                      330                      335
```

| | | | | | | | | | | | | | | |
|---|---|---|---|---|---|---|---|---|---|---|---|---|---|---|
| Gly | Lys | Lys | Pro | Ile | Pro | Glu | Asn | Ile | Thr | Val | Tyr | Arg | Trp | Cys | Gly |
| | | | 340 | | | | 345 | | | | | | 350 | | |
| Met | Pro | Glu | Phe | Gly | Tyr | Gln | Ile | Ser | Asp | Pro | Leu | Pro | Ser | Leu | Lys |
| | | 355 | | | | 360 | | | | | 365 | | | | |
| Asp | Phe | Glu | Glu | Gln | Phe | Leu | Asn | Thr | Ile | Lys | Glu | Asp | Lys | Gly | Tyr |
| | 370 | | | | | 375 | | | | | 380 | | | | |
| Met | Ser | Thr | Ser | Leu | Ser | Ser | Glu | Arg | Leu | Ala | Ala | Phe | Gly | Ser | Arg |
| 385 | | | | | 390 | | | | | 395 | | | | | 400 |
| Lys | Ile | Ile | Leu | Arg | Leu | Gln | Val | Pro | Lys | Gly | Ser | Thr | Gly | Ala | Tyr |
| | | | | 405 | | | | | 410 | | | | | 415 | |
| Leu | Ser | Ala | Ile | Gly | Gly | Phe | Ala | Ser | Lys | Glu | Ile | Leu | Leu | Asp |
| | | | 420 | | | | | 425 | | | | | 430 | | |
| Lys | Asp | Ser | Lys | Tyr | His | Ile | Asp | Lys | Val | Thr | Glu | Val | Ile | Ile | Lys |
| | | 435 | | | | 440 | | | | | 445 | | | | |
| Gly | Val | Lys | Arg | Tyr | Val | Val | Asp | Ala | Thr | Leu | Leu | Thr | Asn | Ser | Arg |
| | 450 | | | | | 455 | | | | | 460 | | | | |
| Gly | Pro | Ser | Thr | Pro | Pro | Thr | Pro | Ser | Pro | Ser | Thr | Pro | Pro | Thr | Pro |
| 465 | | | | | 470 | | | | | 475 | | | | | 480 |
| Ser | Asp | Ile | Gly | Ser | Thr | Met | Lys | Thr | Asn | Gln | Ile | Ser | Thr | Thr | Gln |
| | | | | 485 | | | | | 490 | | | | | 495 | |
| Lys | Asn | Gln | Gln | Lys | Glu | Met | Asp | Arg | Lys | Gly | Leu | Leu | Gly | Tyr | Tyr |
| | | | 500 | | | | | 505 | | | | | 510 | | |
| Phe | Lys | Gly | Lys | Asp | Phe | Ser | Asn | Leu | Thr | Met | Phe | Ala | Pro | Thr | Arg |
| | | 515 | | | | 520 | | | | | 525 | | | | |
| Asp | Ser | Thr | Leu | Ile | Tyr | Asp | Gln | Gln | Thr | Ala | Asn | Lys | Leu | Leu | Asp |
| | 530 | | | | | 535 | | | | | 540 | | | | |
| Lys | Lys | Gln | Gln | Glu | Tyr | Gln | Ser | Ile | Arg | Trp | Ile | Gly | Leu | Ile | Gln |
| 545 | | | | | 550 | | | | | 555 | | | | | 560 |
| Ser | Lys | Glu | Thr | Gly | Asp | Phe | Thr | Phe | Asn | Leu | Ser | Glu | Asp | Glu | Gln |
| | | | | 565 | | | | | 570 | | | | | 575 | |
| Ala | Ile | Ile | Glu | Ile | Asn | Gly | Lys | Ile | Ile | Ser | Asn | Lys | Gly | Lys | Glu |
| | | | | 580 | | | | | 585 | | | | | 590 | |
| Lys | Gln | Val | Val | His | Leu | Glu | Lys | Gly | Lys | Leu | Val | Pro | Ile | Lys | Ile |
| | | 595 | | | | 600 | | | | | 605 | | | | |
| Glu | Tyr | Gln | Ser | Asp | Thr | Lys | Phe | Asn | Ile | Asp | Ser | Lys | Thr | Phe | Lys |
| | 610 | | | | | 615 | | | | | 620 | | | | |
| Glu | Leu | Lys | Leu | Phe | Lys | Ile | Asp | Ser | Gln | Asn | Gln | Pro | Gln | Gln | Val |
| 625 | | | | | 630 | | | | | 635 | | | | | 640 |
| Gln | Gln | Asp | Glu | Leu | Arg | Asn | Pro | Glu | Phe | Asn | Lys | Lys | Glu | Ser | Gln |
| | | | | 645 | | | | | 650 | | | | | 655 | |
| Glu | Phe | Leu | Ala | Lys | Pro | Ser | Lys | Ile | Asn | Leu | Phe | Thr | Gln | Gln | Met |
| | | | 660 | | | | | 665 | | | | | 670 | | |
| Lys | Arg | Glu | Ile | Asp | Glu | Asp | Thr | Asp | Thr | Asp | Gly | Asp | Ser | Ile | Pro |
| | | 675 | | | | 680 | | | | | 685 | | | | |
| Asp | Leu | Trp | Glu | Glu | Asn | Gly | Tyr | Thr | Ile | Gln | Asn | Arg | Ile | Ala | Val |
| | 690 | | | | | 695 | | | | | 700 | | | | |
| Lys | Trp | Asp | Asp | Ser | Leu | Ala | Ser | Lys | Gly | Tyr | Thr | Lys | Phe | Val | Ser |
| 705 | | | | | 710 | | | | | 715 | | | | | 720 |
| Asn | Pro | Leu | Glu | Ser | His | Thr | Val | Gly | Asp | Pro | Tyr | Thr | Asp | Tyr | Glu |
| | | | | 725 | | | | | 730 | | | | | 735 | |
| Lys | Ala | Ala | Arg | Asp | Leu | Asp | Leu | Ser | Asn | Ala | Lys | Glu | Thr | Phe | Asn |
| | | | 740 | | | | | 745 | | | | | 750 | | |
| Pro | Leu | Val | Ala | Ala | Phe | Pro | Ser | Val | Asn | Val | Ser | Met | Glu | Lys | Val |

-continued

```
              755                           760                           765
Ile  Leu  Ser  Pro  Asn  Glu  Asn  Leu  Ser  Asn  Ser  Val  Glu  Ser  His  Ser
         770                      775                      780

Ser  Thr  Asn  Trp  Ser  Tyr  Thr  Asn  Thr  Glu  Gly  Ala  Ser  Val  Glu  Ala
785                      790                      795                      800

Gly  Ile  Gly  Pro  Lys  Gly  Ile  Ser  Phe  Gly  Val  Ser  Val  Asn  Tyr  Gln
                   805                      810                      815

His  Ser  Glu  Thr  Val  Ala  Gln  Glu  Trp  Gly  Thr  Ser  Thr  Gly  Asn  Thr
              820                      825                      830

Ser  Gln  Phe  Asn  Thr  Ala  Ser  Ala  Gly  Tyr  Leu  Asn  Ala  Asn  Val  Arg
         835                      840                      845

Tyr  Asn  Asn  Val  Gly  Thr  Gly  Ala  Ile  Tyr  Asp  Val  Lys  Pro  Thr  Thr
    850                      855                      860

Ser  Phe  Val  Leu  Asn  Asn  Asp  Thr  Ile  Ala  Thr  Ile  Thr  Ala  Lys  Ser
865                      870                      875                      880

Asn  Ser  Thr  Ala  Leu  Asn  Ile  Ser  Pro  Glu  Ser  Tyr  Pro  Lys  Lys
                        885                      890                      895

Gly  Gln  Asn  Gly  Ile  Ala  Ile  Thr  Ser  Met  Asp  Asp  Phe  Asn  Ser  His
              900                      905                      910

Pro  Ile  Thr  Leu  Asn  Lys  Lys  Gln  Val  Asp  Asn  Leu  Leu  Asn  Asn  Lys
         915                      920                      925

Pro  Met  Met  Leu  Glu  Thr  Asn  Gln  Thr  Asp  Gly  Val  Tyr  Lys  Ile  Lys
930                      935                      940

Asp  Thr  His  Gly  Asn  Ile  Val  Thr  Gly  Gly  Glu  Trp  Asn  Gly  Val  Ile
945                      950                      955                      960

Gln  Gln  Ile  Lys  Ala  Lys  Thr  Ala  Ser  Ile  Ile  Val  Asp  Asp  Gly  Glu
                   965                      970                      975

Arg  Val  Ala  Glu  Lys  Arg  Val  Ala  Ala  Lys  Asp  Tyr  Glu  Asn  Pro  Glu
              980                      985                      990

Asp  Lys  Thr  Pro  Ser  Leu  Thr  Leu  Lys  Asp  Ala  Leu  Lys  Leu  Ser  Tyr
         995                      1000                     1005

Pro  Asp  Glu  Ile  Lys  Glu  Ile  Glu  Gly  Leu  Leu  Tyr  Tyr  Lys  Asn  Lys
    1010                     1015                     1020

Pro  Ile  Tyr  Glu  Ser  Ser  Val  Met  Thr  Tyr  Leu  Asp  Glu  Asn  Thr  Ala
1025                     1030                     1035                     1040

Lys  Glu  Val  Thr  Lys  Gln  Leu  Asn  Asp  Thr  Thr  Gly  Lys  Phe  Lys  Asp
                   1045                     1050                     1055

Val  Ser  His  Leu  Tyr  Asp  Val  Lys  Leu  Thr  Pro  Lys  Met  Asn  Val  Thr
              1060                     1065                     1070

Ile  Lys  Leu  Ser  Ile  Leu  Tyr  Asp  Asn  Ala  Glu  Ser  Asn  Asp  Asn  Ser
         1075                     1080                     1085

Ile  Gly  Lys  Trp  Thr  Asn  Thr  Asn  Ile  Val  Ser  Gly  Gly  Asn  Asn  Gly
         1090                     1095                     1100

Lys  Lys  Gln  Tyr  Ser  Ser  Asn  Asn  Pro  Asp  Ala  Asn  Leu  Thr  Leu  Asn
1105                     1110                     1115                     1120

Thr  Asp  Ala  Gln  Glu  Lys  Leu  Asn  Lys  Asn  Arg  Asp  Tyr  Tyr  Ile  Ser
                   1125                     1130                     1135

Leu  Tyr  Met  Lys  Ser  Glu  Lys  Asn  Thr  Gln  Cys  Glu  Ile  Thr  Ile  Asp
              1140                     1145                     1150

Gly  Glu  Ile  Tyr  Pro  Ile  Thr  Thr  Lys  Thr  Val  Asn  Val  Asn  Lys  Asp
              1155                     1160                     1165

Asn  Tyr  Lys  Arg  Leu  Asp  Ile  Ile  Ala  His  Asn  Ile  Lys  Ser  Asn  Pro
    1170                     1175                     1180
```

-continued

| | | | | | | | | | | | | | | |
|---|---|---|---|---|---|---|---|---|---|---|---|---|---|---|
| Ile 1185 | Ser | Ser | Leu | His | Ile 1190 | Lys | Thr | Asn | Asp | Glu 1195 | Ile | Thr | Leu | Phe | Trp 1200 |
| Asp | Asp | Ile | Ser | Ile 1205 | Thr | Asp | Val | Ala | Ser 1210 | Ile | Lys | Pro | Glu | Asn 1215 | Leu |
| Thr | Asp | Ser | Glu 1220 | Ile | Lys | Gln | Ile | Tyr 1225 | Ser | Arg | Tyr | Gly | Ile 1230 | Lys | Leu |
| Glu | Asp | Gly 1235 | Ile | Leu | Ile | Asp | Lys 1240 | Lys | Gly | Gly | Ile | His 1245 | Tyr | Gly | Glu |
| Phe | Ile 1250 | Asn | Glu | Ala | Ser | Phe 1255 | Asn | Ile | Glu | Pro | Leu 1260 | Gln | Asn | Tyr | Val |
| Thr 1265 | Lys | Tyr | Glu | Val | Thr 1270 | Tyr | Ser | Ser | Glu | Leu 1275 | Gly | Pro | Asn | Val | Ser 1280 |
| Asp | Thr | Leu | Glu | Ser 1285 | Asp | Lys | Ile | Tyr | Lys 1290 | Asp | Gly | Thr | Ile | Lys 1295 | Phe |
| Asp | Phe | Thr | Lys 1300 | Tyr | Ser | Lys | Asn | Glu 1305 | Gln | Gly | Leu | Phe | Tyr 1310 | Asp | Ser |
| Gly | Leu | Asn | Trp 1315 | Asp | Phe | Lys | Ile | Asn 1320 | Ala | Ile | Thr | Tyr 1325 | Asp | Gly | Lys |
| Glu | Met | Asn 1330 | Val | Phe | His | Arg 1335 | Tyr | Asn | Lys | | | | | | |

What is claimed is:

1. A substantially pure nucleotide sequence which encodes an auxiliary protein having SEQ ID NO:2 or 20, or the complement thereof, wherein said auxiliary protein activates the insecticidal activity of an insect-specific protein.

2. A substantially pure nucleotide sequence which encodes an auxiliary protein having SEQ ID NO:2 or 20, or the complement thereof, wherein said auxiliary protein enhances the insecticidal activity of an insect-specific protein.

3. The nucleotide sequence of claim 1 wherein said sequence is given as VIP2A(a) in SEQ ID NO:1.

4. The nucleotide sequence of claim 1 wherein said sequence is optimized for expression in a plant.

5. The nucleotide sequence of claim 4 wherein said sequence is given in SEQ ID NO:24.

6. The nucleotide sequence of claim 2 wherein said sequence is optimized for expression in a plant.

7. The nucleotide sequence of claim 1 wherein said sequence is given as VIP2A(b) in SEQ ID NO:19.

8. The nucleotide sequence of claim 7 wherein said sequence is optimized for expression in a plant.

9. The nucleotide sequence of claim 6 wherein said sequence in given in SEQ ID NO:27.

10. A nucleotide sequence which hybridizes to the nucleotide sequence of claim 1 or 2 under stringent conditions wherein said stringent conditions are 65° C., 2×SSC, and 0.1% SDS.

* * * * *